United States Patent
Mueller et al.

(10) Patent No.: US 12,300,356 B2
(45) Date of Patent: May 13, 2025

(54) CELL-FREE DETECTION OF METHYLATED TUMOUR DNA

(71) Applicants: QUEEN'S UNIVERSITY AT KINGSTON, Kingston (CA); INSTITUT CURIE, Paris (FR); INSTITUT NATIONAL DE LA SANTE ET DE LA RECHERCHE MEDICALE (INSERM), Paris (FR)

(72) Inventors: Christopher R. Mueller, Kingston (CA); Marc-Henri Stern, Paris (FR)

(73) Assignees: QUEEN'S UNIVERSITY AT KINGSTON, Kingston (CA); INSTITUT CURIE, Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 19 days.

(21) Appl. No.: 16/098,455

(22) PCT Filed: May 4, 2017

(86) PCT No.: PCT/CA2017/000111
§ 371 (c)(1),
(2) Date: Nov. 2, 2018

(87) PCT Pub. No.: WO2017/201606
PCT Pub. Date: Nov. 30, 2017

(65) Prior Publication Data
US 2019/0256921 A1    Aug. 22, 2019

Related U.S. Application Data

(60) Provisional application No. 62/331,585, filed on May 4, 2016.

(51) Int. Cl.
| | | |
|---|---|---|
| *C12Q 1/6886* | (2018.01) | |
| *C12Q 1/6827* | (2018.01) | |
| *G16B 25/00* | (2019.01) | |
| *G16B 25/10* | (2019.01) | |
| *G16B 30/00* | (2019.01) | |
| *G16B 35/00* | (2019.01) | |
| *G16B 99/00* | (2019.01) | |

(52) U.S. Cl.
CPC .......... *G16B 30/00* (2019.02); *C12Q 1/6827* (2013.01); *C12Q 1/6886* (2013.01); *G16B 25/00* (2019.02); *G16B 25/10* (2019.02); *G16B 35/00* (2019.02); *G16B 99/00* (2019.02); *C12Q 2600/106* (2013.01); *C12Q 2600/118* (2013.01); *C12Q 2600/154* (2013.01)

(58) Field of Classification Search
None
See application file for complete search history.

(56) References Cited

U.S. PATENT DOCUMENTS

| | | | | |
|---|---|---|---|---|
| 6,582,908 | B2 * | 6/2003 | Fodor | C07H 21/00 506/30 |
| 2009/0075260 | A1 * | 3/2009 | Distler | C12Q 1/6886 435/6.12 |
| 2009/0305256 | A1 | 12/2009 | Pfeifer et al. | |
| 2012/0064521 | A1 * | 3/2012 | Yen | C12Q 1/6858 435/6.11 |
| 2012/0219946 | A1 | 8/2012 | Laird et al. | |
| 2013/0084328 | A1 * | 4/2013 | Perera | C12Q 1/6869 435/6.12 |
| 2015/0119350 | A1 * | 4/2015 | Kebebew | C12Q 1/6886 514/43 |

FOREIGN PATENT DOCUMENTS

| | | |
|---|---|---|
| WO | 2013/177265 A1 | 11/2013 |
| WO | 2014/043763 A1 | 3/2014 |
| WO | 2014/164874 A2 | 10/2014 |
| WO | 2015/159292 A2 | 10/2015 |

OTHER PUBLICATIONS

Feng (PNAS 2010 vol. 107 No. 19 pp. 8689-8694) (Year: 2010).*
Zhang et al. (Hepatol Int 2013 vol. 7 p. 893) (Year: 2013).*
Walsh et al teaches (Genes & Development (1999) vol. 13, pp. 26-36) (Year: 1999).*
Legendre et al, "Whole-genome bisulfate sequencing of cell-free DNA identifies signature associated with metastatic breast cancer", Clinical Epigenetics, 2015, vol. 7, No. 100.
Farkas et al, "Genome-wide DNA methylation assay reveals novel candidate biomarker genes in cervical cancer", Epigenetics, Nov. 2013, vol. 8, No. 11, pp. 1213-1225.

(Continued)

*Primary Examiner* — Katherine D Salmon
(74) *Attorney, Agent, or Firm* — GREENBLUM & BERNSTEIN, P.L.C.

(57) ABSTRACT

Provided herein is a method for detecting a tumour that can be applied to cell-free samples, e.g., to cell-free detect circulating tumour DNA. The method utilizes detection of adjacent methylation signals within a single sequencing read as the basic positive tumour signal, thereby decreasing false positives. The method comprises extracting DNA from a cell-free sample obtained from a subject, bisulphite converting the DNA, amplifying regions methylated in cancer (e.g., CpG islands, CpG shores, and/or CpG shelves), generating sequencing reads, and detecting tumour signals. To increase sensitivity, biased primers designed based on bisulphite converted methylated sequences can be used. Target methylated regions can be selected from a pre-validated set according to the specific aim of the test. Absolute number, proportion, and/or distribution of tumour signals may be used for tumour detection or classification. The method is also useful in, e.g., predicting, prognosticating, and/or monitoring response to treatment, tumour load, relapse, cancer development, or risk.

9 Claims, 35 Drawing Sheets

Specification includes a Sequence Listing.

(56) References Cited

OTHER PUBLICATIONS

Haldrup et al, "DNA Methylation Signatures for Prediction of Biochemical Recurrence After Radical Prostatectomy of Clinically Localized Prostate Cancer," J Clin Oncol, Sep. 10, 2013, vol. 31, No. 26, pp. 3250-3258.

Tommasi et al, "Methylation of homeobox genes is a frequent and early epigenetic event in breast cancer", Breast Cancer Research, Feb. 27, 2009, vol. 11, No. 1.

Fackler et al, "Novel Methylated Biomarkers and a Robust Assay to Detect Circulating Tumor DNA in Metastatic Breast Cancer", Cancer Research, Oct. 17, 2014, vol. 74, No. 8, pp. 2160-2170.

Ellinger et al, "CpG Island Hypermethylation in Cell-Free Serum DNA Identifies Patients With Localized Prostate Cancer", The Prostate, 2008, vol. 68, pp. 42-49.

Schwarzenbach et al, "Circulating DNA as biomarker in breast cancer", Breast Cancer Research, 2015, vol. 17, No. 136.

Lehmann-Werman et al: "Identification of tissue-specific cell death using methylation patterns of circulating DNA", Proceedings of the National Academy of Sciences, vol. 113, No. 13, pp. E1826-E1834, Mar. 14, 2016.

Anonymous: Infinium(R) HumanMethylation450 BeadChip, Mar. 9, 2012.

Office Action issued Feb. 21, 2023 in European Patent Application No. 17 801 856.0.

Office Action issued Nov. 19, 2021 in European Patent Application No. 17 801 856.0.

Office Action issued Oct. 2, 2020 in European Patent Application No. 17 801 856.0.

International Search Report issued Aug. 29, 2017 in PCT/CA2017/000111.

Written Opinion of the International Searching Authority, issued Aug. 29, 2017 in PCT/CA2017/000111.

Office Action issued Apr. 4, 2023 in Canadian Patent Application No. 3,023,335.

Carson, et al., "Development and initial clinical correlation of a DNA methylation-based blood test for prostate cancer," *The Prostate*, 2020, 80: 1038-1042.

Cristall, et al., "A DNA methylation-based liquid biopsy for triple-negative breast cancer," *Precision Oncology*, (2021) 5:53.

Office Action issued Dec. 20, 2023 in European patent application No. 17 801 856.0.

Office Action issued Sep. 2, 2024 in European patent application No. 17801856.0.

* cited by examiner

| | Area | Std. Error | 95% CI | P value |
|---|---|---|---|---|
| cg03257575 | 0.8773 | 0.01278 | 0.8523 to 0.9024 | < 0.0001 |
| cg25764899 | 0.95 | 0.008397 | 0.9335 to 0.9664 | < 0.0001 |
| cg25191623 | 0.9261 | 0.01008 | 0.9064 to 0.9459 | < 0.0001 |
| cg22336004 | 0.9098 | 0.01053 | 0.8892 to 0.9305 | < 0.0001 |
| cg12071883 | 0.9168 | 0.01006 | 0.8971 to 0.9365 | < 0.0001 |
| cg04550737 | 0.9012 | 0.01089 | 0.8799 to 0.9225 | < 0.0001 |
| cg22877509 | 0.8984 | 0.01148 | 0.8759 to 0.9209 | < 0.0001 |
| cg17816394 | 0.9136 | 0.01019 | 0.8936 to 0.9336 | < 0.0001 |
| cg05099503 | 0.9182 | 0.01046 | 0.8977 to 0.9387 | < 0.0001 |
| cg22831607 | 0.8664 | 0.01502 | 0.8369 to 0.8958 | < 0.0001 |
| cg21384402 | 0.8963 | 0.01125 | 0.8742 to 0.9183 | < 0.0001 |
| cg15556502 | 0.9087 | 0.01014 | 0.8888 to 0.9286 | < 0.0001 |
| cg19897940 | 0.8473 | 0.01317 | 0.8214 to 0.8731 | < 0.0001 |
| cg13691247 | 0.8976 | 0.01212 | 0.8738 to 0.9213 | < 0.0001 |
| cg13879483 | 0.9415 | 0.008398 | 0.9250 to 0.9579 | < 0.0001 |
| cg01940855 | 0.8454 | 0.0144 | 0.8171 to 0.8736 | < 0.0001 |
| cg27398263 | 0.865 | 0.01322 | 0.8391 to 0.8909 | < 0.0001 |
| cg13631572 | 0.8556 | 0.01321 | 0.8297 to 0.8815 | < 0.0001 |
| cg04368094 | 0.8967 | 0.01107 | 0.8750 to 0.9184 | < 0.0001 |
| cg05527869 | 0.8242 | 0.01534 | 0.7941 to 0.8543 | < 0.0001 |
| cg03348973 | 0.8991 | 0.01093 | 0.8776 to 0.9205 | < 0.0001 |
| cg20945565 | 0.8479 | 0.01321 | 0.8220 to 0.8738 | < 0.0001 |
| cg15146853 | 0.9161 | 0.01115 | 0.8942 to 0.9379 | < 0.0001 |
| cg06537894 | 0.9244 | 0.00991 | 0.9050 to 0.9439 | < 0.0001 |
| cg22473620 | 0.8525 | 0.01338 | 0.8263 to 0.8787 | < 0.0001 |
| cg00778995 | 0.8738 | 0.01229 | 0.8497 to 0.8979 | < 0.0001 |
| cg13356895 | 0.8268 | 0.01579 | 0.7959 to 0.8578 | < 0.0001 |
| cg23448584 | 0.8714 | 0.01422 | 0.8435 to 0.8993 | < 0.0001 |
| cg08260891 | 0.9309 | 0.00953 | 0.9122 to 0.9495 | < 0.0001 |
| cg19127283 | 0.8919 | 0.01179 | 0.8688 to 0.9150 | < 0.0001 |
| cg00442112 | 0.8498 | 0.014 | 0.8223 to 0.8772 | < 0.0001 |
| cg14866200 | 0.8071 | 0.01626 | 0.7753 to 0.8390 | < 0.0001 |
| cg24154839 | 0.958 | 0.00663 | 0.9450 to 0.9710 | < 0.0001 |
| cg03205103 | 0.9322 | 0.009127 | 0.9143 to 0.9501 | < 0.0001 |
| cg18148997 | 0.9154 | 0.01079 | 0.8942 to 0.9365 | < 0.0001 |
| cg08516515 | 0.9184 | 0.01039 | 0.8980 to 0.9387 | < 0.0001 |
| cg05766140 | 0.908 | 0.01147 | 0.8855 to 0.9305 | < 0.0001 |
| cg14151253 | 1 | 0 | 1.000 to 1.000 | < 0.0001 |
| cg00124375 | 0.8762 | 0.01189 | 0.8529 to 0.8995 | < 0.0001 |
| cg25459553 | 0.8939 | 0.01131 | 0.8718 to 0.9161 | < 0.0001 |
| cg27363327 | 0.8514 | 0.01377 | 0.8244 to 0.8784 | < 0.0001 |
| cg13315970 | 0.8697 | 0.01282 | 0.8446 to 0.8948 | < 0.0001 |
| cg21684012 | 0.8854 | 0.01139 | 0.8631 to 0.9078 | < 0.0001 |
| cg16924337 | 0.8455 | 0.01437 | 0.8173 to 0.8736 | < 0.0001 |
| cg14045872 | 0.8401 | 0.01494 | 0.8108 to 0.8694 | < 0.0001 |
| cg00158523 | 0.8997 | 0.01093 | 0.8782 to 0.9211 | < 0.0001 |
| cg25832771 | 0.8646 | 0.01259 | 0.8399 to 0.8893 | < 0.0001 |

Fig. 3

| Reference | MCF7 # Reads | MCF7 Mean Me | SKBR3 # Reads | SKBR3 Mean Me | T47D # Reads | T47D Mean Me | MDA MB 231 # Reads | MDA MB 231 Mean Me | MCF10A # Reads | MCF10A Mean Me | hTert # Reads | hTert Mean Me |
|---|---|---|---|---|---|---|---|---|---|---|---|---|
| ADCYFtrim | 204 | 0.968 | 351 | 0.975 | 334 | 0.965 | 40 | 0.781 | 603 | 0.475 | 175 | 0.548 |
| ADCYGtrim | 121 | 0.975 | 219 | 0.981 | 218 | 0.967 | 30 | 0.862 | 427 | 0.522 | 121 | 0.627 |
| ADCYHtrim | 0 | 0 | 0 | 0 | 0 | 0 | 0 | 0 | 0 | 0 | 0 | 0 |
| C1Dtrim | 1597 | 0.942 | 1184 | 0.922 | 1047 | 0.832 | 418 | 0.916 | 215 | 0.575 | 104 | 0.933 |
| C1Etrim | 1423 | 0.784 | 1976 | 0.68 | 726 | 0.762 | 746 | 0.999 | 2289 | 0.675 | 118 | 0.149 |
| C1Ftrim | 1545 | 0.937 | 1156 | 0.919 | 995 | 0.8 | 418 | 0.916 | 214 | 0.758 | 100 | 0.917 |
| C1Gtrim | 1477 | 0.615 | 1980 | 0.646 | 890 | 0.529 | 568 | 0.928 | 700 | 0.501 | 158 | 0.032 |
| MIRBtrim | 300 | 0.783 | 383 | 0.024 | 315 | 0.711 | 311 | 0.78 | 507 | 0.251 | 458 | 0.073 |
| MIRCtrim | 374 | 0.916 | 448 | 0.565 | 471 | 0.884 | 118 | 0.559 | 858 | 0.49 | 929 | 0.643 |
| MIRDtrim | 145 | 0.954 | 6 | 0.148 | 258 | 0.856 | 118 | 0.989 | 134 | 0.189 | 10 | 0.126 |
| MIREtrim | 2078 | 0.976 | 524 | 0.614 | 1295 | 0.965 | 536 | 0.946 | 1818 | 0.484 | 172 | 0.305 |
| MIRFtrim | 170 | 0.895 | 68 | 0.196 | 115 | 0.798 | 14 | 0.801 | 144 | 0.279 | 167 | 0.397 |
| VWCJtrim | 635 | 0.915 | 195 | 0.239 | 1329 | 0.633 | 205 | 0.903 | 261 | 0.622 | 102 | 0.281 |
| VWCKtrim | 44 | 0.975 | 23 | 0.279 | 98 | 0.764 | 7 | 0.971 | 114 | 0.599 | 15 | 0.603 |
| VWCLtrim | 1786 | 0.909 | 747 | 0.472 | 2805 | 0.733 | 125 | 0.896 | 4493 | 0.806 | 2253 | 0.566 |
| VWCMtrim | 952 | 0.964 | 632 | 0.275 | 943 | 0.784 | 1051 | 0.788 | 1408 | 0.767 | 63 | 0.67 |
| VWCNtrim | 1062 | 0.934 | 220 | 0.254 | 1764 | 0.603 | 291 | 0.855 | 326 | 0.659 | 111 | 0.39 |
| CHSAtrim | 223 | 0.914 | 66 | 0.012 | 259 | 0.485 | 7 | 0.048 | 191 | 0.009 | 52 | 0.007 |
| CHSBtrim | 1387 | 0.928 | 5 | 0.02 | 1840 | 0.776 | 0 | 0 | 2 | 0 | 30 | 0 |
| CHSCtrim | 1847 | 0.918 | 108 | 0.016 | 2421 | 0.772 | 59 | 0.006 | 205 | 0.007 | 220 | 0.021 |
| CHSDtrim | 1357 | 0.928 | 5 | 0.02 | 1761 | 0.778 | 0 | 0 | 3 | 0 | 30 | 0 |
| DMBAtrim | 0 | 0 | 0 | 0 | 2 | 0.269 | 0 | 0 | 0 | 0 | 0 | 0 |
| DMBBtrim | 1120 | 0.965 | 113 | 0.098 | 1117 | 0.956 | 885 | 0.955 | 1792 | 0.803 | 2976 | 0.515 |
| DMBCtrim | 795 | 0.971 | 105 | 0.162 | 874 | 0.959 | 814 | 0.964 | 1404 | 0.799 | 2324 | 0.553 |
| FOXAtrim | 481 | 0.871 | 417 | 0.636 | 362 | 0.741 | 169 | 0.001 | 280 | 0.512 | 50 | 0.143 |
| FOXBtrim | 30 | 0.878 | 0 | 0 | 123 | 0.79 | 39 | 0.043 | 4 | 0.167 | 49 | 0.418 |
| FOXCtrim | 0 | 0 | 0 | 0 | 0 | 0 | 1 | 0 | 0 | 0 | 0 | 0 |
| FOXDtrim | 316 | 0.97 | 321 | 0.9 | 496 | 0.885 | 450 | 0.329 | 259 | 0.696 | 627 | 0.783 |
| FOXEtrim | 636 | 0.98 | 1040 | 0.951 | 938 | 0.956 | 800 | 0.88 | 588 | 0.881 | 1128 | 0.906 |
| HOXAAtrim | 1969 | 0.949 | 1561 | 0.088 | 2319 | 0.726 | 796 | 0.902 | 1639 | 0.678 | 1911 | 0.734 |
| HOXABtrim | 2006 | 0.958 | 1703 | 0.305 | 2460 | 0.802 | 780 | 0.924 | 1676 | 0.714 | 1943 | 0.775 |
| HOXACtrim | 13 | 0.85 | 48 | 0.246 | 81 | 0.749 | 135 | 0.841 | 79 | 0.744 | 44 | 0.934 |
| HOXADtrim | 469 | 0.935 | 1108 | 0.395 | 701 | 0.829 | 173 | 0.911 | 543 | 0.295 | 497 | 0.368 |
| SFRAtrim | 594 | 0.901 | 220 | 0.123 | 667 | 0.884 | 662 | 0.978 | 641 | 0.565 | 491 | 0.252 |
| SFRBtrim | 1061 | 0.959 | 0 | 0 | 1046 | 0.946 | 325 | 0.997 | 778 | 0.719 | 629 | 0.4 |
| SFRCtrim | 1256 | 0.984 | 173 | 0.306 | 1254 | 0.968 | 1292 | 0.998 | 853 | 0.689 | 458 | 0.633 |
| SFRDtrim | 643 | 0.867 | 231 | 0.023 | 728 | 0.823 | 731 | 0.926 | 666 | 0.49 | 503 | 0.219 |
| SFREtrim | 1195 | 0.955 | 0 | 0 | 1170 | 0.936 | 307 | 0.997 | 875 | 0.62 | 815 | 0.137 |
| TTBAtrim | 419 | 0.968 | 100 | 0.04 | 674 | 0.77 | 400 | 0.766 | 205 | 0.206 | 478 | 0.343 |
| TTBBtrim | 381 | 0.946 | 0 | 0 | 457 | 0.74 | 242 | 0.933 | 9 | 0.4 | 383 | 0.134 |
| TTBCtrim | 198 | 0.967 | 1 | 1 | 199 | 0.64 | 59 | 0.844 | 15 | 0.4 | 42 | 0.291 |
| TTBDtrim | 656 | 0.974 | 4 | 0.2 | 557 | 0.866 | 377 | 0.957 | 19 | 0.649 | 25 | 0.874 |
| 4th Generation | | | | | | | | | | | | |
| mbBARHL2 Trim | 73 | 0.968 | 50 | 0.515 | | | 76 | 0.961 | 811 | 0.883 | 159 | 0.976 |
| mbBOLL Trim | 46 | 0.974 | 53 | 0.954 | | | 16 | 0.935 | 234 | 0.759 | 54 | 0.873 |
| mbC5orf Trim | 26 | 0.832 | 14 | 0.842 | | | 15 | 0.886 | 1077 | 0.983 | 661 | 0.745 |
| mbCDO Trim | 44 | 0.95 | 59 | 0.556 | | | 48 | 0.988 | 523 | 0.517 | 373 | 0.95 |
| mbCOL1 Trim | 297 | 0.966 | 522 | 0.857 | | | 496 | 0.984 | 917 | 0.841 | 348 | 0.552 |
| mbCYTL Trim | 23 | 0.804 | 3 | 0.778 | | | 4 | 0.25 | 251 | 0.561 | 118 | 0.164 |
| mbDDAH Trim | 5 | 0.4 | 0 | 0 | | | 0 | 0 | 59 | 0.571 | 1 | 0.4 |
| mbDMRTA Trim | 48 | 0.964 | 59 | 0.199 | | | 106 | 0.907 | 517 | 0.811 | 346 | 0.714 |
| mbEGFLAM Trim | 76 | 0.936 | 11 | 0 | | | 66 | 0.867 | 826 | 0.632 | 15 | 0.35 |
| mbGABRA A Trim | 1 | 0.909 | 0 | 0 | | | 11 | 0.873 | 15 | 0.713 | 4 | 0.907 |
| mbGABRA B Trim | 55 | 0.786 | 26 | 0.433 | | | 54 | 0.854 | 557 | 0.682 | 78 | 0.451 |
| mbGNG Trim | 67 | 0.971 | 45 | 0.859 | | | 44 | 0.966 | 222 | 0.931 | 131 | 0.974 |
| mbID4 Trim | 40 | 0.967 | 111 | 0.81 | | | 42 | 0.607 | 264 | 0.909 | 91 | 0.6 |
| mbIRF Trim | 151 | 0.953 | 0 | 0 | | | 112 | 0.895 | 593 | 0.731 | 81 | 0.318 |
| mbNT5E Trim | 136 | 0.957 | 63 | 0.695 | | | 3 | 0.6 | 502 | 0.757 | 0 | 0 |
| mbPDE4 Trim | 58 | 0.922 | 25 | 0.485 | | | 40 | 1 | 503 | 0.691 | 93 | 0.625 |
| mbPOU3F Trim | 178 | 0.776 | 122 | 0.432 | | | 132 | 0.59 | 1439 | 0.695 | 382 | 0.656 |
| mbRUSC Trim | 18 | 0.902 | 71 | 0.902 | | | 27 | 0.984 | 916 | 0.946 | 136 | 0.514 |
| mbSCAND Trim | 111 | 0.014 | 116 | 0.022 | | | 249 | 0.808 | 463 | 0.044 | 238 | 0.039 |

Fig. 12A

| Reference | MCF7 Reads Exp. | MCF7 Mn. Meth. | SKBR3 Reads Exp. | SKBR3 Mn. Meth. | T47D Reads Exp. | T47D Mn. Meth. | MDA MB 231 Reads Exp. | MDA MB 231 Mn. Meth. | MCF10A Reads Exp. | MCF10A Mn. Meth. | hTert Reads Exp. | hTert Mn. Meth. |
|---|---|---|---|---|---|---|---|---|---|---|---|---|
| mbSHISA Trim | 208 | 0.958 | 0 | 0 | | | 0 | 0 | 648 | 0.786 | 7 | 0.167 |
| mbSIM A Trim | 144 | 0.966 | 219 | 0.928 | | | 53 | 0.997 | 374 | 0.848 | 228 | 0.742 |
| mbSIM B Trim | 45 | 0.978 | 103 | 0.728 | | | 113 | 0.997 | 293 | 0.944 | 334 | 0.652 |
| mbSLC Trim | 236 | 0.96 | 38 | 0.23 | | | 8 | 0 | 740 | 0.938 | 52 | 0.976 |
| mbTAL Trim | 300 | 0.939 | 115 | 0.467 | | | 84 | 0.699 | 351 | 0.664 | 411 | 0.772 |
| mbTBX15 Trim | 51 | 0.954 | 9 | 0.358 | | | 41 | 0.897 | 144 | 0.516 | 76 | 0.505 |
| mbTRIM A Trim | 21 | 0.939 | 40 | 0.619 | | | 23 | 0.664 | 77 | 0.608 | 65 | 0.422 |
| mbTRIM B Trim | 118 | 0.97 | 167 | 0.892 | | | 95 | 0.915 | 298 | 0.735 | 133 | 0.619 |
| pbBARHL Trim | 55 | 0.932 | 69 | 0.222 | | | 94 | 0.83 | 515 | 0.762 | 138 | 0.779 |
| pbBOLL Trim | 35 | 0.942 | 18 | 0.719 | | | 18 | 0.681 | 151 | 0.803 | 336 | 0.66 |
| pbCDO Trim | 56 | 0.852 | 81 | 0.149 | | | 62 | 0.824 | 176 | 0.244 | 147 | 0.569 |
| pbCOL1 Trim | 302 | 0.965 | 522 | 0.867 | | | 496 | 0.985 | 890 | 0.863 | 348 | 0.615 |
| pbCYTL Trim | 39 | 0.842 | 29 | 0.913 | | | 7 | 0.25 | 207 | 0.239 | 60 | 0.104 |
| pbCorf Trim | 26 | 0.86 | 21 | 0.838 | | | 13 | 0.904 | 1171 | 0.979 | 785 | 0.687 |
| pbDDAH Trim | 5 | 0.4 | 0 | 0 | | | 0 | 0 | 60 | 0.585 | 1 | 0 |
| pbDMRTA Trim | 61 | 0.956 | 31 | 0.276 | | | 46 | 0.977 | 83 | 0.583 | 64 | 0.732 |
| pbEGFLAM Trim | 43 | 0.944 | 0 | 0 | | | 40 | 0.879 | 256 | 0.664 | 13 | 0.528 |
| pbGABRA Trim | 161 | 0.717 | 68 | 0.222 | | | 114 | 0.849 | 1092 | 0.686 | 156 | 0.417 |
| pbGNG Trim | 125 | 0.952 | 116 | 0.869 | | | 48 | 1 | 359 | 0.794 | 107 | 0.988 |
| pbID4 A Trim | 44 | 0.96 | 104 | 0.911 | | | 36 | 0.847 | 562 | 0.944 | 242 | 0.805 |
| pbID4 B Trim | 70 | 0.929 | 159 | 0.909 | | | 4 | 0.663 | 318 | 0.977 | 43 | 0.902 |
| pbIRF4 Trim | 79 | 0.96 | 0 | 0 | | | 36 | 0.961 | 392 | 0.847 | 211 | 0.703 |
| pbPDE4 Trim | 33 | 0.735 | 20 | 0 | | | 22 | 0.659 | 720 | 0.638 | 149 | 0.675 |
| pbPOU3F Trim | 196 | 0.696 | 135 | 0.056 | | | 144 | 0.184 | 1591 | 0.241 | 427 | 0.289 |
| pbRUSC Trim | 19 | 0.885 | 73 | 0.907 | | | 23 | 0.981 | 1131 | 0.942 | 172 | 0.526 |
| pbSCAND Trim | 108 | 0.012 | 117 | 0.019 | | | 248 | 0.809 | 461 | 0.044 | 236 | 0.037 |
| pbSHISA Trim | 205 | 0.945 | 0 | 0 | | | 0 | 0 | 611 | 0.868 | 8 | 0 |
| pbSIM A Trim | 210 | 0.97 | 330 | 0.943 | | | 58 | 1 | 699 | 0.969 | 520 | 0.726 |
| pbSIM B Trim | 55 | 0.919 | 75 | 0.673 | | | 35 | 0.932 | 261 | 0.897 | 128 | 0.879 |
| pbSIM C Trim | 165 | 0.953 | 261 | 0.89 | | | 49 | 0.995 | 936 | 0.582 | 701 | 0.512 |
| pbSLC Trim | 70 | 0.952 | 38 | 0.553 | | | 0 | 0 | 297 | 0.76 | 226 | 0.965 |
| pbTAL Trim | 100 | 0.952 | 8 | 0 | | | 78 | 0.752 | 326 | 0.513 | 138 | 0.443 |
| pbTBX15 Trim | 1 | 0.875 | 0 | 0 | | | 0 | 0 | 4 | 0.975 | 0 | 0 |
| pbTRIM Trim | 133 | 0.967 | 200 | 0.957 | | | 112 | 0.907 | 689 | 0.822 | 221 | 0.603 |

Fig. 12B

| Reference | A02324 T HER2+ # Reads | A02324 T HER2+ Mean Me | A02324 N HER2+ # Reads | A02324 N HER2+ Mean Me | A02354 T TRIPLE- # Reads | A02354 T TRIPLE- Mean Me | A02354 N TRIPLE- # Reads | A02354 N TRIPLE- Mean Me | B02275 T TRIPLE-GR+ # Reads | B02275 T TRIPLE-GR+ Mean Me | B02275 N TRIPLE-GR+ Mean Me | B02275 N TRIPLE-GR+ Mean Me |
|---|---|---|---|---|---|---|---|---|---|---|---|---|
| ADCYFtrim | 16 | 0.991 | 0 | 0 | 0 | 0 | 4 | 1 | 125 | 0.791 | 251 | 0.529 |
| ADCYGtrim | 10 | 0.987 | 0 | 0 | 0 | 0 | 3 | 1 | 96 | 0.832 | 210 | 0.62 |
| ADCYHtrim | 0 | 0 | 0 | 0 | 0 | 0 | 0 | 0 | 0 | 0 | 0 | 0 |
| C1Dtrim | 344 | 0.843 | 45 | 0.776 | 0 | 0 | 0 | 0 | 955 | 0.912 | 556 | 0.549 |
| C1Etrim | 393 | 0.347 | 728 | 0.036 | 193 | 0.007 | 1 | 0 | 663 | 0.778 | 753 | 0.359 |
| C1Ftrim | 331 | 0.741 | 51 | 0.912 | 0 | 0 | 0 | 0 | 913 | 0.889 | 550 | 0.501 |
| C1Gtrim | 378 | 0.439 | 73 | 1 | 0 | 0 | 0 | 0 | 504 | 0.892 | 246 | 0.581 |
| MIRBtrim | 557 | 0.099 | 485 | 0.031 | 136 | 0.001 | 499 | 0.027 | 253 | 0.471 | 247 | 0.054 |
| MIRCtrim | 23 | 0.64 | 286 | 0.084 | 175 | 0.094 | 9 | 0 | 130 | 0.735 | 328 | 0.242 |
| MIRDtrim | 0 | 0 | 0 | 0 | 63 | 0 | 31 | 0 | 213 | 0.868 | 144 | 0.287 |
| MIREtrim | 248 | 0.996 | 80 | 1 | 0 | 0 | 191 | 0.026 | 475 | 0.944 | 685 | 0.355 |
| MIRFtrim | 88 | 0.214 | 92 | 0.012 | 112 | 0.044 | 603 | 0.082 | 30 | 0.383 | 39 | 0.061 |
| VWCJtrim | 1 | 0 | 78 | 0.55 | 32 | 0.071 | 2 | 0.5 | 604 | 0.879 | 351 | 0.3 |
| VWCKtrim | 0 | 0 | 9 | 0.269 | 0 | 0 | 0 | 0 | 248 | 0.915 | 39 | 0.62 |
| VWCLtrim | 0 | 0 | 3 | 0 | 339 | 0.011 | 0 | 0 | 697 | 0.925 | 476 | 0.47 |
| VWCMtrim | 0 | 0 | 0 | 0 | 92 | 0.153 | 0 | 0 | 454 | 0.981 | 234 | 0.673 |
| VWCNtrim | 1 | 0.2 | 93 | 0.658 | 34 | 0.273 | 2 | 0.6 | 809 | 0.912 | 403 | 0.425 |
| CHSAtrim | 77 | 0.006 | 27 | 0 | 44 | 0.004 | 2 | 0 | 378 | 0.748 | 279 | 0.047 |
| CHSBtrim | 0 | 0 | 0 | 0 | 0 | 0 | 0 | 0 | 1039 | 0.946 | 240 | 0.34 |
| CHSCtrim | 125 | 0.256 | 46 | 0 | 36 | 0.046 | 583 | 0.748 | 1396 | 0.921 | 337 | 0.176 |
| CHSDtrim | 0 | 0 | 0 | 0 | 0 | 0 | 0 | 0 | 1037 | 0.946 | 241 | 0.339 |
| DMBAtrim | 0 | 0 | 0 | 0 | 0 | 0 | 0 | 0 | 0 | 0 | 0 | 0 |
| DMBBtrim | 1078 | 0.876 | 586 | 0.386 | 559 | 0.935 | 219 | 0.486 | 1078 | 0.887 | 544 | 0.373 |
| DMBCtrim | 1000 | 0.891 | 564 | 0.399 | 530 | 0.939 | 202 | 0.461 | 1014 | 0.889 | 506 | 0.399 |
| FOXAtrim | 205 | 0.745 | 12 | 0 | 0 | 0 | 0 | 0 | 240 | 0.232 | 51 | 0.093 |
| FOXBtrim | 155 | 0.355 | 32 | 0.078 | 54 | 0.09 | 2363 | 0.159 | 6 | 0.056 | 12 | 0.069 |
| FOXCtrim | 0 | 0 | 0 | 0 | 0 | 0 | 21 | 0.179 | 0 | 0 | 0 | 0 |
| FOXDtrim | 806 | 0.918 | 0 | 0 | 0 | 0 | 0 | 0 | 44 | 0.023 | 38 | 0 |
| FOXEtrim | 1139 | 0.956 | 0 | 0 | 185 | 0.072 | 173 | 0.888 | 341 | 0.157 | 268 | 0.173 |
| HOXAAtrim | 905 | 0.824 | 536 | 0.376 | 1899 | 0.696 | 781 | 0.589 | 1076 | 0.199 | 1163 | 0.178 |
| HOXABtrim | 896 | 0.824 | 529 | 0.466 | 1877 | 0.764 | 770 | 0.7 | 1079 | 0.225 | 1153 | 0.265 |
| HOXACtrim | 31 | 0.987 | 78 | 0.379 | 190 | 0.668 | 67 | 0.973 | 107 | 0.055 | 118 | 0.469 |
| HOXADtrim | 189 | 0.181 | 189 | 0.056 | 299 | 0.294 | 121 | 0.671 | 750 | 0.124 | 639 | 0.026 |
| SFRAtrim | 353 | 0.351 | 798 | 0.094 | 410 | 0.104 | 192 | 0.089 | 520 | 0.61 | 403 | 0.339 |
| SFRBtrim | 836 | 0.667 | 0 | 0 | 0 | 0 | 583 | 0.998 | 591 | 0.94 | 168 | 0.72 |
| SFRCtrim | 331 | 0.633 | 700 | 0.277 | 370 | 0.282 | 1830 | 0.937 | 1006 | 0.671 | 468 | 0.557 |
| SFRDtrim | 375 | 0.232 | 881 | 0.027 | 458 | 0.028 | 212 | 0.018 | 553 | 0.636 | 435 | 0.326 |
| SFREtrim | 831 | 0.508 | 0 | 0 | 0 | 0 | 595 | 0.999 | 578 | 0.927 | 169 | 0.58 |
| TTBAtrim | 35 | 0 | 12 | 0.15 | 157 | 0.276 | 163 | 0.79 | 434 | 0.691 | 150 | 0.098 |
| TTBBtrim | 1 | 0.4 | 0 | 0 | 0 | 0 | 125 | 0.95 | 131 | 0.937 | 62 | 0.21 |
| TTBCtrim | 0 | 0 | 0 | 0 | 1 | 0.333 | 1 | 0.25 | 69 | 0.782 | 8 | 0.588 |
| TTBDtrim | 0 | 0 | 0 | 0 | 0 | 0 | 0 | 0 | 361 | 0.888 | 126 | 0.484 |

Fig. 13A

| Reference | D01333 T ER+ PR+ # Reads | D01333 T ER+ PR+ Mean Me | D01333 N ER+ PR+ # Reads | D01333 N ER+ PR+ Mean Me | D02291 T ER+ PR+ GR+ # Reads | D02291 T ER+ PR+ GR+ Mean Me | D02291 N ER+ PR+ GR+ # Reads | D02291 N ER+ PR+ GR+ Mean Me | D02610 T ER+ PR+ # Reads | D02610 T ER+ PR+ Mean Me | D02610 N ER+ PR+ # Reads | D02610 N ER+ PR+ Mean Me |
|---|---|---|---|---|---|---|---|---|---|---|---|---|
| ADCYFtrim | 33 | 0.896 | 5 | 0.92 | 30 | 0.966 | 0 | 0 | 216 | 0.776 | 13 | 0 |
| ADCYGtrim | 21 | 0.905 | 4 | 1 | 23 | 0.98 | 0 | 0 | 131 | 0.84 | 14 | 0.217 |
| ADCYHtrim | 0 | 0 | 0 | 0 | 0 | 0 | 0 | 0 | 0 | 0 | 0 | 0 |
| C1Dtrim | 170 | 0.923 | 14 | 0.99 | 342 | 0.967 | 27 | 0.425 | 1009 | 0.968 | 35 | 0.095 |
| C1Etrim | 355 | 0.802 | 77 | 0.148 | 529 | 0.943 | 82 | 0.032 | 808 | 0.906 | 506 | 0.621 |
| C1Ftrim | 165 | 0.926 | 13 | 0.981 | 326 | 0.964 | 26 | 0.506 | 986 | 0.97 | 40 | 0 |
| C1Gtrim | 218 | 0.578 | 14 | 0.381 | 332 | 0.981 | 0 | 0 | 409 | 0.882 | 0 | 0 |
| MIRBtrim | 103 | 0.611 | 435 | 0.121 | 156 | 0.061 | 8 | 0 | 530 | 0.077 | 65 | 0.005 |
| MIRCtrim | 103 | 0.724 | 47 | 0.049 | 87 | 0.918 | 28 | 0.257 | 231 | 0.621 | 5 | 0 |
| MIRDtrim | 91 | 0.782 | 10 | 0.017 | 52 | 0.775 | 0 | 0 | 159 | 0.31 | 70 | 0.149 |
| MIREtrim | 203 | 0.924 | 5 | 0 | 208 | 0.832 | 0 | 0 | 393 | 0.925 | 184 | 0.836 |
| MIRFtrim | 27 | 0.446 | 36 | 0.052 | 3 | 0.167 | 24 | 0.063 | 112 | 0.04 | 56 | 0 |
| VWCJtrim | 56 | 0.969 | 3 | 0.051 | 184 | 0.758 | 0 | 0 | 48 | 0.174 | 6 | 0.013 |
| VWCKtrim | 30 | 0.98 | 0 | 0 | 29 | 0.914 | 0 | 0 | 0 | 0 | 0 | 0 |
| VWCLtrim | 399 | 0.976 | 0 | 0 | 422 | 0.901 | 0 | 0 | 245 | 0.766 | 0 | 0 |
| VWCMtrim | 70 | 0.977 | 3 | 0.267 | 243 | 0.65 | 0 | 0 | 50 | 0.242 | 6 | 0.217 |
| VWCNtrim | 275 | 0.852 | 0 | 0 | 335 | 0.339 | 4 | 0.175 | 477 | 0.505 | 2 | 0 |
| CHSAtrim | 486 | 0.973 | 0 | 0 | 588 | 0.739 | 0 | 0 | 125 | 0.802 | 0 | 0 |
| CHSBtrim | 572 | 0.968 | 3 | 0 | 702 | 0.763 | 0 | 0 | 330 | 0.751 | 4 | 0 |
| CHSCtrim | 483 | 0.972 | 0 | 0 | 589 | 0.737 | 0 | 0 | 125 | 0.802 | 0 | 0 |
| CHSDtrim | 0 | 0 | 0 | 0 | 0 | 0 | 0 | 0 | 0 | 0 | 0 | 0 |
| DMBAtrim | 500 | 0.896 | 175 | 0.65 | 424 | 0.97 | 4 | 0 | 1359 | 0.745 | 0 | 0 |
| DMBBtrim | 470 | 0.909 | 147 | 0.61 | 400 | 0.976 | 4 | 0 | 1291 | 0.771 | 0 | 0 |
| DMBCtrim | 216 | 0.906 | 32 | 0.503 | 382 | 0.906 | 0 | 0 | 401 | 0.714 | 0 | 0 |
| FOXAtrim | 4 | 0.333 | 70 | 0.19 | 12 | 0.417 | 35 | 0.01 | 53 | 0.305 | 1 | 0 |
| FOXBtrim | 0 | 0 | 1 | 0 | 0 | 0 | 0 | 0 | 0 | 0 | 0 | 0 |
| FOXCtrim | 100 | 0.96 | 0 | 0 | 371 | 0.91 | 0 | 0 | 499 | 0.878 | 0 | 0 |
| FOXDtrim | 213 | 0.978 | 9 | 0.667 | 511 | 0.966 | 0 | 0 | 908 | 0.93 | 0 | 0 |
| FOXEtrim | 291 | 0.704 | 277 | 0.205 | 748 | 0.776 | 3 | 0.133 | 1055 | 0.118 | 67 | 0.051 |
| HOXAAtrim | 292 | 0.753 | 277 | 0.423 | 746 | 0.796 | 3 | 0.25 | 1052 | 0.25 | 66 | 0.078 |
| HOXABtrim | 43 | 0.738 | 19 | 0.189 | 194 | 0.61 | 0 | 0 | 296 | 0.453 | 0 | 0 |
| HOXACtrim | 106 | 0.619 | 34 | 0.306 | 245 | 0.614 | 3 | 0.293 | 518 | 0.224 | 60 | 0.003 |
| HOXADtrim | 308 | 0.685 | 104 | 0.078 | 447 | 0.649 | 48 | 0.082 | 594 | 0.339 | 0 | 0 |
| SFRAtrim | 320 | 0.967 | 79 | 0.881 | 438 | 0.742 | 0 | 0 | 534 | 0.825 | 0 | 0 |
| SFRBtrim | 407 | 0.811 | 87 | 0.238 | 726 | 0.907 | 45 | 0.237 | 1050 | 0.682 | 0 | 0 |
| SFRCtrim | 328 | 0.627 | 117 | 0.016 | 485 | 0.613 | 52 | 0.017 | 617 | 0.278 | 0 | 0 |
| SFRDtrim | 314 | 0.966 | 80 | 0.83 | 428 | 0.665 | 0 | 0 | 524 | 0.755 | 0 | 0 |
| SFREtrim | 221 | 0.553 | 54 | 0.119 | 240 | 0.408 | 1 | 0 | 178 | 0.036 | 15 | 0 |
| TTBAtrim | 60 | 0.81 | 0 | 0 | 138 | 0.527 | 0 | 0 | 39 | 0.046 | 0 | 0 |
| TTBBtrim | 116 | 0.355 | 0 | 0 | 79 | 0.417 | 0 | 0 | 1 | 0.25 | 0 | 0 |
| TTBCtrim | 106 | 0.751 | 0 | 0 | 155 | 0.5 | 0 | 0 | 0 | 0 | 0 | 0 |
| TTBDtrim | 341 | 0.963 | 0 | 0 | 356 | 0.995 | 0 | 0 | 0 | 0 | 0 | 0 |

Fig. 13B

| Reference | DU145 # Reads | DU145 Mean Me | PC3 # Reads | PC3 Mean Me | LNCAP # Reads | LNCAP Mean Me | RWPE # Reads | RWPE Mean Me |
|---|---|---|---|---|---|---|---|---|
| ADCYFtrim | 216 | 0.916 | 213 | 0.459 | 199 | 0.903 | 71 | 0.297 |
| ADCYGtrim | 146 | 0.917 | 188 | 0.611 | 161 | 0.921 | 46 | 0.416 |
| ADCYHtrim | 4 | 0.847 | 0 | 0 | 5 | 0.795 | 0 | 0 |
| C1Dtrim | 548 | 0.916 | 616 | 0.95 | 941 | 0.954 | 58 | 0.063 |
| C1Etrim | 621 | 0.74 | 585 | 0.943 | 2458 | 0.956 | 292 | 0.023 |
| C1Ftrim | 526 | 0.93 | 591 | 0.936 | 872 | 0.942 | 61 | 0.049 |
| C1Gtrim | 736 | 0.78 | 523 | 0.721 | 1583 | 0.786 | 0 | 0 |
| MIRBtrim | 187 | 0.096 | 745 | 0.824 | 994 | 0.169 | 775 | 0.032 |
| MIRCtrim | 265 | 0.387 | 461 | 0.876 | 369 | 0.564 | 81 | 0.019 |
| MIRDtrim | 155 | 0.152 | 0 | 0 | 289 | 0.092 | 24 | 0.071 |
| MIREtrim | 566 | 0.377 | 1110 | 0.97 | 1190 | 0.547 | 31 | 0.032 |
| MIRFtrim | 56 | 0.1 | 173 | 0.873 | 62 | 0.095 | 200 | 0.021 |
| VWCJtrim | 494 | 0.948 | 891 | 0.676 | 766 | 0.836 | 379 | 0.103 |
| VWCKtrim | 208 | 0.956 | 44 | 0.911 | 36 | 0.877 | 8 | 1 |
| VWCLtrim | 1041 | 0.923 | 746 | 0.911 | 1419 | 0.851 | 675 | 0.405 |
| VWCMtrim | 1071 | 0.922 | 917 | 0.867 | 1083 | 0.88 | 1 | 0 |
| VWCNtrim | 657 | 0.938 | 1120 | 0.736 | 992 | 0.853 | 425 | 0.268 |
| CHSAtrim | 56 | 0.003 | 986 | 0.482 | 945 | 0.524 | 1194 | 0.194 |
| CHSBtrim | 111 | 0.585 | 734 | 0.931 | 1944 | 0.746 | 1463 | 0.367 |
| CHSCtrim | 345 | 0.246 | 1074 | 0.927 | 2539 | 0.762 | 1983 | 0.218 |
| CHSDtrim | 113 | 0.592 | 730 | 0.93 | 1933 | 0.745 | 1467 | 0.367 |
| DMBAtrim | 0 | 0 | 0 | 0 | 0 | 0 | 0 | 0 |
| DMBBtrim | 1046 | 0.977 | 1388 | 0.967 | 2759 | 0.892 | 3164 | 0.175 |
| DMBCtrim | 1026 | 0.98 | 1282 | 0.974 | 2597 | 0.911 | 3049 | 0.218 |
| FOXAtrim | 1663 | 0.946 | 670 | 0.876 | 710 | 0.619 | 1722 | 0.3 |
| FOXBtrim | 7 | 1 | 4 | 0.667 | 70 | 0.607 | 90 | 0.259 |
| FOXCtrim | 0 | 0 | 0 | 0 | 0 | 0 | 0 | 0 |
| FOXDtrim | 387 | 0.873 | 510 | 0.958 | 964 | 0.919 | 1974 | 0.438 |
| FOXEtrim | 1547 | 0.975 | 1336 | 0.964 | 1619 | 0.903 | 3207 | 0.709 |
| HOXAAtrim | 2289 | 0.965 | 2522 | 0.056 | 1952 | 0.46 | 2234 | 0.135 |
| HOXABtrim | 2298 | 0.972 | 2505 | 0.142 | 1939 | 0.598 | 2216 | 0.199 |
| HOXACtrim | 302 | 0.906 | 38 | 0 | 286 | 0.355 | 116 | 0.016 |
| HOXADtrim | 710 | 0.971 | 1741 | 0.134 | 603 | 0.607 | 1313 | 0.051 |
| SFRAtrim | 452 | 0.357 | 374 | 0.872 | 562 | 0.092 | 920 | 0.101 |
| SFRBtrim | 330 | 0.784 | 531 | 0.855 | 0 | 0 | 855 | 0.609 |
| SFRCtrim | 817 | 0.672 | 933 | 0.932 | 506 | 0.246 | 1400 | 0.133 |
| SFRDtrim | 484 | 0.283 | 412 | 0.832 | 611 | 0.021 | 1006 | 0.081 |
| SFREtrim | 321 | 0.719 | 514 | 0.896 | 18 | 0.993 | 846 | 0.428 |
| TTBAtrim | 823 | 0.673 | 351 | 0.63 | 1197 | 0.6 | 1262 | 0.111 |
| TTBBtrim | 301 | 0.752 | 374 | 0.818 | 343 | 0.822 | 295 | 0.723 |
| TTBCtrim | 161 | 0.678 | 29 | 0.548 | 453 | 0.483 | 51 | 0.634 |
| TTBDtrim | 890 | 0.693 | 428 | 0.854 | 845 | 0.799 | 508 | 0.809 |

Fig. 14

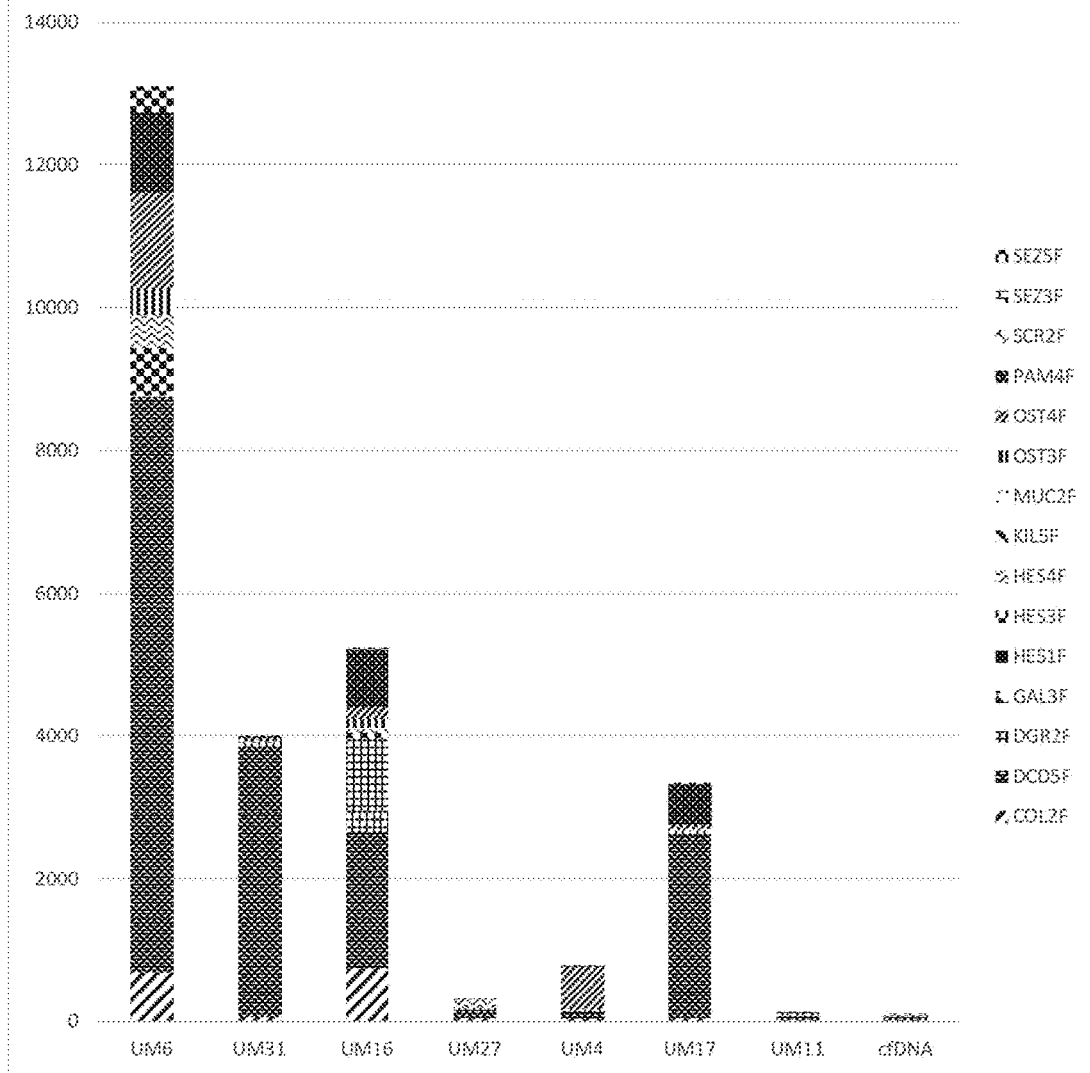

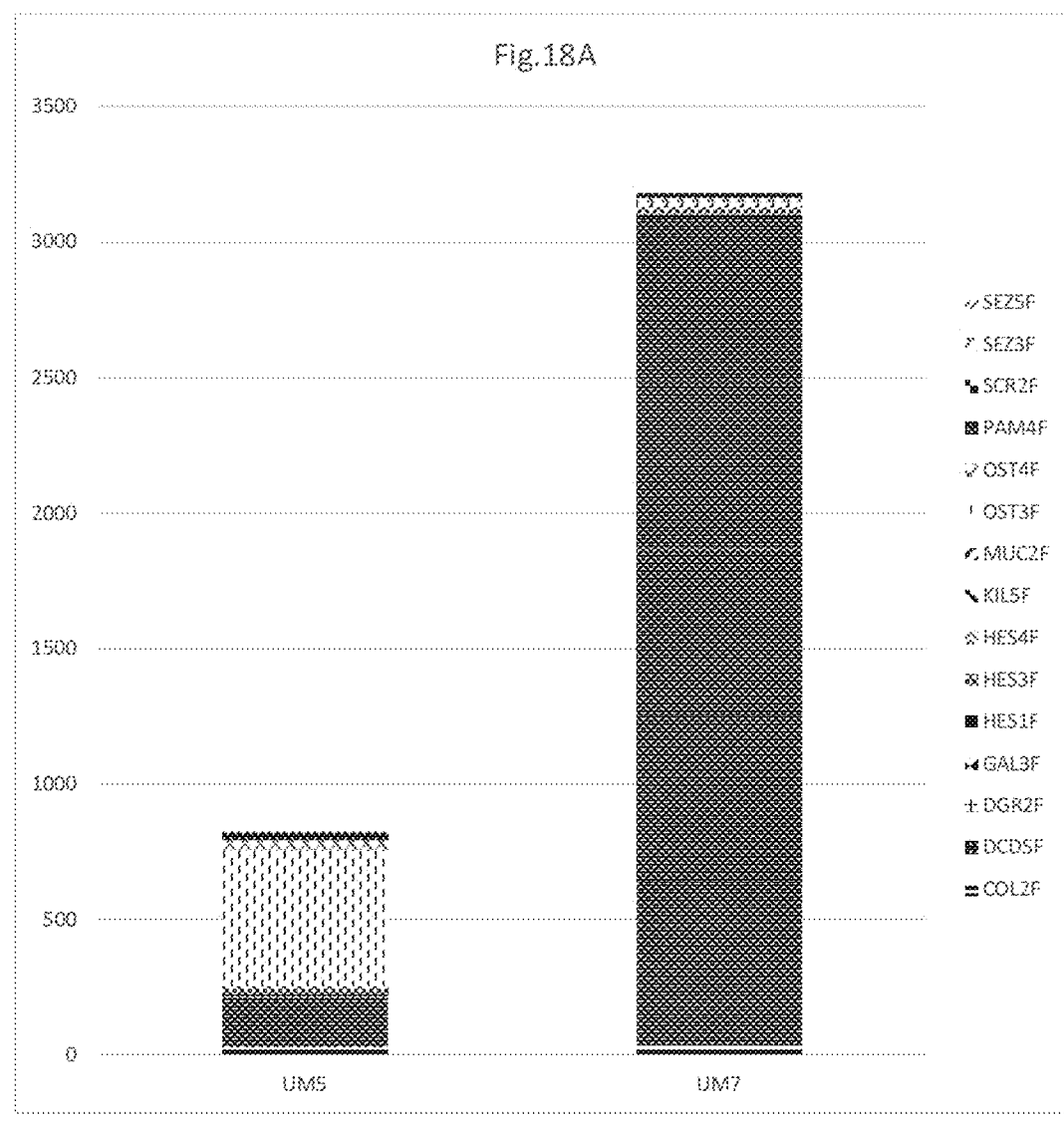

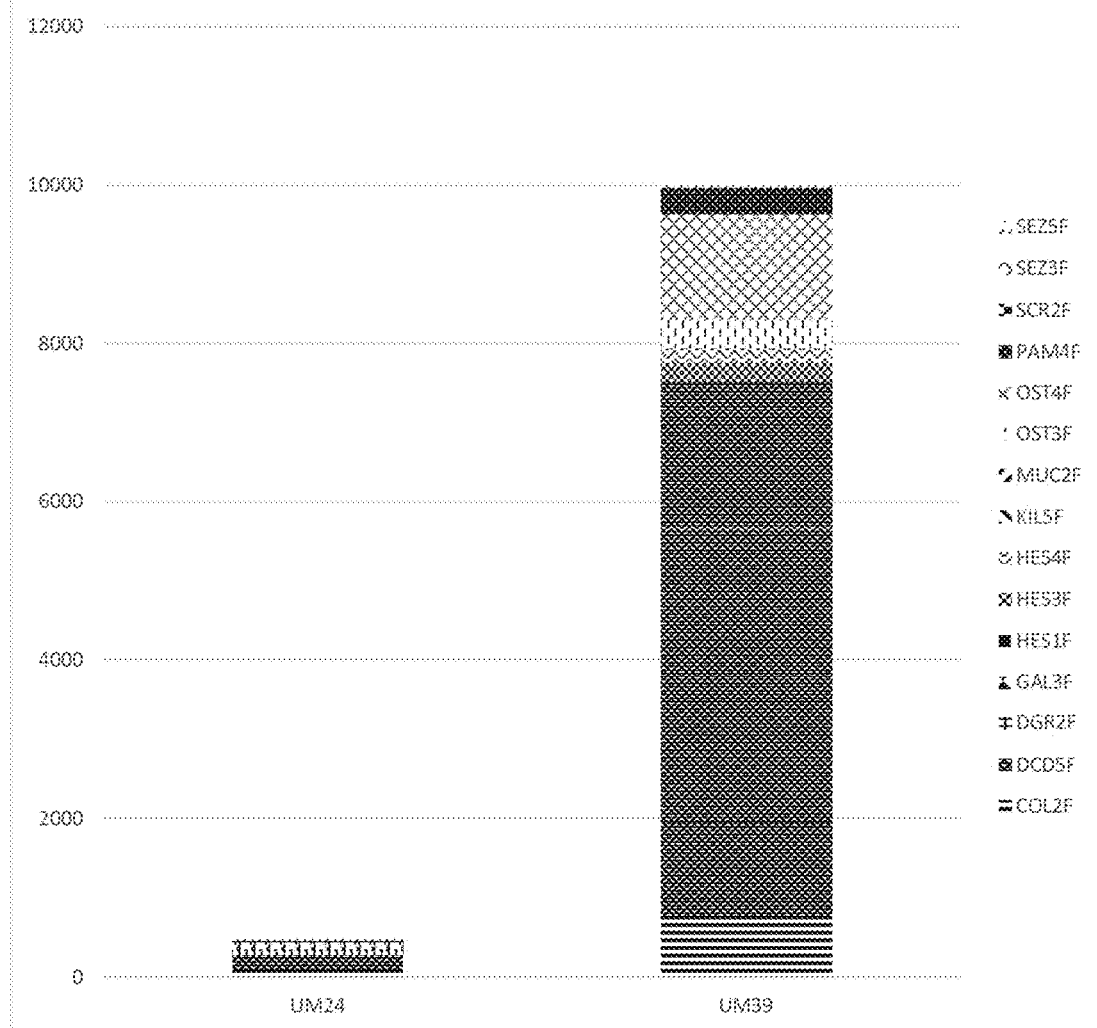

| Name | Chromosome | Nucleotide | Basal | Her2 | LumA | LumB | Normal-LikTissue | |
|---|---|---|---|---|---|---|---|---|
| | | | 82 | 31 | 280 | 127 | 17 | 89 # Tumours |
| CTSA,NEURL2 | chr20 | 43952209 | 0.30 | 0.71 | 0.89 | 0.91 | 0.24 | 0.01 |
| CHR5:43054200 | chr5 | 43054200 | 0.15 | 0.77 | 0.87 | 0.90 | 0.35 | 0.06 |
| ADCY4 | chr14 | 23873713 | 0.26 | 0.94 | 0.83 | 0.90 | 0.41 | 0.06 |
| DDAH2 | chr6 | 31806197 | 0.18 | 0.61 | 0.81 | 0.84 | 0.18 | 0.00 |
| USP44 | chr12 | 94467038 | 0.43 | 0.90 | 0.80 | 0.95 | 0.35 | 0.01 |
| L1TD1 | chr1 | 62433212 | 0.95 | 0.90 | 0.78 | 0.94 | 0.35 | 0.03 |
| PRDM15 | chr21 | 42110158 | 0.37 | 0.74 | 0.78 | 0.79 | 0.53 | 0.02 |
| HOXD11 | chr2 | 176680809 | 0.20 | 0.65 | 0.76 | 0.89 | 0.35 | 0.03 |
| GNG4 | chr1 | 233880632 | 0.35 | 0.87 | 0.75 | 0.91 | 0.24 | 0.02 |
| COL16A1 | chr1 | 31942288 | 0.24 | 0.84 | 0.75 | 0.92 | 0.18 | 0.00 |
| TAL1 | chr1 | 47470535 | 0.77 | 0.87 | 0.74 | 0.90 | 0.35 | 0.02 |
| CDH23 | chr10 | 72826383 | 0.11 | 0.81 | 0.73 | 0.83 | 0.24 | 0.01 |
| SHF | chr15 | 43267047 | 0.21 | 1.00 | 0.72 | 0.91 | 0.53 | 0.03 |
| CHST11 | chr12 | 103376569 | 0.12 | 0.52 | 0.72 | 0.77 | 0.18 | 0.01 |
| PRKCB | chr16 | 23755057 | 0.32 | 0.68 | 0.71 | 0.83 | 0.12 | 0.00 |
| AFF3 | chr2 | 99542136 | 0.00 | 0.32 | 0.71 | 0.57 | 0.18 | 0.04 |
| ATP5G2 | chr12 | 52357357 | 0.40 | 0.74 | 0.70 | 0.89 | 0.12 | 0.03 |
| CHR19:51071769 | chr19 | 51071769 | 0.34 | 0.97 | 0.70 | 0.83 | 0.24 | 0.02 |
| C1orf114 | chr1 | 167663259 | 0.61 | 0.90 | 0.69 | 0.88 | 0.24 | 0.00 |
| CHR1:90967747 | chr1 | 90967747 | 0.52 | 0.74 | 0.68 | 0.80 | 0.12 | 0.01 |
| NT5E | chr6 | 86215916 | 0.45 | 0.61 | 0.68 | 0.79 | 0.12 | 0.01 |
| PLTP | chr20 | 43973373 | 0.20 | 0.84 | 0.68 | 0.82 | 0.18 | 0.00 |
| MAST1 | chr19 | 12839611 | 0.59 | 0.87 | 0.67 | 0.88 | 0.29 | 0.00 |
| ITPRIPL1 | chr2 | 96354641 | 0.61 | 0.90 | 0.67 | 0.84 | 0.18 | 0.00 |
| KIAA1751 | chr1 | 1925149 | 0.18 | 0.71 | 0.66 | 0.70 | 0.18 | 0.01 |
| ACVRL1 | chr12 | 50587178 | 0.38 | 0.81 | 0.66 | 0.89 | 0.18 | 0.02 |
| GABRA4 | chr4 | 46690498 | 0.33 | 0.52 | 0.66 | 0.85 | 0.06 | 0.00 |
| TOB2P1 | chr6 | 28283425 | 0.77 | 0.65 | 0.65 | 0.80 | 0.18 | 0.00 |
| FLI1 | chr11 | 128068895 | 0.12 | 0.61 | 0.65 | 0.77 | 0.06 | 0.00 |
| CD38 | chr4 | 15389336 | 0.21 | 0.77 | 0.65 | 0.79 | 0.18 | 0.00 |
| HOTAIR | chr12 | 52646064 | 0.84 | 1.00 | 0.64 | 0.77 | 0.53 | 0.04 |
| PRDM13 | chr6 | 100167832 | 0.74 | 0.81 | 0.64 | 0.82 | 0.24 | 0.00 |
| HNF1B | chr17 | 33177343 | 0.30 | 0.65 | 0.64 | 0.75 | 0.06 | 0.00 |
| RGS17 | chr6 | 153494417 | 0.10 | 0.77 | 0.64 | 0.79 | 0.24 | 0.02 |
| COL11A2 | chr6 | 33269254 | 0.07 | 0.55 | 0.64 | 0.70 | 0.18 | 0.01 |
| CHR11:68379305 | chr11 | 68379315 | 0.16 | 1.00 | 0.63 | 0.87 | 0.18 | 0.02 |
| RUNX1T1 | chr8 | 93183326 | 0.35 | 0.42 | 0.63 | 0.80 | 0.18 | 0.01 |
| VWC2 | chr7 | 49783648 | 0.11 | 0.65 | 0.63 | 0.76 | 0.18 | 0.00 |
| RTN4RL1 | chr17 | 1827755 | 0.48 | 0.52 | 0.62 | 0.76 | 0.12 | 0.03 |
| CHR17:69460208 | chr17 | 69460208 | 0.35 | 0.90 | 0.62 | 0.79 | 0.18 | 0.01 |
| TMEM132C | chr12 | 127317993 | 0.78 | 0.71 | 0.62 | 0.73 | 0.18 | 0.00 |
| C19orf41 | chr19 | 55358350 | 0.35 | 0.45 | 0.61 | 0.77 | 0.12 | 0.00 |
| SHISA3 | chr4 | 42094600 | 0.04 | 0.26 | 0.61 | 0.75 | 0.18 | 0.00 |
| SOX2OT | chr3 | 182919839 | 0.56 | 0.77 | 0.60 | 0.80 | 0.18 | 0.01 |
| ALX4 | chr11 | 44289229 | 0.28 | 0.68 | 0.60 | 0.79 | 0.41 | 0.03 |
| HLA-F | chr6 | 29799979 | 0.26 | 0.42 | 0.60 | 0.62 | 0.29 | 0.02 |
| KCNJ2 | chr17 | 65676379 | 0.10 | 0.65 | 0.60 | 0.76 | 0.06 | 0.00 |
| ERNA4 | chr1 | 153310037 | 0.59 | 0.90 | 0.60 | 0.78 | 0.18 | 0.01 |
| HIF3A | chr19 | 51491904 | 0.09 | 0.55 | 0.59 | 0.71 | 0.12 | 0.01 |
| CHR8:95315690 | chr8 | 95315690 | 0.57 | 0.84 | 0.59 | 0.80 | 0.29 | 0.02 |
| GIPC2 | chr1 | 78284188 | 0.60 | 0.77 | 0.59 | 0.76 | 0.24 | 0.04 |
| CRYM | chr16 | 21202756 | 0.39 | 0.58 | 0.59 | 0.80 | 0.29 | 0.01 |
| HIVEP3 | chr1 | 41901042 | 0.00 | 0.35 | 0.59 | 0.80 | 0.24 | 0.01 |
| SLC2A2 | chr3 | 172228901 | 0.40 | 0.68 | 0.58 | 0.80 | 0.12 | 0.00 |
| CYTL1 | chr4 | 5072014 | 0.13 | 0.58 | 0.58 | 0.76 | 0.06 | 0.00 |
| PON3 | chr7 | 94863672 | 0.33 | 0.55 | 0.58 | 0.64 | 0.12 | 0.00 |

Fig. 26A

| Name | Chromoso | Nucleotide | Basal | Her2 | LumA | LumB | Normal-LiTissue | |
|---|---|---|---|---|---|---|---|---|
| | | | 82 | 31 | 280 | 127 | 17 | 89 # Tumours |
| TRIM71 | chr3 | 32834411 | 0.27 | 0.52 | 0.58 | 0.74 | 0.18 | 0.00 |
| CHR12:61: | chr12 | 61311757 | 0.18 | 0.55 | 0.58 | 0.69 | 0.24 | 0.00 |
| C5orf39 | chr5 | 43076337 | 0.41 | 0.48 | 0.58 | 0.78 | 0.24 | 0.01 |
| HOXA10 | chr7 | 27180568 | 0.10 | 0.29 | 0.58 | 0.75 | 0.06 | 0.00 |
| ESPN | chr1 | 6430566 | 0.21 | 0.77 | 0.57 | 0.73 | 0.24 | 0.03 |
| POU4F1 | chr13 | 78075701 | 0.12 | 0.58 | 0.57 | 0.74 | 0.18 | 0.00 |
| TXNRD1 | chr12 | 103133606 | 0.38 | 0.77 | 0.56 | 0.78 | 0.24 | 0.00 |
| EGFLAM | chr5 | 38293298 | 0.10 | 0.48 | 0.56 | 0.68 | 0.00 | 0.00 |
| NR5A2 | chr1 | 198278409 | 0.66 | 0.52 | 0.56 | 0.59 | 0.12 | 0.00 |
| LHX1 | chr17 | 32368589 | 0.10 | 0.35 | 0.56 | 0.67 | 0.06 | 0.00 |
| TNFRSF10I | chr8 | 23077458 | 0.28 | 0.35 | 0.56 | 0.76 | 0.06 | 0.00 |
| STK33 | chr11 | 8572251 | 0.05 | 0.65 | 0.56 | 0.65 | 0.18 | 0.00 |
| CHR2:174 | chr2 | 174899291 | 0.26 | 0.65 | 0.55 | 0.75 | 0.06 | 0.00 |
| ID4 | chr6 | 19944994 | 0.35 | 0.68 | 0.55 | 0.67 | 0.18 | 0.00 |
| ZFPM2 | chr8 | 106401171 | 0.38 | 0.52 | 0.55 | 0.69 | 0.29 | 0.00 |
| TTBK1 | chr6 | 43319186 | 0.34 | 0.71 | 0.55 | 0.72 | 0.18 | 0.00 |
| CHR5:429 | chr5 | 42987870 | 0.24 | 0.52 | 0.55 | 0.67 | 0.00 | 0.00 |
| NKX2-1 | chr14 | 36058194 | 0.15 | 0.52 | 0.55 | 0.69 | 0.24 | 0.00 |
| INA | chr10 | 105026691 | 0.22 | 0.52 | 0.54 | 0.72 | 0.12 | 0.00 |
| CHST2 | chr3 | 144322268 | 0.04 | 0.58 | 0.54 | 0.72 | 0.12 | 0.00 |
| HOXD8 | chr2 | 176702611 | 0.27 | 0.48 | 0.53 | 0.56 | 0.12 | 0.00 |
| PTPRN2 | chr7 | 157176096 | 0.67 | 0.58 | 0.53 | 0.67 | 0.12 | 0.00 |
| CHR1:238 | chr1 | 238227872 | 0.29 | 0.58 | 0.52 | 0.75 | 0.24 | 0.00 |
| ALX1 | chr12 | 84198427 | 0.27 | 0.77 | 0.52 | 0.66 | 0.18 | 0.00 |
| TSPAN33 | chr7 | 128596336 | 0.54 | 0.77 | 0.51 | 0.70 | 0.18 | 0.01 |
| FOXL2,C3c | chr3 | 140148674 | 0.38 | 0.74 | 0.51 | 0.72 | 0.18 | 0.00 |
| CDK5R2 | chr2 | 219532295 | 0.26 | 0.61 | 0.51 | 0.50 | 0.18 | 0.00 |
| RECK | chr9 | 36027340 | 0.02 | 0.52 | 0.51 | 0.69 | 0.24 | 0.00 |
| SHOX2 | chr3 | 159304101 | 0.46 | 0.68 | 0.51 | 0.78 | 0.06 | 0.00 |
| SFRP5 | chr10 | 99521787 | 0.12 | 0.52 | 0.51 | 0.60 | 0.18 | 0.00 |
| CHR8:680 | chr8 | 68037587 | 0.11 | 0.52 | 0.51 | 0.70 | 0.29 | 0.01 |
| NRN1 | chr6 | 5952522 | 0.09 | 0.77 | 0.51 | 0.68 | 0.00 | 0.00 |
| MIR129-2 | chr11 | 43559433 | 0.24 | 0.52 | 0.51 | 0.72 | 0.06 | 0.00 |
| LRRC4,SN | chr7 | 127459694 | 0.48 | 0.61 | 0.50 | 0.69 | 0.41 | 0.07 |
| SP9 | chr2 | 174907892 | 0.33 | 0.81 | 0.50 | 0.71 | 0.12 | 0.00 |
| TBX15 | chr1 | 119332123 | 0.30 | 0.61 | 0.49 | 0.68 | 0.18 | 0.00 |
| POU3F3 | chr2 | 104836990 | 0.15 | 0.52 | 0.49 | 0.66 | 0.00 | 0.00 |
| EVX1 | chr7 | 27248876 | 0.39 | 0.77 | 0.49 | 0.74 | 0.18 | 0.00 |
| FABP5 | chr8 | 82355156 | 0.09 | 0.74 | 0.48 | 0.61 | 0.12 | 0.01 |
| PDE4B | chr1 | 66030623 | 0.10 | 0.61 | 0.48 | 0.67 | 0.06 | 0.00 |
| T | chr6 | 166501919 | 0.13 | 0.65 | 0.48 | 0.69 | 0.12 | 0.00 |
| CHR1:119 | chr1 | 119344859 | 0.45 | 0.61 | 0.47 | 0.71 | 0.06 | 0.00 |
| CHR12:52 | chr12 | 52897710 | 0.33 | 0.74 | 0.47 | 0.63 | 0.29 | 0.01 |
| LOC25516 | chr5 | 6636380 | 0.33 | 0.84 | 0.47 | 0.62 | 0.35 | 0.00 |
| NUDT16P | chr3 | 132563617 | 0.77 | 0.81 | 0.47 | 0.56 | 0.47 | 0.04 |
| IRF4 | chr6 | 336743 | 0.57 | 0.74 | 0.47 | 0.72 | 0.18 | 0.00 |
| MSC | chr8 | 72918612 | 0.22 | 0.61 | 0.47 | 0.69 | 0.12 | 0.00 |
| UD8 | chr6 | 29629547 | 0.62 | 0.45 | 0.46 | 0.68 | 0.29 | 0.00 |
| C1orf230 | chr1 | 149960747 | 0.24 | 0.55 | 0.46 | 0.69 | 0.12 | 0.00 |
| HOXA9 | chr7 | 27171749 | 0.50 | 0.42 | 0.46 | 0.68 | 0.06 | 0.01 |
| CARD11 | chr7 | 3049859 | 0.65 | 0.71 | 0.45 | 0.69 | 0.18 | 0.00 |
| SPAG6 | chr10 | 22674438 | 0.78 | 0.61 | 0.45 | 0.68 | 0.12 | 0.00 |
| IRF8 | chr16 | 84490167 | 0.43 | 0.45 | 0.45 | 0.60 | 0.12 | 0.00 |
| CDO1 | chr5 | 115180312 | 0.38 | 0.45 | 0.45 | 0.67 | 0.12 | 0.00 |
| CHR3:148 | chr3 | 14827760 | 0.29 | 0.74 | 0.44 | 0.70 | 0.06 | 0.00 |
| GALR3 | chr22 | 36550955 | 0.70 | 0.81 | 0.43 | 0.70 | 0.24 | 0.02 |

Fig. 26B

| Name | Chromoso | Nucleotide | Basal | Her2 | LumA | LumB | Normal-Li | Tissue |
|---|---|---|---|---|---|---|---|---|
| | | | 82 | 31 | 280 | 127 | 17 | 89 # Tumours |
| CHR7:646 | chr7 | 64675139 | 0.28 | 0.61 | 0.43 | 0.69 | 0.18 | |
| ALOX5 | chr10 | 45234531 | 0.13 | 0.65 | 0.43 | 0.66 | 0.18 | 0.00 |
| PDX1 | chr13 | 27389540 | 0.62 | 0.61 | 0.43 | 0.50 | 0.12 | 0.00 |
| CHR19:48 | chr19 | 48895423 | 0.35 | 0.58 | 0.43 | 0.68 | 0.06 | 0.00 |
| MIR155HG | chr21 | 25856447 | 0.09 | 0.68 | 0.43 | 0.53 | 0.12 | 0.04 |
| AKR1B1 | chr7 | 133794363 | 0.15 | 0.77 | 0.43 | 0.60 | 0.06 | 0.00 |
| TMEM90B | chr20 | 24398353 | 0.61 | 0.58 | 0.42 | 0.52 | 0.18 | 0.00 |
| KCNK17 | chr6 | 39389863 | 0.23 | 0.68 | 0.42 | 0.59 | 0.24 | 0.01 |
| DMBX1 | chr1 | 46723905 | 0.76 | 0.65 | 0.41 | 0.61 | 0.18 | 0.00 |
| DMRTA2 | chr1 | 50659537 | 0.66 | 0.68 | 0.41 | 0.68 | 0.18 | 0.00 |
| chr5:7263 | chr5 | 72634721 | 0.74 | 0.65 | 0.41 | 0.48 | 0.12 | 0.01 |
| CPXM1 | chr20 | 2729316 | 0.38 | 0.94 | 0.40 | 0.62 | 0.18 | 0.01 |
| CHR2:236 | chr2 | 236737696 | 0.59 | 0.68 | 0.39 | 0.57 | 0.12 | 0.00 |
| FLJ41350,L | chr10 | 102980016 | 0.24 | 0.71 | 0.39 | 0.57 | 0.18 | 0.01 |
| NKX6-2 | chr10 | 134449831 | 0.22 | 0.58 | 0.39 | 0.69 | 0.06 | 0.00 |
| SNX32 | chr11 | 65357904 | 0.12 | 0.81 | 0.38 | 0.66 | 0.24 | 0.00 |
| SFRP2 | chr4 | 154929278 | 0.16 | 0.65 | 0.38 | 0.54 | 0.12 | 0.00 |
| CHR10:43 | chr10 | 43138371 | 0.48 | 0.77 | 0.38 | 0.63 | 0.12 | 0.00 |
| GALR1 | chr18 | 73090725 | 0.43 | 0.48 | 0.37 | 0.62 | 0.18 | 0.00 |
| NOTUM | chr17 | 77512868 | 0.15 | 0.77 | 0.37 | 0.64 | 0.12 | 0.01 |
| CD8A | chr2 | 86871615 | 0.10 | 0.68 | 0.37 | 0.54 | 0.24 | 0.00 |
| NPHS2 | chr1 | 177811696 | 0.30 | 0.23 | 0.37 | 0.51 | 0.06 | 0.00 |
| BOLL | chr2 | 198359232 | 0.62 | 0.74 | 0.36 | 0.64 | 0.29 | 0.00 |
| FZD2 | chr17 | 39990836 | 0.37 | 0.58 | 0.36 | 0.61 | 0.18 | 0.01 |
| CDKL2 | chr4 | 76774796 | 0.72 | 0.61 | 0.35 | 0.43 | 0.18 | 0.01 |
| BARHL2 | chr1 | 90965039 | 0.68 | 0.23 | 0.35 | 0.50 | 0.00 | 0.00 |
| SYNGR3 | chr16 | 1980982 | 0.30 | 0.58 | 0.34 | 0.60 | 0.06 | 0.00 |
| EPSTI1 | chr13 | 42464421 | 0.49 | 0.48 | 0.34 | 0.61 | 0.06 | 0.00 |
| OSTM1/NF | chr6 | 108546973 | 0.61 | 0.77 | 0.33 | 0.51 | 0.12 | 0.00 |
| AP3B1 | chr5 | 77304490 | 0.30 | 0.19 | 0.32 | 0.57 | 0.00 | 0.00 |
| LASS1,GDF | chr19 | 18868311 | 0.04 | 0.65 | 0.32 | 0.52 | 0.18 | 0.00 |
| DRD4 | chr11 | 627035 | 0.56 | 0.61 | 0.32 | 0.54 | 0.12 | 0.00 |
| PAX6 | chr11 | 31797204 | 0.84 | 0.71 | 0.30 | 0.47 | 0.18 | 0.00 |
| HSPA12B | chr20 | 3661341 | 0.21 | 0.65 | 0.30 | 0.58 | 0.12 | 0.01 |
| TLX1NB | chr10 | 102871266 | 0.40 | 0.61 | 0.30 | 0.54 | 0.12 | 0.00 |
| C6orf186 | chr6 | 110785613 | 0.11 | 0.68 | 0.30 | 0.54 | 0.00 | 0.00 |
| CCDC8 | chr19 | 51608360 | 0.48 | 0.52 | 0.29 | 0.55 | 0.00 | 0.00 |
| SALL3 | chr18 | 74841079 | 0.37 | 0.42 | 0.29 | 0.59 | 0.06 | 0.00 |
| KCNK4 | chr11 | 63816492 | 0.11 | 0.68 | 0.29 | 0.52 | 0.06 | 0.00 |
| C17orf64 | chr17 | 55853653 | 0.32 | 0.52 | 0.28 | 0.54 | 0.06 | 0.00 |
| NHC | chr19 | 3386252 | 0.63 | 0.52 | 0.27 | 0.36 | 0.24 | 0.01 |
| DPP10 | chr2 | 115635476 | 0.38 | 0.42 | 0.27 | 0.44 | 0.18 | 0.00 |
| CCL28 | chr5 | 43432924 | 0.88 | 0.23 | 0.24 | 0.28 | 0.06 | 0.04 |
| MIR548G,F | chr3 | 101077583 | 0.79 | 0.19 | 0.24 | 0.39 | 0.06 | 0.03 |
| NR2E1 | chr6 | 108596488 | 0.55 | 0.71 | 0.23 | 0.42 | 0.18 | 0.00 |
| C20orf56 | chr20 | 22507676 | 0.44 | 0.16 | 0.23 | 0.34 | 0.00 | 0.00 |
| SLC7A4 | chr22 | 19716885 | 0.65 | 0.77 | 0.23 | 0.54 | 0.12 | 0.00 |
| TCTEX1D1 | chr1 | 66990668 | 0.57 | 0.39 | 0.19 | 0.38 | 0.00 | 0.00 |
| PHOX2B | chr4 | 41447005 | 0.57 | 0.42 | 0.19 | 0.22 | 0.06 | 0.02 |
| CA9 | chr9 | 35666104 | 0.55 | 0.52 | 0.15 | 0.37 | 0.12 | 0.00 |
| LEF1,LOC6 | chr4 | 109307487 | 0.63 | 0.32 | 0.10 | 0.13 | 0.06 | 0.01 |
| PRSS27 | chr16 | 2705621 | 0.68 | 0.23 | 0.09 | 0.15 | 0.12 | 0.02 |
| SIM1 | chr6 | 101021823 | 0.59 | 0.26 | 0.07 | 0.13 | 0.00 | 0.00 |
| PPFIA3 | chr19 | 54337905 | 0.82 | 0.58 | 0.05 | 0.16 | 0.29 | 0.00 |
| CHR10:12! | chr10 | 125024561 | 0.59 | 0.03 | 0.00 | 0.00 | 0.00 | 0.00 |

Fig. 26C

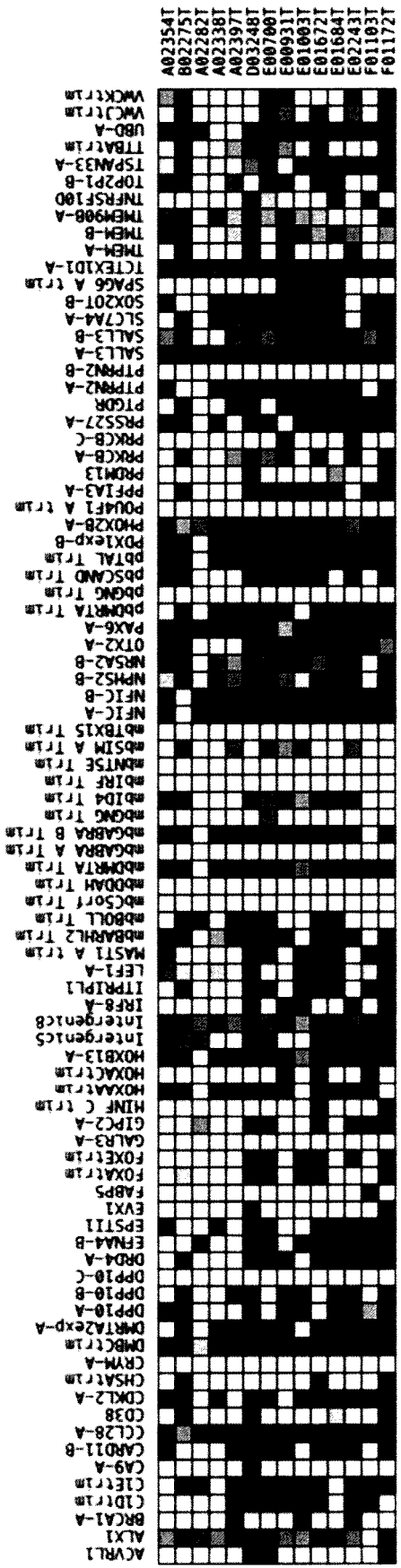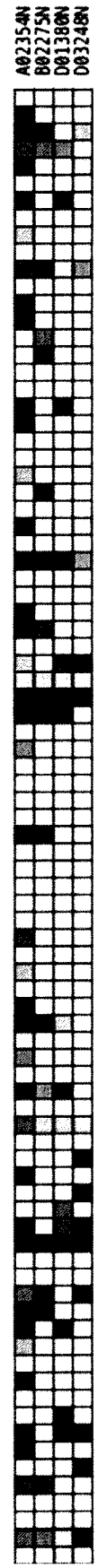
Fig. 28

SEQUENCE LISTING

```
<160> NUMBER OF SEQ ID NOS: 1008

<210> SEQ ID NO 1
<211> LENGTH: 22
<212> TYPE: DNA
<213> ORGANISM: Homo sapiens

<400> SEQUENCE: 1
ttgaggtaaa ggagatttcg gt                                              22

<210> SEQ ID NO 2
<211> LENGTH: 23
<212> TYPE: DNA
<213> ORGANISM: Homo sapiens

<400> SEQUENCE: 2
acatacgcct acgcaaattt tta                                             23

<210> SEQ ID NO 3
<211> LENGTH: 21
<212> TYPE: DNA
<213> ORGANISM: Homo sapiens

<400> SEQUENCE: 3
ttcggtgttt gcgaagggtt a                                               21
```

```
<210> SEQ ID NO 4
<211> LENGTH: 23
<212> TYPE: DNA
<213> ORGANISM: Homo sapiens

<400> SEQUENCE: 4
tcacaaccaa cacaacgaca ctt                                              23

<210> SEQ ID NO 5
<211> LENGTH: 21
<212> TYPE: DNA
<213> ORGANISM: Homo sapiens

<400> SEQUENCE: 5
acaaccaaca caacgacact t                                                21

<210> SEQ ID NO 6
<211> LENGTH: 20
<212> TYPE: DNA
<213> ORGANISM: Homo sapiens

<400> SEQUENCE: 6
tcggtatttg ttttcgcggt                                                  20

<210> SEQ ID NO 7
<211> LENGTH: 22
<212> TYPE: DNA
<213> ORGANISM: Homo sapiens

<400> SEQUENCE: 7
cgcctacgca aattttatc gc                                                22

<210> SEQ ID NO 8
<211> LENGTH: 22
<212> TYPE: DNA
<213> ORGANISM: Homo sapiens

<400> SEQUENCE: 8
cgagagcgat aaaaatttgc gt                                               22

<210> SEQ ID NO 9
<211> LENGTH: 20
<212> TYPE: DNA
<213> ORGANISM: Homo sapiens

<400> SEQUENCE: 9
acccttcgca aacaccgaaa                                                  20

<210> SEQ ID NO 10
<211> LENGTH: 19
<212> TYPE: DNA
<213> ORGANISM: Homo sapiens

<400> SEQUENCE: 10
ggtaatagcg tgtttttgc                                                   19

<210> SEQ ID NO 11
<211> LENGTH: 22
<212> TYPE: DNA
<213> ORGANISM: Homo sapiens

<400> SEQUENCE: 11
atattacata cgcctacgca aa                                               22
```

<210> SEQ ID NO 12
<211> LENGTH: 20
<212> TYPE: DNA
<213> ORGANISM: Homo sapiens

<400> SEQUENCE: 12
tttgtgtaaa atgcggcggt                                               20

<210> SEQ ID NO 13
<211> LENGTH: 22
<212> TYPE: DNA
<213> ORGANISM: Homo sapiens

<400> SEQUENCE: 13
ctaccgcgaa aacaaatacc ga                                            22

<210> SEQ ID NO 14
<211> LENGTH: 20
<212> TYPE: DNA
<213> ORGANISM: Homo sapiens

<400> SEQUENCE: 14
atttcggtgt ttgcgaaggg                                               20

<210> SEQ ID NO 15
<211> LENGTH: 20
<212> TYPE: DNA
<213> ORGANISM: Homo sapiens

<400> SEQUENCE: 15
acaaccaaca caacgacact                                               20

<210> SEQ ID NO 16
<211> LENGTH: 20
<212> TYPE: DNA
<213> ORGANISM: Homo sapiens

<400> SEQUENCE: 16
tttcggttgt cgggtttgga                                               20

<210> SEQ ID NO 17
<211> LENGTH: 22
<212> TYPE: DNA
<213> ORGANISM: Homo sapiens

<400> SEQUENCE: 17
tatttcggtt gtcgggtttg ga                                            22

<210> SEQ ID NO 18
<211> LENGTH: 20
<212> TYPE: DNA
<213> ORGANISM: Homo sapiens

<400> SEQUENCE: 18
ccctcaatcg ctcatcctcc                                               20

<210> SEQ ID NO 19
<211> LENGTH: 20
<212> TYPE: DNA
<213> ORGANISM: Homo sapiens

<400> SEQUENCE: 19

| | |
|---|---|
| tcgtcggtcg gtttaggatg | 20 |

<210> SEQ ID NO 20
<211> LENGTH: 22
<212> TYPE: DNA
<213> ORGANISM: Homo sapiens

<400> SEQUENCE: 20

| | |
|---|---|
| aaaaccgacg ccaaacctac at | 22 |

<210> SEQ ID NO 21
<211> LENGTH: 20
<212> TYPE: DNA
<213> ORGANISM: Homo sapiens

<400> SEQUENCE: 21

| | |
|---|---|
| aaccgacgcc aaacctacat | 20 |

<210> SEQ ID NO 22
<211> LENGTH: 20
<212> TYPE: DNA
<213> ORGANISM: Homo sapiens

<400> SEQUENCE: 22

| | |
|---|---|
| cggaggatga gcgattgagg | 20 |

<210> SEQ ID NO 23
<211> LENGTH: 20
<212> TYPE: DNA
<213> ORGANISM: Homo sapiens

<400> SEQUENCE: 23

| | |
|---|---|
| taacgcgcac accgaactaa | 20 |

<210> SEQ ID NO 24
<211> LENGTH: 20
<212> TYPE: DNA
<213> ORGANISM: Homo sapiens

<400> SEQUENCE: 24

| | |
|---|---|
| cgagttgggg tcgcgattat | 20 |

<210> SEQ ID NO 25
<211> LENGTH: 20
<212> TYPE: DNA
<213> ORGANISM: Homo sapiens

<400> SEQUENCE: 25

| | |
|---|---|
| catcctaaac cgaccgacga | 20 |

<210> SEQ ID NO 26
<211> LENGTH: 20
<212> TYPE: DNA
<213> ORGANISM: Homo sapiens

<400> SEQUENCE: 26

| | |
|---|---|
| cgacgcgtta cggttgttta | 20 |

<210> SEQ ID NO 27
<211> LENGTH: 20
<212> TYPE: DNA
<213> ORGANISM: Homo sapiens

<400> SEQUENCE: 27

```
ccgcttctcc gaaaccaaac                                               20
```

<210> SEQ ID NO 28
<211> LENGTH: 20
<212> TYPE: DNA
<213> ORGANISM: Homo sapiens

<400> SEQUENCE: 28

```
taaggcgggg tttttagagc                                               20
```

<210> SEQ ID NO 29
<211> LENGTH: 18
<212> TYPE: DNA
<213> ORGANISM: Homo sapiens

<400> SEQUENCE: 29

```
taaaaactaa cgcgcccg                                                 18
```

<210> SEQ ID NO 30
<211> LENGTH: 18
<212> TYPE: DNA
<213> ORGANISM: Homo sapiens

<400> SEQUENCE: 30

```
ggtttcggtg ttattcgc                                                 18
```

<210> SEQ ID NO 31
<211> LENGTH: 19
<212> TYPE: DNA
<213> ORGANISM: Homo sapiens

<400> SEQUENCE: 31

```
ctcctctccg cgaaaaaat                                                19
```

<210> SEQ ID NO 32
<211> LENGTH: 20
<212> TYPE: DNA
<213> ORGANISM: Homo sapiens

<400> SEQUENCE: 32

```
cggaggatga gcgattgagg                                               20
```

<210> SEQ ID NO 33
<211> LENGTH: 20
<212> TYPE: DNA
<213> ORGANISM: Homo sapiens

<400> SEQUENCE: 33

```
taacgcgcac accgaactaa                                               20
```

<210> SEQ ID NO 34
<211> LENGTH: 20
<212> TYPE: DNA
<213> ORGANISM: Homo sapiens

<400> SEQUENCE: 34

```
tcgtcggtcg gtttaggatg                                               20
```

<210> SEQ ID NO 35
<211> LENGTH: 20
<212> TYPE: DNA
<213> ORGANISM: Homo sapiens

```
<400> SEQUENCE: 35
aaccgacgcc aaacctacat                                              20

<210> SEQ ID NO 36
<211> LENGTH: 20
<212> TYPE: DNA
<213> ORGANISM: Homo sapiens

<400> SEQUENCE: 36
gtcggacgcg ttttagttgg                                              20

<210> SEQ ID NO 37
<211> LENGTH: 20
<212> TYPE: DNA
<213> ORGANISM: Homo sapiens

<400> SEQUENCE: 37
tccctaccga cctcaacact                                              20

<210> SEQ ID NO 38
<211> LENGTH: 20
<212> TYPE: DNA
<213> ORGANISM: Homo sapiens

<400> SEQUENCE: 38 tggttgggggg attttgaggg                                             20

<210> SEQ ID NO 39
<211> LENGTH: 20
<212> TYPE: DNA
<213> ORGANISM: Homo sapiens

<400> SEQUENCE: 39
aaacctcccc gcctacctat                                              20

<210> SEQ ID NO 40
<211> LENGTH: 20
<212> TYPE: DNA
<213> ORGANISM: Homo sapiens

<400> SEQUENCE: 40
gcggacggtt tggagaaatg                                              20

<210> SEQ ID NO 41
<211> LENGTH: 20
<212> TYPE: DNA
<213> ORGANISM: Homo sapiens

<400> SEQUENCE: 41
cgcgactcaa tctcaccact                                              20

<210> SEQ ID NO 42
<211> LENGTH: 20
<212> TYPE: DNA
<213> ORGANISM: Homo sapiens

<400> SEQUENCE: 42
ggaggttggg tttcgggatt                                              20

<210> SEQ ID NO 43
<211> LENGTH: 20
<212> TYPE: DNA
<213> ORGANISM: Homo sapiens
```

<400> SEQUENCE: 43
gcgcccctaa actcgtatct                                              20

<210> SEQ ID NO 44
<211> LENGTH: 20
<212> TYPE: DNA
<213> ORGANISM: Homo sapiens

<400> SEQUENCE: 44
gcggagtggt gagattgagt                                              20

<210> SEQ ID NO 45
<211> LENGTH: 20
<212> TYPE: DNA
<213> ORGANISM: Homo sapiens

<400> SEQUENCE: 45
accgacttct tcgattcgcc                                              20

<210> SEQ ID NO 46
<211> LENGTH: 20
<212> TYPE: DNA
<213> ORGANISM: Homo sapiens

<400> SEQUENCE: 46
ataggtaggc ggggaggttt                                              20

<210> SEQ ID NO 47
<211> LENGTH: 19
<212> TYPE: DNA
<213> ORGANISM: Homo sapiens

<400> SEQUENCE: 47
cgatccccca actcaaccc                                               19

<210> SEQ ID NO 48
<211> LENGTH: 20
<212> TYPE: DNA
<213> ORGANISM: Homo sapiens

<400> SEQUENCE: 48
tgagttggcg gtttcgtttg                                              20

<210> SEQ ID NO 49
<211> LENGTH: 20
<212> TYPE: DNA
<213> ORGANISM: Homo sapiens

<400> SEQUENCE: 49
cccgaatccc ctcttatccc                                              20

<210> SEQ ID NO 50
<211> LENGTH: 20
<212> TYPE: DNA
<213> ORGANISM: Homo sapiens

<400> SEQUENCE: 50
cgcgattttg tagtcggggt                                              20

<210> SEQ ID NO 51
<211> LENGTH: 20
<212> TYPE: DNA

```
<213> ORGANISM: Homo sapiens

<400> SEQUENCE: 51
tttcctatcg ccccaacacc                                              20

<210> SEQ ID NO 52
<211> LENGTH: 20
<212> TYPE: DNA
<213> ORGANISM: Homo sapiens

<400> SEQUENCE: 52
ggaggttggg tttcgggatt                                              20

<210> SEQ ID NO 53
<211> LENGTH: 20
<212> TYPE: DNA
<213> ORGANISM: Homo sapiens

<400> SEQUENCE: 53
gcgcccctaa actcgtatct                                              20

<210> SEQ ID NO 54
<211> LENGTH: 20
<212> TYPE: DNA
<213> ORGANISM: Homo sapiens

<400> SEQUENCE: 54
gattgagtcg cgatggaacg                                              20

<210> SEQ ID NO 55
<211> LENGTH: 20
<212> TYPE: DNA
<213> ORGANISM: Homo sapiens

<400> SEQUENCE: 55
gccgccttca acccaaaata                                              20

<210> SEQ ID NO 56
<211> LENGTH: 20
<212> TYPE: DNA
<213> ORGANISM: Homo sapiens

<400> SEQUENCE: 56
cgcgagcgta tagagtacga                                              20

<210> SEQ ID NO 57
<211> LENGTH: 20
<212> TYPE: DNA
<213> ORGANISM: Homo sapiens

<400> SEQUENCE: 57
accctaacca accccgaaac                                              20

<210> SEQ ID NO 58
<211> LENGTH: 20
<212> TYPE: DNA
<213> ORGANISM: Homo sapiens

<400> SEQUENCE: 58
tagcgtcgcg agcgtataga                                              20

<210> SEQ ID NO 59
<211> LENGTH: 20
```

<212> TYPE: DNA
<213> ORGANISM: Homo sapiens

<400> SEQUENCE: 59
aaaaataacc cgacgcccga                                              20

<210> SEQ ID NO 60
<211> LENGTH: 21
<212> TYPE: DNA
<213> ORGANISM: Homo sapiens

<400> SEQUENCE: 60
ggtttcgtag aagaggtttt c                                            21

<210> SEQ ID NO 61
<211> LENGTH: 20
<212> TYPE: DNA
<213> ORGANISM: Homo sapiens

<400> SEQUENCE: 61
cgcgaaataa taacgacttt                                              20

<210> SEQ ID NO 62
<211> LENGTH: 21
<212> TYPE: DNA
<213> ORGANISM: Homo sapiens

<400> SEQUENCE: 62
agaagaggtt ttcgttgggg g                                            21

<210> SEQ ID NO 63
<211> LENGTH: 20
<212> TYPE: DNA
<213> ORGANISM: Homo sapiens

<400> SEQUENCE: 63
accaaccccg aaactcgaaa                                              20

<210> SEQ ID NO 64
<211> LENGTH: 20
<212> TYPE: DNA
<213> ORGANISM: Homo sapiens

<400> SEQUENCE: 64
taggatttgg ggttggtgcg                                              20

<210> SEQ ID NO 65
<211> LENGTH: 20
<212> TYPE: DNA
<213> ORGANISM: Homo sapiens

<400> SEQUENCE: 65
aacgcaacga cgaacgtaac                                              20

<210> SEQ ID NO 66
<211> LENGTH: 20
<212> TYPE: DNA
<213> ORGANISM: Homo sapiens

<400> SEQUENCE: 66
tggtagtggg gagatcgagg                                              20

<210> SEQ ID NO 67

```
<211> LENGTH: 20
<212> TYPE: DNA
<213> ORGANISM: Homo sapiens

<400> SEQUENCE: 67
aaacgccccc aactctaacc                                               20

<210> SEQ ID NO 68
<211> LENGTH: 18
<212> TYPE: DNA
<213> ORGANISM: Homo sapiens

<400> SEQUENCE: 68
gttgcggacg gcgtagat                                                 18

<210> SEQ ID NO 69
<211> LENGTH: 21
<212> TYPE: DNA
<213> ORGANISM: Homo sapiens

<400> SEQUENCE: 69
acgctccccg aaacaataac t                                             21

<210> SEQ ID NO 70
<211> LENGTH: 21
<212> TYPE: DNA
<213> ORGANISM: Homo sapiens

<400> SEQUENCE: 70
ttgttagttt tgttagcgcg g                                             21

<210> SEQ ID NO 71
<211> LENGTH: 21
<212> TYPE: DNA
<213> ORGANISM: Homo sapiens

<400> SEQUENCE: 71
cgtccgcaac gattcatcat c                                             21

<210> SEQ ID NO 72
<211> LENGTH: 22
<212> TYPE: DNA
<213> ORGANISM: Homo sapiens

<400> SEQUENCE: 72
tgtttaggag atggttcgtg gt                                            22

<210> SEQ ID NO 73
<211> LENGTH: 20
<212> TYPE: DNA
<213> ORGANISM: Homo sapiens

<400> SEQUENCE: 73
gcatctacgc cgtccgcaac                                               20

<210> SEQ ID NO 74
<211> LENGTH: 18
<212> TYPE: DNA
<213> ORGANISM: Homo sapiens

<400> SEQUENCE: 74
atctacgccg tccgcaac                                                 18
```

```
<210> SEQ ID NO 75
<211> LENGTH: 20
<212> TYPE: DNA
<213> ORGANISM: Homo sapiens

<400> SEQUENCE: 75
tgtttagacg tgggttgggg                                              20

<210> SEQ ID NO 76
<211> LENGTH: 20
<212> TYPE: DNA
<213> ORGANISM: Homo sapiens

<400> SEQUENCE: 76
tcaactccac tcaccccgta                                              20

<210> SEQ ID NO 77
<211> LENGTH: 20
<212> TYPE: DNA
<213> ORGANISM: Homo sapiens

<400> SEQUENCE: 77
gaggagggtg gagagggtag                                              20

<210> SEQ ID NO 78
<211> LENGTH: 20
<212> TYPE: DNA
<213> ORGANISM: Homo sapiens

<400> SEQUENCE: 78
ataccgcacg tactcccaac                                              20

<210> SEQ ID NO 79
<211> LENGTH: 20
<212> TYPE: DNA
<213> ORGANISM: Homo sapiens

<400> SEQUENCE: 79
ggagtggagt aggtagcggt                                              20

<210> SEQ ID NO 80
<211> LENGTH: 20
<212> TYPE: DNA
<213> ORGANISM: Homo sapiens

<400> SEQUENCE: 80
ttcctaaccc tctccgacca                                              20

<210> SEQ ID NO 81
<211> LENGTH: 20
<212> TYPE: DNA
<213> ORGANISM: Homo sapiens

<400> SEQUENCE: 81
tttttgagcg gtgaagggga                                              20

<210> SEQ ID NO 82
<211> LENGTH: 20
<212> TYPE: DNA
<213> ORGANISM: Homo sapiens

<400> SEQUENCE: 82
aattattaac gcgaccgccg                                              20
```

<210> SEQ ID NO 83
<211> LENGTH: 24
<212> TYPE: DNA
<213> ORGANISM: Homo sapiens

<400> SEQUENCE: 83
gtaataattt ggtggtatcg gggg         24

<210> SEQ ID NO 84
<211> LENGTH: 23
<212> TYPE: DNA
<213> ORGANISM: Homo sapiens

<400> SEQUENCE: 84
tctactaaac gaacacgtaa cgc          23

<210> SEQ ID NO 85
<211> LENGTH: 21
<212> TYPE: DNA
<213> ORGANISM: Homo sapiens

<400> SEQUENCE: 85
ataatttggt ggtatcgggg g             21

<210> SEQ ID NO 86
<211> LENGTH: 25
<212> TYPE: DNA
<213> ORGANISM: Homo sapiens

<400> SEQUENCE: 86
acgcgttatt attctactaa acgaa         25

<210> SEQ ID NO 87
<211> LENGTH: 23
<212> TYPE: DNA
<213> ORGANISM: Homo sapiens

<400> SEQUENCE: 87
tggggtttgt tttaattgtg gtt           23

<210> SEQ ID NO 88
<211> LENGTH: 22
<212> TYPE: DNA
<213> ORGANISM: Homo sapiens

<400> SEQUENCE: 88
gcgaaacccg cgccttctta at            22

<210> SEQ ID NO 89
<211> LENGTH: 20
<212> TYPE: DNA
<213> ORGANISM: Homo sapiens

<400> SEQUENCE: 89
gaaacccgcg ccttcttaat               20

<210> SEQ ID NO 90
<211> LENGTH: 27
<212> TYPE: DNA
<213> ORGANISM: Homo sapiens

<400> SEQUENCE: 90
ggggaagtat agttatttaa taagttg        27

```
<210> SEQ ID NO 91
<211> LENGTH: 23
<212> TYPE: DNA
<213> ORGANISM: Homo sapiens

<400> SEQUENCE: 91
acaaaacatc raaccattaa taa                                              23

<210> SEQ ID NO 92
<211> LENGTH: 20
<212> TYPE: DNA
<213> ORGANISM: Homo sapiens

<400> SEQUENCE: 92
ttcgcgaagg agagcgtatc                                                  20

<210> SEQ ID NO 93
<211> LENGTH: 20
<212> TYPE: DNA
<213> ORGANISM: Homo sapiens

<400> SEQUENCE: 93
ccctacgtac acccccaaac                                                  20

<210> SEQ ID NO 94
<211> LENGTH: 20
<212> TYPE: DNA
<213> ORGANISM: Homo sapiens

<400> SEQUENCE: 94 cgtttgggggg tgtacgtagg                                                 20

<210> SEQ ID NO 95
<211> LENGTH: 20
<212> TYPE: DNA
<213> ORGANISM: Homo sapiens

<400> SEQUENCE: 95
aaacccaata cacgcgacga                                                  20

<210> SEQ ID NO 96
<211> LENGTH: 20
<212> TYPE: DNA
<213> ORGANISM: Homo sapiens

<400> SEQUENCE: 96
tttgtcgggg aggttggttt                                                  20

<210> SEQ ID NO 97
<211> LENGTH: 20
<212> TYPE: DNA
<213> ORGANISM: Homo sapiens

<400> SEQUENCE: 97
ttcctactaa acgccgacgc                                                  20

<210> SEQ ID NO 98
<211> LENGTH: 20
<212> TYPE: DNA
<213> ORGANISM: Homo sapiens

<400> SEQUENCE: 98
```
tagcgtttgg ttcgttcggt 20

<210> SEQ ID NO 99
<211> LENGTH: 20
<212> TYPE: DNA
<213> ORGANISM: Homo sapiens

<400> SEQUENCE: 99
ataaaaacgc gaacgccgac 20

<210> SEQ ID NO 100
<211> LENGTH: 20
<212> TYPE: DNA
<213> ORGANISM: Homo sapiens

<400> SEQUENCE: 100
gcgggcgttt cgattgattt 20

<210> SEQ ID NO 101
<211> LENGTH: 22
<212> TYPE: DNA
<213> ORGANISM: Homo sapiens

<400> SEQUENCE: 101
ttgcgggcgt ttcgattgat tt 22

<210> SEQ ID NO 102
<211> LENGTH: 20
<212> TYPE: DNA
<213> ORGANISM: Homo sapiens

<400> SEQUENCE: 102
taaaaaccgc ccccactacc 20

<210> SEQ ID NO 103
<211> LENGTH: 20
<212> TYPE: DNA
<213> ORGANISM: Homo sapiens

<400> SEQUENCE: 103
tgttcggcgg tttaggtgtt 20

<210> SEQ ID NO 104
<211> LENGTH: 20
<212> TYPE: DNA
<213> ORGANISM: Homo sapiens

<400> SEQUENCE: 104
aaatcaatcg aaacgcccgc 20

<210> SEQ ID NO 105
<211> LENGTH: 20
<212> TYPE: DNA
<213> ORGANISM: Homo sapiens

<400> SEQUENCE: 105
tagttcgggt ttcgtcgtgc 20

<210> SEQ ID NO 106
<211> LENGTH: 22
<212> TYPE: DNA
<213> ORGANISM: Homo sapiens

<400> SEQUENCE: 106

```
aaaactaaaa accgccccca ct                                         22

<210> SEQ ID NO 107
<211> LENGTH: 20
<212> TYPE: DNA
<213> ORGANISM: Homo sapiens

<400> SEQUENCE: 107
aactaaaaac cgcccccact                                            20

<210> SEQ ID NO 108
<211> LENGTH: 20
<212> TYPE: DNA
<213> ORGANISM: Homo sapiens

<400> SEQUENCE: 108
gtgggtggta gtttgcgttg                                            20

<210> SEQ ID NO 109
<211> LENGTH: 20
<212> TYPE: DNA
<213> ORGANISM: Homo sapiens

<400> SEQUENCE: 109
cactacctcc ccgccttaaa                                            20

<210> SEQ ID NO 110
<211> LENGTH: 20
<212> TYPE: DNA
<213> ORGANISM: Homo sapiens

<400> SEQUENCE: 110
gcgtgcgttt tcggttttga                                            20

<210> SEQ ID NO 111
<211> LENGTH: 22
<212> TYPE: DNA
<213> ORGANISM: Homo sapiens

<400> SEQUENCE: 111
cggcgtgcgt tttcggtttt ga                                         22

<210> SEQ ID NO 112
<211> LENGTH: 20
<212> TYPE: DNA
<213> ORGANISM: Homo sapiens

<400> SEQUENCE: 112
aacgcaaact accacccacc                                            20

<210> SEQ ID NO 113
<211> LENGTH: 21
<212> TYPE: DNA
<213> ORGANISM: Homo sapiens

<400> SEQUENCE: 113
ggacgttggg ttgagttagg a                                          21

<210> SEQ ID NO 114
<211> LENGTH: 20
<212> TYPE: DNA
<213> ORGANISM: Homo sapiens
```

-continued

<400> SEQUENCE: 114
acgaccctac aactcccta                                            20

<210> SEQ ID NO 115
<211> LENGTH: 20
<212> TYPE: DNA
<213> ORGANISM: Homo sapiens

<400> SEQUENCE: 115
ggtgttcgaa ttgtacggcg                                           20

<210> SEQ ID NO 116
<211> LENGTH: 20
<212> TYPE: DNA
<213> ORGANISM: Homo sapiens

<400> SEQUENCE: 116
ctacgcgccg ctcataaaaa                                           20

<210> SEQ ID NO 117
<211> LENGTH: 20
<212> TYPE: DNA
<213> ORGANISM: Homo sapiens

<400> SEQUENCE: 117
gcgcgtacgg tttcgtatag                                           20

<210> SEQ ID NO 118
<211> LENGTH: 20
<212> TYPE: DNA
<213> ORGANISM: Homo sapiens

<400> SEQUENCE: 118
atactcgctc tttacgcccg                                           20

<210> SEQ ID NO 119
<211> LENGTH: 20
<212> TYPE: DNA
<213> ORGANISM: Homo sapiens

<400> SEQUENCE: 119
tagagcggta ggtcggtagg                                           20

<210> SEQ ID NO 120
<211> LENGTH: 20
<212> TYPE: DNA
<213> ORGANISM: Homo sapiens

<400> SEQUENCE: 120
aacaaaccga accgctacac                                           20

<210> SEQ ID NO 121
<211> LENGTH: 20
<212> TYPE: DNA
<213> ORGANISM: Homo sapiens

<400> SEQUENCE: 121
gcggcgtggg aatgaatttt                                           20

<210> SEQ ID NO 122
<211> LENGTH: 22
<212> TYPE: DNA
<213> ORGANISM: Homo sapiens

```
<400> SEQUENCE: 122
gggcggcgtg ggaatgaatt tt                                              22

<210> SEQ ID NO 123
<211> LENGTH: 20
<212> TYPE: DNA
<213> ORGANISM: Homo sapiens

<400> SEQUENCE: 123
ctttccctcg cacccctaaa                                                 20

<210> SEQ ID NO 124
<211> LENGTH: 20
<212> TYPE: DNA
<213> ORGANISM: Homo sapiens

<400> SEQUENCE: 124
tgcgagggaa agtttgggtt                                                 20

<210> SEQ ID NO 125
<211> LENGTH: 20
<212> TYPE: DNA
<213> ORGANISM: Homo sapiens

<400> SEQUENCE: 125
ccgcgttacc cgaaaaactt                                                 20

<210> SEQ ID NO 126
<211> LENGTH: 20
<212> TYPE: DNA
<213> ORGANISM: Homo sapiens

<400> SEQUENCE: 126
ttttaggggt gcgagggaaa                                                 20

<210> SEQ ID NO 127
<211> LENGTH: 20
<212> TYPE: DNA
<213> ORGANISM: Homo sapiens

<400> SEQUENCE: 127
cgcaaccgaa ctactcaccc                                                 20

<210> SEQ ID NO 128
<211> LENGTH: 20
<212> TYPE: DNA
<213> ORGANISM: Homo sapiens

<400> SEQUENCE: 128
gtgcgaggga aagtttgggt                                                 20

<210> SEQ ID NO 129
<211> LENGTH: 19
<212> TYPE: DNA
<213> ORGANISM: Homo sapiens

<400> SEQUENCE: 129
acccgcgtta cccgaaaaa                                                  19

<210> SEQ ID NO 130
<211> LENGTH: 19
<212> TYPE: DNA
```

<210> SEQ ID NO 130
<211> LENGTH: 19
<212> TYPE: DNA
<213> ORGANISM: Homo sapiens

<400> SEQUENCE: 130
tttttttggt tgtcgggtc                                                    19

<210> SEQ ID NO 131
<211> LENGTH: 18
<212> TYPE: DNA
<213> ORGANISM: Homo sapiens

<400> SEQUENCE: 131
cgaaacccga aacacgta                                                     18

<210> SEQ ID NO 132
<211> LENGTH: 20
<212> TYPE: DNA
<213> ORGANISM: Homo sapiens

<400> SEQUENCE: 132
agagtggtcg ggtgtttagc                                                   20

<210> SEQ ID NO 133
<211> LENGTH: 21
<212> TYPE: DNA
<213> ORGANISM: Homo sapiens

<400> SEQUENCE: 133
acgtaaccca aaaactcgaa a                                                 21

<210> SEQ ID NO 134
<211> LENGTH: 18
<212> TYPE: DNA
<213> ORGANISM: Homo sapiens

<400> SEQUENCE: 134
gtcgtttttt aggggtgc                                                     18

<210> SEQ ID NO 135
<211> LENGTH: 20
<212> TYPE: DNA
<213> ORGANISM: Homo sapiens

<400> SEQUENCE: 135
taaacttcgc aaccgaacta                                                   20

<210> SEQ ID NO 136
<211> LENGTH: 21
<212> TYPE: DNA
<213> ORGANISM: Homo sapiens

<400> SEQUENCE: 136
tattaagttt gcgtttgggt c                                                 21

<210> SEQ ID NO 137
<211> LENGTH: 20
<212> TYPE: DNA
<213> ORGANISM: Homo sapiens

<400> SEQUENCE: 137
aaaaccgtct atccctacgc                                                   20

<210> SEQ ID NO 138
<211> LENGTH: 20

```
<212> TYPE: DNA
<213> ORGANISM: Homo sapiens

<400> SEQUENCE: 138
cgaggtagga agttttgcgg                                               20

<210> SEQ ID NO 139
<211> LENGTH: 20
<212> TYPE: DNA
<213> ORGANISM: Homo sapiens

<400> SEQUENCE: 139
cgactcctcc cgcgaaataa                                               20

<210> SEQ ID NO 140
<211> LENGTH: 20
<212> TYPE: DNA
<213> ORGANISM: Homo sapiens

<400> SEQUENCE: 140
cggggtgttg ttgtagggtt                                               20

<210> SEQ ID NO 141
<211> LENGTH: 19
<212> TYPE: DNA
<213> ORGANISM: Homo sapiens

<400> SEQUENCE: 141
aatcacacct acccacgcc                                                19

<210> SEQ ID NO 142
<211> LENGTH: 20
<212> TYPE: DNA
<213> ORGANISM: Homo sapiens

<400> SEQUENCE: 142
tagggcggtt aggtttgggg                                               20

<210> SEQ ID NO 143
<211> LENGTH: 20
<212> TYPE: DNA
<213> ORGANISM: Homo sapiens

<400> SEQUENCE: 143
gacgaataac cccaccctcc                                               20

<210> SEQ ID NO 144
<211> LENGTH: 20
<212> TYPE: DNA
<213> ORGANISM: Homo sapiens

<400> SEQUENCE: 144
ttgtcgcgtt ggttttcgt                                                20

<210> SEQ ID NO 145
<211> LENGTH: 20
<212> TYPE: DNA
<213> ORGANISM: Homo sapiens

<400> SEQUENCE: 145
acctttctct cgaccccaat                                               20

<210> SEQ ID NO 146
```

```
<211> LENGTH: 21
<212> TYPE: DNA
<213> ORGANISM: Homo sapiens

<400> SEQUENCE: 146
cgttttgtcg gttgcgtgtt a                                              21

<210> SEQ ID NO 147
<211> LENGTH: 21
<212> TYPE: DNA
<213> ORGANISM: Homo sapiens

<400> SEQUENCE: 147
attccccgac ctacccaaaa c                                              21

<210> SEQ ID NO 148
<211> LENGTH: 24
<212> TYPE: DNA
<213> ORGANISM: Homo sapiens

<400> SEQUENCE: 148
ggtaggtgat aacgttagtg ggtt                                           24

<210> SEQ ID NO 149
<211> LENGTH: 20
<212> TYPE: DNA
<213> ORGANISM: Homo sapiens

<400> SEQUENCE: 149
acctccatcc cctacccaac                                                20

<210> SEQ ID NO 150
<211> LENGTH: 20
<212> TYPE: DNA
<213> ORGANISM: Homo sapiens

<400> SEQUENCE: 150
agtaggggga ggtggttttg                                                20

<210> SEQ ID NO 151
<211> LENGTH: 20
<212> TYPE: DNA
<213> ORGANISM: Homo sapiens

<400> SEQUENCE: 151
tcctcctccc caacttaacc                                                20

<210> SEQ ID NO 152
<211> LENGTH: 20
<212> TYPE: DNA
<213> ORGANISM: Homo sapiens

<400> SEQUENCE: 152
agtttgggtg tggcggttta                                                20

<210> SEQ ID NO 153
<211> LENGTH: 22
<212> TYPE: DNA
<213> ORGANISM: Homo sapiens

<400> SEQUENCE: 153
accaacttcg ccatattaac ca                                             22
```

```
<210> SEQ ID NO 154
<211> LENGTH: 20
<212> TYPE: DNA
<213> ORGANISM: Homo sapiens

<400> SEQUENCE: 154
cgcggtgtat tgtgggtagt                                              20

<210> SEQ ID NO 155
<211> LENGTH: 20
<212> TYPE: DNA
<213> ORGANISM: Homo sapiens

<400> SEQUENCE: 155
ccttccgacc cgaatcatcc                                              20

<210> SEQ ID NO 156
<211> LENGTH: 19
<212> TYPE: DNA
<213> ORGANISM: Homo sapiens

<400> SEQUENCE: 156
ggtcgtcgga acgtgatgt                                               19

<210> SEQ ID NO 157
<211> LENGTH: 20
<212> TYPE: DNA
<213> ORGANISM: Homo sapiens

<400> SEQUENCE: 157
gccaacatca acaccaaccc                                              20

<210> SEQ ID NO 158
<211> LENGTH: 20
<212> TYPE: DNA
<213> ORGANISM: Homo sapiens

<400> SEQUENCE: 158
tcgttttgtc gttgtcgtcg                                              20

<210> SEQ ID NO 159
<211> LENGTH: 21
<212> TYPE: DNA
<213> ORGANISM: Homo sapiens

<400> SEQUENCE: 159
ttaaataacc cgctccctcc g                                            21

<210> SEQ ID NO 160
<211> LENGTH: 20
<212> TYPE: DNA
<213> ORGANISM: Homo sapiens

<400> SEQUENCE: 160
gtcgtgatgt tagagcgggc                                              20

<210> SEQ ID NO 161
<211> LENGTH: 20
<212> TYPE: DNA
<213> ORGANISM: Homo sapiens

<400> SEQUENCE: 161
accccgatcc tccttaaacg                                              20
```

```
<210> SEQ ID NO 162
<211> LENGTH: 18
<212> TYPE: DNA
<213> ORGANISM: Homo sapiens

<400> SEQUENCE: 162
ttaaggagga tcggggtc                                                      18

<210> SEQ ID NO 163
<211> LENGTH: 22
<212> TYPE: DNA
<213> ORGANISM: Homo sapiens

<400> SEQUENCE: 163
tcaatacgac gttaaataac cc                                                 22

<210> SEQ ID NO 164
<211> LENGTH: 20
<212> TYPE: DNA
<213> ORGANISM: Homo sapiens

<400> SEQUENCE: 164
tggagttaag cgggtggtag                                                    20

<210> SEQ ID NO 165
<211> LENGTH: 21
<212> TYPE: DNA
<213> ORGANISM: Homo sapiens

<400> SEQUENCE: 165
cccgctctaa catcacgact c                                                  21

<210> SEQ ID NO 166
<211> LENGTH: 20
<212> TYPE: DNA
<213> ORGANISM: Homo sapiens

<400> SEQUENCE: 166
gtattgtcgc gggttcgttc                                                    20

<210> SEQ ID NO 167
<211> LENGTH: 20
<212> TYPE: DNA
<213> ORGANISM: Homo sapiens

<400> SEQUENCE: 167
ctcaaccaat ccccactccc                                                    20

<210> SEQ ID NO 168
<211> LENGTH: 23
<212> TYPE: DNA
<213> ORGANISM: Homo sapiens

<400> SEQUENCE: 168
gttttaggtt tcgttagtat ggg                                                23

<210> SEQ ID NO 169
<211> LENGTH: 29
<212> TYPE: DNA
<213> ORGANISM: Homo sapiens

<400> SEQUENCE: 169
caaattaaaa taaatcattt aacccataa                                          29
```

<210> SEQ ID NO 170
<211> LENGTH: 25
<212> TYPE: DNA
<213> ORGANISM: Homo sapiens

<400> SEQUENCE: 170
ttaaaataaa tcatttaacc cataa                                          25

<210> SEQ ID NO 171
<211> LENGTH: 20
<212> TYPE: DNA
<213> ORGANISM: Homo sapiens

<400> SEQUENCE: 171
cgaagatttc gtaggcgggt                                                20

<210> SEQ ID NO 172
<211> LENGTH: 22
<212> TYPE: DNA
<213> ORGANISM: Homo sapiens

<400> SEQUENCE: 172
acgacgcaaa taacgctacg ca                                             22

<210> SEQ ID NO 173
<211> LENGTH: 20
<212> TYPE: DNA
<213> ORGANISM: Homo sapiens

<400> SEQUENCE: 173
gacgcaaata acgctacgca                                                20

<210> SEQ ID NO 174
<211> LENGTH: 21
<212> TYPE: DNA
<213> ORGANISM: Homo sapiens

<400> SEQUENCE: 174
tgttttagaa gcgggagaaa g                                              21

<210> SEQ ID NO 175
<211> LENGTH: 22
<212> TYPE: DNA
<213> ORGANISM: Homo sapiens

<400> SEQUENCE: 175
aaataaaacc cccgtatcca at                                             22

<210> SEQ ID NO 176
<211> LENGTH: 23
<212> TYPE: DNA
<213> ORGANISM: Homo sapiens

<400> SEQUENCE: 176
aatgttttag aagcgggaga aag                                            23

<210> SEQ ID NO 177
<211> LENGTH: 24
<212> TYPE: DNA
<213> ORGANISM: Homo sapiens

<400> SEQUENCE: 177

```
aaaaataaaa cccccgtatc caat                                           24

<210> SEQ ID NO 178
<211> LENGTH: 28
<212> TYPE: DNA
<213> ORGANISM: Homo sapiens

<400> SEQUENCE: 178
gcggcggtta gcgttagttt ttcggtag                                       28

<210> SEQ ID NO 179
<211> LENGTH: 28
<212> TYPE: DNA
<213> ORGANISM: Homo sapiens

<400> SEQUENCE: 179
cgaaacgcca acgtatcata acgacgca                                       28

<210> SEQ ID NO 180
<211> LENGTH: 20
<212> TYPE: DNA
<213> ORGANISM: Homo sapiens

<400> SEQUENCE: 180
acgttttagg gacggcgaat                                                20

<210> SEQ ID NO 181
<211> LENGTH: 20
<212> TYPE: DNA
<213> ORGANISM: Homo sapiens

<400> SEQUENCE: 181
aatcccaacg accgtctacc                                                20

<210> SEQ ID NO 182
<211> LENGTH: 26
<212> TYPE: DNA
<213> ORGANISM: Homo sapiens

<400> SEQUENCE: 182
tttcgttttg tatttatggt agatgt                                         26

<210> SEQ ID NO 183
<211> LENGTH: 20
<212> TYPE: DNA
<213> ORGANISM: Homo sapiens

<400> SEQUENCE: 183
ccaacgaccg tctaccacta                                                20

<210> SEQ ID NO 184
<211> LENGTH: 20
<212> TYPE: DNA
<213> ORGANISM: Homo sapiens

<400> SEQUENCE: 184
cgtggtatgg atttcggggt                                                20

<210> SEQ ID NO 185
<211> LENGTH: 20
<212> TYPE: DNA
<213> ORGANISM: Homo sapiens

<400> SEQUENCE: 185
```
actcctaacc ctaaacgcga                                          20

<210> SEQ ID NO 186
<211> LENGTH: 22
<212> TYPE: DNA
<213> ORGANISM: Homo sapiens

<400> SEQUENCE: 186
gtttttttcg gtttttgttc ga                                       22

<210> SEQ ID NO 187
<211> LENGTH: 22
<212> TYPE: DNA
<213> ORGANISM: Homo sapiens

<400> SEQUENCE: 187
tttctcccaa ttccaatatc ca                                       22

<210> SEQ ID NO 188
<211> LENGTH: 24
<212> TYPE: DNA
<213> ORGANISM: Homo sapiens

<400> SEQUENCE: 188
tggttttttt cggttttttgt tcga                                    24

<210> SEQ ID NO 189
<211> LENGTH: 24
<212> TYPE: DNA
<213> ORGANISM: Homo sapiens

<400> SEQUENCE: 189
actttctccc aattccaata tcca                                     24

<210> SEQ ID NO 190
<211> LENGTH: 20
<212> TYPE: DNA
<213> ORGANISM: Homo sapiens

<400> SEQUENCE: 190
gcgatcggcg attggttttt                                          20

<210> SEQ ID NO 191
<211> LENGTH: 20
<212> TYPE: DNA
<213> ORGANISM: Homo sapiens

<400> SEQUENCE: 191
gcgacgacac acgacctaaa                                          20

<210> SEQ ID NO 192
<211> LENGTH: 20
<212> TYPE: DNA
<213> ORGANISM: Homo sapiens

<400> SEQUENCE: 192
tgaggtttta ggtcgtgtgt                                          20

<210> SEQ ID NO 193
<211> LENGTH: 22
<212> TYPE: DNA
<213> ORGANISM: Homo sapiens

<400> SEQUENCE: 193
ggtgaggttt taggtcgtgt gt                                      22

<210> SEQ ID NO 194
<211> LENGTH: 25
<212> TYPE: DNA
<213> ORGANISM: Homo sapiens

<400> SEQUENCE: 194
aaaaccttaa tcgactcaaa taaaa                                   25

<210> SEQ ID NO 195
<211> LENGTH: 20
<212> TYPE: DNA
<213> ORGANISM: Homo sapiens

<400> SEQUENCE: 195
gggtgtagtt gcgtagcgta                                         20

<210> SEQ ID NO 196
<211> LENGTH: 20
<212> TYPE: DNA
<213> ORGANISM: Homo sapiens

<400> SEQUENCE: 196
ccgaaccctc ctcaccaaaa                                         20

<210> SEQ ID NO 197
<211> LENGTH: 20
<212> TYPE: DNA
<213> ORGANISM: Homo sapiens

<400> SEQUENCE: 197
tagttgcgta gcgtagggta                                         20

<210> SEQ ID NO 198
<211> LENGTH: 21
<212> TYPE: DNA
<213> ORGANISM: Homo sapiens

<400> SEQUENCE: 198
tcaccaaaat cctcctaaaa c                                       21

<210> SEQ ID NO 199
<211> LENGTH: 25
<212> TYPE: DNA
<213> ORGANISM: Homo sapiens

<400> SEQUENCE: 199
acgtagtgtt ggtaagattt gtaga                                   25

<210> SEQ ID NO 200
<211> LENGTH: 24
<212> TYPE: DNA
<213> ORGANISM: Homo sapiens

<400> SEQUENCE: 200
acaaaaaccg cttataaacg acga                                    24

<210> SEQ ID NO 201
<211> LENGTH: 22
<212> TYPE: DNA
<213> ORGANISM: Homo sapiens

<400> SEQUENCE: 201
gtaggttttt gcgttggaga tt                                    22

<210> SEQ ID NO 202
<211> LENGTH: 26
<212> TYPE: DNA
<213> ORGANISM: Homo sapiens

<400> SEQUENCE: 202
attttcgtta cttctctatt cccaaa                                26

<210> SEQ ID NO 203
<211> LENGTH: 20
<212> TYPE: DNA
<213> ORGANISM: Homo sapiens

<400> SEQUENCE: 203
ggggtttcgc gttttgagtt                                       20

<210> SEQ ID NO 204
<211> LENGTH: 20
<212> TYPE: DNA
<213> ORGANISM: Homo sapiens

<400> SEQUENCE: 204
aacaccaaaa cccccgctaa                                       20

<210> SEQ ID NO 205
<211> LENGTH: 22
<212> TYPE: DNA
<213> ORGANISM: Homo sapiens

<400> SEQUENCE: 205
aaaagtaatt aatcggaacg gt                                    22

<210> SEQ ID NO 206
<211> LENGTH: 23
<212> TYPE: DNA
<213> ORGANISM: Homo sapiens

<400> SEQUENCE: 206
acactttccc aaatacaaaa aaa                                   23

<210> SEQ ID NO 207
<211> LENGTH: 20
<212> TYPE: DNA
<213> ORGANISM: Homo sapiens

<400> SEQUENCE: 207
tttcgagtcg gggcgtttta                                       20

<210> SEQ ID NO 208
<211> LENGTH: 20
<212> TYPE: DNA
<213> ORGANISM: Homo sapiens

<400> SEQUENCE: 208
tacctaaccg ctcgctctct                                       20

<210> SEQ ID NO 209
<211> LENGTH: 19
<212> TYPE: DNA

```
<213> ORGANISM: Homo sapiens

<400> SEQUENCE: 209
gttcggtttt gggattttt                                           19

<210> SEQ ID NO 210
<211> LENGTH: 19
<212> TYPE: DNA
<213> ORGANISM: Homo sapiens

<400> SEQUENCE: 210
aatcccaaaa accgactct                                           19

<210> SEQ ID NO 211
<211> LENGTH: 23
<212> TYPE: DNA
<213> ORGANISM: Homo sapiens

<400> SEQUENCE: 211
gagggttcgg ttttgggatt ttt                                      23

<210> SEQ ID NO 212
<211> LENGTH: 22
<212> TYPE: DNA
<213> ORGANISM: Homo sapiens

<400> SEQUENCE: 212
accaatccca aaaccgact ct                                        22

<210> SEQ ID NO 213
<211> LENGTH: 20
<212> TYPE: DNA
<213> ORGANISM: Homo sapiens

<400> SEQUENCE: 213
cggaggaatt tgtgtcgtcg                                          20

<210> SEQ ID NO 214
<211> LENGTH: 20
<212> TYPE: DNA
<213> ORGANISM: Homo sapiens

<400> SEQUENCE: 214
caccaaaaca acgctacccg                                          20

<210> SEQ ID NO 215
<211> LENGTH: 21
<212> TYPE: DNA
<213> ORGANISM: Homo sapiens

<400> SEQUENCE: 215
ttgggaattt ttttcgttta t                                        21

<210> SEQ ID NO 216
<211> LENGTH: 22
<212> TYPE: DNA
<213> ORGANISM: Homo sapiens

<400> SEQUENCE: 216
tcctccgaat aacttaaaaa cc                                       22

<210> SEQ ID NO 217
<211> LENGTH: 24
```

```
<212> TYPE: DNA
<213> ORGANISM: Homo sapiens

<400> SEQUENCE: 217
tcgttggata gtggtattta atgt                                           24

<210> SEQ ID NO 218
<211> LENGTH: 20
<212> TYPE: DNA
<213> ORGANISM: Homo sapiens

<400> SEQUENCE: 218
aaaatcaccg actcactcaa                                                20

<210> SEQ ID NO 219
<211> LENGTH: 19
<212> TYPE: DNA
<213> ORGANISM: Homo sapiens

<400> SEQUENCE: 219
cggagtacgg cggtaggaa                                                 19

<210> SEQ ID NO 220
<211> LENGTH: 23
<212> TYPE: DNA
<213> ORGANISM: Homo sapiens

<400> SEQUENCE: 220 aatacccga aacccgcta ata                                              23

<210> SEQ ID NO 221
<211> LENGTH: 20
<212> TYPE: DNA
<213> ORGANISM: Homo sapiens

<400> SEQUENCE: 221
accccgaaaa cccgctaata                                                20

<210> SEQ ID NO 222
<211> LENGTH: 22
<212> TYPE: DNA
<213> ORGANISM: Homo sapiens

<400> SEQUENCE: 222
atgatatttt gtaggaaagc gt                                             22

<210> SEQ ID NO 223
<211> LENGTH: 22
<212> TYPE: DNA
<213> ORGANISM: Homo sapiens

<400> SEQUENCE: 223
caaattccgt ttctaaaaaa ac                                             22

<210> SEQ ID NO 224
<211> LENGTH: 20
<212> TYPE: DNA
<213> ORGANISM: Homo sapiens

<400> SEQUENCE: 224
gggttcgtat gcgggagtag                                                20

<210> SEQ ID NO 225
```

-continued

```
<211> LENGTH: 20
<212> TYPE: DNA
<213> ORGANISM: Homo sapiens

<400> SEQUENCE: 225
acgaaactac accaacgcct                                                      20

<210> SEQ ID NO 226
<211> LENGTH: 21
<212> TYPE: DNA
<213> ORGANISM: Homo sapiens

<400> SEQUENCE: 226 ggggttttc gttaggagta g                                                     21

<210> SEQ ID NO 227
<211> LENGTH: 18
<212> TYPE: DNA
<213> ORGANISM: Homo sapiens

<400> SEQUENCE: 227
aaaccgccct aaaccacc                                                        18

<210> SEQ ID NO 228
<211> LENGTH: 20
<212> TYPE: DNA
<213> ORGANISM: Homo sapiens

<400> SEQUENCE: 228
gaagggcggt agcgatagtt                                                      20

<210> SEQ ID NO 229
<211> LENGTH: 22
<212> TYPE: DNA
<213> ORGANISM: Homo sapiens

<400> SEQUENCE: 229
ctacgaattc cgcaaaccga aa                                                   22

<210> SEQ ID NO 230
<211> LENGTH: 20
<212> TYPE: DNA
<213> ORGANISM: Homo sapiens

<400> SEQUENCE: 230
acgaattccg caaaccgaaa                                                      20

<210> SEQ ID NO 231
<211> LENGTH: 18
<212> TYPE: DNA
<213> ORGANISM: Homo sapiens

<400> SEQUENCE: 231 attgttttg tcggcgtt                                                         18

<210> SEQ ID NO 232
<211> LENGTH: 19
<212> TYPE: DNA
<213> ORGANISM: Homo sapiens

<400> SEQUENCE: 232
tacactacga attccgcaa                                                       19
```

```
<210> SEQ ID NO 233
<211> LENGTH: 20
<212> TYPE: DNA
<213> ORGANISM: Homo sapiens

<400> SEQUENCE: 233
gcgtgcgtat attcgcgttt                                              20

<210> SEQ ID NO 234
<211> LENGTH: 22
<212> TYPE: DNA
<213> ORGANISM: Homo sapiens

<400> SEQUENCE: 234
cggcgtgcgt atattcgcgt tt                                           22

<210> SEQ ID NO 235
<211> LENGTH: 20
<212> TYPE: DNA
<213> ORGANISM: Homo sapiens

<400> SEQUENCE: 235
aaattccgcc tcccctaacc                                              20

<210> SEQ ID NO 236
<211> LENGTH: 24
<212> TYPE: DNA
<213> ORGANISM: Homo sapiens

<400> SEQUENCE: 236
tttagcgttt aatgtgtatg taga                                         24

<210> SEQ ID NO 237
<211> LENGTH: 26
<212> TYPE: DNA
<213> ORGANISM: Homo sapiens

<400> SEQUENCE: 237
cgaaattaca atcgaaacaa acttac                                       26

<210> SEQ ID NO 238
<211> LENGTH: 24
<212> TYPE: DNA
<213> ORGANISM: Homo sapiens

<400> SEQUENCE: 238
aaattacaat cgaaacaaac ttac                                         24

<210> SEQ ID NO 239
<211> LENGTH: 19
<212> TYPE: DNA
<213> ORGANISM: Homo sapiens

<400> SEQUENCE: 239
gttttgagta gggtgcgag                                               19

<210> SEQ ID NO 240
<211> LENGTH: 19
<212> TYPE: DNA
<213> ORGANISM: Homo sapiens

<400> SEQUENCE: 240
aaaaaaacaa attccgcct                                               19
```

```
<210> SEQ ID NO 241
<211> LENGTH: 22
<212> TYPE: DNA
<213> ORGANISM: Homo sapiens

<400> SEQUENCE: 241
gatgttttga gtagggtgcg ag                                    22

<210> SEQ ID NO 242
<211> LENGTH: 24
<212> TYPE: DNA
<213> ORGANISM: Homo sapiens

<400> SEQUENCE: 242
aaacgaaaaa aacaaattcc gcct                                  24

<210> SEQ ID NO 243
<211> LENGTH: 20
<212> TYPE: DNA
<213> ORGANISM: Homo sapiens

<400> SEQUENCE: 243
tggtagcgtt gtaaggtggg                                       20

<210> SEQ ID NO 244
<211> LENGTH: 20
<212> TYPE: DNA
<213> ORGANISM: Homo sapiens

<400> SEQUENCE: 244
aaaaacaaac gcgaccctcg                                       20

<210> SEQ ID NO 245
<211> LENGTH: 22
<212> TYPE: DNA
<213> ORGANISM: Homo sapiens

<400> SEQUENCE: 245
tcgagttttg gtagcgttgt aa                                    22

<210> SEQ ID NO 246
<211> LENGTH: 24
<212> TYPE: DNA
<213> ORGANISM: Homo sapiens

<400> SEQUENCE: 246 aatacccgc aaaaaaaatc taca                                   24

<210> SEQ ID NO 247
<211> LENGTH: 20
<212> TYPE: DNA
<213> ORGANISM: Homo sapiens

<400> SEQUENCE: 247
ccccgcaaaa aaaatctaca                                       20

<210> SEQ ID NO 248
<211> LENGTH: 20
<212> TYPE: DNA
<213> ORGANISM: Homo sapiens

<400> SEQUENCE: 248
acgagaaatt ggcgcgttga                                       20
```

<210> SEQ ID NO 249
<211> LENGTH: 20
<212> TYPE: DNA
<213> ORGANISM: Homo sapiens

<400> SEQUENCE: 249
aacaacaccc tttacgacgc                                                     20

<210> SEQ ID NO 250
<211> LENGTH: 23
<212> TYPE: DNA
<213> ORGANISM: Homo sapiens

<400> SEQUENCE: 250
tgtttgttag ggttttgttt taa                                                 23

<210> SEQ ID NO 251
<211> LENGTH: 22
<212> TYPE: DNA
<213> ORGANISM: Homo sapiens

<400> SEQUENCE: 251
cgccaaaacg aatatttatt ta                                                  22

<210> SEQ ID NO 252
<211> LENGTH: 26
<212> TYPE: DNA
<213> ORGANISM: Homo sapiens

<400> SEQUENCE: 252
aattgtttgt tagggttttg ttttaa                                              26

<210> SEQ ID NO 253
<211> LENGTH: 25
<212> TYPE: DNA
<213> ORGANISM: Homo sapiens

<400> SEQUENCE: 253
cgacgccaaa acgaatattt attta                                               25

<210> SEQ ID NO 254
<211> LENGTH: 20
<212> TYPE: DNA
<213> ORGANISM: Homo sapiens

<400> SEQUENCE: 254
ggtagcgtag tggattcggg                                                     20

<210> SEQ ID NO 255
<211> LENGTH: 20
<212> TYPE: DNA
<213> ORGANISM: Homo sapiens

<400> SEQUENCE: 255
ctcgtcctcc ctccgaaaac                                                     20

<210> SEQ ID NO 256
<211> LENGTH: 22
<212> TYPE: DNA
<213> ORGANISM: Homo sapiens

<400> SEQUENCE: 256

```
gtttgtttta tttcgtgggg ag                                            22

<210> SEQ ID NO 257
<211> LENGTH: 21
<212> TYPE: DNA
<213> ORGANISM: Homo sapiens

<400> SEQUENCE: 257
ccaactcctt aactcgctca a                                             21

<210> SEQ ID NO 258
<211> LENGTH: 20
<212> TYPE: DNA
<213> ORGANISM: Homo sapiens

<400> SEQUENCE: 258
tcgcgggaaa cggttttagt                                               20

<210> SEQ ID NO 259
<211> LENGTH: 18
<212> TYPE: DNA
<213> ORGANISM: Homo sapiens

<400> SEQUENCE: 259
gcccttaacg accctccg                                                 18

<210> SEQ ID NO 260
<211> LENGTH: 23
<212> TYPE: DNA
<213> ORGANISM: Homo sapiens

<400> SEQUENCE: 260
ttttcgcggg aaacggtttt agt                                           23

<210> SEQ ID NO 261
<211> LENGTH: 20
<212> TYPE: DNA
<213> ORGANISM: Homo sapiens

<400> SEQUENCE: 261
gcgcccttaa cgaccctccg                                               20

<210> SEQ ID NO 262
<211> LENGTH: 20
<212> TYPE: DNA
<213> ORGANISM: Homo sapiens

<400> SEQUENCE: 262
cgttttgtaa agcgaagttt                                               20

<210> SEQ ID NO 263
<211> LENGTH: 26
<212> TYPE: DNA
<213> ORGANISM: Homo sapiens

<400> SEQUENCE: 263
gttatacgtt ttgtaaagcg aagttt                                        26

<210> SEQ ID NO 264
<211> LENGTH: 24
<212> TYPE: DNA
<213> ORGANISM: Homo sapiens

<400> SEQUENCE: 264
```

```
aaaccaatca atcactaaac taca                                          24

<210> SEQ ID NO 265
<211> LENGTH: 20
<212> TYPE: DNA
<213> ORGANISM: Homo sapiens

<400> SEQUENCE: 265 ggttttggg cgtcgtgtta                                                20

<210> SEQ ID NO 266
<211> LENGTH: 20
<212> TYPE: DNA
<213> ORGANISM: Homo sapiens

<400> SEQUENCE: 266
aaattcactc tccaccgccc                                               20

<210> SEQ ID NO 267
<211> LENGTH: 22
<212> TYPE: DNA
<213> ORGANISM: Homo sapiens

<400> SEQUENCE: 267
aggcgaataa tgaaacggag ga                                            22

<210> SEQ ID NO 268
<211> LENGTH: 20
<212> TYPE: DNA
<213> ORGANISM: Homo sapiens

<400> SEQUENCE: 268
taacacgacg cccaaaaacc                                               20

<210> SEQ ID NO 269
<211> LENGTH: 20
<212> TYPE: DNA
<213> ORGANISM: Homo sapiens

<400> SEQUENCE: 269
attttacgga tggagtgatg                                               20

<210> SEQ ID NO 270
<211> LENGTH: 23
<212> TYPE: DNA
<213> ORGANISM: Homo sapiens

<400> SEQUENCE: 270
ggaattttac ggatggagtg atg                                           23

<210> SEQ ID NO 271
<211> LENGTH: 26
<212> TYPE: DNA
<213> ORGANISM: Homo sapiens

<400> SEQUENCE: 271
cttatcccga ctaaactact aaaaaa                                        26

<210> SEQ ID NO 272
<211> LENGTH: 20
<212> TYPE: DNA
<213> ORGANISM: Homo sapiens
```

<400> SEQUENCE: 272
aattcgtttc gcgacgtgag    20

<210> SEQ ID NO 273
<211> LENGTH: 22
<212> TYPE: DNA
<213> ORGANISM: Homo sapiens

<400> SEQUENCE: 273
ttaattcgtt tcgcgacgtg ag    22

<210> SEQ ID NO 274
<211> LENGTH: 22
<212> TYPE: DNA
<213> ORGANISM: Homo sapiens

<400> SEQUENCE: 274
acacgcctta aaacctactc at    22

<210> SEQ ID NO 275
<211> LENGTH: 20
<212> TYPE: DNA
<213> ORGANISM: Homo sapiens

<400> SEQUENCE: 275
cgtgagggag aatttaggag    20

<210> SEQ ID NO 276
<211> LENGTH: 26
<212> TYPE: DNA
<213> ORGANISM: Homo sapiens

<400> SEQUENCE: 276
taaaaaaaca cacgccttaa aaccta    26

<210> SEQ ID NO 277
<211> LENGTH: 20
<212> TYPE: DNA
<213> ORGANISM: Homo sapiens

<400> SEQUENCE: 277
tcgtttagcg agcgttgttt    20

<210> SEQ ID NO 278
<211> LENGTH: 20
<212> TYPE: DNA
<213> ORGANISM: Homo sapiens

<400> SEQUENCE: 278
gatccgccgt tacgctattc    20

<210> SEQ ID NO 279
<211> LENGTH: 22
<212> TYPE: DNA
<213> ORGANISM: Homo sapiens

<400> SEQUENCE: 279
tgttagaaat cggtatcgtt ta    22

<210> SEQ ID NO 280
<211> LENGTH: 20
<212> TYPE: DNA
<213> ORGANISM: Homo sapiens -continued

```
<400> SEQUENCE: 280
tctacgaaac gtttacaacc                                               20

<210> SEQ ID NO 281
<211> LENGTH: 27
<212> TYPE: DNA
<213> ORGANISM: Homo sapiens

<400> SEQUENCE: 281 tttttttgtta gaaatcggta tcgttta                                      27

<210> SEQ ID NO 282
<211> LENGTH: 24
<212> TYPE: DNA
<213> ORGANISM: Homo sapiens

<400> SEQUENCE: 282
aaaatctacg aaacgtttac aacc                                          24

<210> SEQ ID NO 283
<211> LENGTH: 20
<212> TYPE: DNA
<213> ORGANISM: Homo sapiens

<400> SEQUENCE: 283
tttagggatc gcgttcggag                                               20

<210> SEQ ID NO 284
<211> LENGTH: 22
<212> TYPE: DNA
<213> ORGANISM: Homo sapiens

<400> SEQUENCE: 284
aaactccttt cccctctcat ac                                            22

<210> SEQ ID NO 285
<211> LENGTH: 20
<212> TYPE: DNA
<213> ORGANISM: Homo sapiens

<400> SEQUENCE: 285
cggagttttt aatcggatat                                               20

<210> SEQ ID NO 286
<211> LENGTH: 21
<212> TYPE: DNA
<213> ORGANISM: Homo sapiens

<400> SEQUENCE: 286
tcccttctct ttaaaactcc t                                             21

<210> SEQ ID NO 287
<211> LENGTH: 22
<212> TYPE: DNA
<213> ORGANISM: Homo sapiens

<400> SEQUENCE: 287
gtcggatttt attttaatcg tg                                            22

<210> SEQ ID NO 288
<211> LENGTH: 26
<212> TYPE: DNA
```

```
<213> ORGANISM: Homo sapiens

<400> SEQUENCE: 288
aaacaaaaaa atctcaaaaa ctaaaa                                          26

<210> SEQ ID NO 289
<211> LENGTH: 25
<212> TYPE: DNA
<213> ORGANISM: Homo sapiens

<400> SEQUENCE: 289
gttgtcggat tttattttaa tcgtg                                           25

<210> SEQ ID NO 290
<211> LENGTH: 29
<212> TYPE: DNA
<213> ORGANISM: Homo sapiens

<400> SEQUENCE: 290
cttaaacaaa aaatctcaa aaactaaaa                                        29

<210> SEQ ID NO 291
<211> LENGTH: 20
<212> TYPE: DNA
<213> ORGANISM: Homo sapiens

<400> SEQUENCE: 291
gttaggggcg aggcgtttat                                                 20

<210> SEQ ID NO 292
<211> LENGTH: 20
<212> TYPE: DNA
<213> ORGANISM: Homo sapiens

<400> SEQUENCE: 292
cgaaacctaa acgcgcgaaa                                                 20

<210> SEQ ID NO 293
<211> LENGTH: 20
<212> TYPE: DNA
<213> ORGANISM: Homo sapiens

<400> SEQUENCE: 293
aggttaatag gtggcgcgtt                                                 20

<210> SEQ ID NO 294
<211> LENGTH: 20
<212> TYPE: DNA
<213> ORGANISM: Homo sapiens

<400> SEQUENCE: 294
cccgcaactc cgcgataata                                                 20

<210> SEQ ID NO 295
<211> LENGTH: 20
<212> TYPE: DNA
<213> ORGANISM: Homo sapiens

<400> SEQUENCE: 295
agtcgttttt cgcgcgttta                                                 20

<210> SEQ ID NO 296
<211> LENGTH: 22
```

```
<212> TYPE: DNA
<213> ORGANISM: Homo sapiens

<400> SEQUENCE: 296
cgagtcgttt ttcgcgcgtt ta                                          22

<210> SEQ ID NO 297
<211> LENGTH: 21
<212> TYPE: DNA
<213> ORGANISM: Homo sapiens

<400> SEQUENCE: 297
gacccgacac cctaaactca t                                           21

<210> SEQ ID NO 298
<211> LENGTH: 22
<212> TYPE: DNA
<213> ORGANISM: Homo sapiens

<400> SEQUENCE: 298
aggcgtttat tggttaatag gg                                          22

<210> SEQ ID NO 299
<211> LENGTH: 22
<212> TYPE: DNA
<213> ORGANISM: Homo sapiens

<400> SEQUENCE: 299
cgacccgaca ccctaaactc at                                          22

<210> SEQ ID NO 300
<211> LENGTH: 20
<212> TYPE: DNA
<213> ORGANISM: Homo sapiens

<400> SEQUENCE: 300
acccgacacc ctaaactcat                                             20

<210> SEQ ID NO 301
<211> LENGTH: 25
<212> TYPE: DNA
<213> ORGANISM: Homo sapiens

<400> SEQUENCE: 301
tttaatttgg gttttaagtt tgagg                                       25

<210> SEQ ID NO 302
<211> LENGTH: 21
<212> TYPE: DNA
<213> ORGANISM: Homo sapiens

<400> SEQUENCE: 302
acgctactaa accccgctta t                                           21

<210> SEQ ID NO 303
<211> LENGTH: 18
<212> TYPE: DNA
<213> ORGANISM: Homo sapiens

<400> SEQUENCE: 303
gcgtttaggt agcgacgc                                               18

<210> SEQ ID NO 304
```

```
<211> LENGTH: 19
<212> TYPE: DNA
<213> ORGANISM: Homo sapiens

<400> SEQUENCE: 304 atacccgac gaaaacgac                                                  19

<210> SEQ ID NO 305
<211> LENGTH: 18
<212> TYPE: DNA
<213> ORGANISM: Homo sapiens

<400> SEQUENCE: 305
tttgggattt ggtcgagc                                                  18

<210> SEQ ID NO 306
<211> LENGTH: 19
<212> TYPE: DNA
<213> ORGANISM: Homo sapiens

<400> SEQUENCE: 306
aaaattaaat cccgcgtcg                                                 19

<210> SEQ ID NO 307
<211> LENGTH: 19
<212> TYPE: DNA
<213> ORGANISM: Homo sapiens

<400> SEQUENCE: 307
cgtttaggtt tgtggacgc                                                 19

<210> SEQ ID NO 308
<211> LENGTH: 22
<212> TYPE: DNA
<213> ORGANISM: Homo sapiens

<400> SEQUENCE: 308
aaaaacgaaa tcgctaatac gc                                             22

<210> SEQ ID NO 309
<211> LENGTH: 18
<212> TYPE: DNA
<213> ORGANISM: Homo sapiens

<400> SEQUENCE: 309
tttttcgaat ttttgcgc                                                  18

<210> SEQ ID NO 310
<211> LENGTH: 20
<212> TYPE: DNA
<213> ORGANISM: Homo sapiens

<400> SEQUENCE: 310
aacacgctcc gactaacttc                                                20

<210> SEQ ID NO 311
<211> LENGTH: 24
<212> TYPE: DNA
<213> ORGANISM: Homo sapiens

<400> SEQUENCE: 311
ggttgttttt tcgaattttt gcgc                                           24
```

```
<210> SEQ ID NO 312
<211> LENGTH: 22
<212> TYPE: DNA
<213> ORGANISM: Homo sapiens

<400> SEQUENCE: 312
taaacacgct ccgactaact tc                                              22

<210> SEQ ID NO 313
<211> LENGTH: 19
<212> TYPE: DNA
<213> ORGANISM: Homo sapiens

<400> SEQUENCE: 313
cgttcgcgtt attatttgc                                                  19

<210> SEQ ID NO 314
<211> LENGTH: 18
<212> TYPE: DNA
<213> ORGANISM: Homo sapiens

<400> SEQUENCE: 314
cgcccaataa caactcgt                                                   18

<210> SEQ ID NO 315
<211> LENGTH: 24
<212> TYPE: DNA
<213> ORGANISM: Homo sapiens

<400> SEQUENCE: 315
attatcgttc gcgttattat ttgc                                            24

<210> SEQ ID NO 316
<211> LENGTH: 21
<212> TYPE: DNA
<213> ORGANISM: Homo sapiens

<400> SEQUENCE: 316
cctcgcccaa taacaactcg t                                               21

<210> SEQ ID NO 317
<211> LENGTH: 20
<212> TYPE: DNA
<213> ORGANISM: Homo sapiens

<400> SEQUENCE: 317
gtcgagtcgt cgttacgatc                                                 20

<210> SEQ ID NO 318
<211> LENGTH: 21
<212> TYPE: DNA
<213> ORGANISM: Homo sapiens

<400> SEQUENCE: 318
ctaccctcct cgaactctac g                                               21

<210> SEQ ID NO 319
<211> LENGTH: 22
<212> TYPE: DNA
<213> ORGANISM: Homo sapiens

<400> SEQUENCE: 319
gttttcggat gggaaatttt ag                                              22
```

```
<210> SEQ ID NO 320
<211> LENGTH: 22
<212> TYPE: DNA
<213> ORGANISM: Homo sapiens

<400> SEQUENCE: 320
aaaccatcta catcgaaatc gc                                              22

<210> SEQ ID NO 321
<211> LENGTH: 25
<212> TYPE: DNA
<213> ORGANISM: Homo sapiens

<400> SEQUENCE: 321
gtggttttcg gatgggaaat tttag                                           25

<210> SEQ ID NO 322
<211> LENGTH: 26
<212> TYPE: DNA
<213> ORGANISM: Homo sapiens

<400> SEQUENCE: 322
aacaaaacca tctacatcga aatcgc                                          26

<210> SEQ ID NO 323
<211> LENGTH: 25
<212> TYPE: DNA
<213> ORGANISM: Homo sapiens

<400> SEQUENCE: 323
tttttaggag taagtatttt gtgtg                                           25

<210> SEQ ID NO 324
<211> LENGTH: 21
<212> TYPE: DNA
<213> ORGANISM: Homo sapiens

<400> SEQUENCE: 324
ccctcttcct cccctactaa t                                               21

<210> SEQ ID NO 325
<211> LENGTH: 19
<212> TYPE: DNA
<213> ORGANISM: Homo sapiens

<400> SEQUENCE: 325
taggtatatt tcggtcggc                                                  19

<210> SEQ ID NO 326
<211> LENGTH: 18
<212> TYPE: DNA
<213> ORGANISM: Homo sapiens

<400> SEQUENCE: 326
aactcgaaac ctcatccg                                                   18

<210> SEQ ID NO 327
<211> LENGTH: 19
<212> TYPE: DNA
<213> ORGANISM: Homo sapiens

<400> SEQUENCE: 327
acgggagggt aaatttagc                                                  19
```

```
<210> SEQ ID NO 328
<211> LENGTH: 20
<212> TYPE: DNA
<213> ORGANISM: Homo sapiens

<400> SEQUENCE: 328
taccaaacaa ttcgacgtta                                              20

<210> SEQ ID NO 329
<211> LENGTH: 18
<212> TYPE: DNA
<213> ORGANISM: Homo sapiens

<400> SEQUENCE: 329
gcgtacgtcg gtttattc                                                18

<210> SEQ ID NO 330
<211> LENGTH: 18
<212> TYPE: DNA
<213> ORGANISM: Homo sapiens

<400> SEQUENCE: 330
acgctctacg cgatcaaa                                                18

<210> SEQ ID NO 331
<211> LENGTH: 22
<212> TYPE: DNA
<213> ORGANISM: Homo sapiens

<400> SEQUENCE: 331
aagtgcgtac gtcggtttat tc                                           22

<210> SEQ ID NO 332
<211> LENGTH: 21
<212> TYPE: DNA
<213> ORGANISM: Homo sapiens

<400> SEQUENCE: 332
gcgacgctct acgcgatcaa a                                            21

<210> SEQ ID NO 333
<211> LENGTH: 20
<212> TYPE: DNA
<213> ORGANISM: Homo sapiens

<400> SEQUENCE: 333
cgagcgattg tggggttaga                                              20

<210> SEQ ID NO 334
<211> LENGTH: 19
<212> TYPE: DNA
<213> ORGANISM: Homo sapiens

<400> SEQUENCE: 334
caactcgcga ccgcctaaa                                               19

<210> SEQ ID NO 335
<211> LENGTH: 20
<212> TYPE: DNA
<213> ORGANISM: Homo sapiens

<400> SEQUENCE: 335
```

```
ttcgggcgtt tatagagttc                                            20

<210> SEQ ID NO 336
<211> LENGTH: 18
<212> TYPE: DNA
<213> ORGANISM: Homo sapiens

<400> SEQUENCE: 336
aaaatcaaaa cgcgaacg                                              18

<210> SEQ ID NO 337
<211> LENGTH: 19
<212> TYPE: DNA
<213> ORGANISM: Homo sapiens

<400> SEQUENCE: 337
tagcgtcgcg ttagaaagc                                             19

<210> SEQ ID NO 338
<211> LENGTH: 20
<212> TYPE: DNA
<213> ORGANISM: Homo sapiens

<400> SEQUENCE: 338
atcgctcaaa acctaacgaa                                            20

<210> SEQ ID NO 339
<211> LENGTH: 22
<212> TYPE: DNA
<213> ORGANISM: Homo sapiens

<400> SEQUENCE: 339
ttttagcgtc gcgttagaaa gc                                         22

<210> SEQ ID NO 340
<211> LENGTH: 24
<212> TYPE: DNA
<213> ORGANISM: Homo sapiens

<400> SEQUENCE: 340
aaaaatcgct caaaacctaa cgaa                                       24

<210> SEQ ID NO 341
<211> LENGTH: 20
<212> TYPE: DNA
<213> ORGANISM: Homo sapiens

<400> SEQUENCE: 341
aggtttagtt tcgaaatcgc                                            20

<210> SEQ ID NO 342
<211> LENGTH: 18
<212> TYPE: DNA
<213> ORGANISM: Homo sapiens

<400> SEQUENCE: 342
aaccgaacga ttccctaa                                              18

<210> SEQ ID NO 343
<211> LENGTH: 24
<212> TYPE: DNA
<213> ORGANISM: Homo sapiens

<400> SEQUENCE: 343
```
gttaaggttt agtttcgaaa tcgc                                          24

<210> SEQ ID NO 344
<211> LENGTH: 24
<212> TYPE: DNA
<213> ORGANISM: Homo sapiens

<400> SEQUENCE: 344
ctaaaaaacc gaacgattcc ctaa                                          24

<210> SEQ ID NO 345
<211> LENGTH: 21
<212> TYPE: DNA
<213> ORGANISM: Homo sapiens

<400> SEQUENCE: 345
gaatttttgg aaaagtcggg a                                             21

<210> SEQ ID NO 346
<211> LENGTH: 20
<212> TYPE: DNA
<213> ORGANISM: Homo sapiens

<400> SEQUENCE: 346
ctcctacaaa aaaaactccc                                               20

<210> SEQ ID NO 347
<211> LENGTH: 25
<212> TYPE: DNA
<213> ORGANISM: Homo sapiens

<400> SEQUENCE: 347
ttcggaattt ttggaaaagt cggga                                         25

<210> SEQ ID NO 348
<211> LENGTH: 23
<212> TYPE: DNA
<213> ORGANISM: Homo sapiens

<400> SEQUENCE: 348
cgactcctac aaaaaaaact ccc                                           23

<210> SEQ ID NO 349
<211> LENGTH: 18
<212> TYPE: DNA
<213> ORGANISM: Homo sapiens

<400> SEQUENCE: 349
agaaggtggt cggtaagc                                                 18

<210> SEQ ID NO 350
<211> LENGTH: 22
<212> TYPE: DNA
<213> ORGANISM: Homo sapiens

<400> SEQUENCE: 350
acgtaattat aaaaaacacg cc                                            22

<210> SEQ ID NO 351
<211> LENGTH: 20
<212> TYPE: DNA
<213> ORGANISM: Homo sapiens

<400> SEQUENCE: 351
ggagaaggtg gtcggtaagc                                               20

<210> SEQ ID NO 352
<211> LENGTH: 25
<212> TYPE: DNA
<213> ORGANISM: Homo sapiens

<400> SEQUENCE: 352
aaaacgtaat tataaaaaac acgcc                                         25

<210> SEQ ID NO 353
<211> LENGTH: 20
<212> TYPE: DNA
<213> ORGANISM: Homo sapiens

<400> SEQUENCE: 353 tagtttttttg gagggagagg                                              20

<210> SEQ ID NO 354
<211> LENGTH: 21
<212> TYPE: DNA
<213> ORGANISM: Homo sapiens

<400> SEQUENCE: 354
atcctcgtcc tcttaaaaaa c                                             21

<210> SEQ ID NO 355
<211> LENGTH: 20
<212> TYPE: DNA
<213> ORGANISM: Homo sapiens

<400> SEQUENCE: 355
gtcgagtttg ggattttggt                                               20

<210> SEQ ID NO 356
<211> LENGTH: 21
<212> TYPE: DNA
<213> ORGANISM: Homo sapiens

<400> SEQUENCE: 356
aaactcctac tcgccctaac c                                             21

<210> SEQ ID NO 357
<211> LENGTH: 23
<212> TYPE: DNA
<213> ORGANISM: Homo sapiens

<400> SEQUENCE: 357
ggggtcgagt ttgggatttt ggt                                           23

<210> SEQ ID NO 358
<211> LENGTH: 23
<212> TYPE: DNA
<213> ORGANISM: Homo sapiens

<400> SEQUENCE: 358
aaaaactcct actcgcccta acc                                           23

<210> SEQ ID NO 359
<211> LENGTH: 20
<212> TYPE: DNA
<213> ORGANISM: Homo sapiens

```
<400> SEQUENCE: 359
tcgagttgga taaggcgtac                                                  20

<210> SEQ ID NO 360
<211> LENGTH: 20
<212> TYPE: DNA
<213> ORGANISM: Homo sapiens

<400> SEQUENCE: 360
ccgataacac gaccgacata                                                  20

<210> SEQ ID NO 361
<211> LENGTH: 20
<212> TYPE: DNA
<213> ORGANISM: Homo sapiens

<400> SEQUENCE: 361
tgtatgtcgg tcgtgttatc                                                  20

<210> SEQ ID NO 362
<211> LENGTH: 20
<212> TYPE: DNA
<213> ORGANISM: Homo sapiens

<400> SEQUENCE: 362
taaacgtact acctccgacc                                                  20

<210> SEQ ID NO 363
<211> LENGTH: 25
<212> TYPE: DNA
<213> ORGANISM: Homo sapiens

<400> SEQUENCE: 363
ggatgtggga ggttcggttc gggtg                                            25

<210> SEQ ID NO 364
<211> LENGTH: 25
<212> TYPE: DNA
<213> ORGANISM: Homo sapiens

<400> SEQUENCE: 364
ccgctcgccc ctcgctaaaa ctaca                                            25

<210> SEQ ID NO 365
<211> LENGTH: 30
<212> TYPE: DNA
<213> ORGANISM: Homo sapiens

<400> SEQUENCE: 365
ggcgcgaggt agttttagta cgtagttttt                                       30

<210> SEQ ID NO 366
<211> LENGTH: 28
<212> TYPE: DNA
<213> ORGANISM: Homo sapiens

<400> SEQUENCE: 366
ataacaacgt cgtcctttcc gcaaaacg                                         28

<210> SEQ ID NO 367
<211> LENGTH: 28
<212> TYPE: DNA
```

```
<213> ORGANISM: Homo sapiens

<400> SEQUENCE: 367
ggggattttg taagttcgcg cgtggttt                              28

<210> SEQ ID NO 368
<211> LENGTH: 28
<212> TYPE: DNA
<213> ORGANISM: Homo sapiens

<400> SEQUENCE: 368
acactctccg cgcgacctat attaacga                              28

<210> SEQ ID NO 369
<211> LENGTH: 28
<212> TYPE: DNA
<213> ORGANISM: Homo sapiens

<400> SEQUENCE: 369
ggagacggtt tgttatggtt gttgcgtt                              28

<210> SEQ ID NO 370
<211> LENGTH: 28
<212> TYPE: DNA
<213> ORGANISM: Homo sapiens

<400> SEQUENCE: 370
acgccctttc taccgacctc acgaacta                              28

<210> SEQ ID NO 371
<211> LENGTH: 27
<212> TYPE: DNA
<213> ORGANISM: Homo sapiens

<400> SEQUENCE: 371
tttttcgggg gcgtggtttg tatgttt                               27

<210> SEQ ID NO 372
<211> LENGTH: 28
<212> TYPE: DNA
<213> ORGANISM: Homo sapiens

<400> SEQUENCE: 372
tacctaacga aacgctcact ccacctcg                              28

<210> SEQ ID NO 373
<211> LENGTH: 28
<212> TYPE: DNA
<213> ORGANISM: Homo sapiens

<400> SEQUENCE: 373
ttttgcggtt aggtgaaggc gtagaggt                              28

<210> SEQ ID NO 374
<211> LENGTH: 28
<212> TYPE: DNA
<213> ORGANISM: Homo sapiens

<400> SEQUENCE: 374
gaccgaatac cccgctttct ctctcgac                              28

<210> SEQ ID NO 375
<211> LENGTH: 28
```

<212> TYPE: DNA
<213> ORGANISM: Homo sapiens

<400> SEQUENCE: 375
gaggtcgaga gagaaagcgg ggtattcg                                              28

<210> SEQ ID NO 376
<211> LENGTH: 28
<212> TYPE: DNA
<213> ORGANISM: Homo sapiens

<400> SEQUENCE: 376
aacgctctca acccaacccc taaactca                                              28

<210> SEQ ID NO 377
<211> LENGTH: 28
<212> TYPE: DNA
<213> ORGANISM: Homo sapiens

<400> SEQUENCE: 377
aggatagtag cggtgagtcg ttagcgtt                                              28

<210> SEQ ID NO 378
<211> LENGTH: 28
<212> TYPE: DNA
<213> ORGANISM: Homo sapiens

<400> SEQUENCE: 378
cgctcccact tttctccttt ctccctcc                                              28

<210> SEQ ID NO 379
<211> LENGTH: 28
<212> TYPE: DNA
<213> ORGANISM: Homo sapiens

<400> SEQUENCE: 379
ttttgataaa gtggggaggg cgtagggg                                              28

<210> SEQ ID NO 380
<211> LENGTH: 28
<212> TYPE: DNA
<213> ORGANISM: Homo sapiens

<400> SEQUENCE: 380
acactctcaa atacccgtcg cgctctat                                              28

<210> SEQ ID NO 381
<211> LENGTH: 28
<212> TYPE: DNA
<213> ORGANISM: Homo sapiens

<400> SEQUENCE: 381
ttttgataaa gtggggaggg cgtagggg                                              28

<210> SEQ ID NO 382
<211> LENGTH: 28
<212> TYPE: DNA
<213> ORGANISM: Homo sapiens

<400> SEQUENCE: 382
acactctcaa atacccgtcg cgctctat                                              28

<210> SEQ ID NO 383

```
<211> LENGTH: 28
<212> TYPE: DNA
<213> ORGANISM: Homo sapiens

<400> SEQUENCE: 383
agcgtagcgt agttggagta gttgcgaa                                    28

<210> SEQ ID NO 384
<211> LENGTH: 30
<212> TYPE: DNA
<213> ORGANISM: Homo sapiens

<400> SEQUENCE: 384
cgacgactct cttcccaatc taaaacccca                                  30

<210> SEQ ID NO 385
<211> LENGTH: 28
<212> TYPE: DNA
<213> ORGANISM: Homo sapiens

<400> SEQUENCE: 385
cggagtttag aagggcgttc ggttacgg                                    28

<210> SEQ ID NO 386
<211> LENGTH: 28
<212> TYPE: DNA
<213> ORGANISM: Homo sapiens

<400> SEQUENCE: 386
ctccacgaat cgcatctttc aataccca                                    28

<210> SEQ ID NO 387
<211> LENGTH: 28
<212> TYPE: DNA
<213> ORGANISM: Homo sapiens

<400> SEQUENCE: 387
aaaggtggtt cgagtgagga aattgcgg                                    28

<210> SEQ ID NO 388
<211> LENGTH: 28
<212> TYPE: DNA
<213> ORGANISM: Homo sapiens

<400> SEQUENCE: 388
gcgtccctaa acgacacacg acgaaatc                                    28

<210> SEQ ID NO 389
<211> LENGTH: 28
<212> TYPE: DNA
<213> ORGANISM: Homo sapiens

<400> SEQUENCE: 389
gtcgacggcg gttttatcgt attgtcgc                                    28

<210> SEQ ID NO 390
<211> LENGTH: 28
<212> TYPE: DNA
<213> ORGANISM: Homo sapiens

<400> SEQUENCE: 390
ccttctcccg aaccttcctt cgtatcct                                    28
```

```
<210> SEQ ID NO 391
<211> LENGTH: 28
<212> TYPE: DNA
<213> ORGANISM: Homo sapiens

<400> SEQUENCE: 391
ttagaggtat ggcggggttt ttgtgacg                                          28

<210> SEQ ID NO 392
<211> LENGTH: 28
<212> TYPE: DNA
<213> ORGANISM: Homo sapiens

<400> SEQUENCE: 392
aatactccct aaacctccta accgcgcc                                          28

<210> SEQ ID NO 393
<211> LENGTH: 25
<212> TYPE: DNA
<213> ORGANISM: Homo sapiens

<400> SEQUENCE: 393
gaggtttaat tgtttcgttg gtcgc                                             25

<210> SEQ ID NO 394
<211> LENGTH: 23
<212> TYPE: DNA
<213> ORGANISM: Homo sapiens

<400> SEQUENCE: 394
acgcaaaacc gcgtatatca cct                                               23

<210> SEQ ID NO 395
<211> LENGTH: 28
<212> TYPE: DNA
<213> ORGANISM: Homo sapiens

<400> SEQUENCE: 395
ggttttaggg acgcggttgg aatttggg                                          28

<210> SEQ ID NO 396
<211> LENGTH: 29
<212> TYPE: DNA
<213> ORGANISM: Homo sapiens

<400> SEQUENCE: 396
cccaacgcct cgaccatatt aaataactt                                         29

<210> SEQ ID NO 397
<211> LENGTH: 28
<212> TYPE: DNA
<213> ORGANISM: Homo sapiens

<400> SEQUENCE: 397
gcgattaagg cgtatcggtg ggtattgc                                          28

<210> SEQ ID NO 398
<211> LENGTH: 28
<212> TYPE: DNA
<213> ORGANISM: Homo sapiens

<400> SEQUENCE: 398
aacaccaccc gacgaactct cgactaac                                          28
```

```
<210> SEQ ID NO 399
<211> LENGTH: 28
<212> TYPE: DNA
<213> ORGANISM: Homo sapiens

<400> SEQUENCE: 399
taggacgttg tttggttcga agttcggg                                              28

<210> SEQ ID NO 400
<211> LENGTH: 28
<212> TYPE: DNA
<213> ORGANISM: Homo sapiens

<400> SEQUENCE: 400
ctccgaaccg accgaaaaac gcaacttt                                              28

<210> SEQ ID NO 401
<211> LENGTH: 21
<212> TYPE: DNA
<213> ORGANISM: Homo sapiens

<400> SEQUENCE: 401
ggcggggtat tgttttgttt c                                                     21

<210> SEQ ID NO 402
<211> LENGTH: 24
<212> TYPE: DNA
<213> ORGANISM: Homo sapiens

<400> SEQUENCE: 402
tctaccgata tcataacacc gact                                                  24

<210> SEQ ID NO 403
<211> LENGTH: 28
<212> TYPE: DNA
<213> ORGANISM: Homo sapiens

<400> SEQUENCE: 403
aaaggtagag ggaaggagag ttgttttt                                              28

<210> SEQ ID NO 404
<211> LENGTH: 29
<212> TYPE: DNA
<213> ORGANISM: Homo sapiens

<400> SEQUENCE: 404
actcctacct cctccgaatc ctaaaacct                                             29

<210> SEQ ID NO 405
<211> LENGTH: 28
<212> TYPE: DNA
<213> ORGANISM: Homo sapiens

<400> SEQUENCE: 405
cggaatgaag gtgtttcgta ggaaggcg                                              28

<210> SEQ ID NO 406
<211> LENGTH: 27
<212> TYPE: DNA
<213> ORGANISM: Homo sapiens

<400> SEQUENCE: 406
gctacgacac ccaacgaccc atcgaaa                                               27
```

<210> SEQ ID NO 407
<211> LENGTH: 28
<212> TYPE: DNA
<213> ORGANISM: Homo sapiens

<400> SEQUENCE: 407
aatgattttg ttgggttcgg tggagcgg                                28

<210> SEQ ID NO 408
<211> LENGTH: 28
<212> TYPE: DNA
<213> ORGANISM: Homo sapiens

<400> SEQUENCE: 408
ccgacaactt ccgcgccatc tcttaaac                                28

<210> SEQ ID NO 409
<211> LENGTH: 28
<212> TYPE: DNA
<213> ORGANISM: Homo sapiens

<400> SEQUENCE: 409
ttgtgttttg agcgtaggtt gcgcgtag                                28

<210> SEQ ID NO 410
<211> LENGTH: 28
<212> TYPE: DNA
<213> ORGANISM: Homo sapiens

<400> SEQUENCE: 410
gccttcccgt cgtaaaacaa ctccgaca                                28

<210> SEQ ID NO 411
<211> LENGTH: 29
<212> TYPE: DNA
<213> ORGANISM: Homo sapiens

<400> SEQUENCE: 411
gttttagggg gttgggggtt tgttaggga                               29

<210> SEQ ID NO 412
<211> LENGTH: 28
<212> TYPE: DNA
<213> ORGANISM: Homo sapiens

<400> SEQUENCE: 412
aacccgaaac gaaactatac accccgca                                28

<210> SEQ ID NO 413
<211> LENGTH: 28
<212> TYPE: DNA
<213> ORGANISM: Homo sapiens

<400> SEQUENCE: 413
tcgatgttcg tagtgttgtt gtagcggt                                28

<210> SEQ ID NO 414
<211> LENGTH: 28
<212> TYPE: DNA
<213> ORGANISM: Homo sapiens

<400> SEQUENCE: 414 ccatcccgc ctaacgaaaa ctaaccct                                    28

<210> SEQ ID NO 415
<211> LENGTH: 28
<212> TYPE: DNA
<213> ORGANISM: Homo sapiens

<400> SEQUENCE: 415
cgtttcgaga agaagtttcg cggttggt                                   28

<210> SEQ ID NO 416
<211> LENGTH: 28
<212> TYPE: DNA
<213> ORGANISM: Homo sapiens

<400> SEQUENCE: 416
atctaaaccc aaatcgaaaa ccgccgcc                                   28

<210> SEQ ID NO 417
<211> LENGTH: 28
<212> TYPE: DNA
<213> ORGANISM: Homo sapiens

<400> SEQUENCE: 417
ttggagttgt cgtagatcgt cgtggtgg                                   28

<210> SEQ ID NO 418
<211> LENGTH: 28
<212> TYPE: DNA
<213> ORGANISM: Homo sapiens

<400> SEQUENCE: 418
aaatcgcccc actaccgcat ccttactc                                   28

<210> SEQ ID NO 419
<211> LENGTH: 28
<212> TYPE: DNA
<213> ORGANISM: Homo sapiens

<400> SEQUENCE: 419
gcggttaggt gtggtaaagt agttggcg                                   28

<210> SEQ ID NO 420
<211> LENGTH: 28
<212> TYPE: DNA
<213> ORGANISM: Homo sapiens

<400> SEQUENCE: 420
gcgcacaacc aacctataaa ctccgacg                                   28

<210> SEQ ID NO 421
<211> LENGTH: 22
<212> TYPE: DNA
<213> ORGANISM: Homo sapiens

<400> SEQUENCE: 421
gggatttgtg aaggcggatt tg                                         22

<210> SEQ ID NO 422
<211> LENGTH: 27
<212> TYPE: DNA
<213> ORGANISM: Homo sapiens

<400> SEQUENCE: 422

-continued aatattccgt cgataccgaa aacccga                                    27

<210> SEQ ID NO 423
<211> LENGTH: 27
<212> TYPE: DNA
<213> ORGANISM: Homo sapiens

<400> SEQUENCE: 423
cggttggagc gcgttttcga gaagaat                                    27

<210> SEQ ID NO 424
<211> LENGTH: 28
<212> TYPE: DNA
<213> ORGANISM: Homo sapiens

<400> SEQUENCE: 424
aacgcaaaac aaaccgcgac cgaaaata                                   28

<210> SEQ ID NO 425
<211> LENGTH: 22
<212> TYPE: DNA
<213> ORGANISM: Homo sapiens

<400> SEQUENCE: 425
aggagaagtc gtagcgggcg tc                                         22

<210> SEQ ID NO 426
<211> LENGTH: 24
<212> TYPE: DNA
<213> ORGANISM: Homo sapiens

<400> SEQUENCE: 426
gactaaacct tctaccgccc accg                                       24

<210> SEQ ID NO 427
<211> LENGTH: 28
<212> TYPE: DNA
<213> ORGANISM: Homo sapiens

<400> SEQUENCE: 427
tagttgcgat ggggtgggaa gttacgtt                                   28

<210> SEQ ID NO 428
<211> LENGTH: 28
<212> TYPE: DNA
<213> ORGANISM: Homo sapiens

<400> SEQUENCE: 428
aaaaccatcg ccatccacga aaacgaca                                   28

<210> SEQ ID NO 429
<211> LENGTH: 30
<212> TYPE: DNA
<213> ORGANISM: Homo sapiens

<400> SEQUENCE: 429
aggaggatga tagtttagaa agaagagggt                                 30

<210> SEQ ID NO 430
<211> LENGTH: 28
<212> TYPE: DNA
<213> ORGANISM: Homo sapiens

<400> SEQUENCE: 430
cgcgaccgcg acgataacga taaaaact                               28

<210> SEQ ID NO 431
<211> LENGTH: 28
<212> TYPE: DNA
<213> ORGANISM: Homo sapiens

<400> SEQUENCE: 431
gaaacgtgta ggcgtcggcg tttatgag                               28

<210> SEQ ID NO 432
<211> LENGTH: 28
<212> TYPE: DNA
<213> ORGANISM: Homo sapiens

<400> SEQUENCE: 432
cgacctctcg aacgcctcct acaaacaa                               28

<210> SEQ ID NO 433
<211> LENGTH: 21
<212> TYPE: DNA
<213> ORGANISM: Homo sapiens

<400> SEQUENCE: 433
gtggaggagg aagttcgttt c                                      21

<210> SEQ ID NO 434
<211> LENGTH: 24
<212> TYPE: DNA
<213> ORGANISM: Homo sapiens

<400> SEQUENCE: 434
aactactacc aaacacgaaa cgca                                   24

<210> SEQ ID NO 435
<211> LENGTH: 23
<212> TYPE: DNA
<213> ORGANISM: Homo sapiens

<400> SEQUENCE: 435
ggttagagtc ggttgcgtag ttt                                    23

<210> SEQ ID NO 436
<211> LENGTH: 27
<212> TYPE: DNA
<213> ORGANISM: Homo sapiens

<400> SEQUENCE: 436
tttttgttag gcgaagtata gagagcg                                27

<210> SEQ ID NO 437
<211> LENGTH: 27
<212> TYPE: DNA
<213> ORGANISM: Homo sapiens

<400> SEQUENCE: 437
tttttcgatt ggtcgacggc gagagag                                27

<210> SEQ ID NO 438
<211> LENGTH: 28
<212> TYPE: DNA
<213> ORGANISM: Homo sapiens

```
<400> SEQUENCE: 438
tttccgaact acaaacgcac actaaaac                                          28

<210> SEQ ID NO 439
<211> LENGTH: 26
<212> TYPE: DNA
<213> ORGANISM: Homo sapiens

<400> SEQUENCE: 439
gattcgtatg ggttttatcg agtttc                                            26

<210> SEQ ID NO 440
<211> LENGTH: 25
<212> TYPE: DNA
<213> ORGANISM: Homo sapiens

<400> SEQUENCE: 440
acttaaaaat aaactcgccc gtacg                                             25

<210> SEQ ID NO 441
<211> LENGTH: 28
<212> TYPE: DNA
<213> ORGANISM: Homo sapiens

<400> SEQUENCE: 441
tcgttggtga aggtgtagtg ttcgttcg                                          28

<210> SEQ ID NO 442
<211> LENGTH: 28
<212> TYPE: DNA
<213> ORGANISM: Homo sapiens

<400> SEQUENCE: 442
taacgcgcgc gctcacaaat aaaacgac                                          28

<210> SEQ ID NO 443
<211> LENGTH: 28
<212> TYPE: DNA
<213> ORGANISM: Homo sapiens

<400> SEQUENCE: 443
tttttagtgg ttcgagcgtt tgcgttgc                                          28

<210> SEQ ID NO 444
<211> LENGTH: 29
<212> TYPE: DNA
<213> ORGANISM: Homo sapiens

<400> SEQUENCE: 444
tccgtcctcg aaataattct aaccgacgc                                         29

<210> SEQ ID NO 445
<211> LENGTH: 25
<212> TYPE: DNA
<213> ORGANISM: Homo sapiens

<400> SEQUENCE: 445
cgtggtatag ttaatcgcgc ggcgt                                             25

<210> SEQ ID NO 446
<211> LENGTH: 28
<212> TYPE: DNA
```

```
<213> ORGANISM: Homo sapiens

<400> SEQUENCE: 446
tacaacccca acgccataac tcgccaat                                          28

<210> SEQ ID NO 447
<211> LENGTH: 28
<212> TYPE: DNA
<213> ORGANISM: Homo sapiens

<400> SEQUENCE: 447
tgtcgtcgtc gtcggggttt tgttattt                                          28

<210> SEQ ID NO 448
<211> LENGTH: 28
<212> TYPE: DNA
<213> ORGANISM: Homo sapiens

<400> SEQUENCE: 448
acgacgataa actcccgcta aacccgaa                                          28

<210> SEQ ID NO 449
<211> LENGTH: 27
<212> TYPE: DNA
<213> ORGANISM: Homo sapiens

<400> SEQUENCE: 449
gaacgaggat ttgcgttttt ggatcgc                                           27

<210> SEQ ID NO 450
<211> LENGTH: 29
<212> TYPE: DNA
<213> ORGANISM: Homo sapiens

<400> SEQUENCE: 450
cctaaactcc tctacatatt cctctacct                                         29

<210> SEQ ID NO 451
<211> LENGTH: 27
<212> TYPE: DNA
<213> ORGANISM: Homo sapiens

<400> SEQUENCE: 451
gaatggttgc gatatggggt tcgacgg                                           27

<210> SEQ ID NO 452
<211> LENGTH: 27
<212> TYPE: DNA
<213> ORGANISM: Homo sapiens

<400> SEQUENCE: 452
ccacgatatc cgccgcgatc caaaaac                                           27

<210> SEQ ID NO 453
<211> LENGTH: 25
<212> TYPE: DNA
<213> ORGANISM: Homo sapiens

<400> SEQUENCE: 453
taagggtcgg ttgttgtttt ttttc                                             25

<210> SEQ ID NO 454
<211> LENGTH: 25
```

```
<212> TYPE: DNA
<213> ORGANISM: Homo sapiens

<400> SEQUENCE: 454
accgacgcct tccttataaa atacg                                          25

<210> SEQ ID NO 455
<211> LENGTH: 28
<212> TYPE: DNA
<213> ORGANISM: Homo sapiens

<400> SEQUENCE: 455
tgtgggataa tttggcgaag ggagtaga                                       28

<210> SEQ ID NO 456
<211> LENGTH: 28
<212> TYPE: DNA
<213> ORGANISM: Homo sapiens

<400> SEQUENCE: 456
aactcgaaat taactacgaa cgcccgcc                                       28

<210> SEQ ID NO 457
<211> LENGTH: 28
<212> TYPE: DNA
<213> ORGANISM: Homo sapiens

<400> SEQUENCE: 457 ggcggggggta gttttttgtat taaggcga                                     28

<210> SEQ ID NO 458
<211> LENGTH: 28
<212> TYPE: DNA
<213> ORGANISM: Homo sapiens

<400> SEQUENCE: 458
cctacgctac tactcttctc gaccccccg                                      28

<210> SEQ ID NO 459
<211> LENGTH: 27
<212> TYPE: DNA
<213> ORGANISM: Homo sapiens

<400> SEQUENCE: 459
cgtttcgttc gtcggtcgta gcgattg                                        27

<210> SEQ ID NO 460
<211> LENGTH: 28
<212> TYPE: DNA
<213> ORGANISM: Homo sapiens

<400> SEQUENCE: 460
ccgacgaaac attttcgcac cacaacac                                       28

<210> SEQ ID NO 461
<211> LENGTH: 28
<212> TYPE: DNA
<213> ORGANISM: Homo sapiens

<400> SEQUENCE: 461
cgcggtttcg gggtatacgg agttttttg                                      28

<210> SEQ ID NO 462
```

```
<211> LENGTH: 28
<212> TYPE: DNA
<213> ORGANISM: Homo sapiens

<400> SEQUENCE: 462
gcaattcaat cgctacgacc gacgaacg                                              28

<210> SEQ ID NO 463
<211> LENGTH: 28
<212> TYPE: DNA
<213> ORGANISM: Homo sapiens

<400> SEQUENCE: 463
cgtcgtagcg ggtacggtta acgagttg                                              28

<210> SEQ ID NO 464
<211> LENGTH: 27
<212> TYPE: DNA
<213> ORGANISM: Homo sapiens

<400> SEQUENCE: 464
tttctccact cgaaacgccc gacaacc                                               27

<210> SEQ ID NO 465
<211> LENGTH: 28
<212> TYPE: DNA
<213> ORGANISM: Homo sapiens

<400> SEQUENCE: 465
cgggggagaa cggtttgagt ttcgagta                                              28

<210> SEQ ID NO 466
<211> LENGTH: 28
<212> TYPE: DNA
<213> ORGANISM: Homo sapiens

<400> SEQUENCE: 466
tcatatttca acctcgccgc cgctaaac                                              28

<210> SEQ ID NO 467
<211> LENGTH: 28
<212> TYPE: DNA
<213> ORGANISM: Homo sapiens

<400> SEQUENCE: 467
agtagggatg gtcgttcgtt gttcggtg                                              28

<210> SEQ ID NO 468
<211> LENGTH: 28
<212> TYPE: DNA
<213> ORGANISM: Homo sapiens

<400> SEQUENCE: 468
gacaaacgac cgaaaatact cgcgcaac                                              28

<210> SEQ ID NO 469
<211> LENGTH: 28
<212> TYPE: DNA
<213> ORGANISM: Homo sapiens

<400> SEQUENCE: 469
ttttacggtc ggggcgatag ttgaaggt                                              28
```

```
<210> SEQ ID NO 470
<211> LENGTH: 28
<212> TYPE: DNA
<213> ORGANISM: Homo sapiens

<400> SEQUENCE: 470
tcacgccaat acccgctaat ccctccta                                          28

<210> SEQ ID NO 471
<211> LENGTH: 27
<212> TYPE: DNA
<213> ORGANISM: Homo sapiens

<400> SEQUENCE: 471
ggggatggat aatttttagg cgttaac                                           27

<210> SEQ ID NO 472
<211> LENGTH: 22
<212> TYPE: DNA
<213> ORGANISM: Homo sapiens

<400> SEQUENCE: 472
taacctcgtc tttatccccg cg                                                22

<210> SEQ ID NO 473
<211> LENGTH: 29
<212> TYPE: DNA
<213> ORGANISM: Homo sapiens

<400> SEQUENCE: 473
agtgtgtagt cgtttgtggg tgaggagtt                                         29

<210> SEQ ID NO 474
<211> LENGTH: 28
<212> TYPE: DNA
<213> ORGANISM: Homo sapiens

<400> SEQUENCE: 474
caccgcgaaa aacgcccaca atcttacc                                          28

<210> SEQ ID NO 475
<211> LENGTH: 29
<212> TYPE: DNA
<213> ORGANISM: Homo sapiens

<400> SEQUENCE: 475 cgcggggag tttatttttg aggattcgg                                          29

<210> SEQ ID NO 476
<211> LENGTH: 28
<212> TYPE: DNA
<213> ORGANISM: Homo sapiens

<400> SEQUENCE: 476
actcctcacc cacaaacgac tacacact                                          28

<210> SEQ ID NO 477
<211> LENGTH: 29
<212> TYPE: DNA
<213> ORGANISM: Homo sapiens

<400> SEQUENCE: 477
tagtatttgt acggagtttt tcggcggtc                                         29
```

```
<210> SEQ ID NO 478
<211> LENGTH: 29
<212> TYPE: DNA
<213> ORGANISM: Homo sapiens

<400> SEQUENCE: 478
tacgacgcaa ccaacgatac tatcaccaa                                    29

<210> SEQ ID NO 479
<211> LENGTH: 27
<212> TYPE: DNA
<213> ORGANISM: Homo sapiens

<400> SEQUENCE: 479
tagtgattgg ttatttgggc gcggggc                                      27

<210> SEQ ID NO 480
<211> LENGTH: 28
<212> TYPE: DNA
<213> ORGANISM: Homo sapiens

<400> SEQUENCE: 480
aaacgacatc catcatctcc ctcgaccc                                     28

<210> SEQ ID NO 481
<211> LENGTH: 20
<212> TYPE: DNA
<213> ORGANISM: Homo sapiens

<400> SEQUENCE: 481
aggtcgcgtt ttggtcgtgc                                              20

<210> SEQ ID NO 482
<211> LENGTH: 25
<212> TYPE: DNA
<213> ORGANISM: Homo sapiens

<400> SEQUENCE: 482
acttaaaaat aaactcgccc gtacg                                        25

<210> SEQ ID NO 483
<211> LENGTH: 28
<212> TYPE: DNA
<213> ORGANISM: Homo sapiens

<400> SEQUENCE: 483
attttacgta gggtggggtt gagggcgt                                     28

<210> SEQ ID NO 484
<211> LENGTH: 28
<212> TYPE: DNA
<213> ORGANISM: Homo sapiens

<400> SEQUENCE: 484
atcctaaccg tcccgcctca aaaccgta                                     28

<210> SEQ ID NO 485
<211> LENGTH: 26
<212> TYPE: DNA
<213> ORGANISM: Homo sapiens

<400> SEQUENCE: 485
cgtcgtagta tttggcggcg cgtttc                                       26
```

```
<210> SEQ ID NO 486
<211> LENGTH: 28
<212> TYPE: DNA
<213> ORGANISM: Homo sapiens

<400> SEQUENCE: 486
aacgtaccta atccccaaac ccactcct                                    28

<210> SEQ ID NO 487
<211> LENGTH: 29
<212> TYPE: DNA
<213> ORGANISM: Homo sapiens

<400> SEQUENCE: 487
tcgttgtgcg cgtttcgttt gttggatta                                   29

<210> SEQ ID NO 488
<211> LENGTH: 28
<212> TYPE: DNA
<213> ORGANISM: Homo sapiens

<400> SEQUENCE: 488
tcgataatat ctccgtcgcc tccgcaaa                                    28

<210> SEQ ID NO 489
<211> LENGTH: 28
<212> TYPE: DNA
<213> ORGANISM: Homo sapiens

<400> SEQUENCE: 489
gcgcgtttaa tcgtgggatt tttgggag                                    28

<210> SEQ ID NO 490
<211> LENGTH: 27
<212> TYPE: DNA
<213> ORGANISM: Homo sapiens

<400> SEQUENCE: 490
caaattcgcg acaccctacc ccaacac                                     27

<210> SEQ ID NO 491
<211> LENGTH: 21
<212> TYPE: DNA
<213> ORGANISM: Homo sapiens

<400> SEQUENCE: 491
gggtgtcgcg aatttggggt a                                           21

<210> SEQ ID NO 492
<211> LENGTH: 28
<212> TYPE: DNA
<213> ORGANISM: Homo sapiens

<400> SEQUENCE: 492
ctaaacctct ccctcccaa atttacct                                     28

<210> SEQ ID NO 493
<211> LENGTH: 28
<212> TYPE: DNA
<213> ORGANISM: Homo sapiens

<400> SEQUENCE: 493
```
atcgagtttt tagcggtttt tggggcgg                                        28

<210> SEQ ID NO 494
<211> LENGTH: 28
<212> TYPE: DNA
<213> ORGANISM: Homo sapiens

<400> SEQUENCE: 494
actaacatcg cgcacttaaa tctttccg                                        28

<210> SEQ ID NO 495
<211> LENGTH: 21
<212> TYPE: DNA
<213> ORGANISM: Homo sapiens

<400> SEQUENCE: 495
ggtagcggcg ggtaaaaagt c                                               21

<210> SEQ ID NO 496
<211> LENGTH: 22
<212> TYPE: DNA
<213> ORGANISM: Homo sapiens

<400> SEQUENCE: 496
tacaactttt tacctccgcc gc                                              22

<210> SEQ ID NO 497
<211> LENGTH: 28
<212> TYPE: DNA
<213> ORGANISM: Homo sapiens

<400> SEQUENCE: 497
cgtcgatttg cggaatttcg tcgtcgtt                                        28

<210> SEQ ID NO 498
<211> LENGTH: 28
<212> TYPE: DNA
<213> ORGANISM: Homo sapiens

<400> SEQUENCE: 498
acatccgcgt aaactcgccc tttaacac                                        28

<210> SEQ ID NO 499
<211> LENGTH: 28
<212> TYPE: DNA
<213> ORGANISM: Homo sapiens

<400> SEQUENCE: 499
tttcgggatt agggtttcgg agggtgtc                                        28

<210> SEQ ID NO 500
<211> LENGTH: 28
<212> TYPE: DNA
<213> ORGANISM: Homo sapiens

<400> SEQUENCE: 500
cgtatcgatc cgtccctccc gcttaaaa                                        28

<210> SEQ ID NO 501
<211> LENGTH: 26
<212> TYPE: DNA
<213> ORGANISM: Homo sapiens

<400> SEQUENCE: 501
cggttttggt ggtagttttg gtaatc                                          26

<210> SEQ ID NO 502
<211> LENGTH: 28
<212> TYPE: DNA
<213> ORGANISM: Homo sapiens

<400> SEQUENCE: 502
aaaacctccc gaacgacgaa ataatcca                                        28

<210> SEQ ID NO 503
<211> LENGTH: 21
<212> TYPE: DNA
<213> ORGANISM: Homo sapiens

<400> SEQUENCE: 503
gtaggcggtc ggaacgtgaa c                                               21

<210> SEQ ID NO 504
<211> LENGTH: 29
<212> TYPE: DNA
<213> ORGANISM: Homo sapiens

<400> SEQUENCE: 504
cgataaaaac tacaataact cgacaacca                                       29

<210> SEQ ID NO 505
<211> LENGTH: 24
<212> TYPE: DNA
<213> ORGANISM: Homo sapiens

<400> SEQUENCE: 505
gttgtgaggg ttttcggcgg tatc                                            24

<210> SEQ ID NO 506
<211> LENGTH: 21
<212> TYPE: DNA
<213> ORGANISM: Homo sapiens

<400> SEQUENCE: 506
cataacaacg cgcgaccect a                                               21

<210> SEQ ID NO 507
<211> LENGTH: 29
<212> TYPE: DNA
<213> ORGANISM: Homo sapiens

<400> SEQUENCE: 507
tgattataaa ttaggggtt tggtcgtcg                                        29

<210> SEQ ID NO 508
<211> LENGTH: 28
<212> TYPE: DNA
<213> ORGANISM: Homo sapiens

<400> SEQUENCE: 508
aaaccctcca ccctcgcaat actactcc                                        28

<210> SEQ ID NO 509
<211> LENGTH: 28
<212> TYPE: DNA
<213> ORGANISM: Homo sapiens

```
<400> SEQUENCE: 509
tgtaggagat aatgggagtg aagaggga                                      28

<210> SEQ ID NO 510
<211> LENGTH: 28
<212> TYPE: DNA
<213> ORGANISM: Homo sapiens

<400> SEQUENCE: 510
ttccacgaaa cgcgcgactt cctaacta                                     28

<210> SEQ ID NO 511
<211> LENGTH: 24
<212> TYPE: DNA
<213> ORGANISM: Homo sapiens

<400> SEQUENCE: 511
gttgagttag gagaggtcga tagc                                         24

<210> SEQ ID NO 512
<211> LENGTH: 28
<212> TYPE: DNA
<213> ORGANISM: Homo sapiens

<400> SEQUENCE: 512
cccgaaaaca acgactatcg aaatccaa                                     28

<210> SEQ ID NO 513
<211> LENGTH: 28
<212> TYPE: DNA
<213> ORGANISM: Homo sapiens

<400> SEQUENCE: 513
ataaggtttg gtggaagcgt aggagcgt                                     28

<210> SEQ ID NO 514
<211> LENGTH: 28
<212> TYPE: DNA
<213> ORGANISM: Homo sapiens

<400> SEQUENCE: 514
acgccgaata aaaatcccgc aaccacaa                                     28

<210> SEQ ID NO 515
<211> LENGTH: 28
<212> TYPE: DNA
<213> ORGANISM: Homo sapiens

<400> SEQUENCE: 515
ggaggggagg agatagcgtt atttaggg                                     28

<210> SEQ ID NO 516
<211> LENGTH: 28
<212> TYPE: DNA
<213> ORGANISM: Homo sapiens

<400> SEQUENCE: 516
aaacaaaacc cgaaacccca cctacacc                                     28

<210> SEQ ID NO 517
<211> LENGTH: 28
<212> TYPE: DNA
<213> ORGANISM: Homo sapiens
```

```
<400> SEQUENCE: 517
gcgtggtagt tgaggatgta gacgtggt                                              28

<210> SEQ ID NO 518
<211> LENGTH: 28
<212> TYPE: DNA
<213> ORGANISM: Homo sapiens

<400> SEQUENCE: 518
tccgaactac ttaaaaatcc ccgccgcc                                              28

<210> SEQ ID NO 519
<211> LENGTH: 28
<212> TYPE: DNA
<213> ORGANISM: Homo sapiens

<400> SEQUENCE: 519
tcgttggttg tgatttttat gcgggcgt                                              28

<210> SEQ ID NO 520
<211> LENGTH: 28
<212> TYPE: DNA
<213> ORGANISM: Homo sapiens

<400> SEQUENCE: 520
acctctccga taaaccaaat cctccgcc                                              28

<210> SEQ ID NO 521
<211> LENGTH: 28
<212> TYPE: DNA
<213> ORGANISM: Homo sapiens

<400> SEQUENCE: 521
cgggtgaggt ttgtggttaa tttcgcgt                                              28

<210> SEQ ID NO 522
<211> LENGTH: 28
<212> TYPE: DNA
<213> ORGANISM: Homo sapiens

<400> SEQUENCE: 522
ctcaaccaaa ctacaacgtt cccgcctc                                              28

<210> SEQ ID NO 523
<211> LENGTH: 28
<212> TYPE: DNA
<213> ORGANISM: Homo sapiens

<400> SEQUENCE: 523
aatggaggcg tagattaacg agcggtgt                                              28

<210> SEQ ID NO 524
<211> LENGTH: 28
<212> TYPE: DNA
<213> ORGANISM: Homo sapiens

<400> SEQUENCE: 524
atccttaaca accccgccga ctaacgtc                                              28

<210> SEQ ID NO 525
<211> LENGTH: 28
<212> TYPE: DNA
```

<213> ORGANISM: Homo sapiens

<400> SEQUENCE: 525
acgggtacgg agaaacgtcg gatttagt                                28

<210> SEQ ID NO 526
<211> LENGTH: 28
<212> TYPE: DNA
<213> ORGANISM: Homo sapiens

<400> SEQUENCE: 526
tccccgcgac actctaccta taacgtcc                                28

<210> SEQ ID NO 527
<211> LENGTH: 22
<212> TYPE: DNA
<213> ORGANISM: Homo sapiens

<400> SEQUENCE: 527
cgtttggcgg gtattgttgt tc                                      22

<210> SEQ ID NO 528
<211> LENGTH: 20
<212> TYPE: DNA
<213> ORGANISM: Homo sapiens

<400> SEQUENCE: 528
cccgacgcaa actccctctc                                         20

<210> SEQ ID NO 529
<211> LENGTH: 25
<212> TYPE: DNA
<213> ORGANISM: Homo sapiens

<400> SEQUENCE: 529
gaagttgttt tttaggggtt tgcgc                                   25

<210> SEQ ID NO 530
<211> LENGTH: 25
<212> TYPE: DNA
<213> ORGANISM: Homo sapiens

<400> SEQUENCE: 530
actcaaatct accctcgctt caacg                                   25

<210> SEQ ID NO 531
<211> LENGTH: 28
<212> TYPE: DNA
<213> ORGANISM: Homo sapiens

<400> SEQUENCE: 531 gcgcggggt attttggagg gttagtta                                 28

<210> SEQ ID NO 532
<211> LENGTH: 28
<212> TYPE: DNA
<213> ORGANISM: Homo sapiens

<400> SEQUENCE: 532
tccctactcg cccgctacga ctataaca                                28

<210> SEQ ID NO 533
<211> LENGTH: 28

```
<212> TYPE: DNA
<213> ORGANISM: Homo sapiens

<400> SEQUENCE: 533 cggatttttgt tttcgggagt cgttcggg                              28

<210> SEQ ID NO 534
<211> LENGTH: 28
<212> TYPE: DNA
<213> ORGANISM: Homo sapiens

<400> SEQUENCE: 534
aactaaacgc ctaacccttc cctcccac                               28

<210> SEQ ID NO 535
<211> LENGTH: 28
<212> TYPE: DNA
<213> ORGANISM: Homo sapiens

<400> SEQUENCE: 535
ttcgttttgt ttttcggttg gagcgggt                               28

<210> SEQ ID NO 536
<211> LENGTH: 28
<212> TYPE: DNA
<213> ORGANISM: Homo sapiens

<400> SEQUENCE: 536
tataacctaa cccttcaacc gcgcctcg                               28

<210> SEQ ID NO 537
<211> LENGTH: 28
<212> TYPE: DNA
<213> ORGANISM: Homo sapiens

<400> SEQUENCE: 537
aggcggcggt ttttggcgat tgtttttc                               28

<210> SEQ ID NO 538
<211> LENGTH: 27
<212> TYPE: DNA
<213> ORGANISM: Homo sapiens

<400> SEQUENCE: 538
ttccgttacc ataaaactac ccgcccc                                27

<210> SEQ ID NO 539
<211> LENGTH: 21
<212> TYPE: DNA
<213> ORGANISM: Homo sapiens

<400> SEQUENCE: 539
gatttcgcgt atcgtcgtgt c                                      21

<210> SEQ ID NO 540
<211> LENGTH: 21
<212> TYPE: DNA
<213> ORGANISM: Homo sapiens

<400> SEQUENCE: 540
taatatcccc cgtacccccc g                                      21

<210> SEQ ID NO 541
```

<211> LENGTH: 28
<212> TYPE: DNA
<213> ORGANISM: Homo sapiens

<400> SEQUENCE: 541
tttcgataat agcgttttg cggcgtgg 28

<210> SEQ ID NO 542
<211> LENGTH: 28
<212> TYPE: DNA
<213> ORGANISM: Homo sapiens

<400> SEQUENCE: 542
caaaaacacg cgacctacgc cctcctaa 28

<210> SEQ ID NO 543
<211> LENGTH: 28
<212> TYPE: DNA
<213> ORGANISM: Homo sapiens

<400> SEQUENCE: 543
cgagtcggag tgagcgttaa gtgagggg 28

<210> SEQ ID NO 544
<211> LENGTH: 28
<212> TYPE: DNA
<213> ORGANISM: Homo sapiens

<400> SEQUENCE: 544
cctatcaacg accacccaac tactccct 28

<210> SEQ ID NO 545
<211> LENGTH: 28
<212> TYPE: DNA
<213> ORGANISM: Homo sapiens

<400> SEQUENCE: 545
tcgggtttag cgtcgtttgt agtttcgg 28

<210> SEQ ID NO 546
<211> LENGTH: 28
<212> TYPE: DNA
<213> ORGANISM: Homo sapiens

<400> SEQUENCE: 546
aaaaacgtct ccttaattcc ccgcgctt 28

<210> SEQ ID NO 547
<211> LENGTH: 30
<212> TYPE: DNA
<213> ORGANISM: Homo sapiens

<400> SEQUENCE: 547
gcggttggag tagaagtgtt agcggttaga 30

<210> SEQ ID NO 548
<211> LENGTH: 28
<212> TYPE: DNA
<213> ORGANISM: Homo sapiens

<400> SEQUENCE: 548
tcaccctaca aaaaccgata accgacga 28

```
<210> SEQ ID NO 549
<211> LENGTH: 28
<212> TYPE: DNA
<213> ORGANISM: Homo sapiens

<400> SEQUENCE: 549
agttggttat aggcggcgaa ttgggttt                                          28

<210> SEQ ID NO 550
<211> LENGTH: 28
<212> TYPE: DNA
<213> ORGANISM: Homo sapiens

<400> SEQUENCE: 550
tcaacacccc ctctcctaac ctctccaa                                          28

<210> SEQ ID NO 551
<211> LENGTH: 28
<212> TYPE: DNA
<213> ORGANISM: Homo sapiens

<400> SEQUENCE: 551
cggggaagag tttcggttcg cgttttag                                          28

<210> SEQ ID NO 552
<211> LENGTH: 28
<212> TYPE: DNA
<213> ORGANISM: Homo sapiens

<400> SEQUENCE: 552
ccctcctata accccgacct acccgaaa                                          28

<210> SEQ ID NO 553
<211> LENGTH: 28
<212> TYPE: DNA
<213> ORGANISM: Homo sapiens

<400> SEQUENCE: 553
gcgcggtagg tgttttcgg gttgtaaa                                           28

<210> SEQ ID NO 554
<211> LENGTH: 28
<212> TYPE: DNA
<213> ORGANISM: Homo sapiens

<400> SEQUENCE: 554
acctttacct aactacactc ccatccaa                                          28

<210> SEQ ID NO 555
<211> LENGTH: 21
<212> TYPE: DNA
<213> ORGANISM: Homo sapiens

<400> SEQUENCE: 555
agagtaggtc gtgggggatt c                                                 21

<210> SEQ ID NO 556
<211> LENGTH: 21
<212> TYPE: DNA
<213> ORGANISM: Homo sapiens

<400> SEQUENCE: 556
cgcgctaacc gcgataaaaa c                                                 21
```

```
<210> SEQ ID NO 557
<211> LENGTH: 28
<212> TYPE: DNA
<213> ORGANISM: Homo sapiens

<400> SEQUENCE: 557
aggagcggga gagggaaaaa tagttaag                                          28

<210> SEQ ID NO 558
<211> LENGTH: 27
<212> TYPE: DNA
<213> ORGANISM: Homo sapiens

<400> SEQUENCE: 558
actacgccca aaactcaact actaaat                                           27

<210> SEQ ID NO 559
<211> LENGTH: 28
<212> TYPE: DNA
<213> ORGANISM: Homo sapiens

<400> SEQUENCE: 559
tgggaacggg atagggacgc gttttaat                                          28

<210> SEQ ID NO 560
<211> LENGTH: 28
<212> TYPE: DNA
<213> ORGANISM: Homo sapiens

<400> SEQUENCE: 560 gaatcccta aactacccgc catcccac                                           28

<210> SEQ ID NO 561
<211> LENGTH: 29
<212> TYPE: DNA
<213> ORGANISM: Homo sapiens

<400> SEQUENCE: 561
tgtacgcgta tttttggagg gtggtttgc                                         29

<210> SEQ ID NO 562
<211> LENGTH: 28
<212> TYPE: DNA
<213> ORGANISM: Homo sapiens

<400> SEQUENCE: 562
cgatctaatc gaccacctcc tctcctcc                                          28

<210> SEQ ID NO 563
<211> LENGTH: 28
<212> TYPE: DNA
<213> ORGANISM: Homo sapiens

<400> SEQUENCE: 563
aagtttcgtc gagttggggt cgttggtt                                          28

<210> SEQ ID NO 564
<211> LENGTH: 27
<212> TYPE: DNA
<213> ORGANISM: Homo sapiens

<400> SEQUENCE: 564
gacccttccc gacaaccatc tcgaaca                                           27
```

<210> SEQ ID NO 565
<211> LENGTH: 28
<212> TYPE: DNA
<213> ORGANISM: Homo sapiens

<400> SEQUENCE: 565
gaaaattgcg cggttgggtt agtagggg                    28

<210> SEQ ID NO 566
<211> LENGTH: 28
<212> TYPE: DNA
<213> ORGANISM: Homo sapiens

<400> SEQUENCE: 566
acctacaaat accgtcccca cccgaaac                    28

<210> SEQ ID NO 567
<211> LENGTH: 28
<212> TYPE: DNA
<213> ORGANISM: Homo sapiens

<400> SEQUENCE: 567
aagaggggtg tgattcgcga gtttagat                    28

<210> SEQ ID NO 568
<211> LENGTH: 23
<212> TYPE: DNA
<213> ORGANISM: Homo sapiens

<400> SEQUENCE: 568
ccgcgcgcga ctcgaacgaa aaa                         23

<210> SEQ ID NO 569
<211> LENGTH: 28
<212> TYPE: DNA
<213> ORGANISM: Homo sapiens

<400> SEQUENCE: 569
aagggtgcga tgttttcgtt taggatcg                    28

<210> SEQ ID NO 570
<211> LENGTH: 29
<212> TYPE: DNA
<213> ORGANISM: Homo sapiens

<400> SEQUENCE: 570
taactaacta aaccgcgat aaaacgact                    29

<210> SEQ ID NO 571
<211> LENGTH: 28
<212> TYPE: DNA
<213> ORGANISM: Homo sapiens

<400> SEQUENCE: 571
tggtaatcgc gtaggtgtgt gatagggc                    28

<210> SEQ ID NO 572
<211> LENGTH: 28
<212> TYPE: DNA
<213> ORGANISM: Homo sapiens

<400> SEQUENCE: 572

```
aaaatacaaa atacgccccc gaccccga                                        28

<210> SEQ ID NO 573
<211> LENGTH: 28
<212> TYPE: DNA
<213> ORGANISM: Homo sapiens

<400> SEQUENCE: 573
tgaggagaga ttcggagtag ttagtaga                                        28

<210> SEQ ID NO 574
<211> LENGTH: 28
<212> TYPE: DNA
<213> ORGANISM: Homo sapiens

<400> SEQUENCE: 574
ccctatcaca cacctacgcg attaccaa                                        28

<210> SEQ ID NO 575
<211> LENGTH: 28
<212> TYPE: DNA
<213> ORGANISM: Homo sapiens

<400> SEQUENCE: 575
tttcgaaaag ttggtagtcg gcggttgg                                        28

<210> SEQ ID NO 576
<211> LENGTH: 28
<212> TYPE: DNA
<213> ORGANISM: Homo sapiens

<400> SEQUENCE: 576
cattctactc ccccgaatcg aaacccccc                                       28

<210> SEQ ID NO 577
<211> LENGTH: 28
<212> TYPE: DNA
<213> ORGANISM: Homo sapiens

<400> SEQUENCE: 577
aagaggaaga gttcgcgcgt cgagttta                                        28

<210> SEQ ID NO 578
<211> LENGTH: 28
<212> TYPE: DNA
<213> ORGANISM: Homo sapiens

<400> SEQUENCE: 578
gaaatcgcgc gcccacgata ctacaaaa                                        28

<210> SEQ ID NO 579
<211> LENGTH: 25
<212> TYPE: DNA
<213> ORGANISM: Homo sapiens

<400> SEQUENCE: 579
ttattagtag gcggcgtcgg gggtt                                           25

<210> SEQ ID NO 580
<211> LENGTH: 29
<212> TYPE: DNA
<213> ORGANISM: Homo sapiens

<400> SEQUENCE: 580
```
cgaaaacccc tactccgaaa aatcgtccg                                          29

<210> SEQ ID NO 581
<211> LENGTH: 28
<212> TYPE: DNA
<213> ORGANISM: Homo sapiens

<400> SEQUENCE: 581
gttgagatat cgaggggttc gggttagg                                           28

<210> SEQ ID NO 582
<211> LENGTH: 30
<212> TYPE: DNA
<213> ORGANISM: Homo sapiens

<400> SEQUENCE: 582
cgccaacaac gataaaataa ataccgcgcc                                         30

<210> SEQ ID NO 583
<211> LENGTH: 29
<212> TYPE: DNA
<213> ORGANISM: Homo sapiens

<400> SEQUENCE: 583
cgtttgttcg atcggggtcg tacgagtat                                          29

<210> SEQ ID NO 584
<211> LENGTH: 28
<212> TYPE: DNA
<213> ORGANISM: Homo sapiens

<400> SEQUENCE: 584
tttccgcctc ctaccttcta acccgact                                           28

<210> SEQ ID NO 585
<211> LENGTH: 28
<212> TYPE: DNA
<213> ORGANISM: Homo sapiens

<400> SEQUENCE: 585 ggttgggggα gtgggaggta aattcgtt                                           28

<210> SEQ ID NO 586
<211> LENGTH: 28
<212> TYPE: DNA
<213> ORGANISM: Homo sapiens

<400> SEQUENCE: 586
ctaaacgctc cctcacgcct taccttca                                           28

<210> SEQ ID NO 587
<211> LENGTH: 28
<212> TYPE: DNA
<213> ORGANISM: Homo sapiens

<400> SEQUENCE: 587
ttgagggaaa cgcggtggga atcgtttt                                           28

<210> SEQ ID NO 588
<211> LENGTH: 28
<212> TYPE: DNA
<213> ORGANISM: Homo sapiens

```
<400> SEQUENCE: 588
ccgtaactcg cccgaaaaac taaccgaa                                  28

<210> SEQ ID NO 589
<211> LENGTH: 22
<212> TYPE: DNA
<213> ORGANISM: Homo sapiens

<400> SEQUENCE: 589
tgattggttg cggggtagtt tc                                        22

<210> SEQ ID NO 590
<211> LENGTH: 24
<212> TYPE: DNA
<213> ORGANISM: Homo sapiens

<400> SEQUENCE: 590
acacccgctt taaaataccg ctaa                                      24

<210> SEQ ID NO 591
<211> LENGTH: 28
<212> TYPE: DNA
<213> ORGANISM: Homo sapiens

<400> SEQUENCE: 591
gcgtttcggg tcgttcgttt tatttcgc                                  28

<210> SEQ ID NO 592
<211> LENGTH: 28
<212> TYPE: DNA
<213> ORGANISM: Homo sapiens

<400> SEQUENCE: 592
cgacaaccta cgccgaatat acgcacct                                  28

<210> SEQ ID NO 593
<211> LENGTH: 28
<212> TYPE: DNA
<213> ORGANISM: Homo sapiens

<400> SEQUENCE: 593
gaagggatga ggttgaggtt ggaggtcg                                  28

<210> SEQ ID NO 594
<211> LENGTH: 29
<212> TYPE: DNA
<213> ORGANISM: Homo sapiens

<400> SEQUENCE: 594
acctcctacc caccaattcc gaaaaacaa                                 29

<210> SEQ ID NO 595
<211> LENGTH: 24
<212> TYPE: DNA
<213> ORGANISM: Homo sapiens

<400> SEQUENCE: 595
ttacggagtt ttaggcggcg ttac                                      24

<210> SEQ ID NO 596
<211> LENGTH: 23
<212> TYPE: DNA
<213> ORGANISM: Homo sapiens
```

```
<400> SEQUENCE: 596
catttccctc tctacgcgcg aac                                              23

<210> SEQ ID NO 597
<211> LENGTH: 28
<212> TYPE: DNA
<213> ORGANISM: Homo sapiens

<400> SEQUENCE: 597
cgtaggtttt gttggagcga gagatcgg                                         28

<210> SEQ ID NO 598
<211> LENGTH: 29
<212> TYPE: DNA
<213> ORGANISM: Homo sapiens

<400> SEQUENCE: 598
acatataaaa ccgcgctacc cgaaaaccg                                        29

<210> SEQ ID NO 599
<211> LENGTH: 28
<212> TYPE: DNA
<213> ORGANISM: Homo sapiens

<400> SEQUENCE: 599
tgaaagggga gagggaatg ttattgtt                                          28

<210> SEQ ID NO 600
<211> LENGTH: 28
<212> TYPE: DNA
<213> ORGANISM: Homo sapiens

<400> SEQUENCE: 600
aatattctcg caaacccacc gccaaacc                                         28

<210> SEQ ID NO 601
<211> LENGTH: 28
<212> TYPE: DNA
<213> ORGANISM: Homo sapiens

<400> SEQUENCE: 601
aaagagattc gtgttgcggc ggatgaag                                         28

<210> SEQ ID NO 602
<211> LENGTH: 28
<212> TYPE: DNA
<213> ORGANISM: Homo sapiens

<400> SEQUENCE: 602
gatcaacact cgaacccgaa ctttccgc                                         28

<210> SEQ ID NO 603
<211> LENGTH: 28
<212> TYPE: DNA
<213> ORGANISM: Homo sapiens

<400> SEQUENCE: 603
aagggaggag ggtggatcga aagcgtta                                         28

<210> SEQ ID NO 604
<211> LENGTH: 29
<212> TYPE: DNA
```

```
<213> ORGANISM: Homo sapiens

<400> SEQUENCE: 604
cgaaaacctt tacacgcgca caaactacg                              29

<210> SEQ ID NO 605
<211> LENGTH: 28
<212> TYPE: DNA
<213> ORGANISM: Homo sapiens

<400> SEQUENCE: 605
tatgggttgc gtcgagggta aggtagtg                               28

<210> SEQ ID NO 606
<211> LENGTH: 29
<212> TYPE: DNA
<213> ORGANISM: Homo sapiens

<400> SEQUENCE: 606
accatcgccg ttcttacctt tcgtctaca                              29

<210> SEQ ID NO 607
<211> LENGTH: 28
<212> TYPE: DNA
<213> ORGANISM: Homo sapiens

<400> SEQUENCE: 607
tttttaattc ggttcggcgt tgatttgt                               28

<210> SEQ ID NO 608
<211> LENGTH: 21
<212> TYPE: DNA
<213> ORGANISM: Homo sapiens

<400> SEQUENCE: 608
acaaccgcgc gctcccgata c                                      21

<210> SEQ ID NO 609
<211> LENGTH: 27
<212> TYPE: DNA
<213> ORGANISM: Homo sapiens

<400> SEQUENCE: 609
tagcgcggaa gttgtgagtt taaggcg                                27

<210> SEQ ID NO 610
<211> LENGTH: 29
<212> TYPE: DNA
<213> ORGANISM: Homo sapiens

<400> SEQUENCE: 610
tcctctaaac accatcgaaa cccccgaac                              29

<210> SEQ ID NO 611
<211> LENGTH: 28
<212> TYPE: DNA
<213> ORGANISM: Homo sapiens

<400> SEQUENCE: 611
agtggcgttc gttgagatta gggaaggg                               28

<210> SEQ ID NO 612
<211> LENGTH: 28
```

```
<212> TYPE: DNA
<213> ORGANISM: Homo sapiens

<400> SEQUENCE: 612
accgtacgct accgaaacga cctttaca                                          28

<210> SEQ ID NO 613
<211> LENGTH: 22
<212> TYPE: DNA
<213> ORGANISM: Homo sapiens

<400> SEQUENCE: 613
gtttgtaatt ggtatgagcg gc                                                22

<210> SEQ ID NO 614
<211> LENGTH: 18
<212> TYPE: DNA
<213> ORGANISM: Homo sapiens

<400> SEQUENCE: 614
ataacgaaac gacgcctc                                                     18

<210> SEQ ID NO 615
<211> LENGTH: 20
<212> TYPE: DNA
<213> ORGANISM: Homo sapiens

<400> SEQUENCE: 615
gtaattggta tgagcggcgt                                                   20

<210> SEQ ID NO 616
<211> LENGTH: 21
<212> TYPE: DNA
<213> ORGANISM: Homo sapiens

<400> SEQUENCE: 616
gcctccgcga aataaaacca t                                                 21

<210> SEQ ID NO 617
<211> LENGTH: 21
<212> TYPE: DNA
<213> ORGANISM: Homo sapiens

<400> SEQUENCE: 617
agttagagtg ggttagggga t                                                 21

<210> SEQ ID NO 618
<211> LENGTH: 20
<212> TYPE: DNA
<213> ORGANISM: Homo sapiens

<400> SEQUENCE: 618
acgcgtaaca caaacacgac                                                   20

<210> SEQ ID NO 619
<211> LENGTH: 20
<212> TYPE: DNA
<213> ORGANISM: Homo sapiens

<400> SEQUENCE: 619
gggggatttt aaagatcgtc                                                   20

<210> SEQ ID NO 620
```

```
<211> LENGTH: 18
<212> TYPE: DNA
<213> ORGANISM: Homo sapiens

<400> SEQUENCE: 620
gacgaacgca atccacaa                                              18

<210> SEQ ID NO 621
<211> LENGTH: 20
<212> TYPE: DNA
<213> ORGANISM: Homo sapiens

<400> SEQUENCE: 621
tggtggagtt gtggattgcg                                            20

<210> SEQ ID NO 622
<211> LENGTH: 20
<212> TYPE: DNA
<213> ORGANISM: Homo sapiens

<400> SEQUENCE: 622
tcccacccaa acctctctct                                            20

<210> SEQ ID NO 623
<211> LENGTH: 18
<212> TYPE: DNA
<213> ORGANISM: Homo sapiens

<400> SEQUENCE: 623
ggtgcgttta cgggtttc                                              18

<210> SEQ ID NO 624
<211> LENGTH: 21
<212> TYPE: DNA
<213> ORGANISM: Homo sapiens

<400> SEQUENCE: 624
acctaatccg atatttcccg a                                          21

<210> SEQ ID NO 625
<211> LENGTH: 20
<212> TYPE: DNA
<213> ORGANISM: Homo sapiens

<400> SEQUENCE: 625
ggtagggttt cggttgcgta                                            20

<210> SEQ ID NO 626
<211> LENGTH: 24
<212> TYPE: DNA
<213> ORGANISM: Homo sapiens

<400> SEQUENCE: 626
tatttcccga aaactccaca tcca                                       24

<210> SEQ ID NO 627
<211> LENGTH: 20
<212> TYPE: DNA
<213> ORGANISM: Homo sapiens

<400> SEQUENCE: 627
tcccgaaaac tccacatcca                                            20
```

```
<210> SEQ ID NO 628
<211> LENGTH: 20
<212> TYPE: DNA
<213> ORGANISM: Homo sapiens

<400> SEQUENCE: 628
atttggatgt ttcgcgtttc                                                 20

<210> SEQ ID NO 629
<211> LENGTH: 20
<212> TYPE: DNA
<213> ORGANISM: Homo sapiens

<400> SEQUENCE: 629
tatcgctacg acccgactaa                                                 20

<210> SEQ ID NO 630
<211> LENGTH: 24
<212> TYPE: DNA
<213> ORGANISM: Homo sapiens

<400> SEQUENCE: 630
gttaatttgg atgtttcgcg tttc                                            24

<210> SEQ ID NO 631
<211> LENGTH: 23
<212> TYPE: DNA
<213> ORGANISM: Homo sapiens

<400> SEQUENCE: 631
gtttatcgct acgacccgac taa                                             23

<210> SEQ ID NO 632
<211> LENGTH: 20
<212> TYPE: DNA
<213> ORGANISM: Homo sapiens

<400> SEQUENCE: 632
aggggagtcg cgttttaggg                                                 20

<210> SEQ ID NO 633
<211> LENGTH: 20
<212> TYPE: DNA
<213> ORGANISM: Homo sapiens

<400> SEQUENCE: 633
tcccgaccga aacccaaatc                                                 20

<210> SEQ ID NO 634
<211> LENGTH: 22
<212> TYPE: DNA
<213> ORGANISM: Homo sapiens

<400> SEQUENCE: 634
gaataacggc gtaagttttt ac                                              22

<210> SEQ ID NO 635
<211> LENGTH: 18
<212> TYPE: DNA
<213> ORGANISM: Homo sapiens

<400> SEQUENCE: 635
atcctcccga acgcaata                                                   18
```

<210> SEQ ID NO 636
<211> LENGTH: 21
<212> TYPE: DNA
<213> ORGANISM: Homo sapiens

<400> SEQUENCE: 636
ttgtacgttt gtgggtgtgg a                                    21

<210> SEQ ID NO 637
<211> LENGTH: 21
<212> TYPE: DNA
<213> ORGANISM: Homo sapiens

<400> SEQUENCE: 637
tcctcccgaa cgcaataatc g                                    21

<210> SEQ ID NO 638
<211> LENGTH: 21
<212> TYPE: DNA
<213> ORGANISM: Homo sapiens

<400> SEQUENCE: 638
ttaacggtta ggttagatcg c                                    21

<210> SEQ ID NO 639
<211> LENGTH: 20
<212> TYPE: DNA
<213> ORGANISM: Homo sapiens

<400> SEQUENCE: 639
caatctctaa aacgcgacac                                      20

<210> SEQ ID NO 640
<211> LENGTH: 21
<212> TYPE: DNA
<213> ORGANISM: Homo sapiens

<400> SEQUENCE: 640
cgggtgtcgc gttttagaga t                                    21

<210> SEQ ID NO 641
<211> LENGTH: 21
<212> TYPE: DNA
<213> ORGANISM: Homo sapiens

<400> SEQUENCE: 641
ttctccgatc tcatacccccc t                                   21

<210> SEQ ID NO 642
<211> LENGTH: 19
<212> TYPE: DNA
<213> ORGANISM: Homo sapiens

<400> SEQUENCE: 642
gagaaaagtt gtttcggtc                                       19

<210> SEQ ID NO 643
<211> LENGTH: 20
<212> TYPE: DNA
<213> ORGANISM: Homo sapiens

<400> SEQUENCE: 643
gctacgtctc tactatccga                                      20

<210> SEQ ID NO 644
<211> LENGTH: 22
<212> TYPE: DNA
<213> ORGANISM: Homo sapiens

<400> SEQUENCE: 644
cgggagaaaa gttgtttcgg tc                                              22

<210> SEQ ID NO 645
<211> LENGTH: 22
<212> TYPE: DNA
<213> ORGANISM: Homo sapiens

<400> SEQUENCE: 645
ccgctacgtc tctactatcc ga                                              22

<210> SEQ ID NO 646
<211> LENGTH: 18
<212> TYPE: DNA
<213> ORGANISM: Homo sapiens

<400> SEQUENCE: 646
ttcggggtga gggtagtc                                                   18

<210> SEQ ID NO 647
<211> LENGTH: 18
<212> TYPE: DNA
<213> ORGANISM: Homo sapiens

<400> SEQUENCE: 647
ccgacgccca actaaaaa                                                   18

<210> SEQ ID NO 648
<211> LENGTH: 21
<212> TYPE: DNA
<213> ORGANISM: Homo sapiens

<400> SEQUENCE: 648
gagttcgggg tgagggtagt c                                               21

<210> SEQ ID NO 649
<211> LENGTH: 23
<212> TYPE: DNA
<213> ORGANISM: Homo sapiens

<400> SEQUENCE: 649
gaatcccgac gcccaactaa aaa                                             23

<210> SEQ ID NO 650
<211> LENGTH: 20
<212> TYPE: DNA
<213> ORGANISM: Homo sapiens

<400> SEQUENCE: 650
ttttcgggtt acgggtcgtt                                                 20

<210> SEQ ID NO 651
<211> LENGTH: 20
<212> TYPE: DNA
<213> ORGANISM: Homo sapiens

<400> SEQUENCE: 651
acgactcctc cgaaaatccg                                        20

<210> SEQ ID NO 652
<211> LENGTH: 19
<212> TYPE: DNA
<213> ORGANISM: Homo sapiens

<400> SEQUENCE: 652
gtcgattttt gttttgagc                                         19

<210> SEQ ID NO 653
<211> LENGTH: 22
<212> TYPE: DNA
<213> ORGANISM: Homo sapiens

<400> SEQUENCE: 653
taaaaataat ctaccgaatc gc                                     22

<210> SEQ ID NO 654
<211> LENGTH: 20
<212> TYPE: DNA
<213> ORGANISM: Homo sapiens

<400> SEQUENCE: 654
ggcgttagcg gggatttaga                                        20

<210> SEQ ID NO 655
<211> LENGTH: 20
<212> TYPE: DNA
<213> ORGANISM: Homo sapiens

<400> SEQUENCE: 655
cgcatcaaac gaaaccctcc                                        20

<210> SEQ ID NO 656
<211> LENGTH: 28
<212> TYPE: DNA
<213> ORGANISM: Homo sapiens

<400> SEQUENCE: 656
cgggaaggtg ttcgtttaat ggttcggt                               28

<210> SEQ ID NO 657
<211> LENGTH: 28
<212> TYPE: DNA
<213> ORGANISM: Homo sapiens

<400> SEQUENCE: 657
gtttccgctc taaatccccg ctaacgcc                               28

<210> SEQ ID NO 658
<211> LENGTH: 28
<212> TYPE: DNA
<213> ORGANISM: Homo sapiens

<400> SEQUENCE: 658
ggaaaaagga ggaggataag aagcgcgg                               28

<210> SEQ ID NO 659
<211> LENGTH: 28
<212> TYPE: DNA
<213> ORGANISM: Homo sapiens

<400> SEQUENCE: 659
ctcgccgaaa atcacgacgc aatcctac                                              28

<210> SEQ ID NO 660
<211> LENGTH: 19
<212> TYPE: DNA
<213> ORGANISM: Homo sapiens

<400> SEQUENCE: 660 tagggaggc gtcgagttc                                                         19

<210> SEQ ID NO 661
<211> LENGTH: 20
<212> TYPE: DNA
<213> ORGANISM: Homo sapiens

<400> SEQUENCE: 661
actcgctaaa cgtcccaacc                                                       20

<210> SEQ ID NO 662
<211> LENGTH: 18
<212> TYPE: DNA
<213> ORGANISM: Homo sapiens

<400> SEQUENCE: 662
gagtttaggg gtcgcgtc                                                         18

<210> SEQ ID NO 663
<211> LENGTH: 20
<212> TYPE: DNA
<213> ORGANISM: Homo sapiens

<400> SEQUENCE: 663
caataccgcc gcctctacta                                                       20

<210> SEQ ID NO 664
<211> LENGTH: 20
<212> TYPE: DNA
<213> ORGANISM: Homo sapiens

<400> SEQUENCE: 664
gagagagtag gagcggatcg                                                       20

<210> SEQ ID NO 665
<211> LENGTH: 20
<212> TYPE: DNA
<213> ORGANISM: Homo sapiens

<400> SEQUENCE: 665
acaaatcaac cccgccctaa                                                       20

<210> SEQ ID NO 666
<211> LENGTH: 20
<212> TYPE: DNA
<213> ORGANISM: Homo sapiens

<400> SEQUENCE: 666
agtgagtgtt cgggagtttc                                                       20

<210> SEQ ID NO 667
<211> LENGTH: 20
<212> TYPE: DNA
<213> ORGANISM: Homo sapiens

```
<400> SEQUENCE: 667
tcatttatta aaaacgcgcg                                              20

<210> SEQ ID NO 668
<211> LENGTH: 22
<212> TYPE: DNA
<213> ORGANISM: Homo sapiens

<400> SEQUENCE: 668
gcagtgagtg ctcgggagcc cc                                           22

<210> SEQ ID NO 669
<211> LENGTH: 25
<212> TYPE: DNA
<213> ORGANISM: Homo sapiens

<400> SEQUENCE: 669
ggttttcatt tgttagaggc gcgcg                                        25

<210> SEQ ID NO 670
<211> LENGTH: 20
<212> TYPE: DNA
<213> ORGANISM: Homo sapiens

<400> SEQUENCE: 670
cgggttcgcg taggattagg                                              20

<210> SEQ ID NO 671
<211> LENGTH: 20
<212> TYPE: DNA
<213> ORGANISM: Homo sapiens

<400> SEQUENCE: 671
actcctcatc ccaacaccct                                              20

<210> SEQ ID NO 672
<211> LENGTH: 19
<212> TYPE: DNA
<213> ORGANISM: Homo sapiens

<400> SEQUENCE: 672
gttcgtagtt cgcggtttc                                               19

<210> SEQ ID NO 673
<211> LENGTH: 18
<212> TYPE: DNA
<213> ORGANISM: Homo sapiens

<400> SEQUENCE: 673
cgatactctc ctcgccct                                                18

<210> SEQ ID NO 674
<211> LENGTH: 22
<212> TYPE: DNA
<213> ORGANISM: Homo sapiens

<400> SEQUENCE: 674
tcggttcgta gttcgcggtt tc                                           22

<210> SEQ ID NO 675
<211> LENGTH: 21
<212> TYPE: DNA
<213> ORGANISM: Homo sapiens
```

```
<400> SEQUENCE: 675
gcacgatact ctcctcgccc t                                            21

<210> SEQ ID NO 676
<211> LENGTH: 19
<212> TYPE: DNA
<213> ORGANISM: Homo sapiens

<400> SEQUENCE: 676
ttgggcgagt gatagtttc                                               19

<210> SEQ ID NO 677
<211> LENGTH: 18
<212> TYPE: DNA
<213> ORGANISM: Homo sapiens

<400> SEQUENCE: 677
gaccgctact acacccga                                                18

<210> SEQ ID NO 678
<211> LENGTH: 23
<212> TYPE: DNA
<213> ORGANISM: Homo sapiens

<400> SEQUENCE: 678
cggtagaaga acgtgtatga ggt                                          23

<210> SEQ ID NO 679
<211> LENGTH: 20
<212> TYPE: DNA
<213> ORGANISM: Homo sapiens

<400> SEQUENCE: 679
gctaccctcg aaaacccgaa                                              20

<210> SEQ ID NO 680
<211> LENGTH: 20
<212> TYPE: DNA
<213> ORGANISM: Homo sapiens

<400> SEQUENCE: 680 gattttttt aaggtcgcgc                                               20

<210> SEQ ID NO 681
<211> LENGTH: 24
<212> TYPE: DNA
<213> ORGANISM: Homo sapiens

<400> SEQUENCE: 681
ttacgatttt ttttaaggtc gcgc                                         24

<210> SEQ ID NO 682
<211> LENGTH: 22
<212> TYPE: DNA
<213> ORGANISM: Homo sapiens

<400> SEQUENCE: 682
actataccta cctaccgccg tc                                           22

<210> SEQ ID NO 683
<211> LENGTH: 20
<212> TYPE: DNA
```

```
<213> ORGANISM: Homo sapiens

<400> SEQUENCE: 683
atttcgaaga aggcgggtcg                                          20

<210> SEQ ID NO 684
<211> LENGTH: 20
<212> TYPE: DNA
<213> ORGANISM: Homo sapiens

<400> SEQUENCE: 684
ctccaaacga tacgccaacg                                          20

<210> SEQ ID NO 685
<211> LENGTH: 18
<212> TYPE: DNA
<213> ORGANISM: Homo sapiens

<400> SEQUENCE: 685
ttttgcgggt aagcgttc                                            18

<210> SEQ ID NO 686
<211> LENGTH: 19
<212> TYPE: DNA
<213> ORGANISM: Homo sapiens

<400> SEQUENCE: 686
ccacaactct ctcgacgac                                           19

<210> SEQ ID NO 687
<211> LENGTH: 22
<212> TYPE: DNA
<213> ORGANISM: Homo sapiens

<400> SEQUENCE: 687 tgtttttgc gggtaagcgt tc                                        22

<210> SEQ ID NO 688
<211> LENGTH: 21
<212> TYPE: DNA
<213> ORGANISM: Homo sapiens

<400> SEQUENCE: 688
gcccacaact ctctcgacga c                                        21

<210> SEQ ID NO 689
<211> LENGTH: 20
<212> TYPE: DNA
<213> ORGANISM: Homo sapiens

<400> SEQUENCE: 689
atttcgggaa agggtgggtc                                          20

<210> SEQ ID NO 690
<211> LENGTH: 20
<212> TYPE: DNA
<213> ORGANISM: Homo sapiens

<400> SEQUENCE: 690
accctaatcc cccttcacca                                          20

<210> SEQ ID NO 691
<211> LENGTH: 20
```

-continued

<212> TYPE: DNA
<213> ORGANISM: Homo sapiens

<400> SEQUENCE: 691
tttcgtttcg tttcggtcgc                                              20

<210> SEQ ID NO 692
<211> LENGTH: 20
<212> TYPE: DNA
<213> ORGANISM: Homo sapiens

<400> SEQUENCE: 692
aacccgcccg aactcaaata                                              20

<210> SEQ ID NO 693
<211> LENGTH: 21
<212> TYPE: DNA
<213> ORGANISM: Homo sapiens

<400> SEQUENCE: 693
attaggagcg tacgttttatt c                                           21

<210> SEQ ID NO 694
<211> LENGTH: 18
<212> TYPE: DNA
<213> ORGANISM: Homo sapiens

<400> SEQUENCE: 694
tacgcactcg aaacacaa                                                18

<210> SEQ ID NO 695
<211> LENGTH: 20
<212> TYPE: DNA
<213> ORGANISM: Homo sapiens

<400> SEQUENCE: 695
cggcgcgttt taagggtttt                                              20

<210> SEQ ID NO 696
<211> LENGTH: 20
<212> TYPE: DNA
<213> ORGANISM: Homo sapiens

<400> SEQUENCE: 696
attactctca cctccgcacg                                              20

<210> SEQ ID NO 697
<211> LENGTH: 19
<212> TYPE: DNA
<213> ORGANISM: Homo sapiens

<400> SEQUENCE: 697
gattgcggga agaaggtac                                               19

<210> SEQ ID NO 698
<211> LENGTH: 19
<212> TYPE: DNA
<213> ORGANISM: Homo sapiens

<400> SEQUENCE: 698
aaacgaaacc aaacgacaa                                               19

<210> SEQ ID NO 699

```
<211> LENGTH: 21
<212> TYPE: DNA
<213> ORGANISM: Homo sapiens

<400> SEQUENCE: 699
cggattgcgg gaagaaggta c                                              21

<210> SEQ ID NO 700
<211> LENGTH: 23
<212> TYPE: DNA
<213> ORGANISM: Homo sapiens

<400> SEQUENCE: 700
gacgaaacga aaccaaacga caa                                            23

<210> SEQ ID NO 701
<211> LENGTH: 20
<212> TYPE: DNA
<213> ORGANISM: Homo sapiens

<400> SEQUENCE: 701
ttttcgagtt tgaagcgttc                                                20

<210> SEQ ID NO 702
<211> LENGTH: 19
<212> TYPE: DNA
<213> ORGANISM: Homo sapiens

<400> SEQUENCE: 702
cgactctcac ctaatccgc                                                 19

<210> SEQ ID NO 703
<211> LENGTH: 23
<212> TYPE: DNA
<213> ORGANISM: Homo sapiens

<400> SEQUENCE: 703
cggttttcga gtttgaagcg ttc                                            23

<210> SEQ ID NO 704
<211> LENGTH: 22
<212> TYPE: DNA
<213> ORGANISM: Homo sapiens

<400> SEQUENCE: 704
taccgactct cacctaatcc gc                                             22

<210> SEQ ID NO 705
<211> LENGTH: 20
<212> TYPE: DNA
<213> ORGANISM: Homo sapiens

<400> SEQUENCE: 705
ttacgacggg gagttcgttc                                                20

<210> SEQ ID NO 706
<211> LENGTH: 24
<212> TYPE: DNA
<213> ORGANISM: Homo sapiens

<400> SEQUENCE: 706
cttaacaacg ttcgcaaatc acga                                           24
```

```
<210> SEQ ID NO 707
<211> LENGTH: 20
<212> TYPE: DNA
<213> ORGANISM: Homo sapiens

<400> SEQUENCE: 707
acaacgttcg caaatcacga                                               20

<210> SEQ ID NO 708
<211> LENGTH: 19
<212> TYPE: DNA
<213> ORGANISM: Homo sapiens

<400> SEQUENCE: 708
gttcgttatt tcggaattc                                                19

<210> SEQ ID NO 709
<211> LENGTH: 21
<212> TYPE: DNA
<213> ORGANISM: Homo sapiens

<400> SEQUENCE: 709
ccgaccgata aaataataatt c                                            21

<210> SEQ ID NO 710
<211> LENGTH: 20
<212> TYPE: DNA
<213> ORGANISM: Homo sapiens

<400> SEQUENCE: 710
gggagggatt taagcgggag                                               20

<210> SEQ ID NO 711
<211> LENGTH: 20
<212> TYPE: DNA
<213> ORGANISM: Homo sapiens

<400> SEQUENCE: 711
cccccttcac taatcccgac                                               20

<210> SEQ ID NO 712
<211> LENGTH: 18
<212> TYPE: DNA
<213> ORGANISM: Homo sapiens

<400> SEQUENCE: 712
agtgttgaga gtcgacgc                                                 18

<210> SEQ ID NO 713
<211> LENGTH: 20
<212> TYPE: DNA
<213> ORGANISM: Homo sapiens

<400> SEQUENCE: 713
aataaaataa cccgaaccgc                                               20

<210> SEQ ID NO 714
<211> LENGTH: 20
<212> TYPE: DNA
<213> ORGANISM: Homo sapiens

<400> SEQUENCE: 714
gggttacggt ttcgggttgt                                               20
```

```
<210> SEQ ID NO 715
<211> LENGTH: 20
<212> TYPE: DNA
<213> ORGANISM: Homo sapiens

<400> SEQUENCE: 715
cgcgtcgact ctcaacacta                                              20

<210> SEQ ID NO 716
<211> LENGTH: 19
<212> TYPE: DNA
<213> ORGANISM: Homo sapiens

<400> SEQUENCE: 716
ggtcgagtcg agtcgttac                                               19

<210> SEQ ID NO 717
<211> LENGTH: 18
<212> TYPE: DNA
<213> ORGANISM: Homo sapiens

<400> SEQUENCE: 717
aaaacgcctc ctaacgaa                                                18

<210> SEQ ID NO 718
<211> LENGTH: 22
<212> TYPE: DNA
<213> ORGANISM: Homo sapiens

<400> SEQUENCE: 718
attggtcgag tcgagtcgtt ac                                           22

<210> SEQ ID NO 719
<211> LENGTH: 23
<212> TYPE: DNA
<213> ORGANISM: Homo sapiens

<400> SEQUENCE: 719
acaaaaaaac gcctcctaac gaa                                          23

<210> SEQ ID NO 720
<211> LENGTH: 21
<212> TYPE: DNA
<213> ORGANISM: Homo sapiens

<400> SEQUENCE: 720
tatttttggg cgaaggcgtt g                                            21

<210> SEQ ID NO 721
<211> LENGTH: 20
<212> TYPE: DNA
<213> ORGANISM: Homo sapiens

<400> SEQUENCE: 721
gtaacgactc gactcgacca                                              20

<210> SEQ ID NO 722
<211> LENGTH: 18
<212> TYPE: DNA
<213> ORGANISM: Homo sapiens

<400> SEQUENCE: 722
tcggcgtttt cgttttc                                                 18
```

```
<210> SEQ ID NO 723
<211> LENGTH: 22
<212> TYPE: DNA
<213> ORGANISM: Homo sapiens

<400> SEQUENCE: 723
cgacgacaca accataaact tt                                          22

<210> SEQ ID NO 724
<211> LENGTH: 20
<212> TYPE: DNA
<213> ORGANISM: Homo sapiens

<400> SEQUENCE: 724
aaggttttgt agttgcggcg                                             20

<210> SEQ ID NO 725
<211> LENGTH: 18
<212> TYPE: DNA
<213> ORGANISM: Homo sapiens

<400> SEQUENCE: 725
tctcacgcgc aaccgaat                                               18

<210> SEQ ID NO 726
<211> LENGTH: 19
<212> TYPE: DNA
<213> ORGANISM: Homo sapiens

<400> SEQUENCE: 726
gtggagtttt aggtagcgc                                              19

<210> SEQ ID NO 727
<211> LENGTH: 19
<212> TYPE: DNA
<213> ORGANISM: Homo sapiens

<400> SEQUENCE: 727
acccgcgata aactaaacc                                              19

<210> SEQ ID NO 728
<211> LENGTH: 22
<212> TYPE: DNA
<213> ORGANISM: Homo sapiens

<400> SEQUENCE: 728
agggtggagt tttaggtagc gc                                          22

<210> SEQ ID NO 729
<211> LENGTH: 23
<212> TYPE: DNA
<213> ORGANISM: Homo sapiens

<400> SEQUENCE: 729
aacaacccgc gataaactaa acc                                         23

<210> SEQ ID NO 730
<211> LENGTH: 20
<212> TYPE: DNA
<213> ORGANISM: Homo sapiens

<400> SEQUENCE: 730
```

```
tgtagtcgtg gttgtcgtgg                                              20

<210> SEQ ID NO 731
<211> LENGTH: 20
<212> TYPE: DNA
<213> ORGANISM: Homo sapiens

<400> SEQUENCE: 731
ccaaataaac gacgtcccgc                                              20

<210> SEQ ID NO 732
<211> LENGTH: 22
<212> TYPE: DNA
<213> ORGANISM: Homo sapiens

<400> SEQUENCE: 732
attttatagt cgcgttaaaa gc                                           22

<210> SEQ ID NO 733
<211> LENGTH: 20
<212> TYPE: DNA
<213> ORGANISM: Homo sapiens

<400> SEQUENCE: 733
acttttatta ctcgcgatcc                                              20

<210> SEQ ID NO 734
<211> LENGTH: 20
<212> TYPE: DNA
<213> ORGANISM: Homo sapiens

<400> SEQUENCE: 734
ggtagggtga gtttggtcgg                                              20

<210> SEQ ID NO 735
<211> LENGTH: 20
<212> TYPE: DNA
<213> ORGANISM: Homo sapiens

<400> SEQUENCE: 735
cgccgaacca cgtaaaaact                                              20

<210> SEQ ID NO 736
<211> LENGTH: 20
<212> TYPE: DNA
<213> ORGANISM: Homo sapiens

<400> SEQUENCE: 736
atttggggcg tttatgtttc                                              20

<210> SEQ ID NO 737
<211> LENGTH: 18
<212> TYPE: DNA
<213> ORGANISM: Homo sapiens

<400> SEQUENCE: 737
ccctcgaaaa acgactcc                                                18

<210> SEQ ID NO 738
<211> LENGTH: 18
<212> TYPE: DNA
<213> ORGANISM: Homo sapiens

<400> SEQUENCE: 738
```

```
aggggttgta gggtcggg                                                 18

<210> SEQ ID NO 739
<211> LENGTH: 21
<212> TYPE: DNA
<213> ORGANISM: Homo sapiens

<400> SEQUENCE: 739
tttaggggtt gtagggtcgg g                                             21

<210> SEQ ID NO 740
<211> LENGTH: 22
<212> TYPE: DNA
<213> ORGANISM: Homo sapiens

<400> SEQUENCE: 740
attttacatt tccctccccc gc                                            22

<210> SEQ ID NO 741
<211> LENGTH: 18
<212> TYPE: DNA
<213> ORGANISM: Homo sapiens

<400> SEQUENCE: 741
agaataaaag taggcggc                                                 18

<210> SEQ ID NO 742
<211> LENGTH: 20
<212> TYPE: DNA
<213> ORGANISM: Homo sapiens

<400> SEQUENCE: 742
tctcgaaacc aaaataaacg                                               20

<210> SEQ ID NO 743
<211> LENGTH: 20
<212> TYPE: DNA
<213> ORGANISM: Homo sapiens

<400> SEQUENCE: 743
agtaggcggc ggatttgtag                                               20

<210> SEQ ID NO 744
<211> LENGTH: 22
<212> TYPE: DNA
<213> ORGANISM: Homo sapiens

<400> SEQUENCE: 744
ccgaaaatac gcgaaatcaa cc                                            22

<210> SEQ ID NO 745
<211> LENGTH: 19
<212> TYPE: DNA
<213> ORGANISM: Homo sapiens

<400> SEQUENCE: 745
gaggagataa aggtgtcgc                                                19

<210> SEQ ID NO 746
<211> LENGTH: 20
<212> TYPE: DNA
<213> ORGANISM: Homo sapiens
```

<400> SEQUENCE: 746
aacgtaccta acccgaaaac 20

<210> SEQ ID NO 747
<211> LENGTH: 22
<212> TYPE: DNA
<213> ORGANISM: Homo sapiens

<400> SEQUENCE: 747
tcggaggaga taaaggtgtc gc 22

<210> SEQ ID NO 748
<211> LENGTH: 22
<212> TYPE: DNA
<213> ORGANISM: Homo sapiens

<400> SEQUENCE: 748
ccaacgtacc taacccgaaa ac 22

<210> SEQ ID NO 749
<211> LENGTH: 18
<212> TYPE: DNA
<213> ORGANISM: Homo sapiens

<400> SEQUENCE: 749
gacggtttcg gtagggtc 18

<210> SEQ ID NO 750
<211> LENGTH: 20
<212> TYPE: DNA
<213> ORGANISM: Homo sapiens

<400> SEQUENCE: 750
ccgaaccgaa tataaaacga 20

<210> SEQ ID NO 751
<211> LENGTH: 20
<212> TYPE: DNA
<213> ORGANISM: Homo sapiens

<400> SEQUENCE: 751
cggacggttt cggtagggtc 20

<210> SEQ ID NO 752
<211> LENGTH: 23
<212> TYPE: DNA
<213> ORGANISM: Homo sapiens

<400> SEQUENCE: 752
gcgccgaacc gaatataaaa cga 23

<210> SEQ ID NO 753
<211> LENGTH: 19
<212> TYPE: DNA
<213> ORGANISM: Homo sapiens

<400> SEQUENCE: 753
ttaggttcgt aaagagggc 19

<210> SEQ ID NO 754
<211> LENGTH: 19
<212> TYPE: DNA
<213> ORGANISM: Homo sapiens

```
<400> SEQUENCE: 754
ttaaaaccac gtccgaata                                              19

<210> SEQ ID NO 755
<211> LENGTH: 20
<212> TYPE: DNA
<213> ORGANISM: Homo sapiens

<400> SEQUENCE: 755
tttcgggcgg gagttatagg                                             20

<210> SEQ ID NO 756
<211> LENGTH: 20
<212> TYPE: DNA
<213> ORGANISM: Homo sapiens

<400> SEQUENCE: 756
acgcgctcta aactcaaccg                                             20

<210> SEQ ID NO 757
<211> LENGTH: 26
<212> TYPE: DNA
<213> ORGANISM: Homo sapiens

<400> SEQUENCE: 757
gcgcgtgggg ttcgtagcgt tttaag                                      26

<210> SEQ ID NO 758
<211> LENGTH: 25
<212> TYPE: DNA
<213> ORGANISM: Homo sapiens

<400> SEQUENCE: 758
ttacccgaaa caccccgcgc ccttc                                       25

<210> SEQ ID NO 759
<211> LENGTH: 28
<212> TYPE: DNA
<213> ORGANISM: Homo sapiens

<400> SEQUENCE: 759
agatacggag atttagcgcg agatcggt                                    28

<210> SEQ ID NO 760
<211> LENGTH: 28
<212> TYPE: DNA
<213> ORGANISM: Homo sapiens

<400> SEQUENCE: 760
aaattaaccg ccgaacactc acaatacg                                    28

<210> SEQ ID NO 761
<211> LENGTH: 28
<212> TYPE: DNA
<213> ORGANISM: Homo sapiens

<400> SEQUENCE: 761
ttgtagtgtc gcgttgcgag tcgattgt                                    28

<210> SEQ ID NO 762
<211> LENGTH: 29
<212> TYPE: DNA
```

<213> ORGANISM: Homo sapiens

<400> SEQUENCE: 762
acaataacgt aacgcccata aaccgaacg                29

<210> SEQ ID NO 763
<211> LENGTH: 28
<212> TYPE: DNA
<213> ORGANISM: Homo sapiens

<400> SEQUENCE: 763
gaggacgggt tgaatcgtgg tttgttgg                 28

<210> SEQ ID NO 764
<211> LENGTH: 28
<212> TYPE: DNA
<213> ORGANISM: Homo sapiens

<400> SEQUENCE: 764
actacgataa tcaaaacgct ccacgcga                 28

<210> SEQ ID NO 765
<211> LENGTH: 27
<212> TYPE: DNA
<213> ORGANISM: Homo sapiens

<400> SEQUENCE: 765
gtgcgcgttt tagtagggcg agaatgg                  27

<210> SEQ ID NO 766
<211> LENGTH: 28
<212> TYPE: DNA
<213> ORGANISM: Homo sapiens

<400> SEQUENCE: 766
cgaaaaccaa atccgaacca ccgtctcc                 28

<210> SEQ ID NO 767
<211> LENGTH: 28
<212> TYPE: DNA
<213> ORGANISM: Homo sapiens

<400> SEQUENCE: 767
tgatttgggt ggatgtagag gttgtggt                 28

<210> SEQ ID NO 768
<211> LENGTH: 28
<212> TYPE: DNA
<213> ORGANISM: Homo sapiens

<400> SEQUENCE: 768
tttcgaataa cgctactccg aaccgcga                 28

<210> SEQ ID NO 769
<211> LENGTH: 28
<212> TYPE: DNA
<213> ORGANISM: Homo sapiens

<400> SEQUENCE: 769
ttgagagtag ggattgtggt gcgtcgtc                 28

<210> SEQ ID NO 770
<211> LENGTH: 28

```
<212> TYPE: DNA
<213> ORGANISM: Homo sapiens

<400> SEQUENCE: 770
ctaactcccg aacgctacat tcgctcca                                28

<210> SEQ ID NO 771
<211> LENGTH: 27
<212> TYPE: DNA
<213> ORGANISM: Homo sapiens

<400> SEQUENCE: 771
ggttgtggtg agtttggttt acgggcg                                 27

<210> SEQ ID NO 772
<211> LENGTH: 26
<212> TYPE: DNA
<213> ORGANISM: Homo sapiens

<400> SEQUENCE: 772
cgtaaaacgc gaccaccgcc aacata                                  26

<210> SEQ ID NO 773
<211> LENGTH: 28
<212> TYPE: DNA
<213> ORGANISM: Homo sapiens

<400> SEQUENCE: 773
gggaggttat tcgtaggatt tggcgcgg                                28

<210> SEQ ID NO 774
<211> LENGTH: 28
<212> TYPE: DNA
<213> ORGANISM: Homo sapiens

<400> SEQUENCE: 774
atcctaacga ctacgcacta cttccgca                                28

<210> SEQ ID NO 775
<211> LENGTH: 24
<212> TYPE: DNA
<213> ORGANISM: Homo sapiens

<400> SEQUENCE: 775
gagttcgttt agttcgtcgg cgtc                                    24

<210> SEQ ID NO 776
<211> LENGTH: 27
<212> TYPE: DNA
<213> ORGANISM: Homo sapiens

<400> SEQUENCE: 776
aaccccgata aactccgata acgacct                                 27

<210> SEQ ID NO 777
<211> LENGTH: 28
<212> TYPE: DNA
<213> ORGANISM: Homo sapiens

<400> SEQUENCE: 777
agagttgggg gcggtatagt tagggtgt                                28

<210> SEQ ID NO 778
```

```
<211> LENGTH: 28
<212> TYPE: DNA
<213> ORGANISM: Homo sapiens

<400> SEQUENCE: 778
ttcaatccct acgaccccaa cgcctaaa                                          28

<210> SEQ ID NO 779
<211> LENGTH: 28
<212> TYPE: DNA
<213> ORGANISM: Homo sapiens

<400> SEQUENCE: 779
cgtggatacg agttttggcg gcgattat                                          28

<210> SEQ ID NO 780
<211> LENGTH: 28
<212> TYPE: DNA
<213> ORGANISM: Homo sapiens

<400> SEQUENCE: 780
gccaccaacc ctacctcctt ccatatcc                                          28

<210> SEQ ID NO 781
<211> LENGTH: 28
<212> TYPE: DNA
<213> ORGANISM: Homo sapiens

<400> SEQUENCE: 781
tttttcggtt tgagttatcg tggcggga                                          28

<210> SEQ ID NO 782
<211> LENGTH: 28
<212> TYPE: DNA
<213> ORGANISM: Homo sapiens

<400> SEQUENCE: 782
cgaaccgtac ttccaaccaa acgcaact                                          28

<210> SEQ ID NO 783
<211> LENGTH: 28
<212> TYPE: DNA
<213> ORGANISM: Homo sapiens

<400> SEQUENCE: 783
taggaagggg tcgatgttgg tttgggtt                                          28

<210> SEQ ID NO 784
<211> LENGTH: 28
<212> TYPE: DNA
<213> ORGANISM: Homo sapiens

<400> SEQUENCE: 784
tctcaccaac tcccatcgaa ttcgcaca                                          28

<210> SEQ ID NO 785
<211> LENGTH: 28
<212> TYPE: DNA
<213> ORGANISM: Homo sapiens

<400> SEQUENCE: 785
gttttggttt cgtttcggag cgcgtaga                                          28
```

```
<210> SEQ ID NO 786
<211> LENGTH: 28
<212> TYPE: DNA
<213> ORGANISM: Homo sapiens

<400> SEQUENCE: 786
tttctctacc gactcaactc cccctccc                                        28

<210> SEQ ID NO 787
<211> LENGTH: 28
<212> TYPE: DNA
<213> ORGANISM: Homo sapiens

<400> SEQUENCE: 787
tcggttgcgt aaatcgcgtt tttggttg                                        28

<210> SEQ ID NO 788
<211> LENGTH: 28
<212> TYPE: DNA
<213> ORGANISM: Homo sapiens

<400> SEQUENCE: 788
ttctcgataa tatctccgtc gcctccgc                                        28

<210> SEQ ID NO 789
<211> LENGTH: 27
<212> TYPE: DNA
<213> ORGANISM: Homo sapiens

<400> SEQUENCE: 789
gtttaggggt ggaggtcggg gttttga                                         27

<210> SEQ ID NO 790
<211> LENGTH: 28
<212> TYPE: DNA
<213> ORGANISM: Homo sapiens

<400> SEQUENCE: 790
ccgaaccccg cgcaaataaa aacaacct                                        28

<210> SEQ ID NO 791
<211> LENGTH: 28
<212> TYPE: DNA
<213> ORGANISM: Homo sapiens

<400> SEQUENCE: 791
ggggcgcgtt tttatggaaa gttagggt                                        28

<210> SEQ ID NO 792
<211> LENGTH: 28
<212> TYPE: DNA
<213> ORGANISM: Homo sapiens

<400> SEQUENCE: 792
ctacgcccta aaacacgcct cgacttct                                        28

<210> SEQ ID NO 793
<211> LENGTH: 28
<212> TYPE: DNA
<213> ORGANISM: Homo sapiens

<400> SEQUENCE: 793
tgtgcgaaag agacgcgggg tttagtta                                        28
```

```
<210> SEQ ID NO 794
<211> LENGTH: 28
<212> TYPE: DNA
<213> ORGANISM: Homo sapiens

<400> SEQUENCE: 794
cccgtaatcg ctaaaacatc cgcccttca                                        28

<210> SEQ ID NO 795
<211> LENGTH: 26
<212> TYPE: DNA
<213> ORGANISM: Homo sapiens

<400> SEQUENCE: 795
cgtcgggcga tgttggtttg ttcgtg                                           26

<210> SEQ ID NO 796
<211> LENGTH: 29
<212> TYPE: DNA
<213> ORGANISM: Homo sapiens

<400> SEQUENCE: 796
gcgacgctcc accgtaaacc caatattta                                        29

<210> SEQ ID NO 797
<211> LENGTH: 27
<212> TYPE: DNA
<213> ORGANISM: Homo sapiens

<400> SEQUENCE: 797
cggggagggt cgagggtttt gtttgag                                          27

<210> SEQ ID NO 798
<211> LENGTH: 28
<212> TYPE: DNA
<213> ORGANISM: Homo sapiens

<400> SEQUENCE: 798
gcgtcccaaa cttcattcaa ccgacgac                                         28

<210> SEQ ID NO 799
<211> LENGTH: 28
<212> TYPE: DNA
<213> ORGANISM: Homo sapiens

<400> SEQUENCE: 799
gcggacgtag taatggatta aacggga                                          28

<210> SEQ ID NO 800
<211> LENGTH: 28
<212> TYPE: DNA
<213> ORGANISM: Homo sapiens

<400> SEQUENCE: 800
aaatccgact ccctacactc ccgacttt                                         28

<210> SEQ ID NO 801
<211> LENGTH: 29
<212> TYPE: DNA
<213> ORGANISM: Homo sapiens

<400> SEQUENCE: 801
gggggttgtg ttagttgttt gtttagcga                                        29
```

<210> SEQ ID NO 802
<211> LENGTH: 28
<212> TYPE: DNA
<213> ORGANISM: Homo sapiens

<400> SEQUENCE: 802
cgaaactatt tcccgccaaa ccgaaccc                                    28

<210> SEQ ID NO 803
<211> LENGTH: 28
<212> TYPE: DNA
<213> ORGANISM: Homo sapiens

<400> SEQUENCE: 803
tttcgggcgg gagtatcggg ttttgtag                                    28

<210> SEQ ID NO 804
<211> LENGTH: 28
<212> TYPE: DNA
<213> ORGANISM: Homo sapiens

<400> SEQUENCE: 804
gctcctttac cccttctcga ccaactcc                                    28

<210> SEQ ID NO 805
<211> LENGTH: 30
<212> TYPE: DNA
<213> ORGANISM: Homo sapiens

<400> SEQUENCE: 805
ttacggattt tatttgtatt cggaatcgta                                  30

<210> SEQ ID NO 806
<211> LENGTH: 29
<212> TYPE: DNA
<213> ORGANISM: Homo sapiens

<400> SEQUENCE: 806
acgcatcaaa ctcgacacaa aatttcatc                                   29

<210> SEQ ID NO 807
<211> LENGTH: 28
<212> TYPE: DNA
<213> ORGANISM: Homo sapiens

<400> SEQUENCE: 807
ggtgttttcg taagacgggg tagtgggt                                    28

<210> SEQ ID NO 808
<211> LENGTH: 28
<212> TYPE: DNA
<213> ORGANISM: Homo sapiens

<400> SEQUENCE: 808
ttctcctccg ctaaaaatcc gaatacga                                    28

<210> SEQ ID NO 809
<211> LENGTH: 28
<212> TYPE: DNA
<213> ORGANISM: Homo sapiens

<400> SEQUENCE: 809

-continued agggattgta tttcgaggtg gtcgaggt					28

<210> SEQ ID NO 810
<211> LENGTH: 28
<212> TYPE: DNA
<213> ORGANISM: Homo sapiens

<400> SEQUENCE: 810
ccgacaaatc gaaaccttcg cccgaaac					28

<210> SEQ ID NO 811
<211> LENGTH: 28
<212> TYPE: DNA
<213> ORGANISM: Homo sapiens

<400> SEQUENCE: 811
tcgcgggtta taaatatttg gttgcggc					28

<210> SEQ ID NO 812
<211> LENGTH: 28
<212> TYPE: DNA
<213> ORGANISM: Homo sapiens

<400> SEQUENCE: 812
gaccgccact acctcgaaaa catttccc					28

<210> SEQ ID NO 813
<211> LENGTH: 28
<212> TYPE: DNA
<213> ORGANISM: Homo sapiens

<400> SEQUENCE: 813
ggtaacggaa aagcgcggga attataga					28

<210> SEQ ID NO 814
<211> LENGTH: 26
<212> TYPE: DNA
<213> ORGANISM: Homo sapiens

<400> SEQUENCE: 814
cccacaacct atcccccgtc caaaaa					26

<210> SEQ ID NO 815
<211> LENGTH: 28
<212> TYPE: DNA
<213> ORGANISM: Homo sapiens

<400> SEQUENCE: 815
ttttgtacgt tgggttacgg gggtttgg					28

<210> SEQ ID NO 816
<211> LENGTH: 28
<212> TYPE: DNA
<213> ORGANISM: Homo sapiens

<400> SEQUENCE: 816
taaacgcgat aaacccctac gaccccca					28

<210> SEQ ID NO 817
<211> LENGTH: 28
<212> TYPE: DNA
<213> ORGANISM: Homo sapiens

<400> SEQUENCE: 817

```
tatcggtttt cgtagttgcg ggaggagg                                              28

<210> SEQ ID NO 818
<211> LENGTH: 28
<212> TYPE: DNA
<213> ORGANISM: Homo sapiens

<400> SEQUENCE: 818
ccgaataaat accaaactcg cccgacgc                                              28

<210> SEQ ID NO 819
<211> LENGTH: 28
<212> TYPE: DNA
<213> ORGANISM: Homo sapiens

<400> SEQUENCE: 819
cgggtagagg ggaggtagga attggaga                                              28

<210> SEQ ID NO 820
<211> LENGTH: 28
<212> TYPE: DNA
<213> ORGANISM: Homo sapiens

<400> SEQUENCE: 820
ccgaataaac gtcacccta cacaccgc                                               28

<210> SEQ ID NO 821
<211> LENGTH: 28
<212> TYPE: DNA
<213> ORGANISM: Homo sapiens

<400> SEQUENCE: 821
ttttgcggtt aggtgaaggc gtagaggt                                              28

<210> SEQ ID NO 822
<211> LENGTH: 28
<212> TYPE: DNA
<213> ORGANISM: Homo sapiens

<400> SEQUENCE: 822
gaccgaatac cccgctttct ctctcgac                                              28

<210> SEQ ID NO 823
<211> LENGTH: 27
<212> TYPE: DNA
<213> ORGANISM: Homo sapiens

<400> SEQUENCE: 823
aggagtagta ttgcgagggt ggagggt                                               27

<210> SEQ ID NO 824
<211> LENGTH: 28
<212> TYPE: DNA
<213> ORGANISM: Homo sapiens

<400> SEQUENCE: 824
taaacccgaa aaacaacgcc aatcccgc                                              28

<210> SEQ ID NO 825
<211> LENGTH: 28
<212> TYPE: DNA
<213> ORGANISM: Homo sapiens
```

```
<400> SEQUENCE: 825
ggggatttgt tgtagagtcg taggagaa                                              28

<210> SEQ ID NO 826
<211> LENGTH: 25
<212> TYPE: DNA
<213> ORGANISM: Homo sapiens

<400> SEQUENCE: 826
ccgcatccca cccttttaaaa ctcta                                                25

<210> SEQ ID NO 827
<211> LENGTH: 28
<212> TYPE: DNA
<213> ORGANISM: Homo sapiens

<400> SEQUENCE: 827
tatgggttgc gtcgagggta aggtagtg                                              28

<210> SEQ ID NO 828
<211> LENGTH: 28
<212> TYPE: DNA
<213> ORGANISM: Homo sapiens

<400> SEQUENCE: 828
tacgacgacc atcgccgttc ttaccttt                                              28

<210> SEQ ID NO 829
<211> LENGTH: 28
<212> TYPE: DNA
<213> ORGANISM: Homo sapiens

<400> SEQUENCE: 829
aaatttggat tgggggaggg acgaggtt                                              28

<210> SEQ ID NO 830
<211> LENGTH: 28
<212> TYPE: DNA
<213> ORGANISM: Homo sapiens

<400> SEQUENCE: 830
cttcgcaacc gaactactca cccccgac                                              28

<210> SEQ ID NO 831
<211> LENGTH: 28
<212> TYPE: DNA
<213> ORGANISM: Homo sapiens

<400> SEQUENCE: 831
ggtcgttgga gtggtcgttt cggtttag                                              28

<210> SEQ ID NO 832
<211> LENGTH: 28
<212> TYPE: DNA
<213> ORGANISM: Homo sapiens

<400> SEQUENCE: 832
cctcaaaccc ccgaacgcgc taaataaa                                              28

<210> SEQ ID NO 833
<211> LENGTH: 28
<212> TYPE: DNA
<213> ORGANISM: Homo sapiens
```

```
<400> SEQUENCE: 833
gttcggggag ggagggagat tcgttttg                                        28

<210> SEQ ID NO 834
<211> LENGTH: 28
<212> TYPE: DNA
<213> ORGANISM: Homo sapiens

<400> SEQUENCE: 834
aactcccgac tttaacctcc caacccaa                                        28

<210> SEQ ID NO 835
<211> LENGTH: 28
<212> TYPE: DNA
<213> ORGANISM: Homo sapiens

<400> SEQUENCE: 835
gttgtagggg tgtttggtcg ggttggta                                        28

<210> SEQ ID NO 836
<211> LENGTH: 28
<212> TYPE: DNA
<213> ORGANISM: Homo sapiens

<400> SEQUENCE: 836
atcaactact ccgtacccca cgtaaccg                                        28

<210> SEQ ID NO 837
<211> LENGTH: 25
<212> TYPE: DNA
<213> ORGANISM: Homo sapiens

<400> SEQUENCE: 837
agtcggggtt ggttggtgga agagg                                           25

<210> SEQ ID NO 838
<211> LENGTH: 28
<212> TYPE: DNA
<213> ORGANISM: Homo sapiens

<400> SEQUENCE: 838
ccctctcaac tcgattcaaa attccccc                                        28

<210> SEQ ID NO 839
<211> LENGTH: 28
<212> TYPE: DNA
<213> ORGANISM: Homo sapiens

<400> SEQUENCE: 839
aaagtaataa gtggtttcgg gcggagtc                                        28

<210> SEQ ID NO 840
<211> LENGTH: 28
<212> TYPE: DNA
<213> ORGANISM: Homo sapiens

<400> SEQUENCE: 840
accccgcata cctacgaaaa cgaaaacc                                        28

<210> SEQ ID NO 841
<211> LENGTH: 27
<212> TYPE: DNA
```

<213> ORGANISM: Homo sapiens

<400> SEQUENCE: 841
cgggattatg gagggtaga gcggtcg                                27

<210> SEQ ID NO 842
<211> LENGTH: 28
<212> TYPE: DNA
<213> ORGANISM: Homo sapiens

<400> SEQUENCE: 842
acgtccttaa cgaacaccta caacaacg                              28

<210> SEQ ID NO 843
<211> LENGTH: 28
<212> TYPE: DNA
<213> ORGANISM: Homo sapiens

<400> SEQUENCE: 843
aggttttgta gtagtaggcg gacgaggc                              28

<210> SEQ ID NO 844
<211> LENGTH: 28
<212> TYPE: DNA
<213> ORGANISM: Homo sapiens

<400> SEQUENCE: 844
acgaatacga aacccgaaac cgaaacgc                              28

<210> SEQ ID NO 845
<211> LENGTH: 25
<212> TYPE: DNA
<213> ORGANISM: Homo sapiens

<400> SEQUENCE: 845
cgtggtatag ttaatcgcgc ggcgt                                 25

<210> SEQ ID NO 846
<211> LENGTH: 28
<212> TYPE: DNA
<213> ORGANISM: Homo sapiens

<400> SEQUENCE: 846
tacaacccca acgccataac tcgccaat                              28

<210> SEQ ID NO 847
<211> LENGTH: 28
<212> TYPE: DNA
<213> ORGANISM: Homo sapiens

<400> SEQUENCE: 847
tagcggggat ttattagggg agaggtgg                              28

<210> SEQ ID NO 848
<211> LENGTH: 28
<212> TYPE: DNA
<213> ORGANISM: Homo sapiens

<400> SEQUENCE: 848
atcacctacg aacactatcc ctcacccg                              28

<210> SEQ ID NO 849
<211> LENGTH: 28

```
<212> TYPE: DNA
<213> ORGANISM: Homo sapiens

<400> SEQUENCE: 849
gcggaatagt tcgcggtttt ggaatgtt                                    28

<210> SEQ ID NO 850
<211> LENGTH: 28
<212> TYPE: DNA
<213> ORGANISM: Homo sapiens

<400> SEQUENCE: 850
aaacgtttcc gctccccgaa aaacgaat                                    28

<210> SEQ ID NO 851
<211> LENGTH: 28
<212> TYPE: DNA
<213> ORGANISM: Homo sapiens

<400> SEQUENCE: 851
ggagatagtt ttgagagggg gaggtcgc                                    28

<210> SEQ ID NO 852
<211> LENGTH: 28
<212> TYPE: DNA
<213> ORGANISM: Homo sapiens

<400> SEQUENCE: 852
cgctacctac gccgatcgta aatcccaa                                    28

<210> SEQ ID NO 853
<211> LENGTH: 28
<212> TYPE: DNA
<213> ORGANISM: Homo sapiens

<400> SEQUENCE: 853
gaatggttgc gatatggggt tcgacgga                                    28

<210> SEQ ID NO 854
<211> LENGTH: 28
<212> TYPE: DNA
<213> ORGANISM: Homo sapiens

<400> SEQUENCE: 854
cgcgatccaa aaacgcaaat cctcgttc                                    28

<210> SEQ ID NO 855
<211> LENGTH: 28
<212> TYPE: DNA
<213> ORGANISM: Homo sapiens

<400> SEQUENCE: 855
ggttttggtc gagatttggg cgggtgag                                    28

<210> SEQ ID NO 856
<211> LENGTH: 28
<212> TYPE: DNA
<213> ORGANISM: Homo sapiens

<400> SEQUENCE: 856
cccgaatcct acgccccaac caaataaa                                    28

<210> SEQ ID NO 857
```

```
<211> LENGTH: 28
<212> TYPE: DNA
<213> ORGANISM: Homo sapiens

<400> SEQUENCE: 857
tgagtgattt cggttcgggg cgtagatt                                          28

<210> SEQ ID NO 858
<211> LENGTH: 29
<212> TYPE: DNA
<213> ORGANISM: Homo sapiens

<400> SEQUENCE: 858
cgaaaatctc tacaaatccc gcaacctcg                                         29

<210> SEQ ID NO 859
<211> LENGTH: 28
<212> TYPE: DNA
<213> ORGANISM: Homo sapiens

<400> SEQUENCE: 859
atggtttcgg ggtgtttagc ggcgattg                                          28

<210> SEQ ID NO 860
<211> LENGTH: 28
<212> TYPE: DNA
<213> ORGANISM: Homo sapiens

<400> SEQUENCE: 860
aacgaaaccg aacgaacccc aatccgta                                          28

<210> SEQ ID NO 861
<211> LENGTH: 27
<212> TYPE: DNA
<213> ORGANISM: Homo sapiens

<400> SEQUENCE: 861
gagtcggagt gagcgttaag tgagggg                                           27

<210> SEQ ID NO 862
<211> LENGTH: 28
<212> TYPE: DNA
<213> ORGANISM: Homo sapiens

<400> SEQUENCE: 862
tccctccgac cgacccaaaa taactacg                                          28

<210> SEQ ID NO 863
<211> LENGTH: 28
<212> TYPE: DNA
<213> ORGANISM: Homo sapiens

<400> SEQUENCE: 863
ttcgttgttc gttttgggta aagggaag                                          28

<210> SEQ ID NO 864
<211> LENGTH: 28
<212> TYPE: DNA
<213> ORGANISM: Homo sapiens

<400> SEQUENCE: 864
aaactcgctt cccaaacttc taaaaatc                                          28
```

<210> SEQ ID NO 865
<211> LENGTH: 28
<212> TYPE: DNA
<213> ORGANISM: Homo sapiens

<400> SEQUENCE: 865
ggggaggcgt cgagttcgga gtttatta                                28

<210> SEQ ID NO 866
<211> LENGTH: 28
<212> TYPE: DNA
<213> ORGANISM: Homo sapiens

<400> SEQUENCE: 866
aaaactcgct aaacgtccca accgcatc                                28

<210> SEQ ID NO 867
<211> LENGTH: 30
<212> TYPE: DNA
<213> ORGANISM: Homo sapiens

<400> SEQUENCE: 867
cgggtattgt tggtttaggt tgtagtaggt                              30

<210> SEQ ID NO 868
<211> LENGTH: 28
<212> TYPE: DNA
<213> ORGANISM: Homo sapiens

<400> SEQUENCE: 868
cgaccctaac caaccccgaa actcgaaa                                28

<210> SEQ ID NO 869
<211> LENGTH: 28
<212> TYPE: DNA
<213> ORGANISM: Homo sapiens

<400> SEQUENCE: 869
agggtagaaa ggaagcggta gtagaaaa                                28

<210> SEQ ID NO 870
<211> LENGTH: 28
<212> TYPE: DNA
<213> ORGANISM: Homo sapiens

<400> SEQUENCE: 870
acaacaactc ctcccttcga acccaacc                                28

<210> SEQ ID NO 871
<211> LENGTH: 28
<212> TYPE: DNA
<213> ORGANISM: Homo sapiens

<400> SEQUENCE: 871
tgtgggaggg aagggaaatc gagattgg                                28

<210> SEQ ID NO 872
<211> LENGTH: 29
<212> TYPE: DNA
<213> ORGANISM: Homo sapiens

<400> SEQUENCE: 872
acgacaaaac gaaacccaca atcctaccc                               29

```
<210> SEQ ID NO 873
<211> LENGTH: 28
<212> TYPE: DNA
<213> ORGANISM: Homo sapiens

<400> SEQUENCE: 873
attcggattg gttagttttt gcggaagt                                      28

<210> SEQ ID NO 874
<211> LENGTH: 28
<212> TYPE: DNA
<213> ORGANISM: Homo sapiens

<400> SEQUENCE: 874
ttcgccacgc aacaacctaa aacgctac                                      28

<210> SEQ ID NO 875
<211> LENGTH: 28
<212> TYPE: DNA
<213> ORGANISM: Homo sapiens

<400> SEQUENCE: 875
ggttgcggcg tttatttagc gggaagtc                                      28

<210> SEQ ID NO 876
<211> LENGTH: 26
<212> TYPE: DNA
<213> ORGANISM: Homo sapiens

<400> SEQUENCE: 876
ctcgccgaac ccgcgacgaa atctac                                        26

<210> SEQ ID NO 877
<211> LENGTH: 28
<212> TYPE: DNA
<213> ORGANISM: Homo sapiens

<400> SEQUENCE: 877
tagaggaatt taaagtgtgg gttggggg                                      28

<210> SEQ ID NO 878
<211> LENGTH: 28
<212> TYPE: DNA
<213> ORGANISM: Homo sapiens

<400> SEQUENCE: 878
accaacttct ctccctttac gccttttt                                      28

<210> SEQ ID NO 879
<211> LENGTH: 29
<212> TYPE: DNA
<213> ORGANISM: Homo sapiens

<400> SEQUENCE: 879
tgggttaagt atttgttatg tgttacgga                                     29

<210> SEQ ID NO 880
<211> LENGTH: 24
<212> TYPE: DNA
<213> ORGANISM: Homo sapiens

<400> SEQUENCE: 880
cgctatccac ccgaatacgc aact                                          24
```

<210> SEQ ID NO 881
<211> LENGTH: 26
<212> TYPE: DNA
<213> ORGANISM: Homo sapiens

<400> SEQUENCE: 881
gcgcggcgtt ttgttatcgg tggatt                                  26

<210> SEQ ID NO 882
<211> LENGTH: 30
<212> TYPE: DNA
<213> ORGANISM: Homo sapiens

<400> SEQUENCE: 882
tctaaaataa cccgcaccaa acaaactaca                              30

<210> SEQ ID NO 883
<211> LENGTH: 28
<212> TYPE: DNA
<213> ORGANISM: Homo sapiens

<400> SEQUENCE: 883
ttataaaggt cggaagcggt tacggggg                                28

<210> SEQ ID NO 884
<211> LENGTH: 28
<212> TYPE: DNA
<213> ORGANISM: Homo sapiens

<400> SEQUENCE: 884 aaccccttc gctcccttcc taaaacga                                 28

<210> SEQ ID NO 885
<211> LENGTH: 28
<212> TYPE: DNA
<213> ORGANISM: Homo sapiens

<400> SEQUENCE: 885
gtatggttgc gatttggggt tggaaggg                                28

<210> SEQ ID NO 886
<211> LENGTH: 28
<212> TYPE: DNA
<213> ORGANISM: Homo sapiens

<400> SEQUENCE: 886
gccgcgatcc aaaaacgcaa atcctaat                                28

<210> SEQ ID NO 887
<211> LENGTH: 27
<212> TYPE: DNA
<213> ORGANISM: Homo sapiens

<400> SEQUENCE: 887
tagggaatgt ttggttgcga tttgggg                                 27

<210> SEQ ID NO 888
<211> LENGTH: 28
<212> TYPE: DNA
<213> ORGANISM: Homo sapiens

<400> SEQUENCE: 888

-continued

```
tccttaccgt cgtaaacata ctactcat                              28

<210> SEQ ID NO 889
<211> LENGTH: 25
<212> TYPE: DNA
<213> ORGANISM: Homo sapiens

<400> SEQUENCE: 889
gcgtaagtgc gaggttgtcg gtagc                                 25

<210> SEQ ID NO 890
<211> LENGTH: 26
<212> TYPE: DNA
<213> ORGANISM: Homo sapiens

<400> SEQUENCE: 890
tttcccgcaa ctctttcccc ctctct                                26

<210> SEQ ID NO 891
<211> LENGTH: 28
<212> TYPE: DNA
<213> ORGANISM: Homo sapiens

<400> SEQUENCE: 891
tgcggttaaa gaattcgttc gcgttcgg                              28

<210> SEQ ID NO 892
<211> LENGTH: 28
<212> TYPE: DNA
<213> ORGANISM: Homo sapiens

<400> SEQUENCE: 892
ctaaacgctc ccgcgaaacc tccaaatc                              28

<210> SEQ ID NO 893
<211> LENGTH: 28
<212> TYPE: DNA
<213> ORGANISM: Homo sapiens

<400> SEQUENCE: 893
ttcgggtatt ttgaggttgt cgtcggga                              28

<210> SEQ ID NO 894
<211> LENGTH: 26
<212> TYPE: DNA
<213> ORGANISM: Homo sapiens

<400> SEQUENCE: 894
gacgacgacg cgtccgacga atttta                                26

<210> SEQ ID NO 895
<211> LENGTH: 28
<212> TYPE: DNA
<213> ORGANISM: Homo sapiens

<400> SEQUENCE: 895
gttttggtcg gggcgtcgtg gatatttt                              28

<210> SEQ ID NO 896
<211> LENGTH: 28
<212> TYPE: DNA
<213> ORGANISM: Homo sapiens

<400> SEQUENCE: 896
```
aaaaaccaac taaaccccctt cccgctcg                                              28

<210> SEQ ID NO 897
<211> LENGTH: 28
<212> TYPE: DNA
<213> ORGANISM: Homo sapiens

<400> SEQUENCE: 897
gtgtggaaag ggtttggcgg ttgttagg                                               28

<210> SEQ ID NO 898
<211> LENGTH: 28
<212> TYPE: DNA
<213> ORGANISM: Homo sapiens

<400> SEQUENCE: 898
ctcgccaaat acgtccaccc aaaaacga                                               28

<210> SEQ ID NO 899
<211> LENGTH: 28
<212> TYPE: DNA
<213> ORGANISM: Homo sapiens

<400> SEQUENCE: 899
taggagggga cgtagagttt acggcgaa                                               28

<210> SEQ ID NO 900
<211> LENGTH: 27
<212> TYPE: DNA
<213> ORGANISM: Homo sapiens

<400> SEQUENCE: 900
gaatacccga cccgacccat ccatcac                                                27

<210> SEQ ID NO 901
<211> LENGTH: 28
<212> TYPE: DNA
<213> ORGANISM: Homo sapiens

<400> SEQUENCE: 901
tgcgtttgta ggagaagtcg ggttggtt                                               28

<210> SEQ ID NO 902
<211> LENGTH: 28
<212> TYPE: DNA
<213> ORGANISM: Homo sapiens

<400> SEQUENCE: 902
actcttcctc gcctcgcact actaccta                                               28

<210> SEQ ID NO 903
<211> LENGTH: 28
<212> TYPE: DNA
<213> ORGANISM: Homo sapiens

<400> SEQUENCE: 903
gtgcgattcg gggtttcgaa aagttggt                                               28

<210> SEQ ID NO 904
<211> LENGTH: 28
<212> TYPE: DNA
<213> ORGANISM: Homo sapiens

<400> SEQUENCE: 904
gaaactacgc gcgaacttac aacgcctc        28

<210> SEQ ID NO 905
<211> LENGTH: 22
<212> TYPE: DNA
<213> ORGANISM: Homo sapiens

<400> SEQUENCE: 905
gagcgtagag cgttgagcgg gg        22

<210> SEQ ID NO 906
<211> LENGTH: 22
<212> TYPE: DNA
<213> ORGANISM: Homo sapiens

<400> SEQUENCE: 906
cgccgccgaa taacacgccc ac        22

<210> SEQ ID NO 907
<211> LENGTH: 28
<212> TYPE: DNA
<213> ORGANISM: Homo sapiens

<400> SEQUENCE: 907
agcggggatt ttcggagttg gagagttt        28

<210> SEQ ID NO 908
<211> LENGTH: 28
<212> TYPE: DNA
<213> ORGANISM: Homo sapiens

<400> SEQUENCE: 908
ctccatccgc ccgacctaac cctaaaaa        28

<210> SEQ ID NO 909
<211> LENGTH: 28
<212> TYPE: DNA
<213> ORGANISM: Homo sapiens

<400> SEQUENCE: 909
gggaagtggc gtagtgggcg tttgtatc        28

<210> SEQ ID NO 910
<211> LENGTH: 28
<212> TYPE: DNA
<213> ORGANISM: Homo sapiens

<400> SEQUENCE: 910
tacctccaac gaccacgccc acaaaata        28

<210> SEQ ID NO 911
<211> LENGTH: 28
<212> TYPE: DNA
<213> ORGANISM: Homo sapiens

<400> SEQUENCE: 911
tggagcgttg agtcgaagtt ttgatttt        28

<210> SEQ ID NO 912
<211> LENGTH: 28
<212> TYPE: DNA
<213> ORGANISM: Homo sapiens

```
<400> SEQUENCE: 912
tcttacccga actttaaccc caaccgct                                              28

<210> SEQ ID NO 913
<211> LENGTH: 28
<212> TYPE: DNA
<213> ORGANISM: Homo sapiens

<400> SEQUENCE: 913
ggttgggagt tcggagttgt agtagagg                                              28

<210> SEQ ID NO 914
<211> LENGTH: 28
<212> TYPE: DNA
<213> ORGANISM: Homo sapiens

<400> SEQUENCE: 914
ctttaaccga ttcaaacaac aaacgcct                                              28

<210> SEQ ID NO 915
<211> LENGTH: 26
<212> TYPE: DNA
<213> ORGANISM: Homo sapiens

<400> SEQUENCE: 915
gtagggcgcg gggtttcgtt agtttc                                                26

<210> SEQ ID NO 916
<211> LENGTH: 28
<212> TYPE: DNA
<213> ORGANISM: Homo sapiens

<400> SEQUENCE: 916
atctaccgtt ctatcctcgt aaccgccg                                              28

<210> SEQ ID NO 917
<211> LENGTH: 28
<212> TYPE: DNA
<213> ORGANISM: Homo sapiens

<400> SEQUENCE: 917
tcgtttggga gggatcgttt ttgggaga                                              28

<210> SEQ ID NO 918
<211> LENGTH: 28
<212> TYPE: DNA
<213> ORGANISM: Homo sapiens

<400> SEQUENCE: 918
aacccgaata ctatccaact accgccgc                                              28

<210> SEQ ID NO 919
<211> LENGTH: 28
<212> TYPE: DNA
<213> ORGANISM: Homo sapiens

<400> SEQUENCE: 919
cgagcgtggg tattaagtcg gtagtgga                                              28

<210> SEQ ID NO 920
<211> LENGTH: 28
<212> TYPE: DNA
```

```
<213> ORGANISM: Homo sapiens

<400> SEQUENCE: 920
gacctcaacc ccctacgcct aacctact                                        28

<210> SEQ ID NO 921
<211> LENGTH: 28
<212> TYPE: DNA
<213> ORGANISM: Homo sapiens

<400> SEQUENCE: 921
gtagatcgcg gttttgtagg ggcgtttg                                        28

<210> SEQ ID NO 922
<211> LENGTH: 28
<212> TYPE: DNA
<213> ORGANISM: Homo sapiens

<400> SEQUENCE: 922
ctaatttcga tttttccacc cccgccgc                                        28

<210> SEQ ID NO 923
<211> LENGTH: 28
<212> TYPE: DNA
<213> ORGANISM: Homo sapiens

<400> SEQUENCE: 923
gagtgtttgt cgagaaggtt gagtaaat                                        28

<210> SEQ ID NO 924
<211> LENGTH: 28
<212> TYPE: DNA
<213> ORGANISM: Homo sapiens

<400> SEQUENCE: 924
caccgcccaa cgcattcgtt ctaaaata                                        28

<210> SEQ ID NO 925
<211> LENGTH: 26
<212> TYPE: DNA
<213> ORGANISM: Homo sapiens

<400> SEQUENCE: 925
ataaaagtgg ggtgggtggc ggaggg                                          26

<210> SEQ ID NO 926
<211> LENGTH: 28
<212> TYPE: DNA
<213> ORGANISM: Homo sapiens

<400> SEQUENCE: 926
gcgccgaaat aacaacccaa cctaccaa                                        28

<210> SEQ ID NO 927
<211> LENGTH: 28
<212> TYPE: DNA
<213> ORGANISM: Homo sapiens

<400> SEQUENCE: 927
tttatcgggg aagttttcga gggtgggc                                        28

<210> SEQ ID NO 928
<211> LENGTH: 28
```

```
<212> TYPE: DNA
<213> ORGANISM: Homo sapiens

<400> SEQUENCE: 928
tcccaactac ctcctacgca cgaacgat                                          28

<210> SEQ ID NO 929
<211> LENGTH: 29
<212> TYPE: DNA
<213> ORGANISM: Homo sapiens

<400> SEQUENCE: 929
atgaaatgtg gttcgtggaa ggtgtttgt                                         29

<210> SEQ ID NO 930
<211> LENGTH: 28
<212> TYPE: DNA
<213> ORGANISM: Homo sapiens

<400> SEQUENCE: 930
acgacccgaa cgttaatcct cttactac                                          28

<210> SEQ ID NO 931
<211> LENGTH: 29
<212> TYPE: DNA
<213> ORGANISM: Homo sapiens

<400> SEQUENCE: 931
acgtagtttt cgagttagtg tcgttagaa                                         29

<210> SEQ ID NO 932
<211> LENGTH: 23
<212> TYPE: DNA
<213> ORGANISM: Homo sapiens

<400> SEQUENCE: 932
gacaaacgcc tcaaacccga ccg                                               23

<210> SEQ ID NO 933
<211> LENGTH: 28
<212> TYPE: DNA
<213> ORGANISM: Homo sapiens

<400> SEQUENCE: 933
aggagcggga gagggaaaaa tagttaag                                          28

<210> SEQ ID NO 934
<211> LENGTH: 26
<212> TYPE: DNA
<213> ORGANISM: Homo sapiens

<400> SEQUENCE: 934
cgctccaaac tacgcccaaa actcaa                                            26

<210> SEQ ID NO 935
<211> LENGTH: 28
<212> TYPE: DNA
<213> ORGANISM: Homo sapiens

<400> SEQUENCE: 935
attagagttg ttttgcgtat tgcggcgg                                          28

<210> SEQ ID NO 936
```

```
<211> LENGTH: 28
<212> TYPE: DNA
<213> ORGANISM: Homo sapiens

<400> SEQUENCE: 936
caaatacccc gtacacccgc taccccaa                                              28

<210> SEQ ID NO 937
<211> LENGTH: 28
<212> TYPE: DNA
<213> ORGANISM: Homo sapiens

<400> SEQUENCE: 937
gggagttgag gtttacgcgg tttcgttg                                              28

<210> SEQ ID NO 938
<211> LENGTH: 27
<212> TYPE: DNA
<213> ORGANISM: Homo sapiens

<400> SEQUENCE: 938
gaccgccaac gcgatccacc cattaac                                               27

<210> SEQ ID NO 939
<211> LENGTH: 28
<212> TYPE: DNA
<213> ORGANISM: Homo sapiens

<400> SEQUENCE: 939
agttttggaa gtagattcgg tgcgggtg                                              28

<210> SEQ ID NO 940
<211> LENGTH: 24
<212> TYPE: DNA
<213> ORGANISM: Homo sapiens

<400> SEQUENCE: 940
gccgcgcaat cgcctctttt tcac                                                  24

<210> SEQ ID NO 941
<211> LENGTH: 28
<212> TYPE: DNA
<213> ORGANISM: Homo sapiens

<400> SEQUENCE: 941
agacgataga tggcgggtag gaagggag                                              28

<210> SEQ ID NO 942
<211> LENGTH: 28
<212> TYPE: DNA
<213> ORGANISM: Homo sapiens

<400> SEQUENCE: 942
gccgcctaca accgacgaac tacaaatc                                              28

<210> SEQ ID NO 943
<211> LENGTH: 28
<212> TYPE: DNA
<213> ORGANISM: Homo sapiens

<400> SEQUENCE: 943
tcgcgggtga ggtttgtggt taatttcg                                              28
```

```
<210> SEQ ID NO 944
<211> LENGTH: 28
<212> TYPE: DNA
<213> ORGANISM: Homo sapiens

<400> SEQUENCE: 944
gctcaaccaa actacaacgt tcccgcct                                              28

<210> SEQ ID NO 945
<211> LENGTH: 28
<212> TYPE: DNA
<213> ORGANISM: Homo sapiens

<400> SEQUENCE: 945
tgagaggcgt attttgttgg ttacggtt                                              28

<210> SEQ ID NO 946
<211> LENGTH: 28
<212> TYPE: DNA
<213> ORGANISM: Homo sapiens

<400> SEQUENCE: 946
cgaaaaccat tccgctaccc ttccaact                                              28

<210> SEQ ID NO 947
<211> LENGTH: 29
<212> TYPE: DNA
<213> ORGANISM: Homo sapiens

<400> SEQUENCE: 947
ggggcgttgg gttatggaga ttacgtttt                                             29

<210> SEQ ID NO 948
<211> LENGTH: 28
<212> TYPE: DNA
<213> ORGANISM: Homo sapiens

<400> SEQUENCE: 948
gtcccgcgct taacgaattc tacgaacg                                              28

<210> SEQ ID NO 949
<211> LENGTH: 22
<212> TYPE: DNA
<213> ORGANISM: Homo sapiens

<400> SEQUENCE: 949
gttcgggtag gggtcggggg tc                                                    22

<210> SEQ ID NO 950
<211> LENGTH: 28
<212> TYPE: DNA
<213> ORGANISM: Homo sapiens

<400> SEQUENCE: 950
cccgaaacga cgtacttaac gacccgaa                                              28

<210> SEQ ID NO 951
<211> LENGTH: 28
<212> TYPE: DNA
<213> ORGANISM: Homo sapiens

<400> SEQUENCE: 951
gggaggtttg agcgtcgaag ttttcgtt                                              28
```

```
<210> SEQ ID NO 952
<211> LENGTH: 28
<212> TYPE: DNA
<213> ORGANISM: Homo sapiens

<400> SEQUENCE: 952
gcccactacc ccgcgaaacc ttatcaac                                    28

<210> SEQ ID NO 953
<211> LENGTH: 28
<212> TYPE: DNA
<213> ORGANISM: Homo sapiens

<400> SEQUENCE: 953
agtcgttagg ttgttaaggc gcgttgtg                                    28

<210> SEQ ID NO 954
<211> LENGTH: 29
<212> TYPE: DNA
<213> ORGANISM: Homo sapiens

<400> SEQUENCE: 954
acaaaaataa aatcgaacct aaccccacg                                   29

<210> SEQ ID NO 955
<211> LENGTH: 25
<212> TYPE: DNA
<213> ORGANISM: Homo sapiens

<400> SEQUENCE: 955
cgtattaagg gttaagcggc gcggt                                       25

<210> SEQ ID NO 956
<211> LENGTH: 29
<212> TYPE: DNA
<213> ORGANISM: Homo sapiens

<400> SEQUENCE: 956
aactttctcg aacgactcga taaacctaa                                   29

<210> SEQ ID NO 957
<211> LENGTH: 28
<212> TYPE: DNA
<213> ORGANISM: Homo sapiens

<400> SEQUENCE: 957
aggttttggg aatttggaag ttcgcggg                                    28

<210> SEQ ID NO 958
<211> LENGTH: 28
<212> TYPE: DNA
<213> ORGANISM: Homo sapiens

<400> SEQUENCE: 958
aaaaacgctc gaacccaacc aatcgacg                                    28

<210> SEQ ID NO 959
<211> LENGTH: 27
<212> TYPE: DNA
<213> ORGANISM: Homo sapiens

<400> SEQUENCE: 959
aaaggaagat cgtgggtagt tcgtgcg                                     27
```

```
<210> SEQ ID NO 960
<211> LENGTH: 28
<212> TYPE: DNA
<213> ORGANISM: Homo sapiens

<400> SEQUENCE: 960
actacaactc acgtttcccc tccaacac                                        28

<210> SEQ ID NO 961
<211> LENGTH: 29
<212> TYPE: DNA
<213> ORGANISM: Homo sapiens

<400> SEQUENCE: 961
aggtttattt gacgttttag gtcgatagt                                       29

<210> SEQ ID NO 962
<211> LENGTH: 28
<212> TYPE: DNA
<213> ORGANISM: Homo sapiens

<400> SEQUENCE: 962
cgatctctcc ctttcttccg cttcctaa                                        28

<210> SEQ ID NO 963
<211> LENGTH: 22
<212> TYPE: DNA
<213> ORGANISM: Homo sapiens

<400> SEQUENCE: 963
ggcgtcggtt gcggttttag at                                              22

<210> SEQ ID NO 964
<211> LENGTH: 30
<212> TYPE: DNA
<213> ORGANISM: Homo sapiens

<400> SEQUENCE: 964
acgcgaaaat ctacctttta attacgaacc                                      30

<210> SEQ ID NO 965
<211> LENGTH: 23
<212> TYPE: DNA
<213> ORGANISM: Homo sapiens

<400> SEQUENCE: 965
tcgtcggtgg tcggcgcgtt ttt                                             23

<210> SEQ ID NO 966
<211> LENGTH: 28
<212> TYPE: DNA
<213> ORGANISM: Homo sapiens

<400> SEQUENCE: 966
aacccgcacc aaacaaacta cacgcaaa                                        28

<210> SEQ ID NO 967
<211> LENGTH: 28
<212> TYPE: DNA
<213> ORGANISM: Homo sapiens

<400> SEQUENCE: 967
```
gaatggtagc gagaggttgc gggttagg                                    28

<210> SEQ ID NO 968
<211> LENGTH: 28
<212> TYPE: DNA
<213> ORGANISM: Homo sapiens

<400> SEQUENCE: 968
ctctaccctc aaaatcgcga cgcaaacg                                    28

<210> SEQ ID NO 969
<211> LENGTH: 28
<212> TYPE: DNA
<213> ORGANISM: Homo sapiens

<400> SEQUENCE: 969
aggagtagta ttgcgagggt ggagggtt                                    28

<210> SEQ ID NO 970
<211> LENGTH: 28
<212> TYPE: DNA
<213> ORGANISM: Homo sapiens

<400> SEQUENCE: 970
cgccaatccc gctccgacac tataacaa                                    28

<210> SEQ ID NO 971
<211> LENGTH: 28
<212> TYPE: DNA
<213> ORGANISM: Homo sapiens

<400> SEQUENCE: 971
ataaggtttg gtggaagcgt aggagcgt                                    28

<210> SEQ ID NO 972
<211> LENGTH: 28
<212> TYPE: DNA
<213> ORGANISM: Homo sapiens

<400> SEQUENCE: 972
acgatattct aacctccgcc gcgaaact                                    28

<210> SEQ ID NO 973
<211> LENGTH: 28
<212> TYPE: DNA
<213> ORGANISM: Homo sapiens

<400> SEQUENCE: 973
ggtagaggga tagggaagag tttggcgt                                    28

<210> SEQ ID NO 974
<211> LENGTH: 28
<212> TYPE: DNA
<213> ORGANISM: Homo sapiens

<400> SEQUENCE: 974
attcaaaacg cgcgcgacga aattcaac                                    28

<210> SEQ ID NO 975
<211> LENGTH: 28
<212> TYPE: DNA
<213> ORGANISM: Homo sapiens

<400> SEQUENCE: 975
gcggagtggg agggttatat tgggagag 28

<210> SEQ ID NO 976
<211> LENGTH: 28
<212> TYPE: DNA
<213> ORGANISM: Homo sapiens

<400> SEQUENCE: 976
ccgaacaaaa ctacgacacc gccgaaaa 28

<210> SEQ ID NO 977
<211> LENGTH: 28
<212> TYPE: DNA
<213> ORGANISM: Homo sapiens

<400> SEQUENCE: 977
acgacgggtt gagataggtg gttggatt 28

<210> SEQ ID NO 978
<211> LENGTH: 28
<212> TYPE: DNA
<213> ORGANISM: Homo sapiens

<400> SEQUENCE: 978
cccgacgcga aacaacgaac taaaacga 28

<210> SEQ ID NO 979
<211> LENGTH: 28
<212> TYPE: DNA
<213> ORGANISM: Homo sapiens

<400> SEQUENCE: 979
tttttgtacg ttttcggggt cggaggag 28

<210> SEQ ID NO 980
<211> LENGTH: 28
<212> TYPE: DNA
<213> ORGANISM: Homo sapiens

<400> SEQUENCE: 980
aatcgccgtc taaacaaatc gcgaacta 28

<210> SEQ ID NO 981
<211> LENGTH: 29
<212> TYPE: DNA
<213> ORGANISM: Homo sapiens

<400> SEQUENCE: 981
cggcggtcgc ggtttgtagt ttagaattg 29

<210> SEQ ID NO 982
<211> LENGTH: 28
<212> TYPE: DNA
<213> ORGANISM: Homo sapiens

<400> SEQUENCE: 982
acgcgcttcc actccgacta acaaatta 28

<210> SEQ ID NO 983
<211> LENGTH: 27
<212> TYPE: DNA
<213> ORGANISM: Homo sapiens -continued

<400> SEQUENCE: 983
ggcgtcgttc gggttaagtt tggttgt                                27

<210> SEQ ID NO 984
<211> LENGTH: 28
<212> TYPE: DNA
<213> ORGANISM: Homo sapiens

<400> SEQUENCE: 984
cacaacttac gcgaaacaac aacctcgc                               28

<210> SEQ ID NO 985
<211> LENGTH: 28
<212> TYPE: DNA
<213> ORGANISM: Homo sapiens

<400> SEQUENCE: 985
tgggttggtg tcgcgcgaat ttttgttt                               28

<210> SEQ ID NO 986
<211> LENGTH: 28
<212> TYPE: DNA
<213> ORGANISM: Homo sapiens

<400> SEQUENCE: 986
cctcctcccg caactacgaa aaccgata                               28

<210> SEQ ID NO 987
<211> LENGTH: 28
<212> TYPE: DNA
<213> ORGANISM: Homo sapiens

<400> SEQUENCE: 987
gttgggggtt atgtttggcg cggaatag                               28

<210> SEQ ID NO 988
<211> LENGTH: 28
<212> TYPE: DNA
<213> ORGANISM: Homo sapiens

<400> SEQUENCE: 988
cgcctatata aaacgtcgac gcgcgaaa                               28

<210> SEQ ID NO 989
<211> LENGTH: 28
<212> TYPE: DNA
<213> ORGANISM: Homo sapiens

<400> SEQUENCE: 989
gttcgggcgt cgcggtcgtt tttatatt                               28

<210> SEQ ID NO 990
<211> LENGTH: 28
<212> TYPE: DNA
<213> ORGANISM: Homo sapiens

<400> SEQUENCE: 990
aaaacgccca ttatcccgc gccaattc                                28

<210> SEQ ID NO 991
<211> LENGTH: 28
<212> TYPE: DNA
<213> ORGANISM: Homo sapiens

```
<400> SEQUENCE: 991
taagaatcgg cggtagttag taggcggg                                         28

<210> SEQ ID NO 992
<211> LENGTH: 28
<212> TYPE: DNA
<213> ORGANISM: Homo sapiens

<400> SEQUENCE: 992
tcctacgccg cgacgaaaac aaaaactc                                         28

<210> SEQ ID NO 993
<211> LENGTH: 28
<212> TYPE: DNA
<213> ORGANISM: Homo sapiens

<400> SEQUENCE: 993
aggtggggcg cgtttattag tttagggg                                         28

<210> SEQ ID NO 994
<211> LENGTH: 28
<212> TYPE: DNA
<213> ORGANISM: Homo sapiens

<400> SEQUENCE: 994
acctctccat cgctaatacc ctaccgct                                         28

<210> SEQ ID NO 995
<211> LENGTH: 28
<212> TYPE: DNA
<213> ORGANISM: Homo sapiens

<400> SEQUENCE: 995
gagtgtttcg agggtaggag gttgtcgg                                         28

<210> SEQ ID NO 996
<211> LENGTH: 28
<212> TYPE: DNA
<213> ORGANISM: Homo sapiens

<400> SEQUENCE: 996
caaaaaccgc ccgcaaaacg aaacctaa                                         28

<210> SEQ ID NO 997
<211> LENGTH: 28
<212> TYPE: DNA
<213> ORGANISM: Homo sapiens

<400> SEQUENCE: 997
acggatcgat cgcggttttg gtaaggat                                         28

<210> SEQ ID NO 998
<211> LENGTH: 28
<212> TYPE: DNA
<213> ORGANISM: Homo sapiens

<400> SEQUENCE: 998
cgcaaaaacg aaaaactacg tacgcgct                                         28

<210> SEQ ID NO 999
<211> LENGTH: 27
<212> TYPE: DNA
```

<213> ORGANISM: Homo sapiens

<400> SEQUENCE: 999
gttgtttgag gacgggtcgt ttagcgg                                27

<210> SEQ ID NO 1000
<211> LENGTH: 28
<212> TYPE: DNA
<213> ORGANISM: Homo sapiens

<400> SEQUENCE: 1000
acccctatcc tacaaccta cgaacgca                                28

<210> SEQ ID NO 1001
<211> LENGTH: 28
<212> TYPE: DNA
<213> ORGANISM: Homo sapiens

<400> SEQUENCE: 1001
tttcgggagg tgtggttacg tttggaga                               28

<210> SEQ ID NO 1002
<211> LENGTH: 28
<212> TYPE: DNA
<213> ORGANISM: Homo sapiens

<400> SEQUENCE: 1002
cccctcctcc caacacccaa cactaaaa                               28

<210> SEQ ID NO 1003
<211> LENGTH: 30
<212> TYPE: DNA
<213> ORGANISM: Homo sapiens

<400> SEQUENCE: 1003
ggttgtggtt tttaaaaggg aaaattcggg                             30

<210> SEQ ID NO 1004
<211> LENGTH: 28
<212> TYPE: DNA
<213> ORGANISM: Homo sapiens

<400> SEQUENCE: 1004
taaacgccga aacccgaacg taacaacc                               28

<210> SEQ ID NO 1005
<211> LENGTH: 28
<212> TYPE: DNA
<213> ORGANISM: Homo sapiens

<400> SEQUENCE: 1005
aggtgattag aagggagagg gggaggtt                               28

<210> SEQ ID NO 1006
<211> LENGTH: 28
<212> TYPE: DNA
<213> ORGANISM: Homo sapiens

<400> SEQUENCE: 1006
tcattataca cgacgcgccc ctccaaat                               28

<210> SEQ ID NO 1007
<211> LENGTH: 28

```
<212> TYPE: DNA
<213> ORGANISM: Homo sapiens

<400> SEQUENCE: 1007
tacgtgggtg taggttaggt cgggttga                                28

<210> SEQ ID NO 1008
<211> LENGTH: 29
<212> TYPE: DNA
<213> ORGANISM: Homo sapiens

<400> SEQUENCE: 1008
accacgcgac taccgtataa acaaccgaa                               29
```

CELL-FREE DETECTION OF METHYLATED TUMOUR DNA

FIELD

This disclosure relates generally to tumour detection. More particularly, this disclosure relates to tumour-specific DNA methylation detection.

BACKGROUND

Cancer screening and monitoring has helped to improve outcomes over the past few decades simply because early detection leads to a better outcome as the cancer can be eliminated before it has spread. In the case of breast cancer, for instance, physical breast exams, mammography, ultrasound and MRI (in high risk patients) have all played a role in improving early diagnosis. The cost/benefit of these modalities for general screening, particularly in relatively younger women, has been controversial.

A primary issue for any screening tool is the compromise between false positive and false negative results (or specificity and sensitivity) which lead to unnecessary investigations in the former case, and ineffectiveness in the latter case. An ideal test is one that has a high Positive Predictive Value (PPV), minimizing unnecessary investigations but detecting the vast majority of cancers. Another key factor is what is called "detection sensitivity", to distinguish it from test sensitivity, and that is the lower limits of detection in terms of the size of the tumour. Screening mammography in breast cancer, for instance, is considered to have a sensitivity from 80 to 90% with a specificity of 90%. However the mean size of tumours detected by mammography remains in the range of 15 to 19 mm. It has been suggested that only 3-13% of women derive an improved treatment outcome from this screening suggesting that the detection of smaller tumours would provide increased benefit. For women at high risk of developing breast cancer the use of MRI has offered some benefit with sensitivities in the range of 75 to 97% and specificities in the area of 90 to 96% and in combination with mammography offering 93-94% sensitivity and 77 to 96% specificities. However, MRI is acknowledged to have a poor PPV, in the area of 10-20%, leading to a large number of false positives and as a consequence unnecessary invasive investigations. All of these screens have likely reached their limit of detection sensitivity (or size of the tumour) and in the case of mammography still involve exposure to radiation, which may be of particular concern in women with familial mutations which render them more sensitive to radiation damage. There are no effective blood based screens for breast cancer based on circulating analytes.

While the above discussion focusses on breast cancer as an example, many of the same challenges exist for other types of cancers as well.

The detection of circulating tumour DNA is increasingly acknowledged as a viable "liquid biopsy" allowing for the detection and informative investigation of tumours in a non-invasive manner. Typically using the identification of tumour specific mutations these techniques have been applied to colon, breast and prostate cancers. Due to the high background of normal DNA present in the circulation these techniques can be limited in sensitivity. As well, the variable nature of tumour mutations in terms of occurrence and location (such as p53 and KRAS mutations) has generally limited these approaches to detecting tumour DNA at 1% of the total DNA in serum. Advanced techniques such as BEAMing have increased sensitivity, but are still limited overall. Even with these limitations the detection of circulating tumour DNA has recently been shown to be useful for detecting metastasis in breast cancer patients.

The detection of tumour specific methylation in the blood has been proposed to offer distinct advantages over the detection of mutations[1-5]. A number of single or multiple methylation biomarkers have been assessed in cancers including lung[6-10], colon[11,12] and breast[13-16]. These have suffered from low sensitivities as they have tended to be insufficiently prevalent in the tumours. Several multi-gene assays have been developed with improved performance. A more advanced multi-gene system using a combination of 10 different genes has been reported and uses a multiplexed PCR based assay[17]. It offers combined sensitivity and specificity of 91% and 96% respectively, due to the better coverage offered and it has been validated in a small cohort of stage IV patients. However, it has a very high background in normal blood which will limit its detection sensitivity. Methylated markers have been used to monitor the response to neoadjuvant therapy[18,19], and recently a methylation gene signature associated with metastatic tumours has been identified[20].

There remains a need for more sensitive and specific screening tools, as well as for straightforward tests that allow for the assessment of tumour burden, chemotherapy response, detection of residual disease, relapse and primary screening in high risk populations.

SUMMARY

It is an object of this disclosure to obviate or mitigate at least one disadvantage of previous approaches.

In a first aspect, this disclosure provides a method for detecting a tumour, comprising: extracting DNA from a cell-free sample obtained from a subject, bisulphite converting at least a portion of the DNA, amplifying regions methylated in cancer from the bisulphite converted DNA, generating sequencing reads from the amplified regions, and detecting tumour signals comprising at least two adjacent methylated sites within a single sequencing read, wherein the detection of at least one of the tumour signals is indicative of a tumour.

In another aspect, there is provided a use of the method for determining response to treatment.

In another aspect, there is provided a use of the method for monitoring tumour load.

In another aspect, there is provided a use of the method for detecting residual tumour post-surgery.

In another aspect, there is provided a use of the method for detecting relapse.

In another aspect, there is provided a use of the method as a secondary screen.

In another aspect, there is provided a use of the method as a primary screen.

In another aspect, there is provided a use of the method for monitoring cancer development.

In another aspect, there is provided a use of the method for monitoring cancer risk.

In another aspect, there is provided a kit for detecting a tumour comprising reagents for carrying out the method, and instructions for detecting the tumour signals.

Other aspects and features of this disclosure will become apparent to those ordinarily skilled in the art upon review of the following description of specific embodiments in conjunction with the accompanying figures.

BRIEF DESCRIPTION OF THE DRAWINGS

Embodiments of this disclosure will now be described, by way of example only, with reference to the attached Figures.

FIG. 3 lists 47 CpG targets selected to identify differentially methylated regions, and shows the results of Receiver Operator Curve (ROC) analysis.

FIGS. 12A and 12B depict a numerical summary of validation data generated for 98 different probes by bisulphite sequencing six different cell lines. #Reads is indicative of the number of reads exported, and Mean Me is indicative of the mean methylation.

FIGS. 13A and 13B depict a numerical summary of generated methylation data for tumour samples. #Reads is indicative of the number of reads exported, and Mean Me is indicative of the mean methylation.

FIG. 14 depicts a numerical summary generated methylation data for prostate cell lines. #Reads is indicative of the number of reads exported, and Mean Me is indicative of the mean methylation.

FIG. 17 is a diagram showing methylation of cfDNA from patients with metastatic uveal melanoma. Methylated reads for each probe were extracted and all reads were normalized for the total number of reads in the sample. Stacked columns represent the total reads from all of the individual probes with different probes identified by shading. The patients are sorted by tumour volume with larger volume on the left and lower volume on the right, and the volume indicated at the bottom. PAP values obtained from these patients is indicated. <5 refers to no detection of ctDNA in these samples. cfDNA is a pool of cell free DNA from 18 normal donors.

FIGS. 18A and 18B are diagrams showing methylation of cfDNA from sequential blood samples of two patients who were part of the patient groups shown in FIGS. 17 and 18. In FIG. 19A the patient was retested after seven months and the tumour at that time was assessed as being 0.5 cm³ in volume. In FIG. 19B the patient was retested after four months where the initial tumour volume was 483 cm³.

FIGS. 26A, 26B, and 26C are charts showing regions used to develop a breast cancer test according to one embodiment. The chromosomal location and nucleotide position of the first CpG residue in the region is indicated. The TCGA breast cancer cohort was divided into sub-groups based on PAM-50 criteria. The fraction of each group that is positive for that probe is indicated. "Tissue" indicates results from normal tissue samples.

FIG. 28 is a heatmap of multiplexed probes for each TNBC tumour sample and selected normal samples. A black square indicates that methylated reads having greater than 80% methylation per read were detected for that probe but does not take into consideration the number of reads for each.

DETAILED DESCRIPTION

Figure 1:
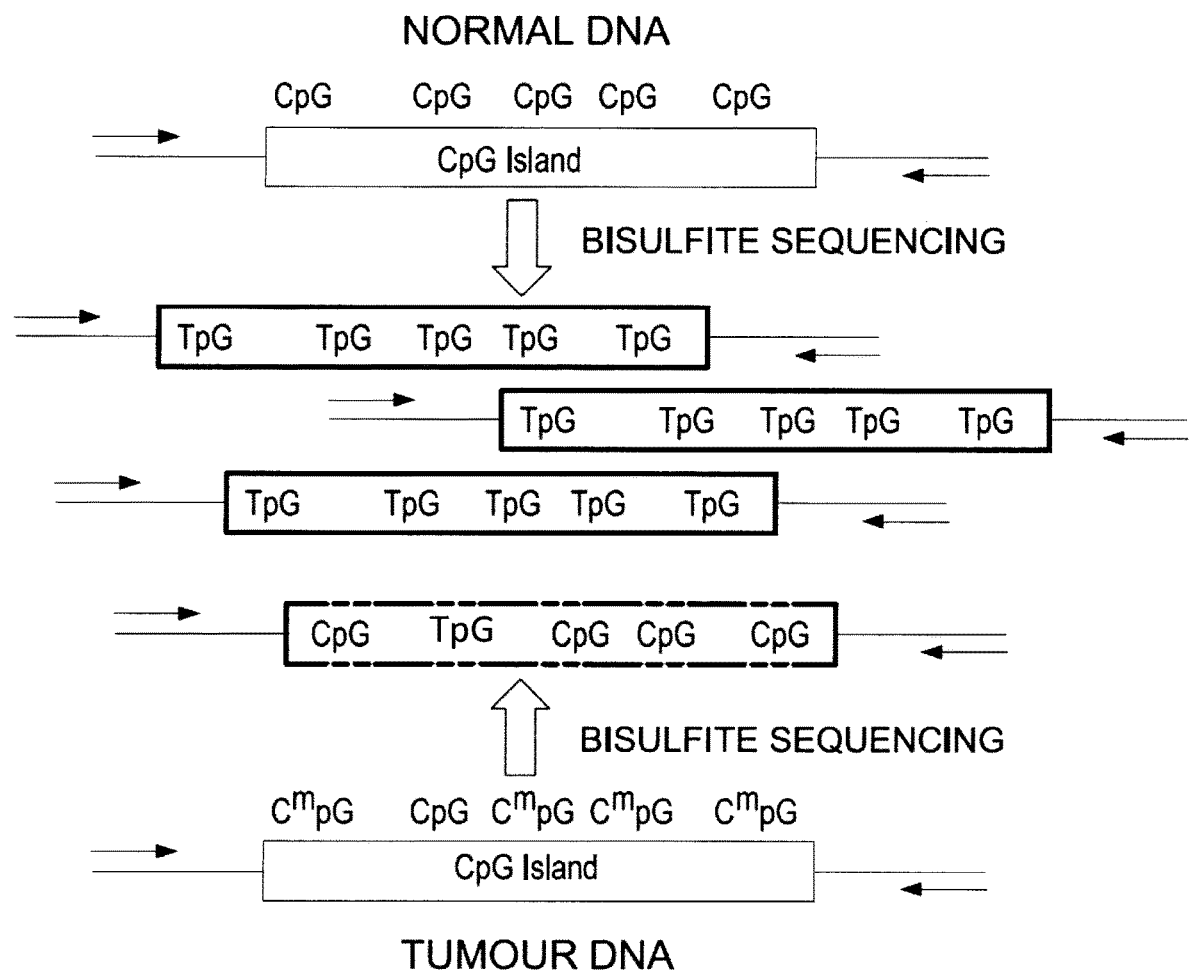
FIG. 1 depicts a schematic of the method.

Generally, this disclosure provides a method for detecting a tumour that can be applied to cell-free samples, e.g., to detect cell-free circulating tumour DNA. The method utilizes detection of adjacent methylation signals within a single sequencing read as the basic "positive" tumour signal.

In one aspect, there is provided a method for detecting a tumour, comprising: extracting DNA from a cell-free sample obtained from a subject, bisulphite converting at least a portion of the DNA, amplifying regions methylated in cancer from the bisulphite converted DNA, generating sequencing reads from the amplified regions, and detecting tumour signals comprising at least two adjacent methylated sites within a single sequencing read, wherein the detection of at least one of the tumour signals is indicative of a tumour.

By "cell-free DNA (cfDNA)" is meant DNA in a biological sample that is not contained in a cell. cfDNA may circulate freely in in a bodily fluid, such as in the bloodstream.

"Cell-free sample", as used herein, is meant a biological sample that is substantially devoid of intact cells. This may be a derived from a biological sample that is itself substantially devoid of cells, or may be derived from a sample from which cells have been removed. Example cell-free samples include those derived from blood, such as serum or plasma; urine; or samples derived from other sources, such as semen, sputum, feces, ductal exudate, lymph, or recovered lavage.

"Circulating tumour DNA", as used herein, accordingly refers to cfDNA originating from a tumour.

By "region methylated in cancer" is meant a segment of the genome containing methylation sites (CpG dinucleotides), methylation of which is associated with a malignant cellular state. Methylation of a region may be associated with more than one different type of cancer, or with one type of cancer specifically. Within this, methylation of a region may be associated with more than one subtype, or with one subtype specifically.

The terms cancer "type" and "subtype" are used relatively herein, such that one "type" of cancer, such as breast cancer, may be "subtypes" based on e.g., stage, morphology, histology, gene expression, receptor profile, mutation profile, aggressiveness, prognosis, malignant characteristics, etc. Likewise, "type" and "subtype" may be applied at a finer level, e.g., to differentiate one histological "type" into "subtypes", e.g., defined according to mutation profile or gene expression.

By "adjacent methylated sites" is meant two methylated sites that are, sequentially, next to each other. It will be understood that this term does not necessarily require the sites to actually be directly beside each other in the physical DNA structure. Rather, in a sequence of DNA including spaced apart methylation sites A, B, and C in the context A-(n)$_n$-B-(n)$_n$-C, wherein (n), refers to the number of base pairs (bp) (e.g., up to 300 bp), sites A and B would be recognized as "adjacent" as would sites B and C. Sites A and C, however, would not be considered to be adjacent methylated sites.

In one embodiment, the regions methylated in cancer comprise CpG islands.

"CpG islands" are regions of the genome having a high frequency of CpG sites. CpG islands are usually 300-3000 bp in length and are found at or near promotors of approximately 40% of mammalian genes. They show a tendency to occur upstream of so-called "housekeeping genes". A concrete definition is elusive, but CpG islands may be said to have an absolute GC content of at least 50%, and a CpG dinucleotide content of at least 60% of what would be statistically expected. Their occurrence at or upstream of the 5' end of genes may reflect a role in the regulation of transcription, and methylation of CpG sites within the promoters of genes may lead to silencing. Silencing of tumour suppressors by methylation is, in turn, a hallmark of a number of human cancers.

In one embodiment, the regions methylated in cancer comprise CpG shores.

"CpG shores" are regions extending short distances from CpG islands in which methylation may also occur. CpG shores may be found in the region 0 to 2 kb upstream and downstream of a CpG island.

In one embodiment, the regions methylated in cancer comprise CpG shelves.

"CpG shelves" are regions extending short distances from CpG shores in which methylation may also occur. CpG shelves may generally be found in the region between 2 kb and 4 kb upstream and downstream of a CpG island (i.e., extending a further 2 kb out from a CpG shore).

In one embodiment, the regions methylated in cancer comprise CpG islands and CpG shores.

In one embodiment, the regions methylated in cancer comprise CpG islands, CpG shores, and CpG shelves.

In one embodiment, the regions methylated in cancer comprise CpG islands and sequences 0 to 4 kb upstream and downstream. The regions methylated in cancer may also comprise CpG islands and sequences 0 to 3 kb upstream and downstream, 0 to 2 kb upstream and downstream, 0 to 1 kb upstream and downstream, 0 to 500 bp upstream and downstream, 0 to 400 bp upstream and downstream, 0 to 300 bp upstream and downstream, 0 to 200 bp upstream and downstream, or 0 to 100 bp upstream and downstream.

In one embodiment, the step of amplifying is carried out with primers designed to anneal to bisulphite converted target sequences having at least one methylated site therein. Bisulphite conversion results in unmethylated cytosines being converted to uracil, while 5-methylcytosine is unaffected. "Bisulphite converted target sequences" are thus understood to be sequences in which cytosines known to be methylation sites are fixed as "C" (cytosine), while cytosines known to be unmethylated are fixed as "U" (uracil; which can be treated as "T" (thymine) for primer design purposes). Primers designed to target such sequences may exhibit a degree of bias towards converted methylated sequences. However, in one embodiment, the primers are designed without preference as to location of the at least one methylated site within target sequences. Often, to achieve optimal discrimination, it may be desirable to place a discriminatory base at the ultimate or penultimate 3' position of an oligonucleotide PCR primer. In this embodiment, however, no preference is given to the location of the discriminatory sites of methylation, such that overall primer design is optimized based on sequence (not discrimination). This results in a degree of bias for some primer sets, but usually not complete specificity towards methylated sequences (some individual primer pairs, however, may be specific if a discriminatory site is fortuitously placed). As will be described herein, this permits some embodiments of the method to be quantitative or semi-quantitative.

In one embodiment, the PCR primers are designed to be methylation specific. This may allow for greater sensitivity in some applications. For instance, primers may be designed to include a discriminatory nucleotide (specific to a methylated sequence following bisulphite conversion) positioned to achieve optimal discrimination, e.g. in PCR applications. The discriminatory may be positioned at the 3' ultimate or penultimate position.

In one embodiment, the primers are designed to amplify DNA fragments 75 to 150 bp in length. This is the general size range known for circulating DNA, and optimizing primer design to take into account target size may increase the sensitivity of the method according to this embodiment. The primers may be designed to amplify regions that are 50 to 200, 75 to 150, or 100 or 125 bp in length.

In some embodiments, concordant results provide additional confidence in a positive tumour signal. By "concordant" or "concordance", as used herein, is meant methylation status that is consistent by location and/or by repeated observation. As has already been stated, the basic "tumour signal" defined herein comprises at least two adjacent methylated sites within a single sequencing read. However, additional layers of concordance can be used to increase confidence for tumour detection, in some embodiments, and not all of these need be derived from the same sequencing read. Layers of concordance that may provide confidence in tumor detection may include, for example:
  (a) detection of methylation of at least two adjacent methylation sites;
  (b) detection of methylation of more than two adjacent methylation sites;
  (c) detection of methylation at adjacent sites within the same section of a target region amplified by one primer pair;
  (d) detection of methylation at non-adjacent sites within the same section of a region amplified by one primer pair;
  (e) detection of methylation at adjacent sites within the same target region;
  (f) detection of methylation at non-adjacent sites within the same target region;
  (g) any one of (a) to (f) in the same sequencing read;
  (h) any one of (a) to (f) in at least two sequencing reads;
  (i) any one of (a) to (f) in a plurality of sequencing reads;
  (j) detection over methylation at sets of adjacent sites that overlap;
  (k) repeated observation of any one of (a) to (j); or
  (l) any combination or subset of the above.

In one embodiment, each of the regions is amplified in sections using multiple primer pairs. In one embodiment, these sections are non-overlapping. The sections may be immediately adjacent or spaced apart (e.g. spaced apart up to 10, 20, 30, 40, or 50 bp). Since target regions (including CpG islands, CpG shores, and/or CpG shelves) are usually longer than 75 to 150 bp, this embodiment permits the methylation status of sites across more (or all) of a given target region to be assessed.

A person of ordinary skill in the art would be well aware of how to design primers for target regions using available tools such as Primer3, Primer3Plus, Primer-BLAST, etc. As discussed, bisulphite conversion results in cytosine converting to uracil and 5'-methyl-cytosine converting to thymine. Thus, primer positioning or targeting may make use of bisulphite converted methylate sequences, depending on the degree of methylation specificity required.

Target regions for amplification are designed to have at least two CpG dinucleotide methylation sites. In some embodiments, however, it may be advantageous to amplify regions having more than one CpG methylation site. For instance, the amplified regions may have 3, 4, 5, 6, 7, 8, 9, 10, 11, 12, 13, 14, or 15 CpG methylation sites. In one embodiment, the primers are designed to amplify DNA fragments comprising 3 to 12 CpG methylation sites. Overall this permits a larger number of adjacent methylation sites to be queried within a single sequencing read, and provides additional certainty (exclusion of false positives) because multiple concordant methylations can be detected within a single sequencing read. In one embodiment, the tumour signals comprise more than two adjacent methylation sites within the single sequencing read. Detecting more than two adjacent methylation sites provides additional concordance, and additional confidence that the tumour signal is not a false positive in this embodiment. For example, a tumour signal may be designated as 3, 4, 5, 6, 7, 8, 9, 10 or more adjacent detected methylation sites within a single sequencing read. In one embodiment, the detection of more than one of the tumour signals is indicative of a tumour. Detection of multiple tumour signals, in this embodiment, can increase confidence in tumour detection. Such signals can be at the same or at different sites. In one embodiment, the detection of more than one of the tumour signals at the same region is indicative of a tumour. Detection of multiple tumour signals indicative of methylation at the same site in the genome, in this embodiment, can increase confidence in tumour detection. So too can detection of methylation at adjacent sites in the genome, even if the signals are derived from different sequencing reads. This reflects another type of concordance. In one embodiment, the detection of adjacent or overlapping tumour signals across at least two different sequencing reads is indicative of a tumour. In one embodiment, the adjacent or overlapping tumour signals are within the same CpG island. In one embodiment, the detection of 5 to 25 adjacent methylated sites is indicative of a tumour.

Methylated regions can be selected according to the purpose of the intended assay. In one embodiment, the regions comprise at least one region listed Table 1 and/or Table 2. In one embodiment, the regions comprise all regions listed in Table 1 and/or Table 2.

Likewise, primer pairs can be designed based on the intended target regions.

In one embodiment, the step of amplification is carried out with more than 100 primer pairs. The step of amplification may be carried out with 10, 20, 30, 40, 50, 60, 70, 80, 90, 100, 110, 120, 130, 140, 150, or more primer pairs. In one embodiment, the step of amplification is a multiplex amplification. Multiplex amplification permits large amount of methylation information to be gathered from many target regions in the genome in parallel, even from cfDNA samples in which DNA is generally not plentiful. The multiplexing may be scaled up to a platform such as ION AmpliSeq™, in which, e.g. up to 24,000 amplicons may be queried simultaneously. In one embodiment, the step of amplification is nested amplification. A nested amplification may improve sensitivity and specificity.

The nested reaction may be part of a next generation sequencing approach. Barcode and/or sequencing primers may be added in the second (nested) amplification. Alternatively, these may added in the first amplification.

In one embodiment, the method further comprises quantifying the tumour signals, wherein a number in excess of a threshold is indicative of a tumour. In one embodiment, the steps of quantifying and comparing are carried out independently for each of the sites methylated in cancer. Accordingly, a count of positive tumour signals may be established for each site. In one embodiment, the method further comprises determining a proportion of the sequencing reads containing tumour signals, wherein the proportion in excess of a threshold is indicative of a tumour. In one embodiment, the step of determining is carried out independently for each of the sites methylated in cancer.

By "threshold", as used herein, is meant a value that is selected to discriminate between a disease (e.g., malignant) state, and a non-disease (e.g., healthy) state. Thresholds can be set according to the disease in question, and may be based on earlier analysis, e.g., of a training set. Thresholds may also be set for a site according to the predictive value of methylation at a particular site. Thresholds may be different for each methylation site, and data from multiple sites can be combined in the end analysis.

Various design parameters may be used to select the regions subject to amplification in some embodiments. In one embodiment, the regions are not methylated in healthy tissue. Healthy tissue would be understood to be non-malignant. Healthy tissue is often selected based on the origin of the corresponding tumour.

Regions may be selected based on desired aims or required specificity, in some embodiments. For instance, it may be desirable to screen for more than one cancer type. Thus, in one embodiment, the regions are collectively methylated in more than one tumour type. It may be desirable to include regions methylated generally in a group of cancers, and regions methylated in specific cancers in order to provide different tiers of information. Thus, in one embodiment, the regions comprise regions that are specifically methylated in specific tumours, and regions that are methylated in more than one tumour type. Likewise, it may be desirably to include a second tier of regions that can differentiate between tumour types. In one embodiment, the regions specifically methylated in specific tumours comprise a plurality of groups, each specific to one tumour type. However, it may be desirable in some contexts to have a test that is focused on one type of cancer. Thus, in one embodiment, the regions are methylated specifically in one tumour type. In one embodiment, the regions are selected from those listed in Table 3 and the tumour is one carrying a BRCA1 mutation.

More specifically, in some embodiments regions may be selected that are methylated in particular subtypes of a cancer exhibiting particular histology, karyotype, gene expression (or profile thereof), gene mutation (or profile thereof), staging, etc. Accordingly, the regions to be amplified may comprise one or more groups of regions, each being established to be methylated in one particular cancer subtype. In one embodiment the regions to be amplified may be methylated in a cancer subtype bearing particular mutations. With breast cancer in mind, one example subtype defined by mutation is cancer bearing BRCA1 mutations. Another subtype is cancer bearing BRCA2 mutations. Other breast cancer subtypes for which methylated regions may be determined include Basal, Luminal A, Luminal B, HER2 and Normal-like tumours. For uveal melanoma, for example, subtypes may include tumours that have retained or lost chromosome 3 (monosomy 3).

Within the context of such a test of some embodiments, information about not only the presence, but also the pattern and distribution of tumour signals both within specific regions and between different regions may help to detect or validate the presence of a form of cancer. In one embodiment, the method further comprises determining a distribution of tumour signals across the regions, and comparing the distribution to at least one pattern associated with a cancer, wherein similarity between the distribution and the pattern is indicative of the cancer.

"Distribution", as used herein in this context, is meant to indicate the number and location of tumour signals across the regions. Statistical analysis may be used to compare the observed distribution with, e.g., pre-established patterns (data) associated with a form of cancer. In other embodiments, the distribution may be compared to multiple patterns. In one embodiment, the method further comprises determining a distribution of tumour signals across the regions, and comparing the distribution to a plurality of patterns, each one associated with a cancer type, wherein similarity between the distribution and one of the plurality of patterns is indicative of the associated cancer type.

In one embodiment, the step of generating sequencing reads is carried out by next generation sequencing. This permits a very high depth of reads to be achieved for a given region. These are high-throughput methods that include, for example, Ilumina (Solexa) sequencing, Roche 454 sequencing, Ion Torrent sequencing, and SOLID sequencing. The depth of sequencing reads may be adjusted depending on desired sensitivity.

In one embodiment, the step of generating sequencing reads is carried out simultaneously for samples obtained from multiple patients, wherein the amplified CpG islands from is barcoded for each patient. This permits parallel analysis of a plurality of patients in one sequencing run.

A number of design parameters may be considered in the selection of regions methylated in cancer, according to some embodiments. Data for this selection process may be from a variety of sources such as, e.g., The Cancer Genome Atlas (TCGA) (cancergenome.nih.gov/), derived by the use of, e.g., Illumina Infinium HumanMethylation450 BeadChip (www.illumina.com/products/methylation_450_beadchip_kits.html) for a wide range of cancers, or from other sources based on, e.g., bisulphite whole genome sequencing, or other methodologies. For instance, "methylation value" (understood herein as derived from TCGA level 3 methylation data, which is in turn derived from the beta-value, which ranges from −0.5 to 0.5) may be used to select regions. In one embodiment, the step of amplification is carried out with primer sets designed to amplify at least one methylation site having a methylation value of below −0.3 in normal issue. This can be established in a plurality of normal tissue samples, for example 4. The methylation value may be at or below −0.1, −0.2, −0.3, −0.4, or −0.5. In one embodiment, the primer sets are designed to amplify at least one methylation site having a difference between the average methylation value in the cancer and the normal tissue of greater than 0.3. The difference may be greater than 0.1, 0.2, 0.3, 0.4, or 0.5. Proximity of other methylation sites that meet this requirement may also play a role in selecting regions, in some embodiments. In one embodiment, the primer sets include primer pairs amplifying at least one methylation site having at least one methylation site within 200 bp that also has a methylation value of below −0.3 in normal issue, and a difference between the average methylation value in the cancer and the normal tissue of greater than 0.3. In another embodiment the adjacent site having these features may be 300 bp. The adjacent site may be within 100, 200, 300, 400, or 500 bp.

In some embodiments, target regions may be selected for amplification based on the number of tumours in the validation set having methylation at that site. For example, a region may be selected if it is methylated in at least 50%, 55%, 60%, 65%, 70%, 75%, 80, 85%, 90, or 95% of tumours tested. For example, regions may be selected if they are methylated in at least 75% of tumours tested, including within specific subtypes. For some validations, it will be appreciated that tumour-derived cell lines may be used for the testing.

In another embodiment, the method further comprises oxidative bisulphite conversion. In addition to the analysis of methylation of CpG residues, additional information that may be of clinical significance may be derived from the analysis of hydroxymethylation. Bisulphite sequencing results in the conversion of unmethylated cytosine residues into uracil/thymidine residues, while both methylated and hydroxymethylated cytosines remain unconverted. However, oxidative bisulphite treatment allows for the conversion of hydroxymethylated cytosines to uracil/thymidine allowing for the differential analysis of both types of modifications. By comparison of bisulphite to oxidative bisulphite treatments the presence of hydroxymethylation can be deduced. This information may be of significance as its presence or absence may be correlated with clinical features of the tumor which may be clinically useful either as a predictive or prognostic factor. Accordingly, in some embodiments, information about hydroxymethylation could additionally be used in the above-described embodiments.

In one aspect, the presence of specific patterns of methylation is linked to underlying characteristics of particular tumours. In these cases, the methylation patterns detected by the method are indicative of clinically relevant aspects of the tumours such as aggressiveness, likelihood of recurrence, and response to various therapies. Detection of these patterns in the blood may thus provide both prognostic and predictive information related to a patient's tumor.

In another aspect, the forgoing method may be applied to clinical applications involving the detection or monitoring of cancer.

In one embodiment, the forgoing method may be applied to determine and/or predict response to treatment.

In one embodiment, the forgoing method may be applied to monitor and/or predict tumour load.

In one embodiment, the forgoing method may be applied to detect and/or predict residual tumour post-surgery.

In one embodiment, the forgoing method may be applied to detect and/or predict relapse.

In one aspect, the forgoing method may be applied as a secondary screen.

In one aspect, the forgoing method may be applied as a primary screen.

In one aspect, the forgoing method may be applied to monitor cancer development.

In one aspect, the forgoing method may be applied to monitor and/or predict cancer risk.

In another aspect, there is provided a kit for detecting a tumour comprising reagents for carrying out the aforementioned method, and instructions for detecting the tumour signals. Reagents may include, for example, primer sets, PCR reaction components, and/or sequencing reagents.

In one embodiment of the forgoing methods, the regions comprise C2CD4A, COL19A1, DCDC2, DHRS3, GALNT3, HES5, KILLIN, MUC21, NR2E1/OSTM1, PAMR1, SCRN1, and SEZ6, and the tumour is uveal melanoma. In one embodiment, the probes comprise C2C5F, COL2F, DCD5F, DGR2F, GAL1F, GAL3F, HES1F, HES3F, HES4F, KIL5F, KIL6F, MUC2F, OST3F, OST4F, PAM4F, SCR2F, SEZ3F, and SEZ5F.

In one embodiment, the regions comprise ADCY4, ALDH1L1, ALOX5, AMOTL2, ANXA2, CHST11, EFS, EPSTI1, EYA4, HAAO, HAPLN3, HCG4P6, HES5, HIF3A, HLA-F, HLA-J, HOXA7, HSF4, KLK4, LOC376693, LRRC4, NBR1, PAH, PON3, PPM1H, PTRF, RARA, RARB, RHCG, RND2, TMP4, TXNRD1, and ZSCAN12, and the tumour is prostate cancer. In one embodiment, the probes comprise ADCY4-F, ALDH1L1-F, ALOX5-F, AMOTL2-F, ANXA2-F, CHST11-F, EFS-F, EPSTI1-F, EYA4-F, HAAO-F, HAPLN3-F, HCG4P6-F, HES5-F, HIF3A-F, HLA-F-F, HLA-J-1-F, HLA-J-2-F, HOXA7-F, HSF4-F, KLK4-F, LOC376693-F, LRRC4-F, NBR1-F, PAH-F, PON3-F, PPM1H-F, PTRF-F, RARA-F, RARB-F, RHCG-F, RND2-F, TMP4-F, TXNRD1-F, and ZSCAN12-F. In one embodiment, the probes additionally include C1Dtrim, C1Etrim, CHSAtrim, DMBCtrim, FOXAtrim, FOXEtrim, SFRAtrim, SFRCtrim, SFREtrim, TTBAtrim, VWCJtrim, and VWCKtrim.

In one embodiment, the regions comprise ASAP1, BC030768, C18orf62, C6orf141, CADPS2, CORO1C, CYP27A1, CYTH4, DMRTA2, EMX1, HFE, HIST1H3G/1H2BI, HMGCLL1, KCNK4, KJ904227, KRT78, LINC240, Me3, MIR1292, NBPF1, NHLH2, NRN1, PPM1H, PPP2R5C, PRSS3, SFRP2, SLCO4C1, SOX2OT, TUBB2B, USP44, Intergenic (Chr1), Intergenic (Chr2), Intergenic (Chr3), Intergenic (Chr4), Intergenic (Chr8), and Intergenic (Chr10), and the tumour is aggressive prostate cancer. In one embodiment, the aggressive prostate cancer has a Gleason Score greater than 6. In one embodiment, the aggressive prostate cancer has a Gleason Score of 9 or greater. In one embodiment, the probes comprise ASAP1/p, BC030768/p, C18orf62/p, C6orf141/p-1, C6orf141/p-2, CADPS2/p, CORO1C/p-1, CORO1C/p-2, CYP27A1/p, CYTH4/p, DMRTA2/p, EMX1/p, HFE/p-1, HFE/p-2, HIST1H3G/1H2BI/p, HMGCLL1/p, KCNK4/p, KJ904227/p, KRT78/p, LINC240/p-1, LINC240/p-2, Me3/p-1, Me3/p-2, MIR129, NBPF1/p, NHLH2/p, NRN1/p, PPM1H/p-1, PPM1H/p-2, PPP2R5C/p, PRSS3/p, SFRP2/p-1, SFRP2/p-2, SLCO4C1/p, SOX2OT/p, TUBB2B/p, USP44/p, Chr1/p-1, Chr2/p-1, Chr3/p-1, Chr4/p-1, Chr8/p-1, and Chr10/p-1.

In one embodiment, the regions comprise the regions depicted in FIGS. 26A, 26B, and 26C, and the tumour is breast cancer.

In one embodiment, the regions comprise ALX1, ACVRL1, BRCA1, C1orf114, CA9, CARD11, CCL28, CD38, CDKL2, CHST11, CRYM, DMBX1, DPP10, DRD4, ERNA4, EPSTI1, EVX1, FABP5, FOXA3, GALR3, GIPC2, HINF1B, HOXA9, HOXB13, Intergenic5, Intergenic 8, IRF8, ITPRIPL1, LEF1, LOC641518, MAST1, BARHL2, BOLL, C5orf39, DDAH2, DMRTA2, GABRA4, ID4, IRF4, NT5E, SIM1, TBX15, NFIC, NPHS2, NR5A2, OTX2, PAX6, GNG4, SCAND3, TAL1, PDX1, PHOX2B, POU4F1, PFIA3, PRDM13, PRKCB, PRSS27, PTGDR, PTPRN2, SALL3, SLC7A4, SOX2OT, SPAG6, TCTEX1D1, TMEM132C, TMEM90B, TNFRSF10D, TOP2P1, TSPAN33, TTBK1, UDB, and VWC2, and the tumour is triple negative breast cancer (TNBC). In one embodiment, the probes comprise ALX1, AVCRL1, BRCA1-A, C1Dtrim, C1Etrim, CA9-A, CARD11-B, CCL28-A, CD38, CDKL2-A, CHSAtrim, CRYM-A, DMBCtrim, DMRTA2exp-A, DPP10-A, DPP10-B, DPP10-C, DRD4-A, EFNA4-B, EPSTI1, EVX1, FABP5, FOXAtrim, FOXEtrim, GALR3-A, GIPC2-A, HINF C trim, HOXAAtrim, HOXACtrim, HOXB13-A, Int5, Int8, IRF8-A, ITRIPL1, LEF1-A, MAST1 A trim, mbBARHL2 Trim, mbBOLL Trim, mbC5orf Trim, mbDDAH Trim, mbDMRTA Trim, mbGABRA A Trim, mbGABRA B Trim, mbGNG Trim, mbID4 Trim, mbIRF Trim, mbNT5E Trim, mbSIM A Trim, mbTBX15 Trim, NFIC-B, NFIC-A, NPSH2-B, NR5A2-B, OTX2-A, PAX6-A, pbDMRTA Trim, pbGNG Trim, pbSCAND Trim, pbTAL Trim, PDX1exp-B, PHOX2B-A, POU4F1 A trim, PPFIA3-A, PRDM13, PRKCB-A, PRKCB-C, PRSS27-A, PTGDR, PTPRN2-A, PTPRN2-B, SALL3-A, SALL3-B, SLC7A4-A, SOX2OT-B, SPAG6 A trim, TCTEX1D1-A, TMEM-A, TMEM-B, TMEM90B-A, TNFRSF10D, TOP2P1-B, TSPAN33-A, TTBAtrim, UBD-A, VWCJtrim, and VWCKtrim.

In one embodiment, each region is amplified with primer pairs listed for the respective region in Table 15.

In one embodiment, the method further comprises administering a treatment for the tumour detected.

In one aspect, there is provided a method for identifying a methylation signature indicative of a biological characteristic, the method comprising: obtaining data for a population comprising a plurality of genomic methylation data sets, each of said genomic methylation data sets associated with biological information for a corresponding sample, segregating the methylation data sets into a first group corresponding to one tissue or cell type possessing the biological characteristic and a second group corresponding to a plurality of tissue or cell types not possessing the biological characteristic, matching methylation data from the first group to methylation data from the second group on a site-by-site basis across the genome, identifying a set of CpG sites that meet a predetermined threshold for establishing differential methylation between the first and second groups, identifying, using the set of CpG sites, target genomic regions comprising at least two differentially methylated CpGs with 300 bp that meet said predetermined criteria, extending the target genomic regions to encompass at least one adjacent differentially methylated CpG site that does not meet the predetermined criteria, wherein the extended target genomic regions provide the methylation signature indicative of the biological trait.

In one embodiment, the method further comprises validating the extended target genomic regions by testing for differential methylation within the extended target genomic regions using DNA from at least one independent sample possessing the biological trait and DNA from at least one independent sample not possessing the biological sample.

In one embodiment, the step of identifying further comprises limiting the set of CpG sites to CpG sites that further exhibit differential methylation with peripheral blood mononuclear cells from a control sample.

In one embodiment, the plurality of tissue or cell types of the second group comprises at least some tissue or cells of the same type as the first group.

In one embodiment, the plurality of tissue or cell types of the second group comprises a plurality of non-diseased tissue or cell types.

In one embodiment, the predetermined threshold is indicative of methylation in the first group and non-methylation in the second group.

In one embodiment, the predetermined threshold is at least 50% methylation in the first group.

In one embodiment, the predetermined threshold is a difference in average methylation between the first and second groups of 0.3 or greater.

In one embodiment, the biological trait comprises malignancy.

In one embodiment, the biological trait comprises a cancer type.

In one embodiment, the biological trait comprises a cancer classification.

In one embodiment, the cancer classification comprises a cancer grade.

In one embodiment, the cancer classification comprises a histological classification.

In one embodiment, the biological trait comprises a metabolic profile.

In one embodiment, the biological trait comprises a mutation.

In one embodiment, the mutation is a disease-associated mutation.

In one embodiment, the biological trait comprises a clinical outcome.

In one embodiment, the biological trait comprises a drug response.

In one embodiment, the method further comprises designing a plurality of PCR primers pairs to amplify portions of the extended target genomic regions, each of the portions comprising at least one differentially methylated CpG site.

In one embodiment, the step of designing the plurality of primer pairs comprising converting non-methylated cytosines uracil, to simulate bisulphite conversion, and designing the primer pairs using the converted sequence.

In one embodiment, the primer pairs are designed to have a methylation bias.

In one embodiment, the primer pairs are methylation-specific.

In one embodiment, the primer pairs have no CpG residues within them having no preference for methylation status.

In one aspect, there is provided a method for synthesizing primer pairs specific to a methylation signature, the method comprising: carrying out the forgoing method, and synthesizing the designed primer pairs.

In one aspect, there is provided a non-transitory computer-readable medium comprising instructions that direct a processor to carry out the forgoing method.

In one aspect, there is provided a computing device comprising the computer-readable medium.

Example 1

Concept Summary

The embodiments detect circulating tumour DNA using a highly sensitive and specific methylation based assay with detection limits 100 times better than other techniques.

FIG. 1 depicts a schematic of the overall strategy. CpG dinucleotides are often clustered into concentrated regions in the genome referred to as CpG islands (grey box) and are often, but not always, associated with the promoter or enhancer regions of genes. These regions are known to become abnormally methylated in tumours (CmpG) as compared to normal tissue (CpG) which may be linked to the inactivation of tumour suppressor genes by this methylation event. Methylation of CpG islands and the boundary regions (CpG island shores) is extensive and co-ordinated such that most or all of the CpG residues in that region become methylated. The detection of this methylation typically involves bisulphite conversion, PCR amplification of the relevant region (arrows), and sequencing where un-methylated CpG residues are converted to TpG dinucleotides while methylated CpG residues are preserved as CpGs. Sequencing of these PCR-amplified "probes" (BISULFITE SEQUENCING) from tumour DNA (arrows) results in the detection of multiple CpG residues being methylated within the same DNA fragment (Dashed Box) which can easily be distinguished from DNA from normal tissue (Boxes). The co-ordinated/concordant nature of this methylation produces a strong signal which can be detected over random or background changes from DNA sequencing. This is accomplished by first identifying regions of tumour specific DNA methylation with multiple correlated CpG methylation sites within the same region.

Figure 30:
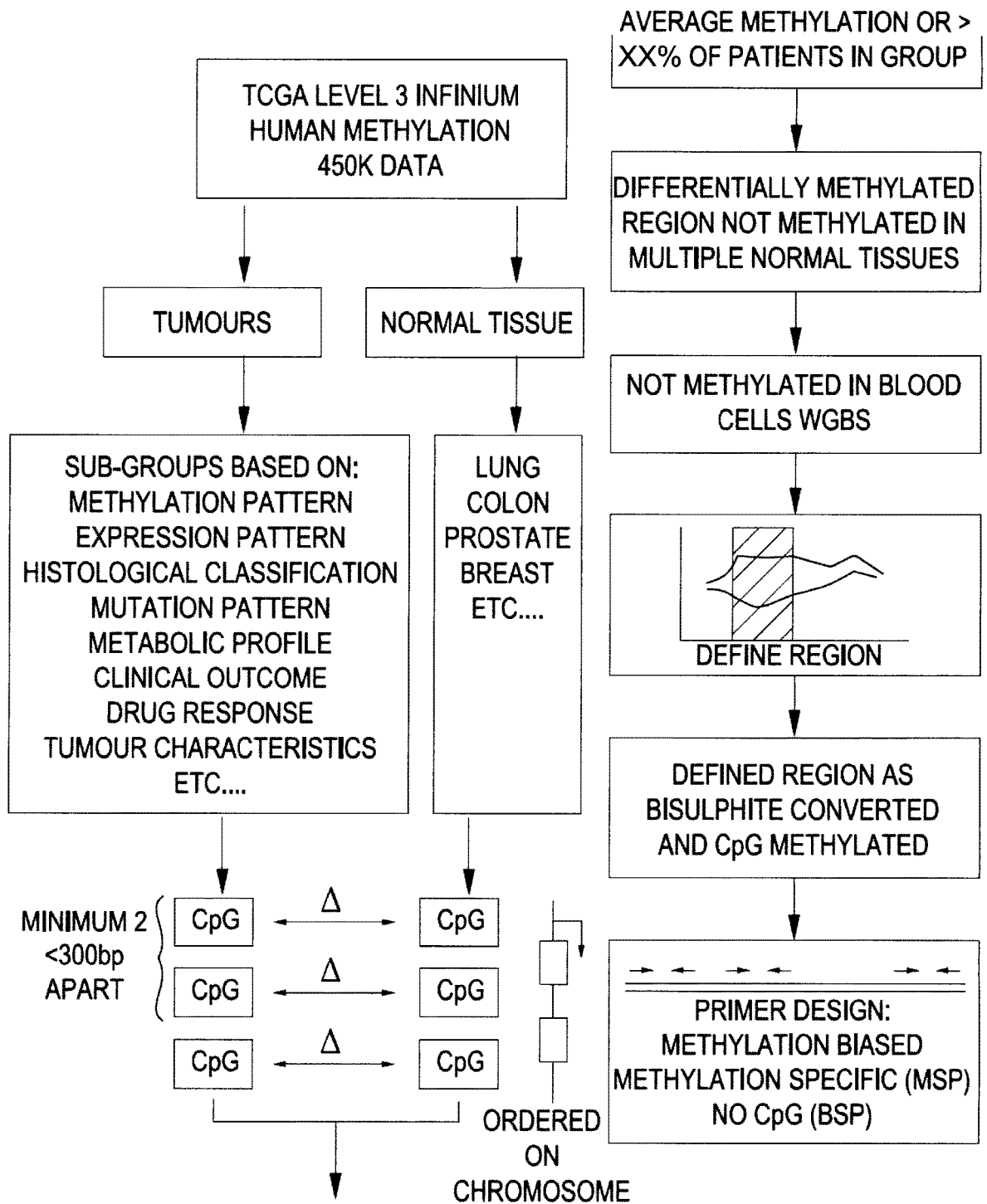
FIG. 30 is a flowchart illustrating a method for determining biological methylation signatures, and for developing probes for their detection.

FIG. 30 depicts a flowchart showing how a methylation signature for a biological trait may be determined. One or more steps of this method may be implemented on a computer. Accordingly, another aspect of this disclosure relates to a non-transitory computer-readable medium comprising instructions that direct a processor to carry out steps of this method.

Generally "probe" is used herein to refer to a target region for amplification and/or the ensuing amplified PCR product. It will be understood that each probe is amplified by a "primer set" or "primer pair".

Figure 2:
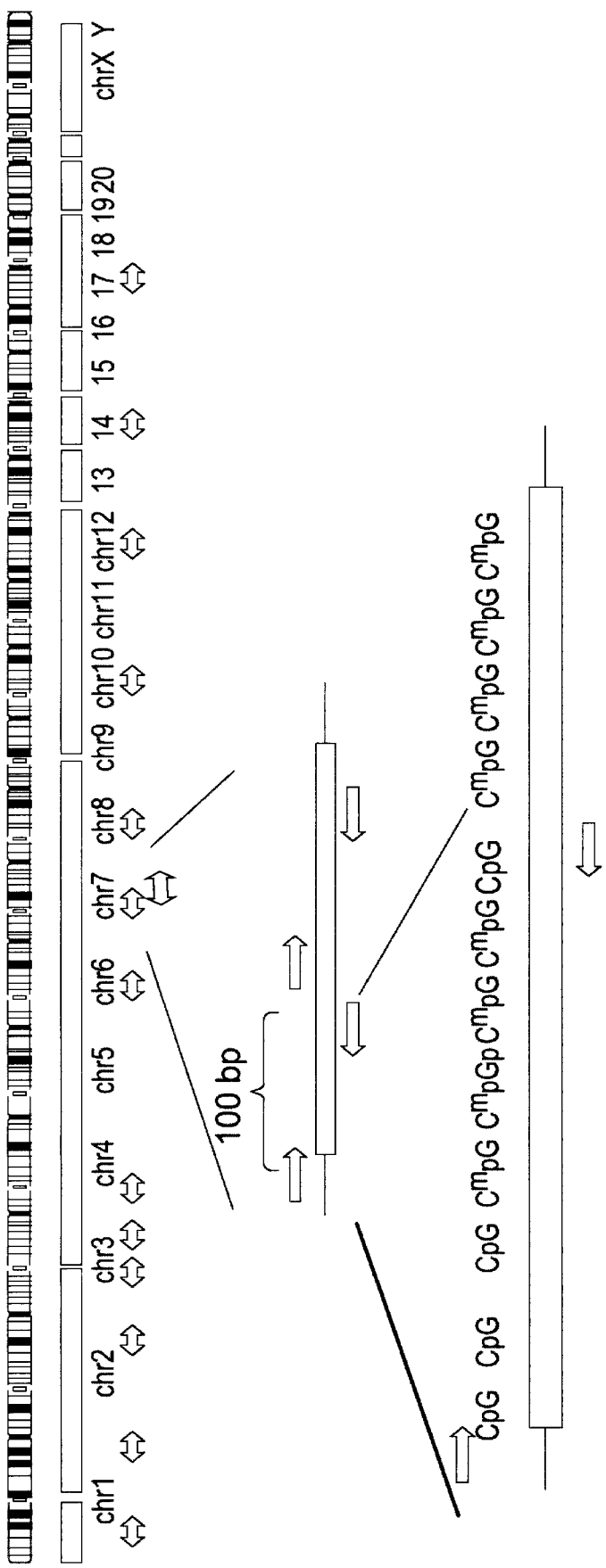
FIG. 2 depicts a schematic of the amplification of multiple target regions.

FIG. 2 depicts a schematic for amplification of target regions. Multiple regions from across the human genome have been identified as being differentially methylated in the DNA from various types of tumours compared to the normal DNA from a variety of different tissues. These regions can be fairly extensive spanning 100 s to 1000 s of base pairs of DNA. These target regions (black boxes, bottom) exhibit coordinated methylation where most or all of the CpG dinucleotides in these regions are methylated in tumour tissue with little or no methylation in normal tissues. As shown in FIG. 2, when sequencing across these regions (arrows) multiple CpG residues are seen to be methylated together in the tumour creating a concordant signal identifiable as being tumour specific. By targeting multiple PCR-amplified probes across individual regions (middle) and across the entire genome (top) large numbers of probes can be designed with the advantage that with more probes comes greater sensitivity due to the greater likelihood of detecting a tumour specific fragment in a given sample. Primers for these probes are designed to amplify regions from 75 to 150 bp in length, corresponding to the typical size of circulating tumour DNA. The primers may include CpG dinucleotides or not, which in the former case can make these primers biased towards the amplification of methylated DNA or exclusively amplify only methylated DNA.

Multiple methylation-biased PCR primer pairs can be created, which are able to preferentially amplify these regions. These multiple regions are sequenced using next generation sequencing (NGS) at a high read depth to detect multiple tumour specific methylation patterns in a single sample. As described herein, features have been incorporated into a blood based cancer detection system that provides advantages over other tests which have been developed, and provides an unprecedented level of sensitivity and specificity as well as enables the detection of minute quantities of DNA (detection sensitivity).

Example 2

Probe and Primer Set Development

The detection of circulating tumour DNA is hampered by both the presence of large amounts of normal DNA as well as by the very low concentrations of tumour DNA in the blood. Compounding this issue, both PCR and sequencing based approaches suffer from the introduction of single nucleotide changes due to the error prone nature of these processes. To deal with these issues, regions of the genome have been identified that exhibit concerted tumour specific methylation over a significant expanse of DNA so that each CpG residue is concordant[21]. Methylation-biased PCR primer pairs were designed for multiple segments of DNA across these regions each containing multiple CpG residues. Sample protocols for selection of differentially methylated regions and design of region specific PCR primers are provided.

Protocol for the Selection of Differentially Methylated Regions

Use of TCGA DATA for Identifying Breast Specific Probes

Level 3 (processed) Illumina Infinium HumanMethylation450 BeadChip array data (www.illumina.com/techniques/microarrays/methylation-arrays.html) was downloaded from The Tumour Genome Atlas (TCGA) site (tcga-data.nci.nih.gov/tcga/tcgaHome2.jsp) for the appropriate tumour types (e.g., breast, prostate, colon, lung, etc.). Tumour and normal samples were separated and the methylation values (from −0.5 to +0.5) for each group were averaged. The individual methylation probes were mapped to their respective genomic location. Probes that fulfilled the following example criteria were then identified:

1. The average methylation values for the normal breast, prostate, colon and lung tissues all below −0.3;
2. The difference between the average breast tumour and average breast normal values greater than 0.3, or at least 50% methylation in the tumour group; and
3. Two probes within 300 bp of each other fulfill criteria 1 and 2.

These criteria establish that the particular probe is not methylated in normal tissue, that the difference between the tumour and normal is significant, and that multiple probes in a relatively small area are co-ordinately methylated. Regions which had multiple positive consecutive probes (i.e., 3 or more) were prioritized for further analysis. Average values for approximately 10 other probes to either side of the positive region were plotted for all tumour and normal tissue samples to define the region exhibiting differential methylation. Regions exhibiting concerted differential methylation between tumour and normal for single or multiple tumour types were identified.

A secondary screen for a lack of methylation of these regions in blood was carried out by examining the methylation status of the defined regions in multiple tissues using nucleotide level genome wide bisulphite sequencing data. Specifically the UCSC Genome Browser (genome.ucsc.edu/) was used to examine methylation data from multiple sources.

Data was processed by the method described in Song Q, et al., A reference methylome database and analysis pipeline to facilitate integrative and comparative epigenomics. PLOS ONE 2013 8(12): e81148 (journals.plos.org/plosone/article?id=10.1371/journal.pone.0081148) for use in the UCSC Browser and to identify hypo-methylated regions (above blue lines).

The following data sources were used:

Gertz J, et al., Analysis of DNA methylation in a three-generation family reveals widespread genetic influence on epigenetic regulation. PLoS Genet. 2011 7(8): e1002228 (journals.plos.org/plosgenetics/article?id=10.1371/journal.pgen.1002228).

Heyn H, et al., Distinct DNA methylomes of newborns and centenarians. Proc. Natl. Acad. Sci. U.S.A. 2012 109(26): 10522-7 (www.pnas.org/content/109/26/10522).

Hon G C, et al., Global DNA hypomethylation coupled to repressive chromatin domain formation and gene silencing in breast cancer. Genome Res. 2012 22 (2): 246-58 (genome.cshlp.org/content/22/2/246).

Heyn H, et al., Whole-genome bisulfite DNA sequencing of a DNMT3B mutant patient. Epigenetics. 2012 7(6):542-50 (www.tandfonline.com/doi/abs/10.4161/epi.20523#.VsS_gdIUVIw).

Hon G C, et al., Global DNA hypomethylation coupled to repressive chromatin domain formation and gene silencing in breast cancer. Genome Res. 2012 22(2):246-58 (genome.cshlp.org/content/22/2/246).

All of the regions identified exhibited hypo-methylation in normal blood cells including Peripheral Blood Mononuclear Cells (PBMC), the prime source of non-tissue DNA in plasma.

Protocol for the Design of Region Specific Primers for PCR Amplification and Next Generation Sequencing For regions identified as being differentially methylated in tumours, PCR primers were designed that are able to recognize bisulphite converted DNA which is methylated. Using Methyprimer Express™ or PyroMark™, or other web based programs, the DNA sequence of the region was converted to the sequence obtained when fully methylated DNA is bisulphite converted (i.e., C residues in a CpG dinucleotide remain Cs, while all other C residues are converted to T residues). The converted DNA was then analysed using PrimerBlast™ (www.ncbi.nlm.nih.gov/tools/primer-blast/) to generate optimal primers. Primers were not expressly selected to contain CpG residues but due to the nature of the regions, generally CpG islands, most had 1 to 3 CpGs within them. This renders them biased towards the amplification of methylated DNA but in many cases they do recognize and amplify non-methylated DNA as well. The region between the primers includes 2 or more CpG residues. Primers were chosen to amplify regions from 75 to 150 base pairs in size with melting temperatures in the range of 52-68° C. Multiple primers were designed for each region to provide increased sensitivity by providing multiple opportunities to detect that region. Adapter sequences (CS1 and CS2) were included at the 5' end of the primers to allow for barcoding and for sequencing on multiple sequencing platforms by the use of adaptor primers for secondary PCR.

Primers were characterized by PCR amplification of breast cancer cell line DNA and DNA from various primary tumours. PCR amplification was done with individual sets of primers and Next Generation Sequencing carried out to characterize the methylation status of specific regions. Primer sets exhibiting appropriate tumour specific methylation were then combined into a multiplex PCR reaction containing many primers.

Results

FIG. 3 lists the 47 CpG probes used to identify differentially methylated regions. These were analyzed by Receiver Operator Curve analysis (ROC). Normal and tumour samples from the entire TCGA breast cancer database were compared. The Area Under the Curve (AUC) analysis for each probe is shown with the standard error, 95% confidence interval and P-value. All of them where shown to have excellent discriminatory capabilities.

Figure 4:
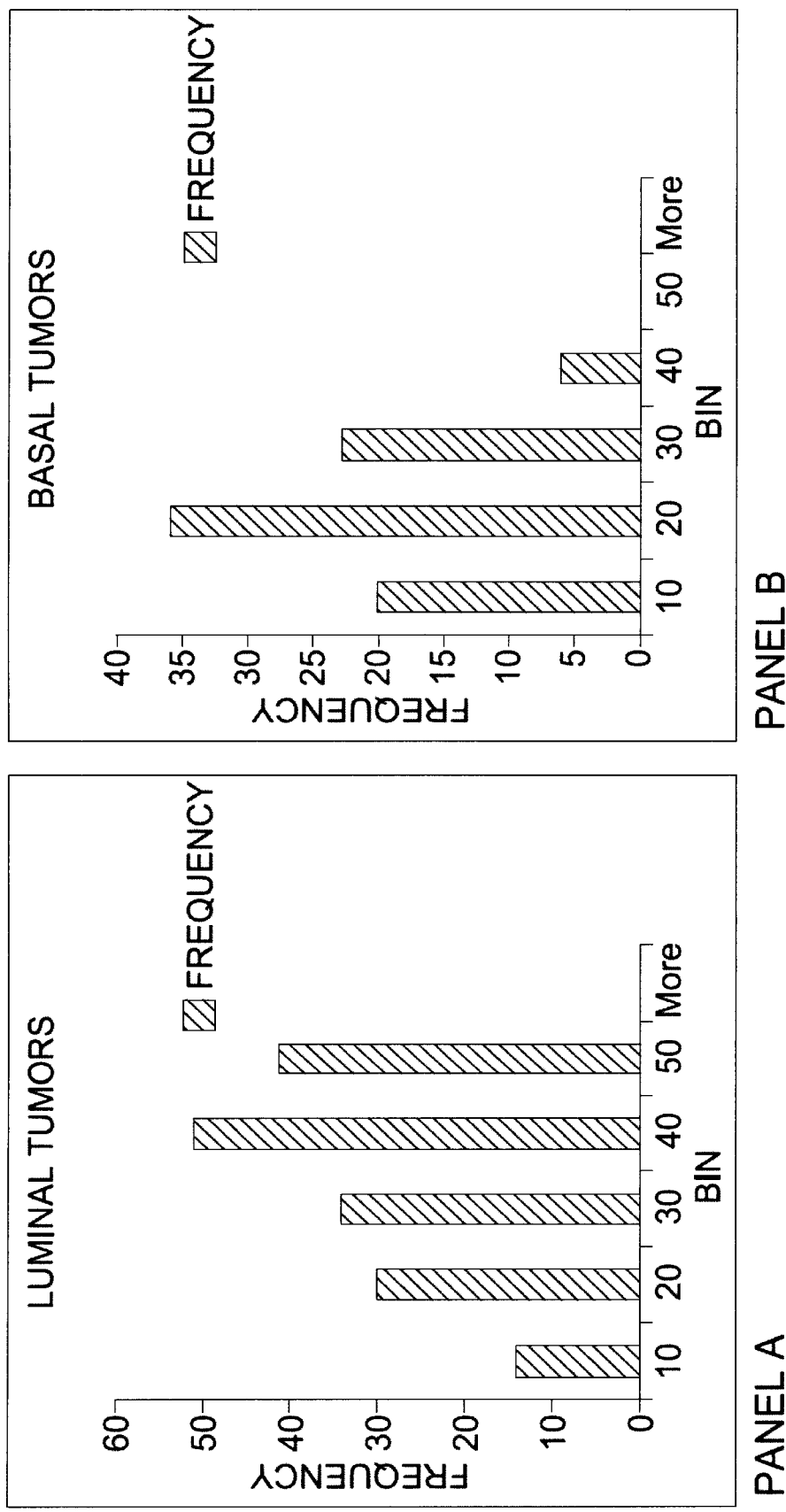
FIG. 4 depicts histograms showing the frequency of patients binned according to positive (methylated) probe frequency. Panel A depicts results for luminal tumours. Panel B depicts results for basal tumours.

FIG. 4 depicts the results of analysis methylation level for each patient in the TCGA database for the 47 CpG. Those exceeding the threshold of −0.1 were considered to be positive for methylation in that patient. The number of probes exceeding this methylation threshold were calculated for each patient. Patients were divided into those with Luminal A and B subtypes (Luminal Tumours; FIG. 4, Panel A) and those with Basal cancers (Basal Tumours; FIG. 4, Panel B) or and the number of patients with a specific range of positive probes was calculated. The histogram shows the frequency of patents within each range of positive probes. While these probes give excellent coverage in both populations, there are more positive probes amongst the Luminal tumours than the Basal tumours. Additional probes specific to the different breast cancer subtypes have been identified and appropriate probe development and validation is underway.

Example 3

Selection of Regions for Cancer and Cancer Types

For breast cancer, 52 regions in the genome were identified that are highly methylated in tumours but where multiple normal tissues do not exhibit methylation of these regions. These serve as highly specific markers for the presence of a tumour with little or no background signal.

Table 1 depicts regions selected for breast cancer screening.

TABLE 1

| Chromosome | Start (hg18) | End (hg18) | General Location | Tumour | Size |
|---|---|---|---|---|---|
| 2nd Generation ||||||
| chr1 | 167663259 | 167663533 | C1orf114 | P/B | 274 |
| chr7 | 49783577 | 49784309 | VWC2 | P/B/C | 732 |
| chr14 | 23873519 | 23873993 | ADCY4 | P/B/C | 474 |
| chr11 | 43559012 | 43559541 | MIR129-2 | B/C | 529 |
| 3rd Generation ||||||
| chr6 | 43319186 | 43319213 | TTBK1 | P/B | 27 |
| chr1 | 46723905 | 46724176 | DMBX1 | P/B/C | 271 |
| chr7 | 27171684 | 27172029 | HOXA9 | B | 345 |
| chr8 | 120720175 | 120720579 | ENPP2 | P/B | 404 |
| chr10 | 99521635 | 99521924 | SFRP5 | P/B | 289 |
| chr12 | 103376281 | 103376485 | CHST11 | P/B/C | 204 |
| chr19 | 51071603 | 51072234 | FOXA3 | P/B | 631 |
| 4th Generation ||||||
| chr1 | 47470535 | 47470713 | TAL1 | B | 178 |
| chr1 | 50658998 | 50659557 | DMRTA2 | B | 559 |
| chr1 | 66030610 | 66030634 | PDE4B | B | 24 |
| chr1 | 90967262 | 90967924 | BARHL2 | B | 662 |
| chr1 | 119331667 | 119332616 | TBX15 | B/C | 949 |
| chr1 | 153557070 | 153557585 | RUSC1, C1orf104 | B | 515 |
| chr1 | 233880632 | 233880962 | GNG4 | B | 330 |
| chr2 | 104836482 | 104837226 | POU3F3 | B | 744 |
| chr2 | 198359230 | 198359743 | BOLL | B/C | 513 |
| chr3 | 32834103 | 32834562 | TRIM71 | B/C | 459 |
| chr3 | 172228723 | 172228985 | SLC2A2 | B | 262 |

TABLE 1-continued

| Chromosome | Start (hg18) | End (hg18) | General Location | Tumour | Size |
|---|---|---|---|---|---|
| chr4 | 5071985 | 5072137 | CYTL1 | B | 152 |
| chr4 | 42094549 | 42094615 | SHISA3 | B | 66 |
| chr4 | 46690266 | 46690578 | GABRA4 | B | 312 |
| chr5 | 38293273 | 38293312 | EGFLAM | B | 39 |
| chr5 | 43076195 | 43076642 | C5orf39 | B | 447 |
| chr5 | 115179918 | 115180393 | CDO1 | B | 475 |
| chr6 | 336189 | 337131 | IRF4 | B/C | 942 |
| chr6 | 19944994 | 19945298 | ID4 | B | 304 |
| chr6 | 28618285 | 28618318 | SCAND3 | B | 33 |
| chr6 | 31806197 | 31806205 | DDAH2 | B | 8 |
| chr6 | 33269254 | 33269355 | COL11A2 | B | 101 |
| chr6 | 86215822 | 86215929 | NT5E | B | 107 |
| chr6 | 101018889 | 101019751 | SIM1 | B | 862 |
| 5th Generation | | | | | |
| chr6 | 153493505 | 153494425 | RGS17 | B | 920 |
| chr7 | 121743738 | 121744126 | CAPDS2 | B | 388 |
| chr8 | 72918338 | 72918895 | MSC | B/C | 557 |
| chr10 | 22674438 | 22674584 | SPAG6 | B/C | 146 |
| chr10 | 105026601 | 105026737 | INA | B | 136 |
| chr11 | 128068895 | 128069316 | FLI1 | B/C | 421 |
| chr12 | 52357158 | 52357378 | ATP5G2 | B | 220 |
| chr12 | 94466892 | 94467095 | USP44 | B/C | 203 |
| chr13 | 78075521 | 78075764 | POU4F1 | B | 243 |
| chr14 | 55656275 | 55656325 | PELI2 | B | 50 |
| chr17 | 33176853 | 33178091 | HNF1B | B | 1238 |
| chr17 | 32368343 | 32368604 | LHX1 | B/C/L | 261 |
| chr17 | 44154844 | 44155027 | PRAC, C17orf93 | B/C | 183 |
| chr18 | 73090725 | 73091121 | GALR1 | B/C | 396 |
| chr19 | 12839383 | 12839805 | MAST1 | B | 422 |
| chr20 | 2729122 | 2729438 | CPXM1 | B/C | 316 |
| chr20 | 43952209 | 43952500 | CTSA, NEURL2 | B | 291 |

In Table 1, 'Start' and 'End' designate the coordinates of the target regions in the hg18 build of the human genome reference sequence. The 'General Location' field gives the name of one or more gene or ORF in the vicinity of the target region. Examination of these sequences relative to nearby genes indicates that they were found, e.g., in upstream, in 5' promoters, in 5' enhancers, in introns, in exons, in distal promoters, in coding regions, or in intergenic regions. The 'Tumour' field indicates whether a region is methylated in prostate (P), breast (B), colon (C), and/or lung (L) cancers. The 'Size' field indicates the size of the target region.

In the discussion here, it should be recognized that reference to genes such as CHST11, FOXA, and NT5 are not intended to be indicative of the genes in question per se, but rather to the associated methylated regions described in Table 1.

In total, 52 regions were found to be methylated in association with breast cancer, 17 were found to be methylated in association with prostate cancer, 9 were found to be methylated in association with prostate cancer, and 1 region was found to be methylated in association with lung cancer. Thus, some regions appear to be generally indicative of the various types of cancers assessed. Other regions methylated in subgroups of these, while others are specific for cancers. In the context of this assay and the types of cancers examined, 25 regions may be described as being "specifically methylated in breast cancer". However, it is noted that the same approach may be used to identify regions methylated specifically in other cancers.

Assays may be developed for cancer generally, or to detect groups of cancers or specific cancers. A multi-tiered assay may be developed using "general" regions (methylated in multiple cancers) and "specific" regions (methylated in only specific cancers). A multi-tiered test of this sort may be run together in one multiplex reaction, or may have its tiers executed separately.

Probes for Breast Cancer

Over 150 different PCR primer pairs were developed to the 52 different regions in the genome shown to exhibit extensive methylation in multiple breast cancer samples from the TCGA database but with no or minimal methylation in multiple normal tissues and in blood cells (Peripheral Blood Mononuclear Cells and others).

As proof of concept, these were then used to amplify bisulphite converted DNA from breast cancer cell lines MCF-7 (ER+, PR+), T47-D (ER+, PR+), SK-BR-3 (HER2+), MDA-MD-231 (Triple Negative) and normal breast lines MCF-10A and 184-hTERT. Sequencing adapters were added and Next Generation Sequencing carried out on an Ion Torrent sequencer. The sequencing reads were then separated by region and the sequence reads were analyzed using the BiqAnalyzer HT program.

Results

Example results of methylation analysis will be discussed herein. CHST11 is an example of a region methylated in prostate, breast, and colon cancer. FOXA is a region methylated in breast and prostate cancer. NT5 is a region methylated specifically in breast cancer.

Figure 5:
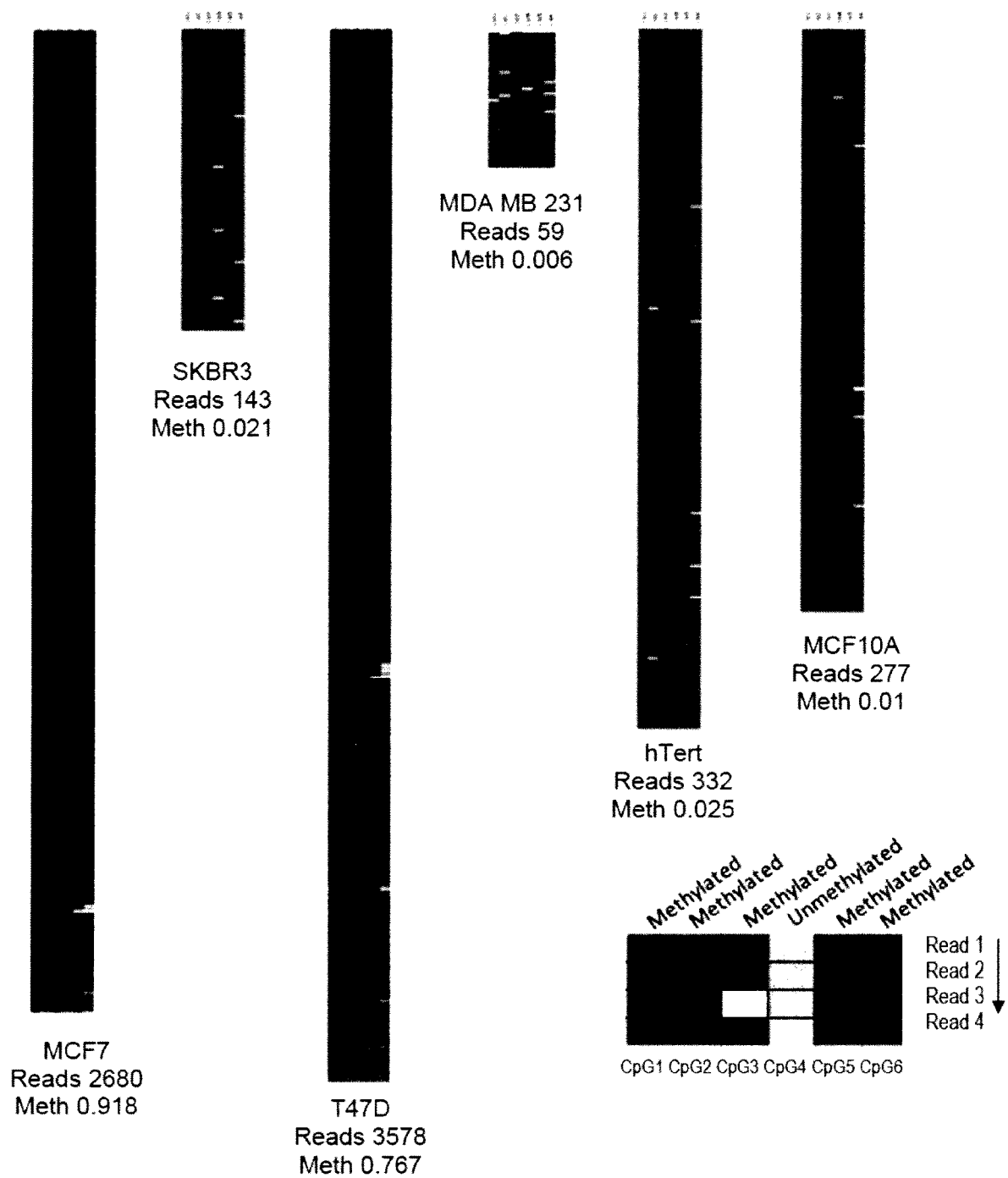
FIG. 5 depicts sequencing results to assess methylation status of a region near the CHST11 gene (CHST11 Probe C) in breast cancer cell lines.

FIG. 5 depicts sequencing results from a region from near the CHST11 gene (Probe C) is shown. For each cell line the results of a single sequencing read is depicted as a horizontal bar with each box representing a single CpG residue from between the PCR primers (in this case there being 6 CpG residues, Illustration at bottom right). Methylated bases are shown in dark grey while un-methylated bases are shown in light grey. Where a CpG could not be identified by the alignment program it is shown as a white box. Multiple sequence reads are shown for each cell line, stacked on top of each other. The numbers at the bottom of each stack indicates the number of sequence reads (Reads) and the overall methylation level determined from these reads (Meth).

When sequenced, these probes produced strong concordant signals that consisted of multiple methylated CpGs (5 to 25) where there is a strong correlation between individual sites being methylated in tumours. This eliminates false positive results due to PCR and sequencing errors. These tumour specific multiple methylated sites can be detected against a high background of normal DNA, being limited only by the read depth of the sequencing. Based on bioinformatic analysis of TCGA tumours, this essentially eliminates false positive signals.

Figure 6:
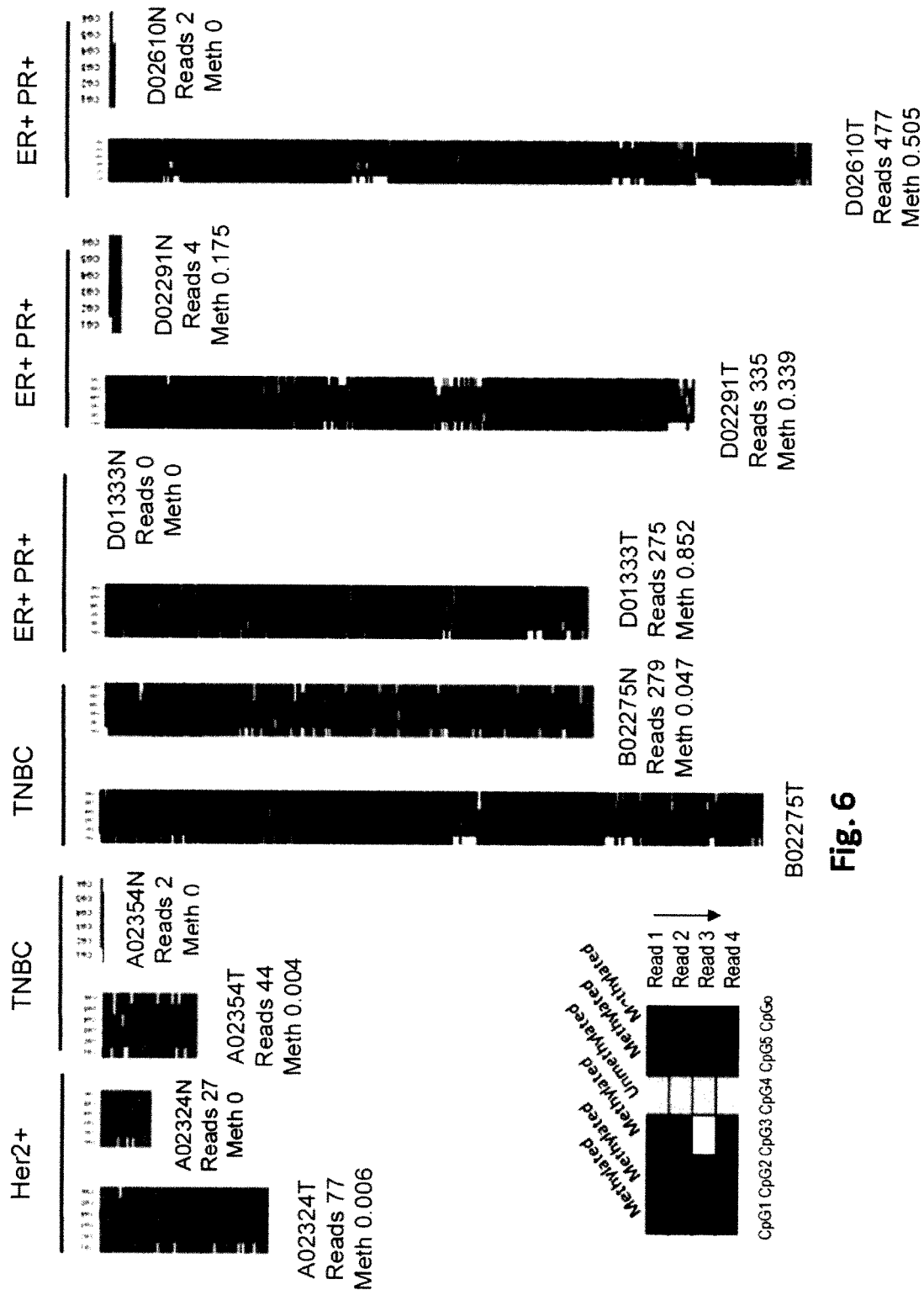
FIG. 6 depicts sequencing results to assess methylation status of CHST11 Probe A in breast cancer tumors and normal breast tissue.

FIG. 6 depicts results for CHST11 Probe A. Methylation in the region was characterized for a variety of breast cancer tumour samples (T) and in normal breast tissue samples (N) from the same patient. As in FIG. 5 the methylated bases are shown in dark grey while un-methylated bases are shown in light grey (illustration bottom left). Tumours of various subtypes were analysed including A02324 which is positive for HER2 amplification (HER2+), A02354 and B02275 which are Triple Negative Breast Cancer (TNBC), and D01333, D02291, D02610 which are all Estrogen and Progesterone Receptor positive tumours (ER+PR+). The values below each column refer to the number of sequence reads obtained by Next Generation Sequencing (Reads) and the overall level of methylation of all of the CpG residues (Meth) based on these reads. Where no sequence reads were obtained for a given sample and box is shown as for sample D01333 N (Normal).

Figure 7:
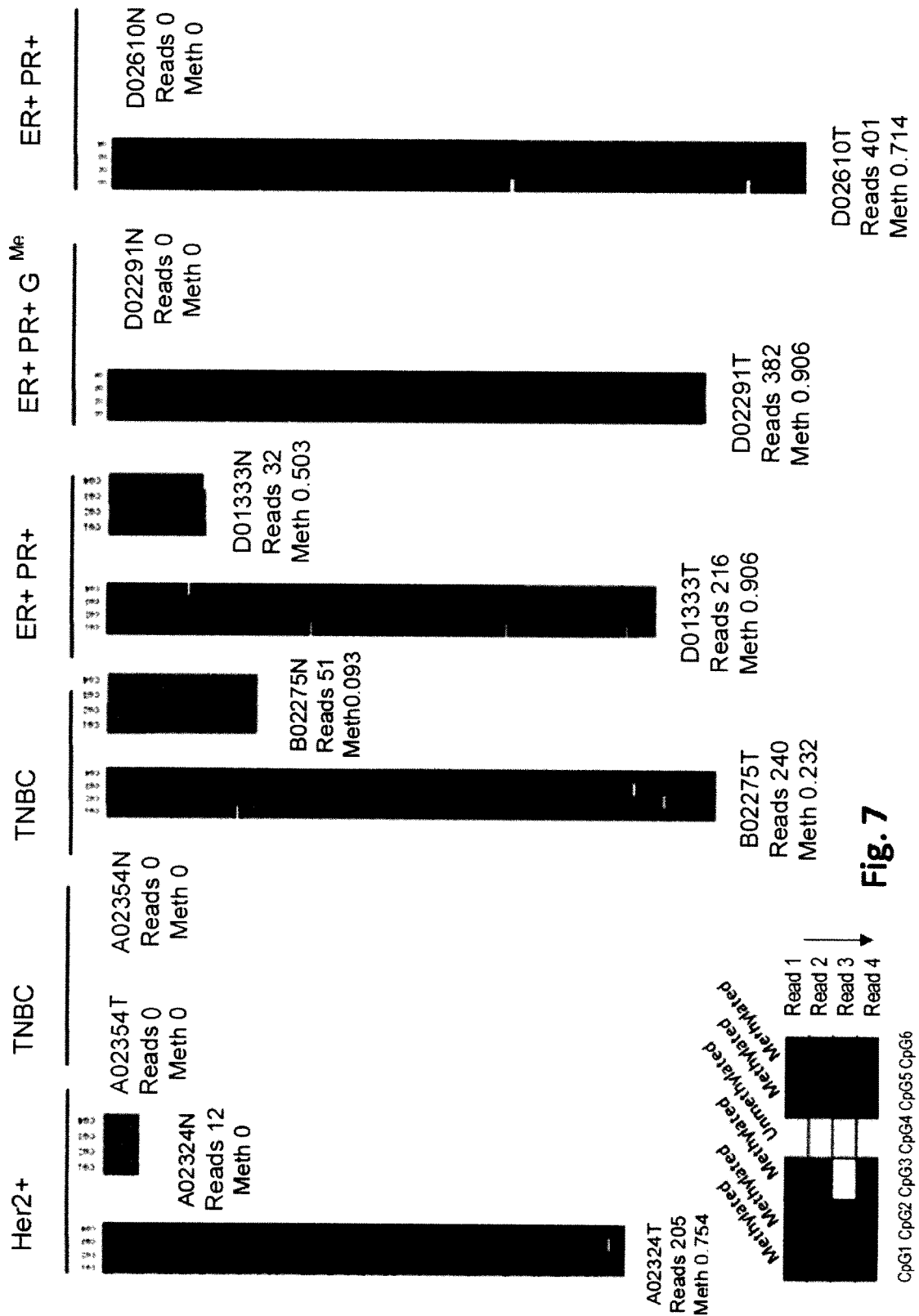
FIG. 7 depicts sequencing results to assess methylation status of FOXA Probe A in breast cancer cell lines.

FIG. 7 depicts results of similar analysis of FOXA Probe A in breast cancer cell lines.

Figure 15:
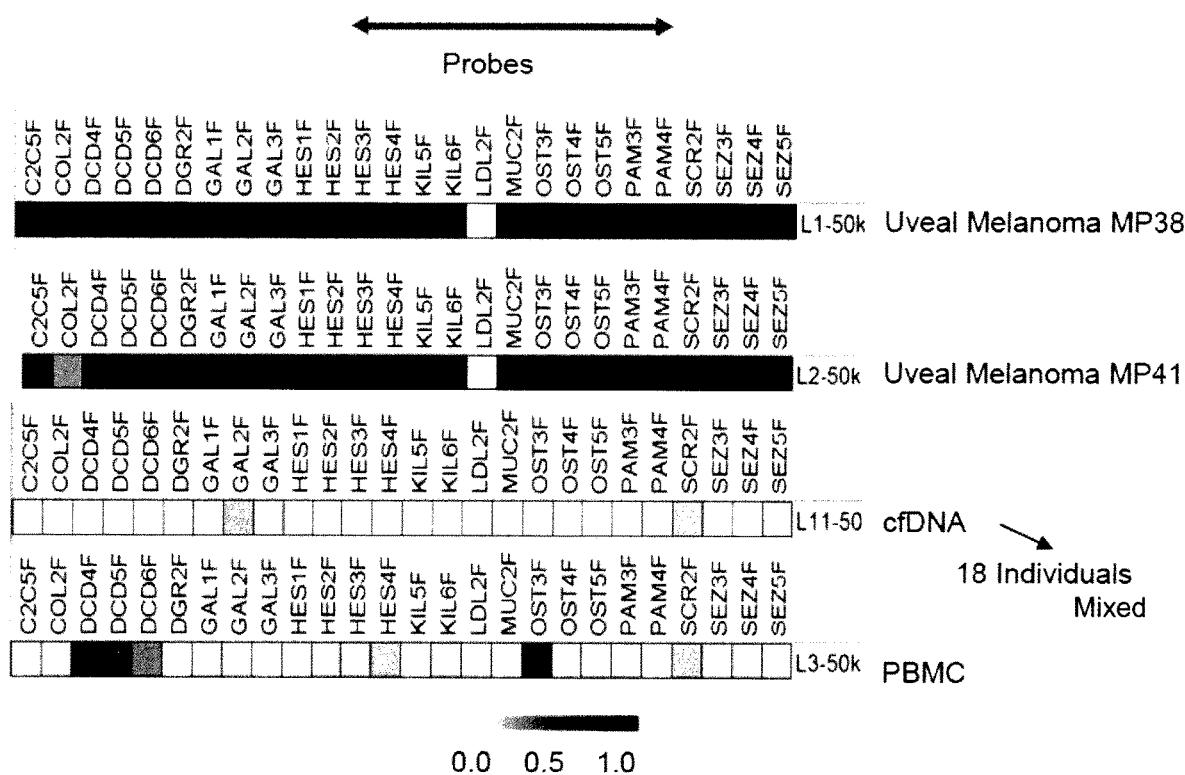
FIG. 15 is a diagram showing validation of various uveal melanoma (UM) probes in two cell lines MP38 (with loss of 3p) and MP41 (3p WT). Negative controls were cell free DNA (cfDNA) consisting of a pool of 18 individuals without cancer and peripheral mononuclear cells (PBMC). Probes for the indicated regions were PCR amplified individually and sequenced. Darker shading indicates higher level of methylation. OST3F was methylated in PBMCs while LDL3F was not methylated in tumours, with the majority showing strong methylation in the UM lines but not in the PBMCs or cfDNA.

FIG. 15 depicts a numerical summary generated methylation data for prostate cell lines. #Reads is indicative of the number of reads exported, and Mean Me is indicative of the mean methylation.

Figure 8:
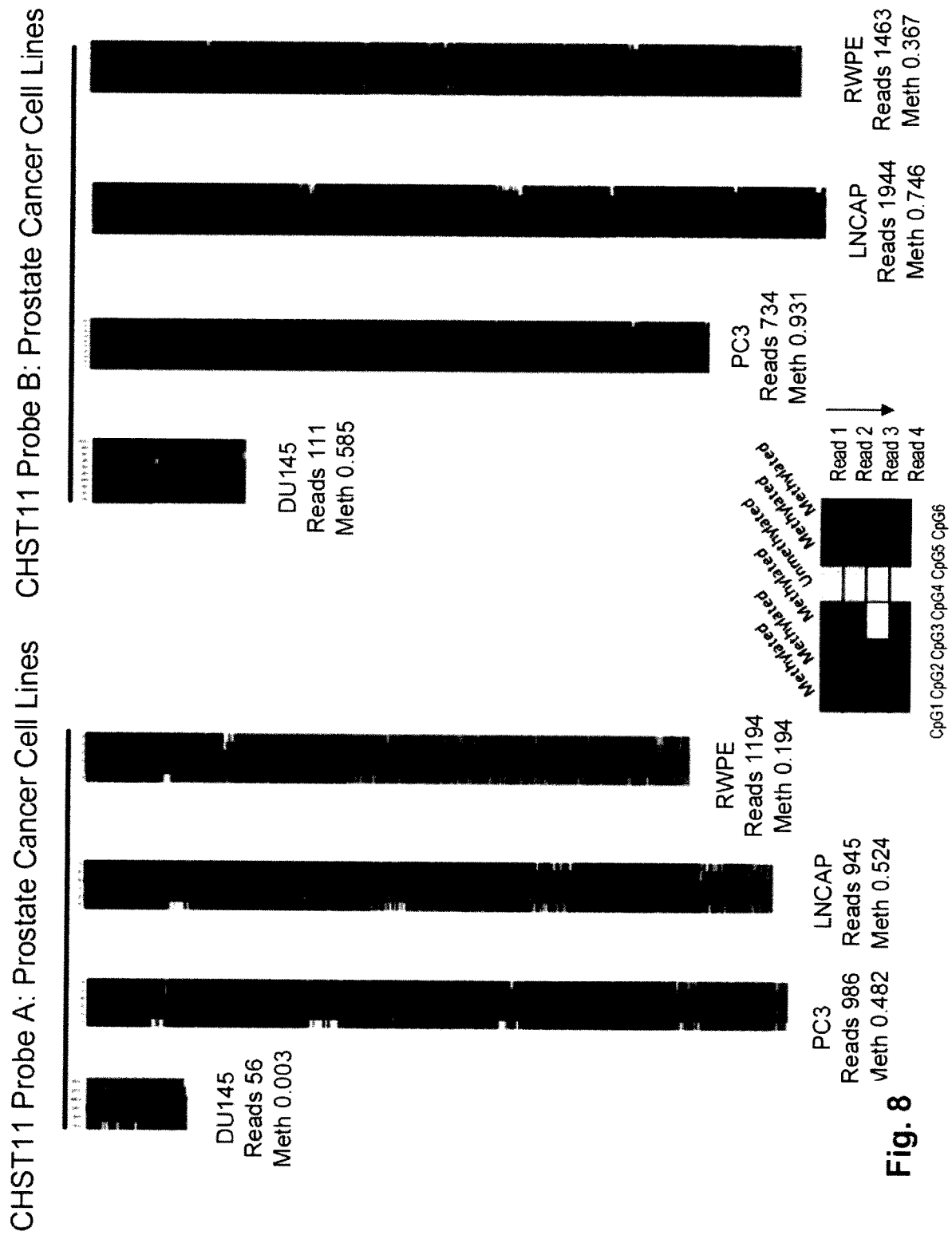
FIG. 8 depicts sequencing results to assess methylation status of CHST Probe A and Probe B in prostate cancer cell lines.

FIG. 8 depicts results of similar analysis of the CHST11 Probe A and CHST11 Probe B in prostate cancer cell lines. DU145 is an Androgen Receptor (AR−) negative cell line which is able to generate metastases in the mouse. PC3 is also AR− and also metastatic. LNCaP is an Androgen Receptor positive line (AR+) which does generate metastases in the mouse while RWPE cells are AR+ and non-metastatic.

Figure 9:
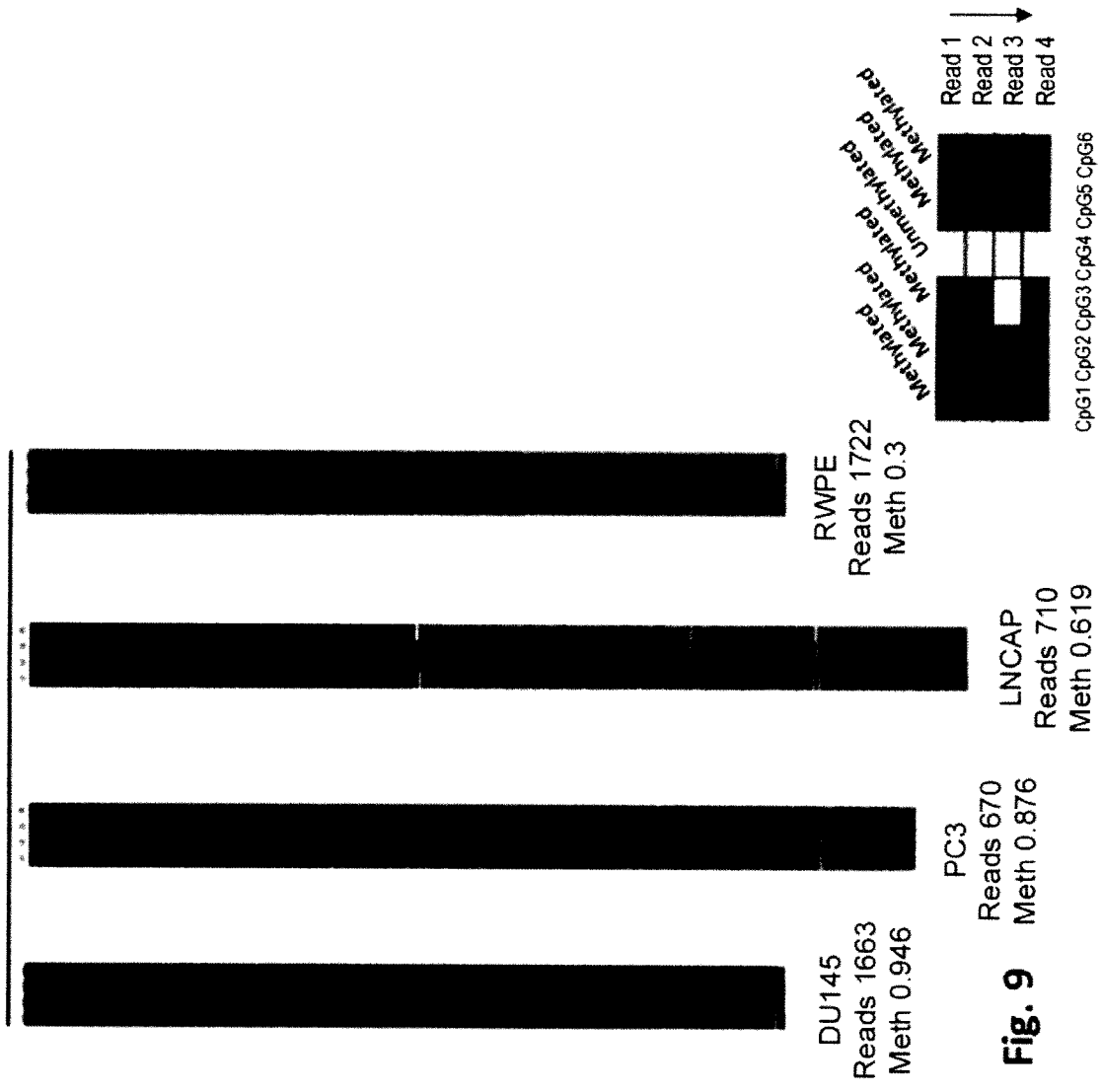
FIG. 9 depicts sequencing results to assess methylation status of FOXA Probe A in prostate cancer cell lines.

FIG. 9 depicts results of similar analysis of FOXA Probe A in prostate cell lines.

Figure 10:
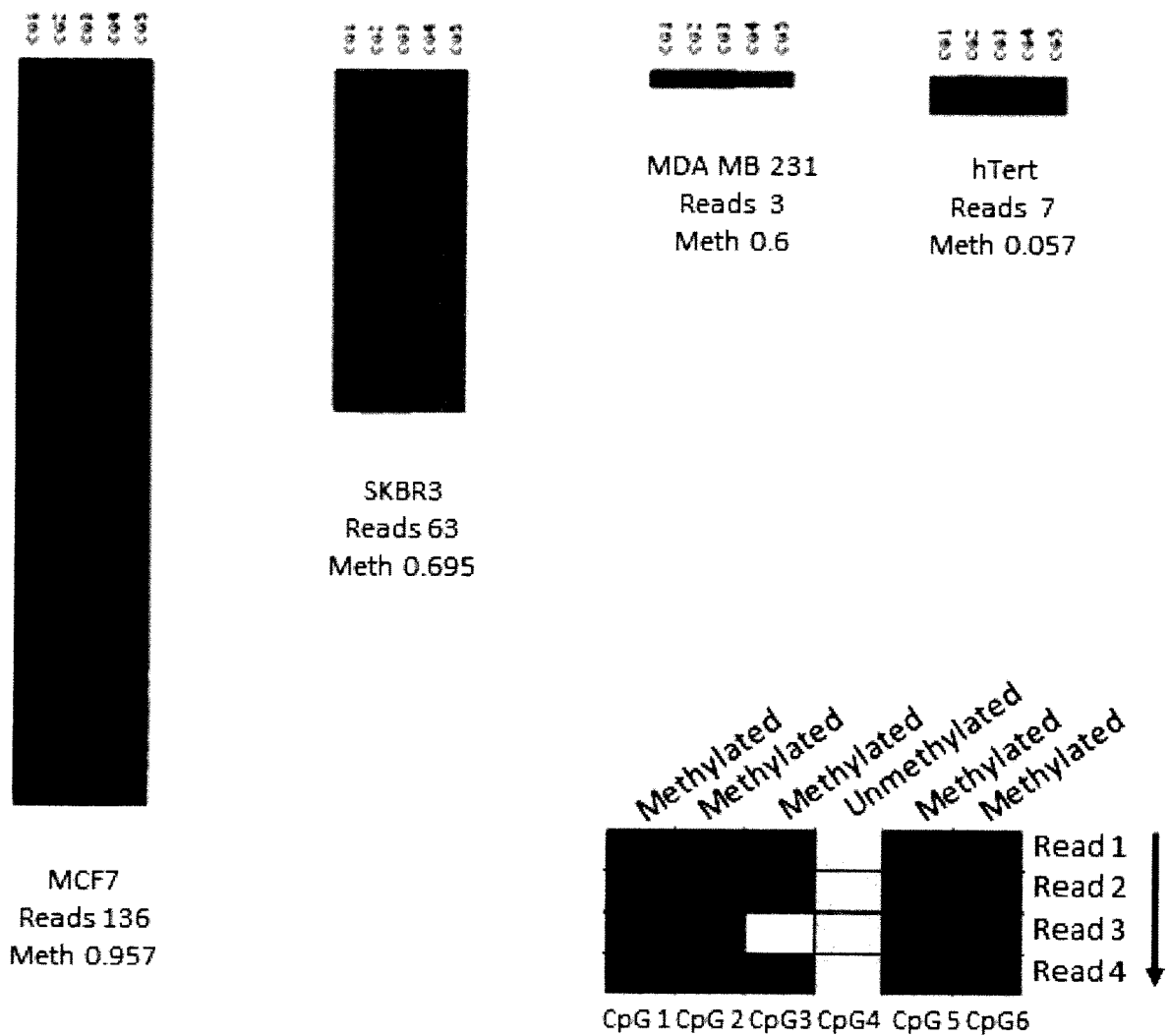
FIG. 10 depicts sequencing results to assess methylation status of NT5 Probe E in breast cancer cell lines.

FIG. 10 depicts sequencing results to assess methylation status NET5 Probe E in breast cancer cell lines.

These results exemplify probes of differing specificities that can be selected using the approach outlined herein.

Example 4

Probes for Uveal Cancer

Using the above-described methodologies, regions were selected for uveal cancer screening. Table 2 depicts these regions.

TABLE 2

| Chromo-some | Start | Stop | General Location | Descriptor | Size |
|---|---|---|---|---|---|
| chr10 | 89611399 | 89611920 | PTEN, KILLIN | Shore CGI | 521 |
| chr11 | 35503400 | 35504124 | PAMR1 | small CGI | 724 |
| chr11 | 1.18E+08 | 1.18E+08 | MPZL2 | Prox Prom | 599 |
| chr15 | 60146043 | 60147120 | C2CD4A | Shore CGI | 1077 |
| chr17 | 24370858 | 24371386 | SEZ6 | small CGI | 528 |
| chr19 | 11060476 | 11060965 | LDLR | Prox Prom | 489 |
| chr2 | 1.66E+08 | 1.66E+08 | GALNT3 | CGI | 1465 |
| chr2 | 2.23E+08 | 2.23E+08 | ccdc140/pax3 | Shore CGI | 4724 |
| chr6 | 21774638 | 21775386 | FLI22536/casc15 | small CGI | 748 |
| chr6 | 24465699 | 24466545 | KAAG1, DCDC2 | CGI | 846 |
| chr6 | 31031220 | 31031651 | MUC21 | CGI | 431 |
| chr6 | 70632889 | 70633262 | COL19A1 | Proc Prom | 373 |
| chr6 | 1.09E+08 | 1.09E+08 | NR2E1/OSTM1 | small CGI | 1001 |
| chr7 | 29996242 | 29996333 | SCRN1 | Shore CGI | 91 |
| chr1 | 2450725 | 2452224 | HES5 | CGI | 1499 |
| chr1 | 12601228 | 12601893 | DHRS3 | Shore CGI | 665 |

Example 5

Tests for Breast Cancer Subtypes

The screen that has been described above, which originally incorporated all breast tumours in the TCGA database, can also be done on subsets of the tumour database.

BRCA1 carriers were taken out of the dataset and analyzed individually to identify target methylated regions specific to this subgroup. Breast cancer can also be divided in other ways: e.g., into five subtypes, Basal, Luminal A., Luminal B, HER2 and Normal-like. Patients in each of these groups were identified and analyzed to identify target methylated regions for each subset.

The screen can also be changed to look at individual patients using the previously described criteria to see who are positive or negative. Target methylated regions can then be ranked based on how many individuals are positive. This can help to remove biasing due to amalgamation (averaging). Targets can then be selected, e.g., if they are present in greater than 75% of patients for each subtype, and then rationalize amongst these.

Test for BRCA Carriers

Current monitoring practices for women at high risk of developing breast cancer due to familial BRCA1 or 2 mutations involve yearly MRI, however the high false positive rates result in a large number of unnecessary biopsies. Using the methodology described herein, a test may be developed to serve as a secondary screen, e.g., to be employed after a positive MRI finding; or to be used for primary screening of high risk patients. The blood test is designed to detect all types of breast cancer but because ER+ breast cancer is the most frequent it is biased towards these cancers, though some of the constituent probes do recognize HER2+ and TNBC tumours. In order to provide optimal sensitivity for the monitoring of BRCA1 and 2 an assay optimized for these patients may be developed.

Both TNBC and BRCA1 and 2 patients were selected from the TCGA 450k methylation database. Generally, most BRCA1 and 2 tumours will present as TNBC but many non-familial cancers are also TNBC. These patients were analyzed using the above-described tumour specific methylation region protocol on both the overall TNBC population and on the BRCA1 and 2 patients. 85 tumour specific regions were identified for TNBC, 67 for BRCA1 and 13 for BRCA2 populations. Of these 39 were present in any two populations and they constitute the starting point for the development of this assay. Appropriate regions for a BRCA1 specific test were identified and assessed in individual patients with known mutations. This population is surprisingly uniform and most patients are recognized by a large number of probes. AUCs for individual probes are for the most part very high. Based on these results, an assay can be developed to detect all three, i.e., TNBC, BRCA1 and 2. If additional detection sensitivity is required, then individual tests can be constructed. For high risk women who are BRCA1 or 2 mutation carriers, their mutation status should be known so that the appropriate test can be applied.

Test for BRCA1 Carriers

Probes have been developed for the detection of cancer in carriers of the BRCA1 mutation. Methylation data from the TCGA Breast cancer cohort were selected from patients known to be carriers of pathogenic BRCA1 mutations. This data was then analyzed as described to identify regions of the genome specifically methylated in this sub-set of breast cancers. Table 3 lists appropriate regions identified and their genomic locations.

TABLE 3

| Target Region (hg18 reference) | | | | |
|---|---|---|---|---|
| chr | Nearest Gene | Start (nt) | End (nt) | Size |
| chr1 | LOC105378683 | 43,023,840 | 43,023,487 | 353 |
| chr1 | NPHS2 | 177,811,942 | 177,811,671 | 271 |
| chr1 | NR5A2 | 198,278,599 | 198,278,409 | 190 |
| chr11 | PAX6 | 31,783,955 | 31,782,545 | 1,410 |
| chr11 | KCNE3 | 73,856,332 | 73,855,762 | 570 |
| chr12 | KCNA6 | 4,789,491 | 4,789,342 | 149 |
| chr12 | TMEM132C | 127,318,539 | 127,317,001 | 1,538 |
| chr13 | PDX1 | 27,390,265 | 27,389,540 | 725 |
| chr13 | EPSTI1 | 42,464,618 | 42,463,901 | 717 |
| chr16 | A2BP1 | 6,009,930 | 6,009,020 | 910 |
| chr16 | CRYM | 21,202,914 | 21,202,448 | 466 |
| chr16 | PRKCB | 23,755,504 | 23,754,826 | 678 |
| chr16 | IRF8 | 84,490,354 | 84,490,167 | 187 |
| chr18 | SALL3 | 74,842,145 | 74,839,705 | 2,440 |
| chr19 | LYPD5 | 49,016,848 | 49,016,696 | 152 |

TABLE 3-continued

| chr | Nearest Gene | Start (nt) | End (nt) | Size |
|---|---|---|---|---|
| chr2: | DPP10 | 115,636,420 | 115,635,215 | 1,205 |
| chr20 | C20orf56 | 22,507,867 | 22,507,676 | 191 |
| chr3 | SOX2OT | 182,919,993 | 182,919,839 | 154 |
| chr4 | CDKL2 | 76,774,880 | 76,774,658 | 222 |
| chr5 | March 11 | 16,233,072 | 16,232,633 | 439 |
| chr5 | CCL28 | 43,433,329 | 43,432,559 | 770 |
| chr5 | AP3B1 | 77,304,644 | 77,304,208 | 436 |
| chr7 | CARD11 | 3,050,299 | 3,049,859 | 440 |
| chr7 | BLACE | 154,859,799 | 154,859,051 | 748 |
| chr7 | PTPRN2 | 157,176,806 | 157,176,096 | 710 |
| chr8 | RUNX1T1 | 93,183,481 | 93,183,326 | 155 |

52 different probes were then developed to various parts of these regions and the methylation pattern in tumor cell lines was characterized, including MDA-MB-436 and HCC1937 which are known to carry BRCA1 mutations. These probes will be combined with previously characterized probes to other regions which are also methylated in tumours from BRCA1 patients. This would provide for a highly sensitive assay able to detect cancer in these high risk women at the earliest possible stage.

Tests for Other Subtypes

A number of breast cell lines from women with known BRCA1 mutations have been isolated such as MDA-MB-436, HCC1937 and HCC1395 (all available from ATCC). These may be used to validate the assay as was done for the general blood test. For BRCA2 mutant lines there is only one ATCC cell line at present, HCC1937. There are several BRCA2 mutant ovarian cancer lines that have been identified and they may be used if the bioinformatic analysis confirms that these methylation markers are also found in ovarian cancer. The development of a single assay that detects both breast and ovarian cancer in BRCA2 carriers represents a distinct advantage as it would simultaneously monitor the two primary cancer risks in these patients.

The development of these assays follows the same course the above-described general assay proceeding from TCGA data to cells lines to patient samples. Tumour banks (some of which have mutation data) can be used for this, and analysis of these tumours provides an indication of their likely BRCA mutation. These samples can also be sequenced to confirm the prediction.

Example 6

Testing of Cell-Free Samples

Proof of concept testing was carried out using cell lines for ease of analysis. However, the assay can be applied to test for cell-free DNA, e.g., circulating cell-free tumour DNA in blood, and finds wide application in this context. A sample protocol for circulating tumour DNA is provided.

Sample Protocol: Test for Circulating Tumour DNA
DNA Preparation

The following example protocol may be used to detect circulating tumour DNA (tDNA).
Obtain DNA to be used for bisulfite conversion and downstream PCR amplification (i.e., cell line, tumour or normal DNA). Determine DNA purity on 0.8% agarose gel.
Determine genomic DNA (gDNA) for concentration in ug/uL by UV spectrophotometry.
Prepare a 1:100 dilution with TE buffer.
Remove RNA contaminates, if necessary, using the purification protocol for the GenElute Mammalian Genomic DNA Miniprep Kit, Sigma Aldrich, CAT #G1N350 (www.sigmaaldrich.com/technical-documents/protocols/biology/genelute-mammalian-genomic-dna-miniprep-kit.html). Follow purification protocol from steps A: 2a-3a, step 4-9.
OPTIONAL: For gDNA from a cell line, sonicate gDNA to approximately 90-120 bp (this represents general size of circulating tDNA). To do this, sonicate 5-10 ug of sample (50-100 ng/100 uL) using a sonicator. Use setting 4, and 15 pulses for 30 seconds with 30 seconds rest on ice in between. Determine sonicated DNA purity and bp size on 0.8% agarose gel.
Bisulfite convert DNA-EpiTect Fast Bisulfite Conversion Kit, QIAgen, CAT #59824 (www.qiagen.com/us/resources/resourcedetail?id=15863f2d-9d1c-4f12-b2e8-a0c6a82b2b1e&lang=en). Follow bisulfite conversion protocol on pages 1-18, 19-23. Refer to trouble shooting guide pages 30-32. Modifications to the protocol include: 1. Prepare reactions in 1.5 mL tubes, 2. High concentration samples at 2 ug, and low concentration samples at 500 ng-1 ug, 3. Perform the bisulfite conversion using 2 heat blocks set at 95° C. and 60° C., 4. Incubation at 60° C. extended to 20 minutes, to achieve complete bisulfite conversion, 5a Elute DNA in 10-20 uL of elution buffer for ~50-100 ng/uL final concentration, and 5b Dilute DNA to 10 ng/uL for use in PCR.
Perform nested PCR with Hot Star Taq Plus DNA Polymerase, Qiagen, CAT #203605 (https://www.qiagen.com/ca/resources/resourcedetail?id=c505b538-7399-43b7-ad10-d27643013d10&lang=en).

Singleplex PCR Amplification
For singleplex PCR amplification of individual probes, carry out a primary PCR reaction with methylation-biased primers (MBP), (primer forward and reverse).
Table 4 recites reaction components.

TABLE 4

| Component | 1X (uL) |
|---|---|
| 10X PCR Buffer | 2.5 |
| 5 mM dNTP's | 1 |
| 5 U Hot Star Taq | 0.1 |
| 25 mM MgCl2 | 3 |
| PCR Grade H2O | 17 |
| [10 ng/uL] DNA | 1 |
| 10 pmol FWD Primer | 0.2 |
| 10 pmol REV Primer | 0.2 |
| Total | 25 |

Table 5 lists thermocycler conditions.

TABLE 5

Thermocycler Conditions

| Temp. | Time | |
|---|---|---|
| 95° C. | 15 min | |
| 95° C. | 30 sec | |
| 58° C. | 30 sec | X 40 |
| 72° C. | 30 sec | |
| 72° C. | 7 min | |
| 4° C. | ∞ | |

Carry out a secondary PCR reaction with universal primers CS1 (Barcode) and CS2 (P1 Adapter). To do this, remove an aliquot from the primary reaction, use as template DNA, this method serves as a two-step dilution PCR reaction Table 6 recites reaction components.

TABLE 6

| Component | 1X (uL) |
|---|---|
| 10X PCR Buffer | 5 |
| 5 mM dNTP's | 2 |
| 5 U Hot Star Taq | 0.2 |
| 25 mM MgCl2 | 6 |
| PCR Grade H2O | 34.4 |
| MBP PCR Template | 2 |
| 10 pmol CS1 Primer | 0.2 |
| 10 pmol CS2 Primer | 0.2 |
| Total | 50 |

Table 7 recites thermocycler conditions.

TABLE 7

| Thermocycler Conditions | | |
|---|---|---|
| Temp. | Time | |
| 95° C. | 15 min | |
| 95° C. | 30 sec | |
| 58° C. | 30 sec | X 3 |
| 72° C. | 30 sec | |
| 72° C. | 7 min | |
| 4° C. | ∞ | |

Determine PCR specificity on 2% agarose gel. Run the methylation-biased PCR product and the CS1 CS2 sequencing PCR product beside one another on the agarose to visualize the banding pattern and increase in bp size. PCR product should be between 200-300 bp For Singleplex PCR products, pool 5-10 uL of each PCR reaction (CS1 CS2 Secondary RXN) into a single tube for each sample type. Purify the pooled PCR with Agencourt AMPure XP beads at a 1.2:1 ratio (90 uL beads+75 uL sample), e.g., as below.

Agencourt Ampure XP Bead Purification

Use freshly prepared 70% ethanol. Allow the beads and pooled DNA to equilibrate to room temperature.

1. Add indicated volume of Agencourt AMPure XP beads to each sample: 90 uL beads+75 uL Pool (1.2:1)
2. Pipet up and down 5 times to thoroughly mix the bead suspension with the DNA. Incubate the suspension at RT for 5 minutes.
3. Place the tube on a magnet for 5 minutes or until the solution clears. Carefully remove the supernatant and store until purified library has been confirmed.
4. Remove the tube from the magnet; add 200 µL of freshly prepared 70% EtOH. Place the tube back on the magnet and incubate for 30 seconds; turn the tube around twice in the magnet to move the beads through the EtOH solution. After the solution clears, remove and discard the supernatant without disturbing the pellet.
5. Repeat step #4 for a second EtOH wash.
6. To remove residual EtOH, pulse-spin the tube. Place the tube back on the magnet, and carefully remove any remaining EtOH with a 20 uL Pipette, without disturbing the pellet.
7. Keeping the tube on the magnet, air-dry the beads at RT for ~5 minutes.
8. Remove the tube from the magnet; add 50 µL of TE directly to the pellet. Flick the tube to mix thoroughly. Incubate at RT for 5 minutes.
9. Pulse-spin and place the tube back on the magnet for ~2 minutes or until the solution clears. Transfer the supernatant containing the eluted DNA to a new 1.5 mL Eppendorf LoBind tube.
10. Remove the tube from the magnet; add 50 µL of TE directly to the pellet. Flick the tube to mix thoroughly. Store the beads, along with the supernatant, at 4° C. until purified library has been confirmed.
11. Visualize the sample pre- and post-purification on an 8% acrylamide gel (higher resolution). Pooled PCR product should be visualized as multiple bands (as each PCR product is a slightly different bp size). Purified sample should eliminate product beneath 150 bp.

Figure 11:
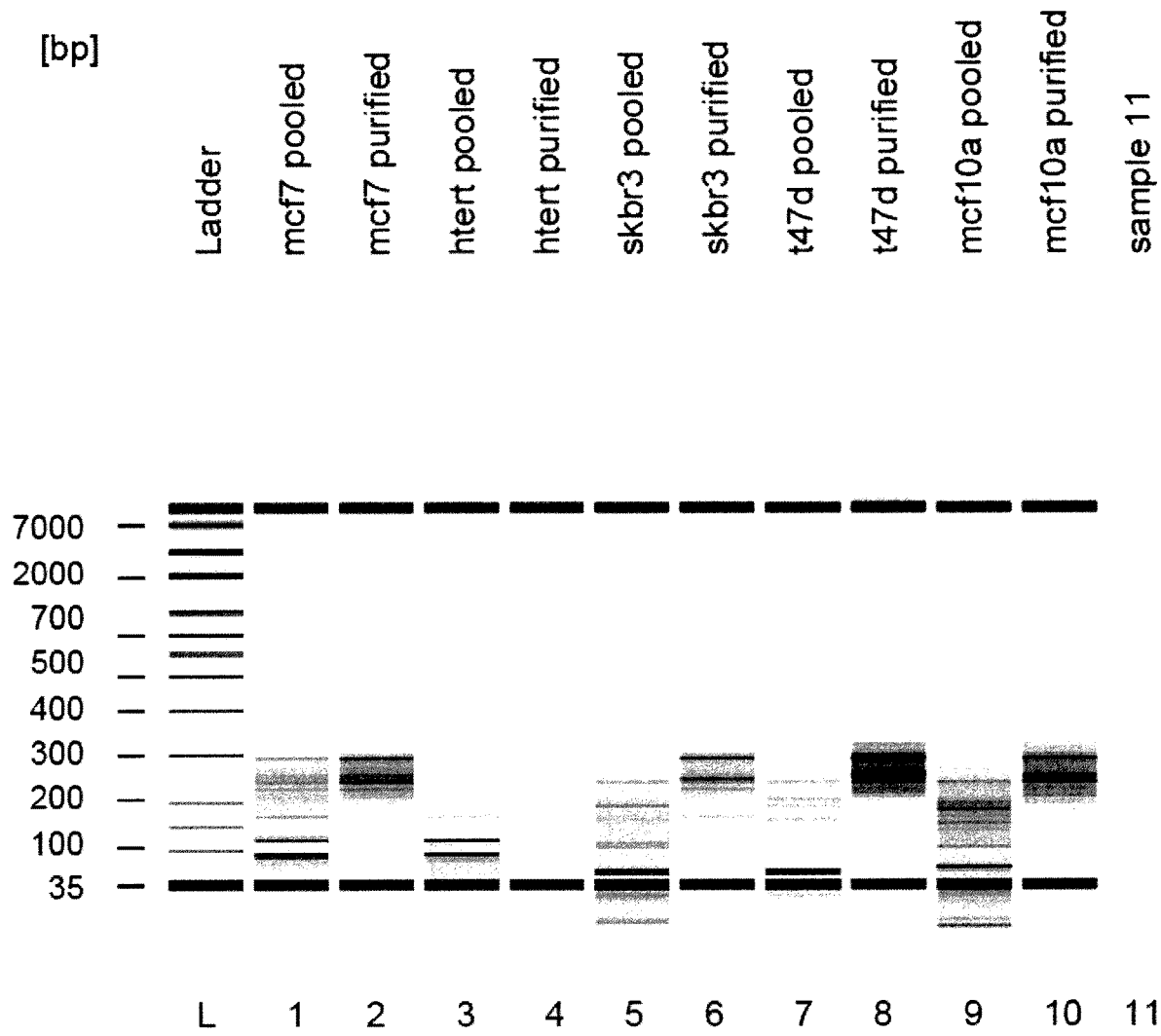
FIG. 11 depicts a summary of BioAnalyzer electrophoresis summary for amplification product generated from various cell lines.

FIG. 11 depicts a summary of BioAnalyzer electrophoresis summary for amplification product generated from various cell lines.

12. Perform nested PCR with Multiplex PCR Plus Kit, Qiagen, CAT #206152 (www.qiagen.com/ca/resources/resourcedetail?id=beb1f99e-0580-42c5-85d4-ea5f37573c07&lang=en), e.g., as below.

Multiplex PCR Amplification of Up to 50 Probes in a Single Reaction

Create multiplex primer mix by aliquot 1 µL of each forward and reverse primer at 10 pmol/uL into a single 1.5 mL tube. Calculate the final concentration of each primer by dividing the initial primer concentration by the final volume of primer mix in the tube, i.e., 15 probes to be multiplexed into a single reaction, would total 30 primers and at 1 uL each, 30 uL final volume. Thus ((10 pmol) (1 uL))/30 uL=0.333 pmol. Primer concentration requires optimization during PCR amplification, as the number of primers in a single reaction can influence the efficiency of the product, e.g.

15 primer sets ~2 pmol final [ ] in PCR 50 primer sets ~0.5 pmol final [ ] in PCR Carry out primary PCR reaction with methylation-biased primers.

Table 8 lists reaction components for multiple amplifications of 15 probes, and Table 9 lists reaction components for multiple amplifications of 50 probes. Table 10 list reaction conditions.

TABLE 8

| 15 primer pairs at 2 pmol | |
|---|---|
| Component | 1X (uL) |
| 2X Multiplex MM | 25 |
| PCR H2O | 18 |
| Primer Mix | 6 |
| [10 ng/µL] DNA | 1 |
| Total | 50 |

TABLE 9

| 50 primer pairs at 0.5 pmol | |
|---|---|
| Component | 1X (uL) |
| 2X Multiplex MM | 25 |
| PCR H2O | 19 |
| Primer Mix | 5 |
| [10 ng/µL] DNA | 1 |
| Total | 50 |

TABLE 10

| Thermocycling Conditions | | |
|---|---|---|
| Temp. | Time | |
| 95° C. | 5 min | |
| 95° C. | 30 sec | |
| 58° C. | 90 sec | X 35 |
| 72° C. | 90 sec | |
| 68° C. | 10 in | |

Determine PCR specificity on 2% agarose gel. Multiplex products should be visualized with multiple banding pattern between 100-300 bp.

Pooling is not required for multiplex products, as the probes have already been combined and amplified into a single tube/reaction.

Purify the pooled PCR with Agencourt AMPure XP beads at a 1.2:1 ratio (60 uL beads+50 uL sample) (refer within document for purification protocol).

After PCR amplification, along with pooling and purifying, the samples can be quantified by qPCR, e.g., Ion Library Quantification Kit, TaqMan assay quantification of Ion Torrent libraries, Thermo Fisher Scientific, CAT #4468802 (tools.thermofisher.com/content/sfs/manuals/4468986_IonLibraryQuantitation-Kit_UG.pdf).

1. Create a standard curve of 6.8 pM, 0.68 pM, 0.068 pM, 0.0068 pM
2. Dilute samples 1:1000, and run in duplicate
3. Perform qPCR assay on the Step One Plus Real Time machine by Life Technologies
4. Sample libraries quantified ≥100 pM can proceed to be sequenced on the Life Technologies Ion Torrent Sequencing platform Life Technologies Ion Torrent PGM Sequencing
Ion PGM Template OT2 200.
    Perform template reaction with Ion PGM Template OT2 200 Kit, Thermo Fisher Scientific, CAT #4480974. Kit contents to be used on the One Touch 2 and Enrichment system (tools.thermofisher.com/content/sfs/manuals/MAN0007220_Ion_PGM_Template_OT2 200_Kit_UG.pdf).
    Utilizing library quant. obtained from qPCR, dilute libraries appropriately to 100 pM. Follow Life Technologies guide on how to further dilute libraries for input into final template reaction.
    Follow reference guide to complete template reaction
    Run the Ion One Touch 2 instrument
    Recover the template positive ISPs
    Enrich the template positive ISPs with the Ion One Touch ES Ion PGM Sequencing 200
    Perform sequencing reaction with Ion PGM Sequencing 200 kit, Thermo Fisher Scientific, CAT #4482006. Kit contents to be used on the Ion PGM system (tools.themofisher.com/content/sfs/manuals/MAN000-7273_IonPGMSequenc_200Kit_v2_UG.pdf).

Plan sequencing run
        Select chip capacity (314, 316 or 318)
        Determine sequencing flows and bp read length (i.e., 500 flows and 200 bp read length)
    Follow reference guide to complete PGM sequencing
        Prepare enriched template positive ISPs
        Anneal the sequencing primer
        Chip check
        Bind sequencing polymerase to the ISPs
        Load the chip
        Select the planned run and perform sequencing analysis
Sequencing Data Analysis and Work Flow
    Obtain run report generated by the PGM and Torrent Browser
    Run report includes the following information
        ISP Density and loading quality
        Total reads generated and ISP summary
        Read length distribution graph
        Barcoded samples: reads generated per sample and mean read length
    Obtain uBAM files generated by the PGM, available for download to an external hard drive
    Bioinformatics data analysis
        Upload uBAM files to a web based bioinformatics platform, Galaxy GenAp
        Perform quality control analysis (i.e., basic statistics and sequence quality check)
        Convert data files: BAM SAM FastQ
        Filter FastQ file: select bp size to trim (i.e., trim sequence <100 bp)
        Convert data files: FastQ FastA
        Download FastA file
    Upload FastA files to BiqAnalyzer software platform
        Create project
        Add sample
        Load reference sequence
        Set gap extension penalty and minimal sequence identity
        Link in FastA files to samples and reference sequences
        Analyze and collect data files (pattern maps and pearl necklace diagrams)

Example 7

Uveal Melanoma Test

The molecular biology of uveal melanoma (UM) is simpler than that of breast cancer, with minimal mutations and rearrangements, and only two major sub-types which correspond to the retention or loss of chromosome 3p. A test was developed for UM which is superior to current state of the art blood assays.

Analysis of 450k methylation TCGA data for 80 UMs allowed for the identification of regions of tumour specific methylation in both 3p- and 3 pWT tumours using our algorithm. Table 11 shows 16 hypermethylated regions in both 3p- and 3 pWT tumours used for probe development and testing, according to one embodiment.

TABLE 11

| Gene | Chr | start | stop | Size | CGI | CpGs |
|---|---|---|---|---|---|---|
| PTEN, KILLIN | chr10 | 89611399 | 89611920 | 521 | Shore CGI | 171 |
| PAMR1 | chr11 | 35503400 | 35504124 | 724 | small CGI | 19 |
| MPZL2 | chr11 | 117640011 | 117640610 | 599 | Prox Prom | |
| C2CD4A | chr15 | 60146043 | 60147120 | 1077 | Shore CGI | 127 |
| SEZ6 | chr17 | 24370858 | 24371386 | 528 | small CGI | 34 |

TABLE 11-continued

| Gene | Chr | start | stop | Size | CGI CpGs |
|---|---|---|---|---|---|
| LDLR | chr19 | 11060476 | 11060965 | 489 Prox Prom | |
| GALNT3 | chr2 | 166358156 | 166359621 | 1465 CGI | 98 |
| ccdc140/pax3 | chr2 | 222881305 | 222886029 | 4724 Shore CGI | 72 |
| FLJ22536/casc15 | chr6 | 21774638 | 21775386 | 748 small CG | 18 |
| KAAG1, DCDC2 | chr6 | 24465699 | 24466545 | 846 CGI | 56 |
| MUC21 | chr6 | 31031220 | 31031651 | 431 CGI | 46 |
| COL19A1 | chr6 | 70632889 | 70633262 | 373 Proc Prom | |
| NR2E1/OSTM1 | chr6 | 108542808 | 108543809 | 1001 small CG | 34 |
| SCRN1 | chr7 | 29996242 | 29996333 | 91 Shore CGI | 133 |
| HES5 | chr1 | 2450725 | 2452224 | 1499 CGI | 111 |
| DHRS3 | chr1 | 12601228 | 12601893 | 665 Shore CGI | 133 |

The top 14 of these common regions were carried forward for probe development and a total of 26 different probes were characterized, with several regions having up to three probes targeting them. Each of these probes was then validated using six different UM cell lines to assess their methylation status. As negative controls, DNA from peripheral blood mononuclear cells (PBMCs), which are the main source of contaminating DNA in blood samples, as well as a pool of cell free DNA (cfDNA) from 16 individuals, were also tested (FIG. 15). These results indicated that the majority of the probes tested showed tumour specific methylation with little or no methylation in the negative controls. A total of 18 probes from 12 different regions were combined into a multiplex PCR reaction and used to analyze cell free DNA from plasma for a previously characterized cohort of metastatic UM patients.

The validated regions were C2CD4A, COL19A1, DCDC2, DHRS3, GALNT3, HES5, KILLIN, MUC21, NR2E1/OSTM1, PAMR1, SCRN1, and SEZ6. The validated probes were C2C5F, COL2F, DCD5F, DGR2F, GAL1F, GAL3F, HES1F, HES3F, HES4F, KIL5F, KIL6F, MUC2F, OST3F, OST4F, PAM4F, SCR2F, SEZ3F, and SEZ5F.

Figure 16:
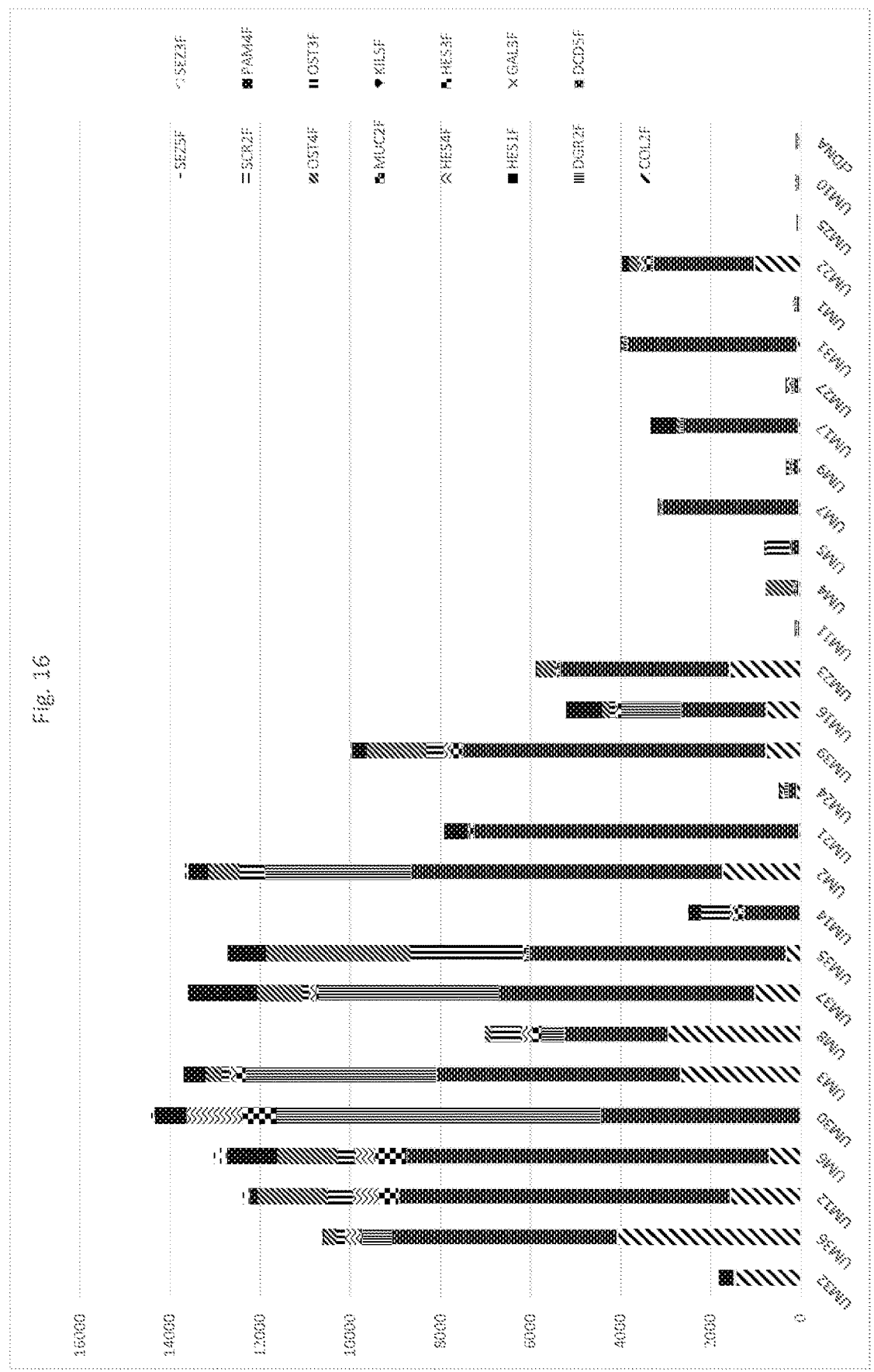
FIG. 16 is a diagram showing methylation of cfDNA from patients with metastatic uveal melanoma. Methylated reads for each probe were extracted and all reads were normalized for the total number of reads in the sample. Stacked columns represent the total reads from all of the individual probes with different probes identified by shading. The patients are sorted by PAP measurements with high values on the left and lower values on the right. cfDNA is a pool of cell free DNA from 18 normal donors.
Figure 19:
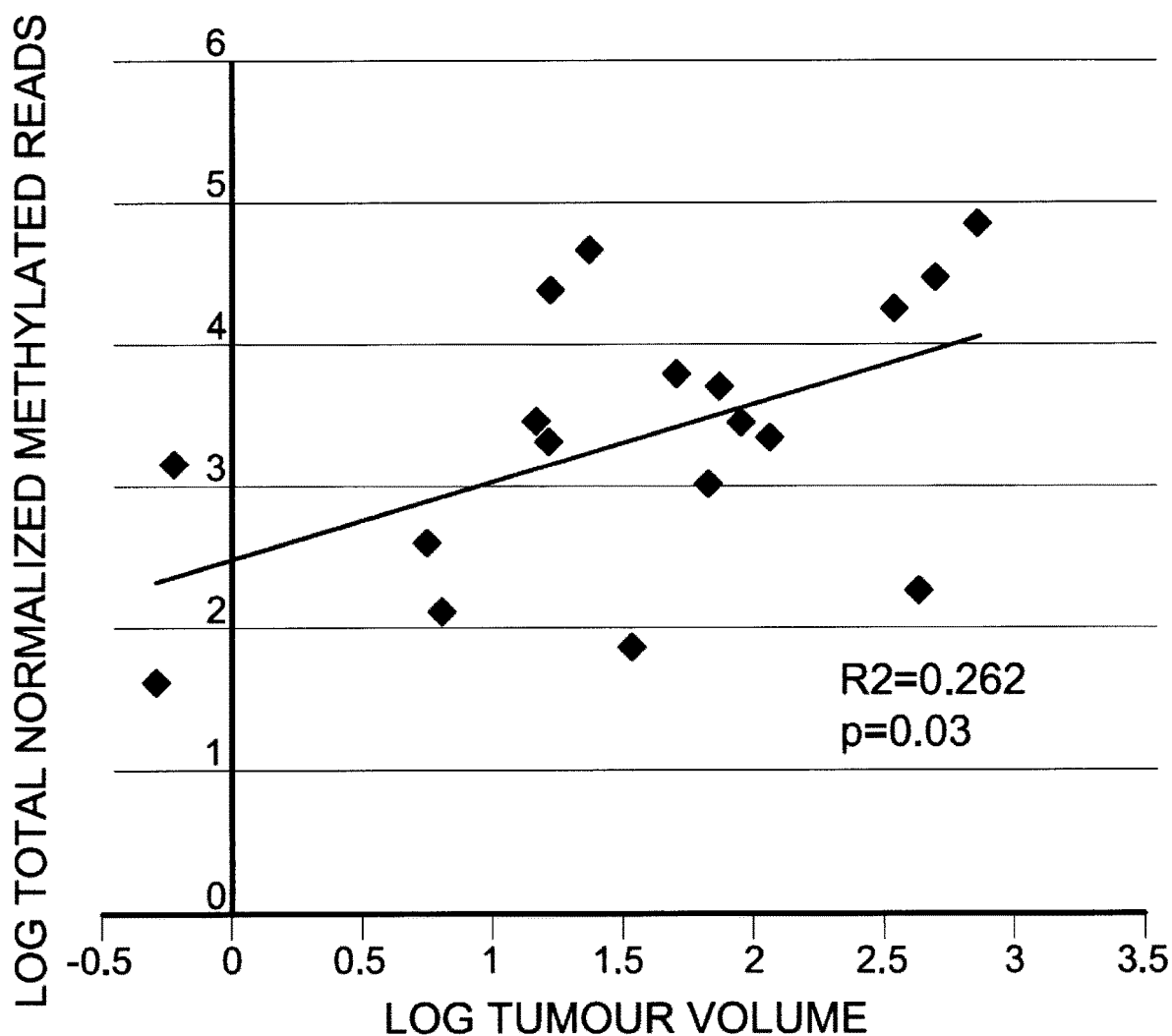
FIG. 19 is a log-log plot showing assay values (methylated reads) are correlated with tumour volume. The character of the metastatic tumour such as whether it is a solid mass or dispersed (miliary) was not taken into account.
Figure 20:
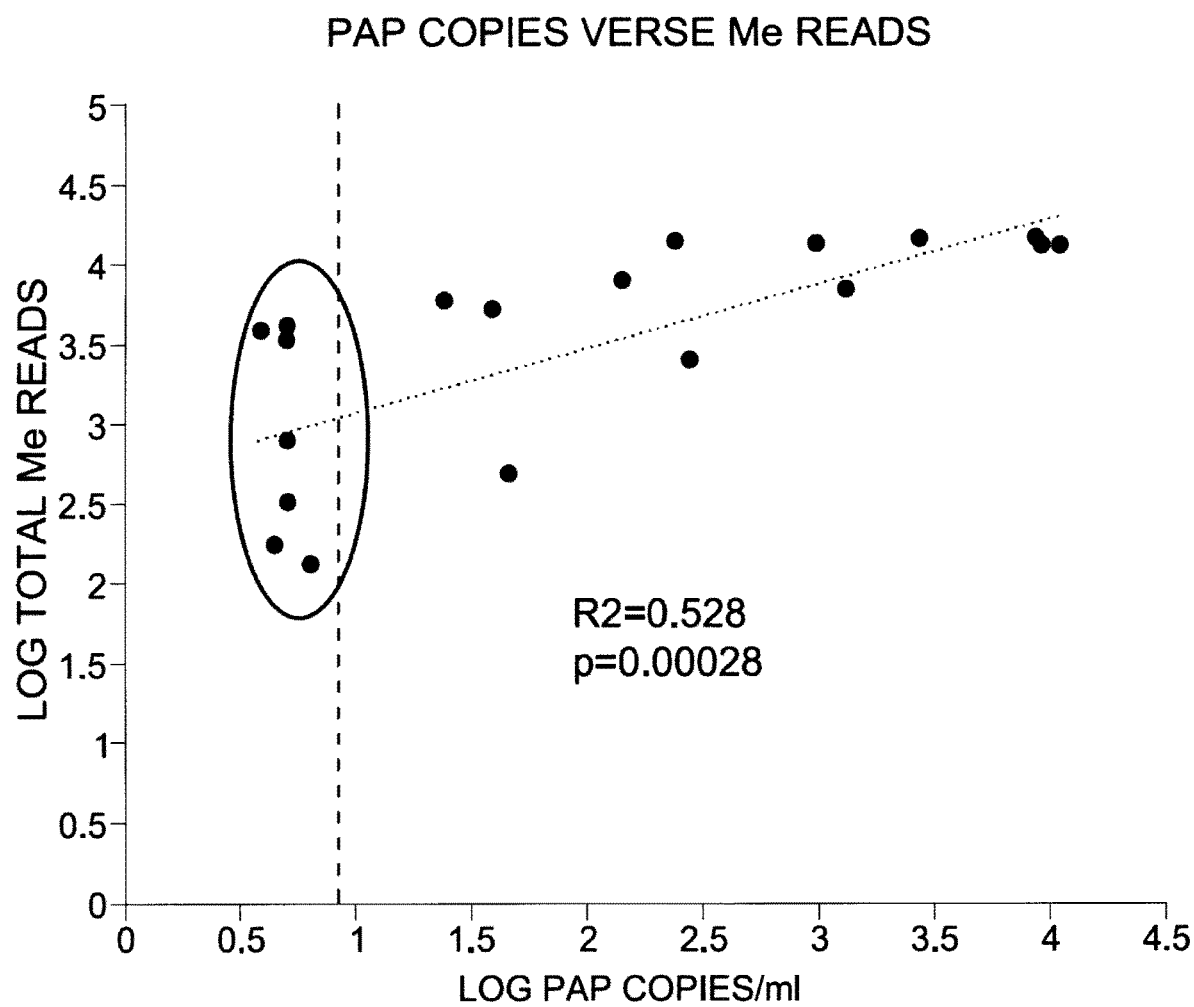
FIG. 20 is a log-log plot showing relationship between test results and PAP signal, where PAP and methylation signals were correlated at higher PAP levels (trend line), although below the detection threshold of PAP at 5 copies/ml (vertical dashed line) the PAP signals were not correlated (ellipse).

These patients were previously tested using the pyrophosphorolysis-activated polymerization (PAP) assay[26], which detects the frequent GNAQ or GNA11 mutations in UM[27]. In all cases the test detected cancer in these patients even when the PAP assay failed to register a signal (FIGS. 16 and 17). Most of the probes functioned like methylation specific PCR reactions, only giving product when there was tumour DNA present though with the additional validation that the specificity of each probe was guaranteed by the presence of multiple methylated CpG residues within each read. In two patients from which serial blood samples were obtained (FIGS. 18A and 18B) the test showed increased tumour levels over time even when the final tumour volume was 0.5 cm³ (FIG. 18A). The test was also generally correlated with the volume of tumour, though the nature of the metastatic tumour as either a solid mass or dispersed has not yet been accounted for (FIG. 19). The levels detected by the test were generally in line with those of the PAP assay and notably gave a signal where PAP failed due to the lack of a mutation (FIG. 16, UM32). Where no or limited amounts of tumour DNA were detected by PAP, the test still gave significant signals (FIG. 20). Even greater sensitivity is expected when the total number of reads analyzed per patient is increased, as this run had less than optimal overall reads due to the presence of large amounts of primer dimer, an issue that has now been resolved. The specificity of the test was demonstrated by the extremely low levels of methylation seen in the pool of 16 cfDNA controls. Overall, the test has been validated in a patient population, and it has been shown to be superior to a state of the art mutation based assay.

Example 8

Prostate Cancer Test

An important aspect of any test is that it should be applicable to all patients. Based on our experience it is essential to consider specific subtypes of a given cancer to ensure that all patients are detected by the assay. The TCGA analysis of a large prostate cohort revealed sub-groups based on specific mutations and transcriptional profiles[28]. Four subtypes were identified based on the overall pattern of methylation found in these tumours. In this example the TCGA prostate cohort was divided into groups based on the methylation pattern and subjected to methylation analysis.

Table 12 lists 40 regions associated with all sub-types of prostate cancer.

TABLE 12

| HES5 | ANXA2 | HLA-F | HAAO |
|---|---|---|---|
| LOC376693 | RHCG | PON3 | RARB |
| CSRP1 | RARA | LRRC4 | ALDH1L1 |
| ALOX5 | PTRF | HLA-J | HIST1H3G |
| PPM1H | RND2 | PAH | ZSCAN12 |
| MON2 | TMP4 | EPSTI1 | HCG4P6 |
| KIAA0984 | HIF3A | ADCY4 | EYA4 |
| TXNRD1 | KLK5 | HAPLN3 | HOXA7 |
| CHST11 | AMOTL2 | AX747633 | HSF4 |
| EFS | SCGB3A1 | NBR1 | TMEM106A |

These regions common to all four methylation subtypes were identified and a total of 38 probes from 33 regions were selected and appropriate "biased" PCR probes were generated. These were characterized using four different prostate cancer lines. DU145 is an androgen receptor (AR−) negative cell line that is able to generate metastases in the mouse. PC3 is also AR− and also metastatic. LNCaP is an androgen receptor positive line (AR+) that is non-metastatic in the mouse while RWPE cells are AR+ and non-metastatic. DNA from PBMC was also tested as this represents the primary source of cell free DNA in the circulation.

Figure 21:
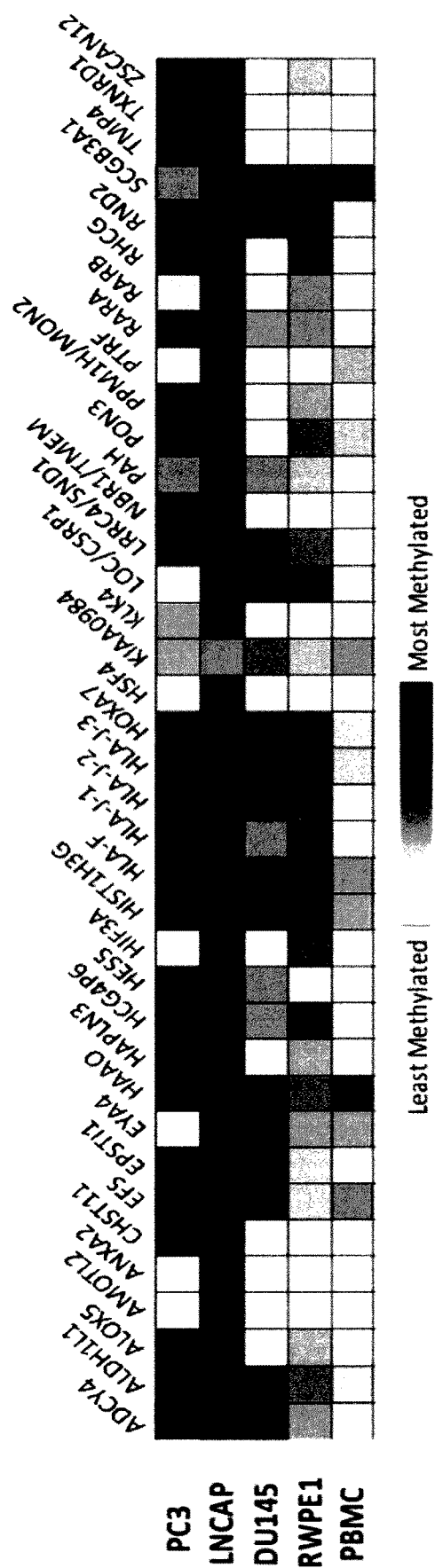
FIG. 21 is a heat map of gene methylation in indicated prostate cancer cell lines.

A total of 34 probes from 33 regions were validated in that they showed little or no methylation in PBMCs while showing large scale methylation in one or more of the tumour cell lines (FIG. 21).

The validated regions were ADCY4, ALDH1L1, ALOX5, AMOTL2, ANXA2, CHST11, EFS, EPSTI1, EYA4, HAAO, HAPLN3, HCG4P6, HES5, HIF3A, HLA-F, HLA-J, HOXA7, HSF4, KLK4, LOC376693, LRRC4, NBR1, PAH, PON3, PPM1H, PTRF, RARA, RARB, RHCG, RND2, TMP4, TXNRD1, and ZSCAN12.

The validated probes were ADCY4-F, ALDH1L1-F, ALOX5-F, AMOTL2-F, ANXA2-F, CHST11-F, EFS-F, EPSTI1-F, EYA4-F, HAAO-F, HAPLN3-F, HCG4P6-F, HES5-F, HIF3A-F, HLA-F-F, HLA-J-1-F, HLA-J-2-F, HOXA7-F, HSF4-F, KLK4-F, LOC376693-F, LRRC4-F, NBR1-F, PAH-F, PON3-F, PPM1H-F, PTRF-F, RARA-F, RARB-F, RHCG-F, RND2-F, TMP4-F, TXNRD1-F, and ZSCAN12-F.

To these 34 probes an additional 12 probes (from 7 regions) were added that had previously been characterized in breast cancer, which were also able to detect prostate cancer, for a total of 46 probes.

The added probes were C1Dtrim, C1Etrim, CHSAtrim, DMBCtrim, FOXAtrim, FOXEtrim, SFRAtrim, SFRCtrim, SFREtrim, TTBAtrim, VWCJtrim, and VWCKtrim.

These probes were multiplexed together and were then used to analyze plasma samples from five patients before they had initiated androgen deprivation therapy (ADT) and 12 months after starting treatment. These patients were part of a small cohort (~40 patients) being followed for depression and the plasma samples at 0.5 ml were much smaller than normally used for the assay (2 mls). All of the patients were MO with no sign of metastatic disease when placed on ADT.

Figure 22:
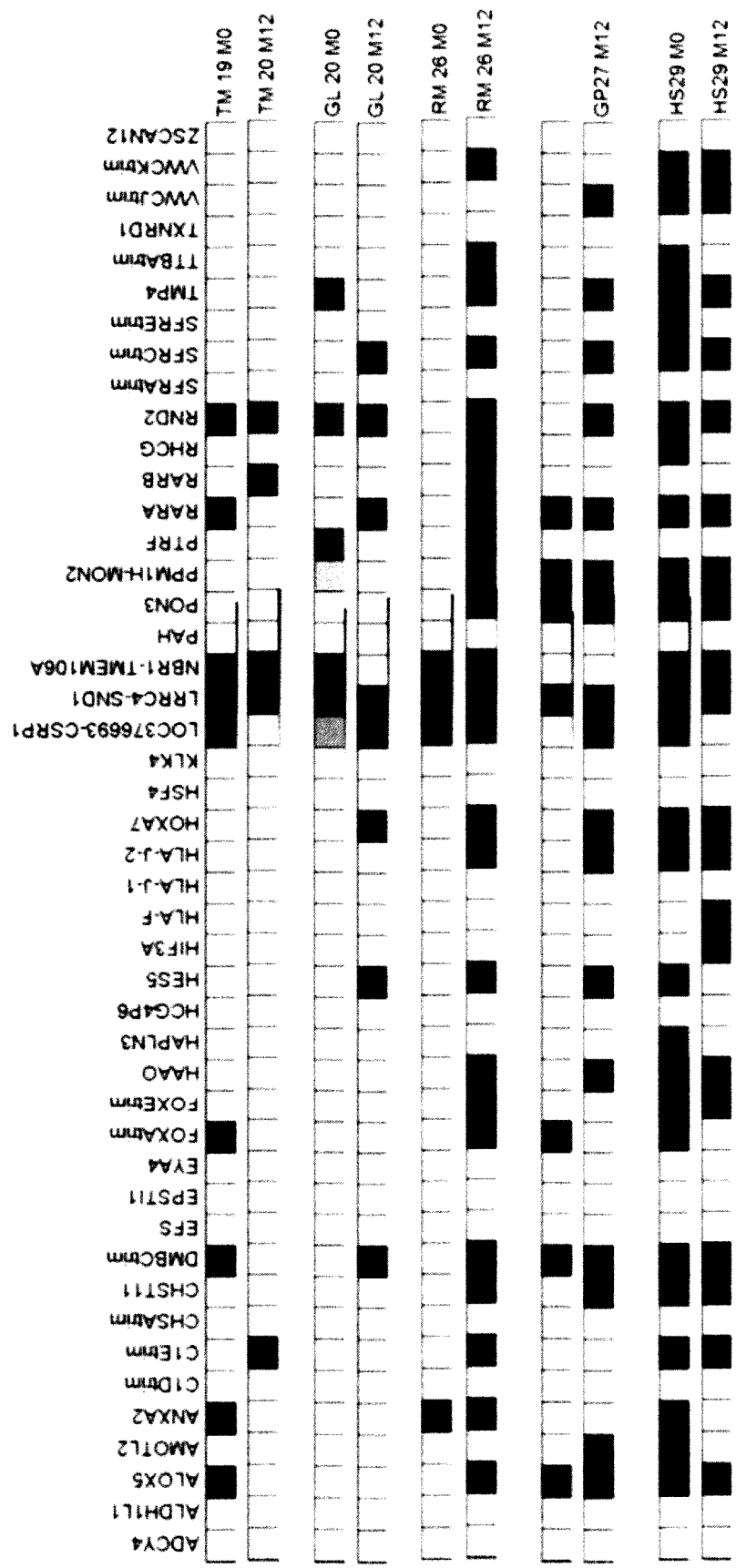
FIG. 22 is a heat map of multiplexed probes for each prostate cancer patient sample. Patient samples were taken before the initiation of ADT (START) and 12 months after (M12). A black square indicates that methylated reads having greater than 80% methylation per read were detected for that probe but does not take into consideration the number of reads for each.
Figure 23:
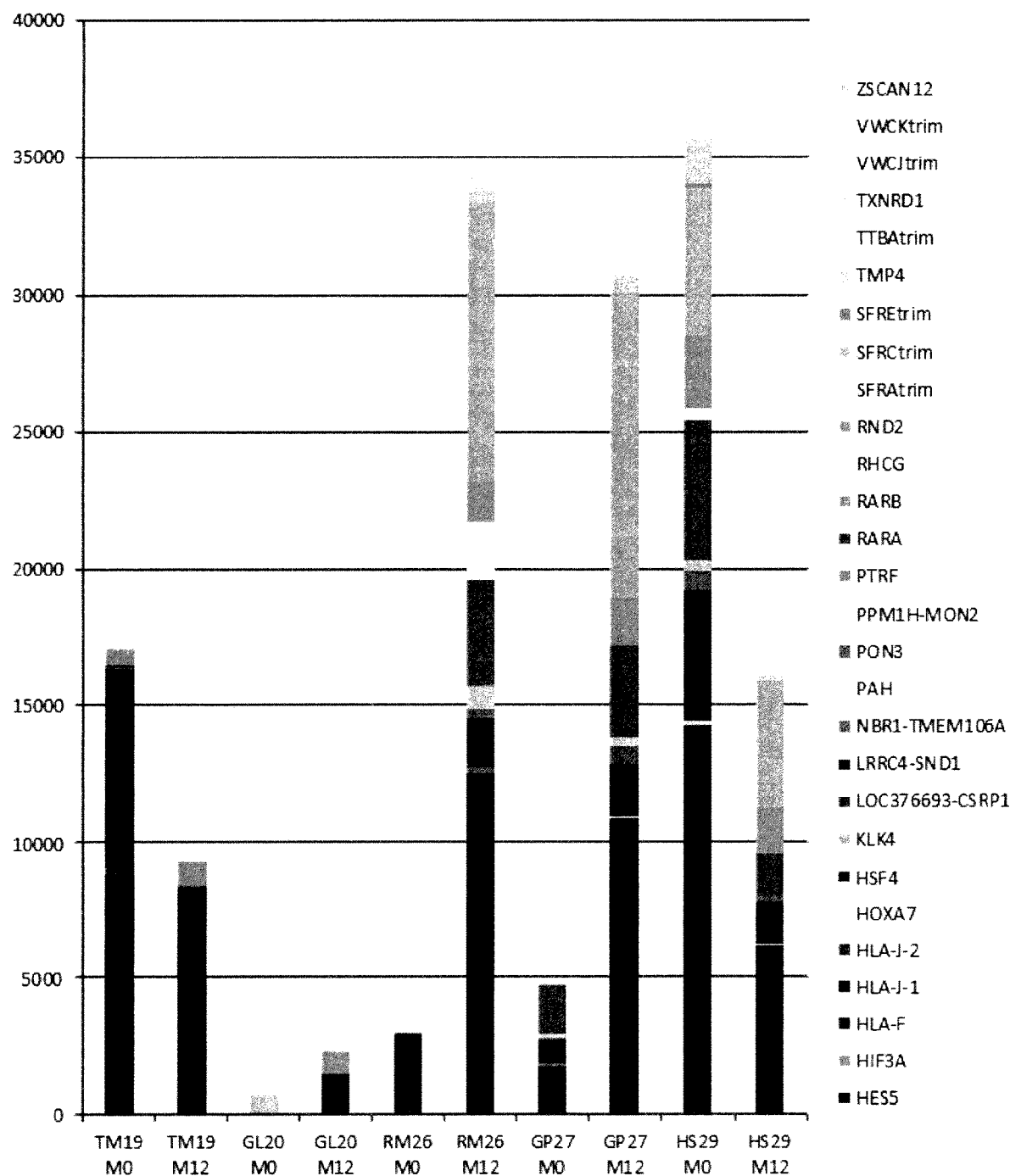
FIG. 23 is a diagram showing number of methylated reads per probe for each prostate cancer patient sample. Different probes are shown in different shading. The number of reads that were at least 80% methylated were determined for each sample and all probes are stacked per sample. Patient samples were taken before the initiation of ADT (START) and 12 months after (M12).
Figure 24:
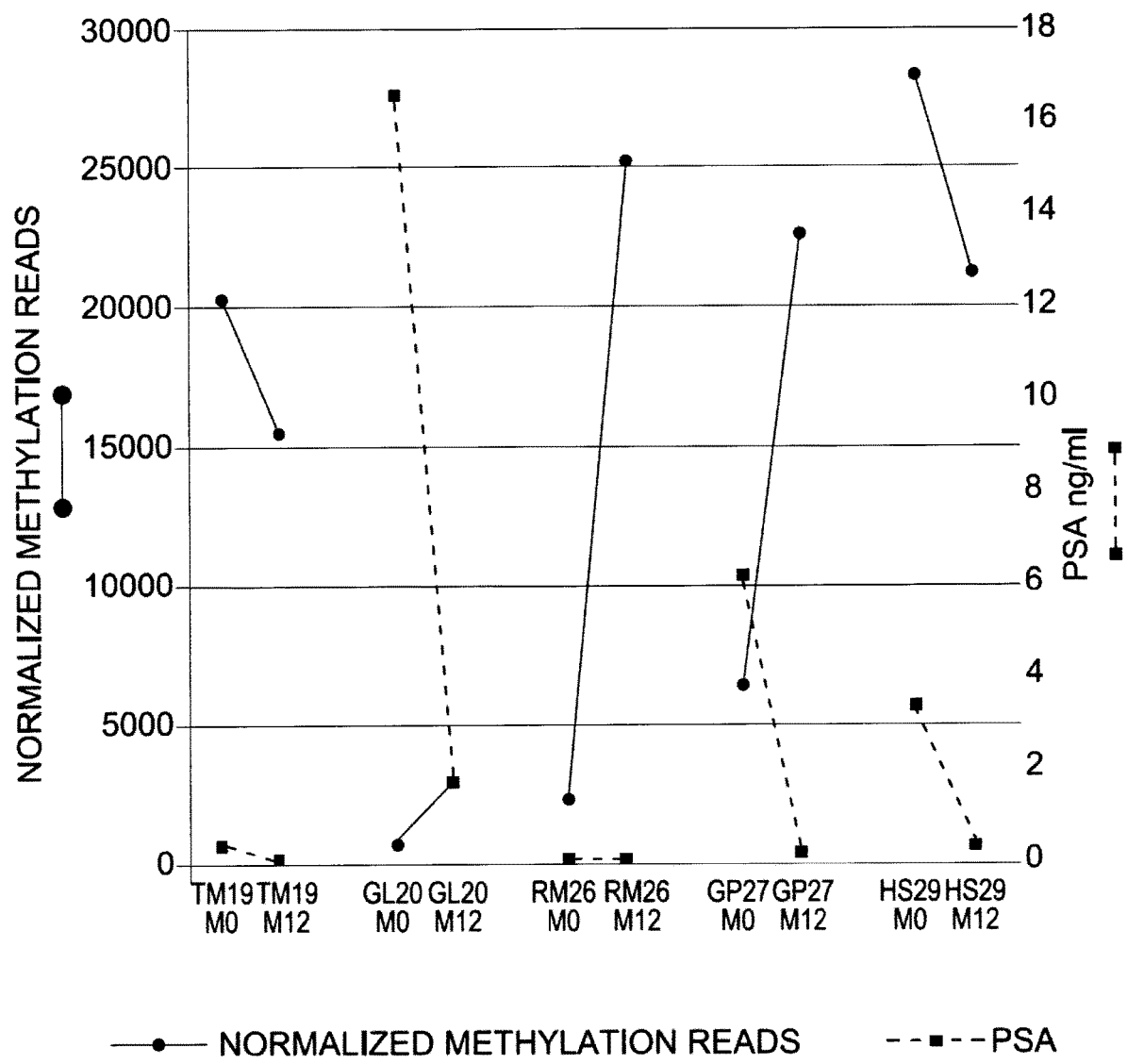
FIG. 24 is a plot showing normalized methylation reads per sample verses PSA levels for each patient. The totals of normalized methylated reads for all probes are plotted with solid lines. Patients initiated androgen deprivation therapy (START) and PSA levels measured at that time and after 12 months of treatment (M12) and are indicated with dashed lines. The methylation detection of circulating tumour DNA (mDETECT) test was performed on 0.5 ml of plasma from these same time points. The Gleason score for each patient at initial diagnosis is shown along with grading, as is the treatment applied as primary therapy (RRP, radical retropubic prostatectomy; BT, brachytherapy; EBR, external beam radiation; RT, radiotherapy).

A variety of probes were positive depending on the particular patient (FIG. 22). The total number of positive probes was in keeping with the total number of methylated reads, which were normalized for total reads for each sample (FIG. 23). In all cases significant ctDNA signals were observed with results that were notably different than PSA results (FIG. 24). Two of the patients, TM19 and RM26 were started on ADT due to their aggressive diseases (T3A and T3B) despite having low PSA levels. PSA levels for both remained low but methylation detection of circulating tumour DNA (mDETECT) either decreased slightly (TM19) or rose dramatically (RM26) suggesting their diseases did not express PSA but had stable or increasing disease. HS29 showed decreased PSA levels which mDETECT paralleled. Both GL20 and GP27 trended in opposite directions to PSA levels with mDETECT increasing even with dramatic drops in PSA levels. GL20 did develop a radiation induced secondary cancer which may be what is detected. Ongoing analysis of additional clinical data is expected to help explain these results.

Based on the literature, three of these regions appear to have prognostic significance as well. C1orf114 or CCDC1 has been shown to be correlated with biochemical relapse. HES5 is a transcription factor that is regulated by the Notch pathway and methylation of its promoter occurs early in prostate cancer development. KLK5 is part of the Kallikrein gene complex that includes KLK3 (the PSA gene). We can demonstrate that KLK5 expression is correlated with methylation and KLK5 expression has previously been shown to be increased in higher grade tumours. These results strongly suggest that the examination of a large number of methylation markers may yield significant insight into the specific processes involved in prostate cancer development and produce diagnostic and prognostic information that would be vital for management of the disease.

Example 9

Predictive Prostate Cancer Methylation Biomarkers

Figure 25:
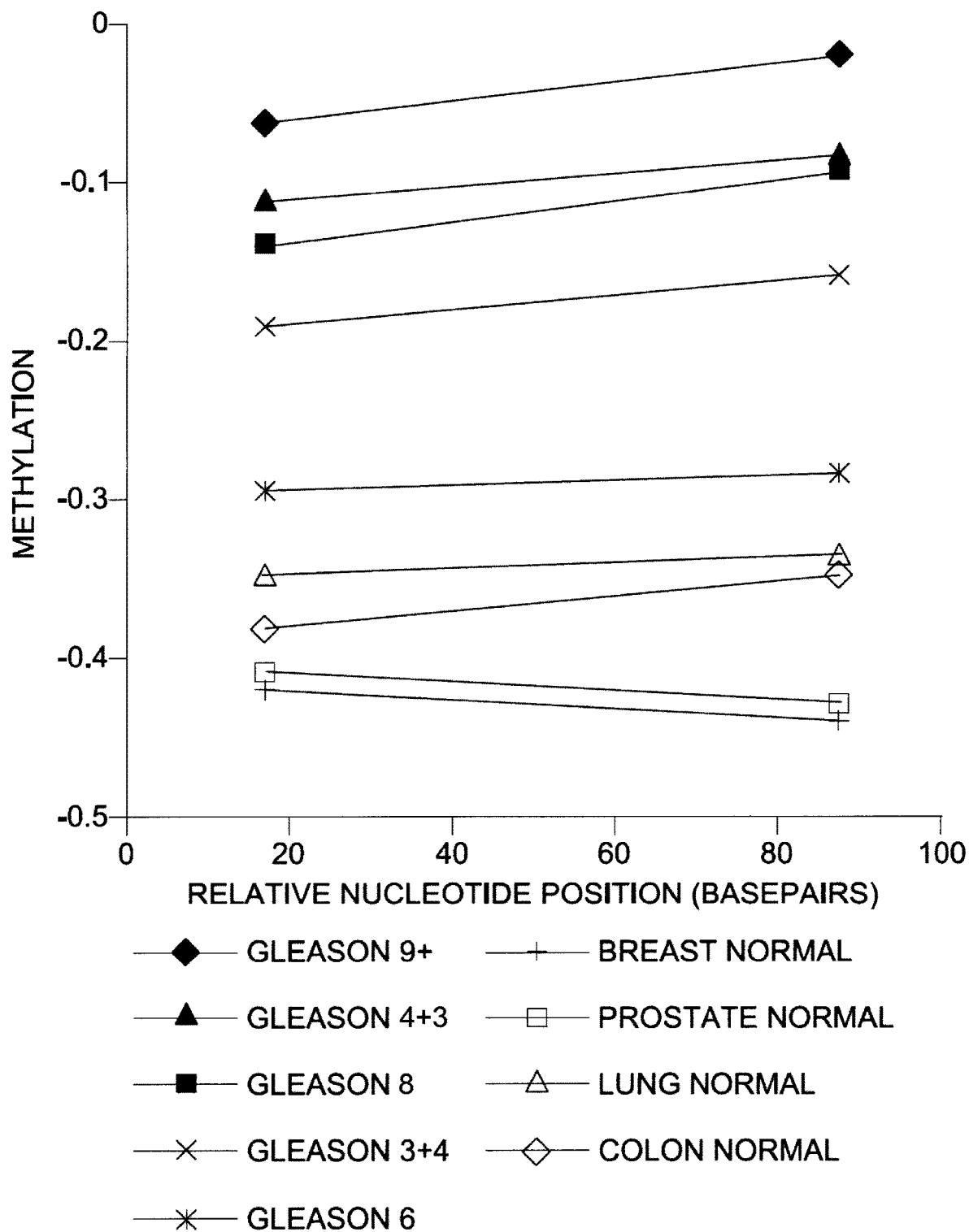
FIG. 25 is a plot of TCGA prostate cancer tumour data, showing the average methylation for each of various Gleason groups, as well as for normal tissue from breast, prostate, lung, and colon, verses position on the genome (in this case on chromosome 8 for the region upstream of the TCF24gene, a transcription factor of unknown function and PRSS3, a serine protease gene on chromosome 9).

The 50 region assay according to embodiments described herein is sufficiently sensitive to easily detect metastatic disease and to follow changes in tumour size over time and, as indicated, has predictive value in itself. As described above, at least three regions, KLK5, HER5, and C1orf114 have potential to predict progression. In order to develop additional probes that are able to predict outcome in this patient population, the prostate cancer TCGA data was reanalysed to divide the patients by Gleason score. An inter-cohort comparison was conducted to identify regions frequently methylated in higher score cancers. Initially, Gleason grades 6 and 9 were compared as these typically represent less and more aggressive tumours and both groups had sufficient numbers of patients to ensure significance of the results. Probe development was carried out under the same criteria as with the original probe sets so that they could be used with ctDNA. No single probe will be absolutely specific for a given grade but a number of the probes showed excellent division between Gleason scores with the proportion of the cohort positive for a given grade increasing with increasing grade (FIG. 25). One of these, PSS3, is a gene whose expression has previously been associated with prostate cancer and particularly metastasis. It should be noted that not all methylation is associated with gene repression. Forty-three new probes were developed based on selection criteria to target the 36 regions shown in Table 13, which are associated with aggressive prostate cancer.

TABLE 13

| ASAP1 | EMX1 | MIR1292 | SOX2OT |
| BC030768 | HFE | NBPF1 | TUBB2B |
| C18orf62 | HIST1H3G/1H2BI | NHLH2 | USP44 |
| C6orf141 | HMGCLL1 | NRN1 | Intergenic (Chr1) |
| CADPS2 | KCNK4 | PPM1H | Intergenic (Chr8) |
| CORO1C | KJ904227 | PPP2R5C | Intergenic (Chr2) |
| CYP27A1 | KRT78 | PRSS3 | Intergenic (Chr3) |
| CYTH4 | LINC240 | SFRP2 | Intergenic (Chr4) |
| DMRTA2 | Me3 | SLCO4C1 | Intergenic (Chr10) |

The probes were ASAP1/p, BC030768/p, C18orf62/p, C6orf141/p-1, C6orf141/p-2, CADPS2/p, CORO1C/p-1, CORO1C/p-2, CYP27A1/p, CYTH4/p, DMRTA2/p, EMX1/p, HFE/p-1, HFE/p-2, HIST1H3G/1H2BI/p, HMGCLL1/p, KCNK4/p, KJ904227/p, KRT78/p, LINC240/p-1, LINC240/p-2, Me3/p-1, Me3/p-2, MIR129, NBPF1/p, NHLH2/p, NRN1/p, PPM1H/p-1, PPM1H/p-2, PPP2R5C/p, PRSS3/p, SFRP2/p-1, SFRP2/p-2, SLCO4C1/p, SOX2OT/p, TUBB2B/p, USP44/p, Chr1/p-1, Chr2/p-1, Chr3/p-1, Chr4/p-1, Chr8/p-1, and Chr10/p-1.

It is expected that it will be an overall pattern of hypermethylation, rather than a single probe, that will have the greatest predictive power.

Example 10

Breast Cancer Test

One approach described herein for identifying hypermethylated regions in breast cancer focused on the most frequently methylated regions within the TCGA database. Due to the large number of LumA and LumB patients in this dataset there was a significant under-detection particularly of the Basal class of tumours.

Figure 27:
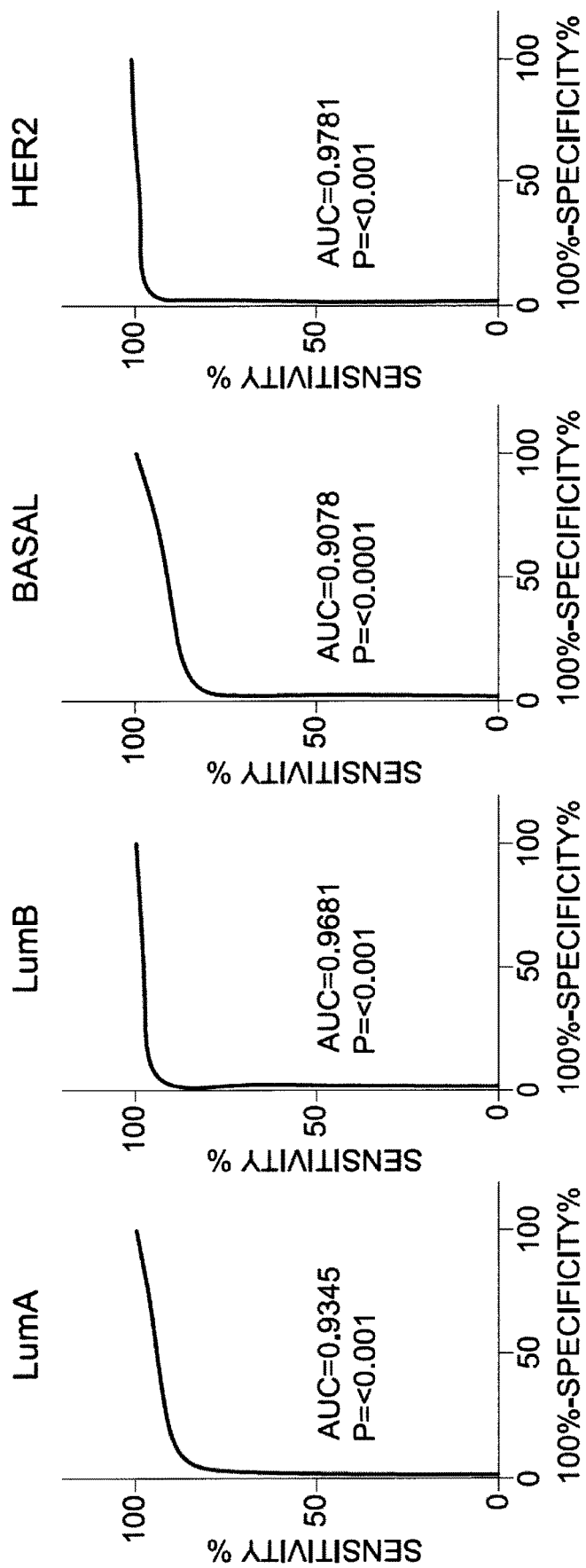
FIG. 27 shows theoretical area under the curve analyses of blood tests using the top 20 probes for each breast cancer subtype (LumA, LumB, Basal, HER2). These values were compared against normal tissue samples for the same probes.

Accordingly, the data were reanalyzed based on the four molecular subtypes LumA, LumB, Her2 and Basal. The Normal-like subtype is not very frequent in the dataset and as expected is very close to normal tissue, however a small number of regions recognizing this subtype were also included. Overall, methods and probes were developed and tested for over 230 different regions (some with multiple probes), and these have been validated using a variety of breast cancer cell lines and tumour samples. Some regions are subtype-specific but most recognize multiple subtypes. These have been assembled into a single test incorporating 167 different probes which recognize all subtypes (FIGS. 26A, 26B, and 26C), with all patients being recognized by a significant number of probes. By looking at just the top 20 probes for each subtype this test has an area under the curve (AUC) per subgroup from 0.9078 to 0.9781, indicating that high detection rates have been achieved for all types of tumours (FIG. 27). This also means that the test is able to identify the subtype of tumour based on the distribution of probe methylation.

Another test specific for the triple negative breast cancer (TNBC) subtype was developed from the larger set of general regions identified as described above. This test incorporates 86 probes from 71 regions, listed in Table 14.

TABLE 14

| CCL28 | PTPRN2 | UDB | IRF4 | HOXA9 | HINF1B | POU4F1 |
|---|---|---|---|---|---|---|
| PAX6 | BARHL2 | TMEM90B | SOX2OT | NT5E | TNFRSF10D | VWC2 |
| PPFIA3 | PRSS27 | C1orf114 | TSPAN33 | DPP10 | CD38 | BRCA1 |
| SPAG6 | DMRTA2 | ITPRIPL1 | CA9 | FOXA3 | CHST11 | HOXB13 |
| TMEM132C | NR5A2 | GIPC2 | IRF8 | C5orf39 | FABP5 | OTX2 |
| DMBX1 | BOLL | ERNA4 | CRYM | PTGDR | Intergenic5 | |
| TAL1 | SLC7A4 | MAST1 | GNG4 | SALL3 | EVX1 | |
| TOP2P1 | LEF1 | DRD4 | DDAH2 | ID4 | ACVRL1 | |
| PRDM13 | CARD11 | Intergenic 8 | EPSTI1 | GABRA4 | TBX15 | |
| GALR3 | NFIC | TCTEX1D1 | TTBK1 | PRKCB | ALX1 | |
| CDKL2 | PDX1 | PHOX2B | SCAND3 | NPHS2 | SIM1 | |

The probes were ALX1, AVCRL1, BRCA1-A, C1Dtrim, C1Etrim, CA9-A, CARD11-B, CCL28-A, CD38, CDKL2-A, CHSAtrim, CRYM-A, DMBCtrim, DMRTA2exp-A, DPP10-A, DPP10-B, DPP10-C, DRD4-A, EFNA4-B, EPSTI1, EVX1, FABP5, FOXAtrim, FOXEtrim, GALR3-A, GIPC2-A, HINF C trim, HOXAAtrim, HOXACtrim, HOXB13-A, Int5, Int8, IRF8-A, ITRIPL1, LEF1-A, MAST1 A trim, mbBARHL2 Trim, mbBOLL Trim, mbC5orf Trim, mbDDAH Trim, mbDMRTA Trim, mbGABRA A Trim, mbGABRA B Trim, mbGNG Trim, mbID4 Trim, mbIRF Trim, mbNT5E Trim, mbSIM A Trim, mbTBX15 Trim, NFIC-B, NFIC-A, NPSH2-B, NR5A2-B, OTX2-A, PAX6-A, pbDMRTA Trim, pbGNG Trim, pbSCAND Trim, pbTAL Trim, PDX1exp-B, PHOX2B-A, POU4F1 A trim, PPFIA3-A, PRDM13, PRKCB-A, PRKCB-C, PRSS27-A, PTGDR, PTPRN2-A, PTPRN2-B, SALL3-A, SALL3-B, SLC7A4-A, SOX2OT-B, SPAG6 A trim, TCTEX1D1-A, TMEM-A, TMEM-B, TMEM90B-A, TNFRSF10D, TOP2P1-B, TSPAN33-A, TTBAtrim, UBD-A, VWCJtrim, and VWCKtrim.

The ability of this test to detect TNBC was validated by the analysis of 14 TNBC primary tumours as well as matched normal tissue from four of these patients. Large scale methylation was observed for the majority of probes and was distinctly different from the normal samples (FIG. 28).

Example 11

Sensitivity of the Tests

Figure 29:
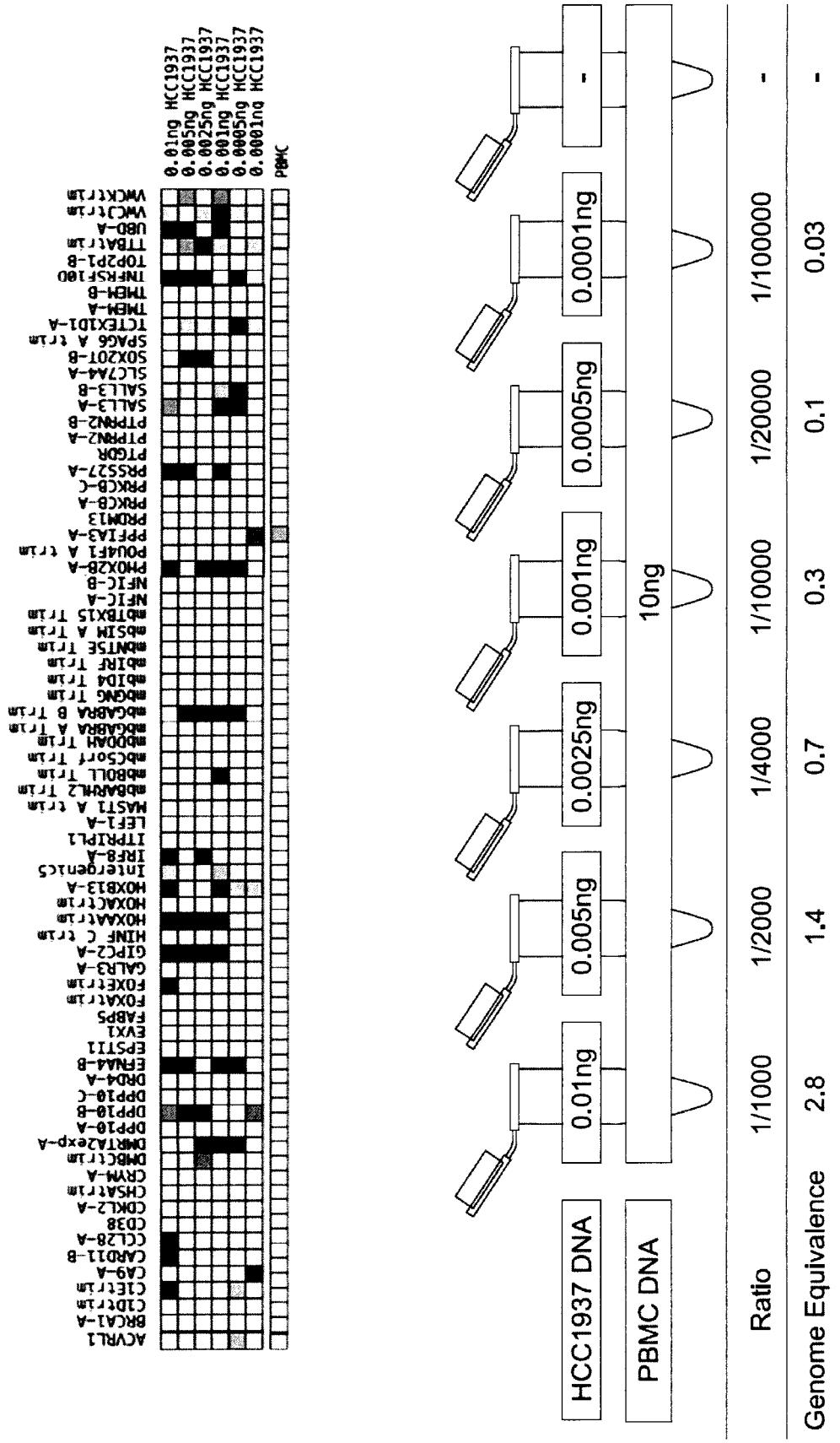
FIG. 29 is a diagram showing results of a sensitivity test for TNBC to detect low levels of tumour DNA, using HCC1937 DNA diluted into a fixed amount of PBMC DNA (10 ng). Shaded squares indicate a distinct methylation signature.

The tests described herein are designed to detect less than one genome's worth of DNA in a sample through the use of multiple regions where a single probe out of many can signal the presence of a tumour. The more regions and probes incorporated into a test the greater is the sensitivity. This is in contrast to mutation detection where the presence of a single mutation per genome equivalent means that random sampling effects rapidly limit sensitivity when the concentration of the tumour DNA falls below one genome equivalent per sample. The presence of large amounts of normal DNA in fluid samples also creates problems for the detection of mutations through the relatively high error rates for PCR and sequencing. To assess the limits of methods and tests described herein, a dilution experiment was performed wherein DNA from a TNBC cell line (HCC1937 DNA) was diluted into a constant amount of PBMC DNA (10 ng) from a normal patient (FIG. 29). These samples were then tested using the TNBC test. A conclusive signal was obtained from the test even when as little as 0.0001 ng of TNBC DNA was present in 10 ng of PBMC DNA. This represents a detection of 0.03 genome equivalents of tumour DNA against a background of 100,000 times more normal DNA.

Example 12

Discussion

The sensitivity of mutation based detection tests is limited by their detection of single unknown mutations in genes, such as p53 or ras. As only a single mutation is present per genome equivalent, this dramatically limits the sensitivity of these assays. Once the concentration of tumour DNA in the blood decreases to less than one genome equivalent per volume of blood analysed, the probability of detecting a mutation decreases dramatically as that particular segment of DNA may not be present in the blood sample. The assay described herein incorporates multiple probes for multiple regions from across the genome to dramatically increase sensitivity. For example, up to 100 or more probes may be incorporated into the assay, making it up to 100 or more times more sensitive than mutation based tests.

Circulating tumour DNA may be produced by the apoptotic or necrotic lysis of tumour cells. This produces very small DNA fragments in the blood. With this in mind, PCR primer pairs were designed to detect DNA in the range of 75 to 150 bp in length, which is optimal for the detection of circulating tumour DNA.

The use of DNA methylation offers one more advantage over mutation based approaches. Mutated genes are typically expressed in the cells (such as p53). They are thus in loosely compacted euchromatin, in comparison to methylated DNA which is in tightly compacted heterochromatin. This methylated and compacted DNA may be protected from apoptotic nucleases, increasing its concentration in the blood in comparison to these less compacted genes.

Extensive analysis of the genome wide methylation patterns in breast, colon, prostate and lung cancers and normal tissue in each of these organs based on TCGA data was carried out. 52 regions were identified for breast cancer which fulfill design criteria, which looks for an optimal difference in methylation between tumour and normal breast tissue, and where there is no methylation in any of the other normal tissues. As well, there should optimally be at least 2 CpG residues within 200 basepairs of each other. This ensured that regions of coordinated tumour specific methylation have been identified.

Within these 52 regions, 17 were found in common with colon cancer, and 9 in common with prostate cancer. Interestingly there were few appropriate regions identified in lung cancer, with only 1 overlapping with breast cancer. Most of these regions are associated with specific genes, though several are distantly intergenic, and almost all were found in CpG islands of various sizes. Probes were first developed for those regions with some commonality between cancers and designed PCR primers which recognize the methylated DNA sequence. This provides a bias in the amplification process for tumour DNA, enriching the tumour signal. These primer pairs amplify regions of 75 to 150 bp in accordance with our design criteria. Typically these regions contain from 3 to 12 CpG residues each, ensuring a robust positive signal when these regions are sequenced. Multiple non-overlapping probes were used as the CpG islands are generally larger than 150 bp, allowing for multiple probes for each appropriate region, providing more power to detect these regions and increasing the detection sensitivity of the assay.

Six different breast cancer lines were used in this validation analysis that have been shown to generally retain tumour specific methylation patterns[22]. MCF-7 and T47D lines are classic ER+ positive cell lines representing the most frequent class of breast cancer. SK-BR-3 cells are a HER2+ line and MDA-MB-231 cells represent a Triple Negative Breast cancer (TNBC), thus the 3 main categories of breast cancer are represented covering 95% of all tumours. Two "normal" lines were also used, the MCF10A line, though this line has been shown to contain some genomic anomalies, and the karyotypically normal 184-hTERT line. DNA was bisulphite converted, and the probes were amplified individually, barcoded then pooled according to cell line and subject to Next Generation Sequencing on an Ion Torrent sequencer. Not all PCR primer pairs produced a product due to the methylation-based nature of the primers, but in general, where a signal was detected, around 1000 reads were obtained per probe for each cell line. These reads were processed through our NGS pipeline using Galaxy and then loaded into the NGS methylation program BiqAnalyzer[23,24]. This program extracts probe specific reads, aligns them against the probe reference sequence, and calls methylated and unmethylated CpGs. It also carries out quality control measures related to bisulphite conversion and alignment criteria. In all of these probes there are several CpG residues within the primer sequence producing a bias towards amplifying methylated DNA. The analysis shown only includes CpGs outside of the primers which are solely representative of the methylation status of the sample being analysed.

FIGS. 5 and 6 depict results for the CHST11 gene, which is a good example where robust PCR primers are able to recognize tumour specific methylation. Four different primer pairs were assessed, three of which amplify probes that partially overlap. In all four cases these regions are completely methylated at all CpGs (not including CpGs in the primers) and are essentially completely unmethylated in the normal lines. CHST11 primers do not recognize the Her2 or TNBC lines, but other primers such as ADCY and MIRD do. The corresponding probes cover a small region of the CpG island and information about the status of the rest of the CpG island is limited due to the relatively coarse resolution of the 450K methylation data. Clearly the remaining part of the CpG island can be developed for additional probes that would increase the sensitivity of detection.

FIG. 7 shows that FOXA probe A had similar characteristics and recognized all but one TNBC tumour. This proves that the target and probe development pipeline moving from TCGA data to cell lines and then to patient normal and tumour tissue successfully identified primer pairs that are able to specifically recognize tumour DNA based on their methylation patterns.

Validation work continues to validate potential probe regions. A further 24 regions were characterized using 52 different probes in the cell lines as an initial screen for their suitability.

FIG. 4 shows the results of analysis of all of the potential CpGs identified in the TCGA cohort for individual patients indicates most patients are recognized by a large proportion of these probes.

FIG. 3 shows the results of ROC analysis[25] and indicates each of these probes has a very high AUC, suggesting excellent performance individually and presumably even better when combined.

It has been noted that there does appear to be a population of patients with relatively few positive probes. This is not subtype specific and other probes specific for this population have been identified. As appropriate, additional probes will be developed for all suitable regions and expanded to include other parts of the associated CpG islands. Overall it is expected that 100-150 separate probes in the assay will provide optimal sensitivity.

FIGS. 12A and 12B depict a numerical summary of validation data, wherein "#Reads" indicates the number of reads, and "Mean" Me indicates the mean methylation observed in results. Approximately half of the probes met the design criteria of having complete methylation of all CpG residues in the tumour samples and little or no methylation in the normal lines.

The next step in validating each of these probes was to examine their methylation patterns in actual patient tumour samples. A small cohort of patient samples was used to investigate GR methylation. From this group three ER+ tumours (one of which is positive for GR methylation), one HER2+ tumour and two TNBC tumours were chosen, as well as their corresponding normal controls. Taking the CHST11A probe as an example, FIG. 6 shows that all six of the normal breast tissue samples had either no reads due to the methylation biased amplification yielding no product or minimal methylation. In no case was there any concerted methylation signal where all CpGs were methylated. In contrast, in one TNBC and one ER+PR+ tumour a strong concordant methylation signal was seen at all six CpG sites. The other 2 ER+PR+ tumours also showed consistent methylation at four or five CpGs with their normal breast tissue controls having minimal reads with only one CpG showing any methylation.

FIGS. 13A and 13B depict a numerical summary of generated methylation data for tumour samples for all probes tested to date. #Reads is indicative of the number of reads exported, and Mean Me is indicative of the mean methylation.

Initial proof of concept work involved mixing experiments where non-methylated and methylated DNA was mixed in increasing ratios. This demonstrated that based in the presence of multiple CpG signatures methylated DNA could easily be detected in the presence of at least a 500 fold excess of unmethylated DNA. These probes were amplified with PCR primers that were not methylation specific or biased, and the probes developed to date do incorporate a bias towards methylated DNA, which further increases the detection sensitivity. However, they do amplify non-methylated DNA (in part because primers were designed with no preference as to the location of methylation sites within the primers). This was done intentionally as it provides for a potential quantitative aspect to this assay. Some of the circulating normal DNA in blood samples is likely from the lysis of nucleated blood cells, which is why serum is preferred over plasma as a source of DNA. However the ratio of tumour to normal DNA in blood may provide some quantitation of the actual concentration of tumour DNA present in the blood, which is thought to be correlated with tumour load. Since tumour can be distinguished from normal DNA reads, the ratio between them can be used as a proxy for the tumour DNA concentration. The number of tumour specific reads per volume of blood, regardless of the number of normal reads, may also prove to be closely linked to circulating tumour DNA levels.

Optimizing this test may include multiplexing to allow all of the probes the opportunity to amplify their targets in a given sample of DNA. Through the use of limited concentrations of primers and cycles, excellent amplification of all probes was obtained within a set of 17 primer pairs. Expanding this to include all of the optimized primers is not expected to be an issue.

The test may be implemented as a blood based breast cancer detection system in patient blood samples.

Based on development and validation work to date, the assay offers significant advantages other current and developing tests based on sensitivity, specificity, and detection sensitivity.

Some potential applications of the embodiments described herein are listed below by level of detection sensitivity:

Determining response to neo-adjuvant chemotherapy;
Monitoring tumour load in diagnosed patients;
Detecting residual disease post-surgery;
Detecting relapse;
Secondary screen after positive MRI in high risk patients;
Direct monitoring of high risk patients; and
Primary population screening.

The analysis of patients with active breast cancer offers the ability to assess a number of different aspects of this blood based test. Patients with locally advanced disease can be recruited preferentially, as these patients generally have larger tumours, receive neo-adjuvant therapy, are more likely to have residual disease and are at higher risk of relapse. By analysing blood samples from these patients upon diagnosis, after any neo-adjuvant treatments, presurgery, and at followup visits post-surgery it is possible to follow the relative tumour burden in these patients over the course of treatment. This will allow the tumour size and type to be correlated with the results of the test described herein.

Patients can be recruited in the clinic after a biopsy confirmed positive diagnosis. Blood can be drawn in conjunction with other routine blood work at diagnosis, after neo-adjuvant treatment, before surgery, within a month after surgery and every 3-6 months following that. Blood from 50 aged matched women without disease can also be collected from the community to provide control samples for the patient cohort. Relevant clinical data can be collected including radiological assessments and/or pathology reports. In particular, the receptor status of the tumours, the size of the tumour based on both radiological assessment and examination of the excised tumour, as well as treatments and response to therapy can be correlated with the circulating DNA analysis.

The assay described herein is expected to be quantitative at different levels. At very low levels of tumour DNA, the random presence of the tumour DNA in a sample will result in a subset of individual probes being positive, with the number of positive probes increasing with greater tumour DNA levels. At higher levels of tumour DNA the number of tumour specific reads will increase, either as an absolute number or in relation to the number of normal DNA reads. As a result methylation data can be treated in three ways:

(1) As a binary outcome where each probe will be considered to be positive if it has any tumour specific methylation pattern present;
(2) An individual threshold of methylation will be established for each probe based on the minimum number of reads required to call a tumour; or
(3) Tumour specific reads per number of normal reads for each probe (or, e.g., per 100,000 total reads).

Each of these approaches may be used to carry out logistic regression on the patient and control sets. Receiver Operating Characteristic (ROC) analysis may be used to define thresholds for each probe that maximizes the sensitivity and sensitivity of the assay. The performance of the entire assay may be characterized using Area Under the Curve (AUC) analysis for overall sensitivity, specificity, classification accuracy and likelihood ratio. Pearson or Spearman correlations may be used to compare patient parameters with the test outcomes.

Changes in methylation may be important drivers of breast cancer development and that these occur very early during the process of transformation. This may explain why many of the observed methylations are common amongst different breast cancer sub-types, while some are even common to other cancers. This may mean that these changes predate the development of full malignancy and suggests that they could also have value in assessing the risk of a women developing breast cancer. It is envisaged that the assay described herein can be used to track the accumulation of risk in the form of increasing gene specific methylation levels and could be used to develop a risk assessment tool. This would be useful for the development and assessment of risk mitigation and prevention strategies.

Table 15 lists the primers used herein for each probe.

TABLE 15

| Gene | Probe | SEQ ID NO. | 5'-3' Primer Sequence (Bisulfite) | Chr: Location | PCR Product Length |
|---|---|---|---|---|---|
| C1orf114/ CCDC18 | C1Df | 1 | TTGAGGTAAAGGAGATTTCGGT | chr1: 167663228-167663361 | 134 |
| | C1Dr | 2 | ACATACGCCTACGCAAATTTTA | | |
| | C1Ef | 3 | TTCGGTGTTTGCGAAGGGTTA | chr1: 167663398-167663508 | 111 |
| | +C1Er | 4 | TCACAACCAACACAACGACACTT | | |
| | C1Er | 5 | ACAACCAACACAACGACACTT | | |
| | C1Ff | 6 | TCGGTATTTGTTTTCGCGGT | chr1: 167663245- | 112 |

TABLE 15-continued

| Gene | Probe | SEQ ID NO. | 5'-3' Primer Sequence (Bisulfite) | Chr: Location | PCR Product Length |
|---|---|---|---|---|---|
| | C1Fr | 7 | CGCCTACGCAAATTTTTATCGC | 167663356 | |
| | C1Gf | 8 | CGAGAGCGATAAAAATTTGCGT | chr1: 167663330- | 88 |
| | C1Gr | 9 | ACCCTTCGCAAACACCGAAA | 167663417 | |
| | C1 eAf | 10 | GGTAATAGCGTGTTTTTGC | chr1: 167663285- | 82 |
| | C1 eAr | 11 | ATATTACATACGCCTACGCAAA | 167663366 | |
| | C1 eBf | 12 | TTTGTGTAAAATGCGGCGGT | chr1: 167663149- | 118 |
| | C1 eBr | 13 | CTACCGCGAAAACAAATACCGA | 167663266 | |
| | C1 eCf | 14 | ATTTCGGTGTTTGCGAAGGG | chr1: 167663395- | 112 |
| | C1 eCr | 15 | ACAACCAACACAACGACACT | 167663506 | |
| VWC2 | VWCJf | 16 | TTTCGGTTGTCGGGTTTGGA | | |
| | +VWCJf | 17 | TATTTCGGTTGTCGGGTTTGGA | chr7: 49783871- | 133 |
| | VWCJr | 18 | CCCTCAATCGCTCATCCTCC | 49784003 | |
| | VWCKf | 19 | TCGTCGGTCGGTTTAGGATG | chr7: 49784151- | 129 |
| | +VWCKr | 20 | AAAACCGACGCCAAACCTACAT | 49784279 | |
| | VWCKr | 21 | AACCGACGCCAAACCTACAT | | |
| | VWCLf | 22 | CGGAGGATGAGCGATTGAGG | chr7: 49783983- | 118 |
| | VWCLr | 23 | TAACGCGCACACCGAACTAA | 49784100 | |
| | VWCMf | 24 | CGAGTTGGGGTCGCGATTAT | chr7: 49784021- | 150 |
| | VWCMr | 25 | CATCCTAAACCGACCGACGA | 49784170 | |
| | VWCNf | 26 | CGACGCGTTACGGTTGTTTA | chr7: 49783849- | 125 |
| | VWCNr | 27 | CCGCTTCTCCGAAACCAAAC | 49783973 | |
| | VWC2 eAf | 28 | TAAGGCGGGGTTTTTAGAGC | chr7: 49783687- | 106 |
| | VWC2 eAr | 29 | TAAAAACTAACGCGCCCG | 49783792 | |
| | VWC2 eBf | 30 | GGTTTCGGTGTTATTCGC | chr7: 49783797- | 126 |
| | VWC2 eBr | 31 | CTCCTCTCCGCGAAAAAAT | 49783922 | |
| | VWC2 eCf | 32 | CGGAGGATGAGCGATTGAGG | chr7: 49783983- | 118 |
| | VWC2 eCr | 33 | TAACGCGCACACCGAACTAA | 49784100 | |
| | VWC2 eDf | 34 | TCGTCGGTCGGTTTAGGATG | chr7: 49784151- | 127 |
| | VWC2 eDr | 35 | AACCGACGCCAAACCTACAT | 49784277 | |
| | VWC2 eEf | 36 | GTCGGACGCGTTTTAGTTGG | chr7: 49784315- | 110 |
| | VWC2 eEr | 37 | TCCCTACCGACCTCAACACT | 49784424 | |
| MIR129-2 | MIRBf | 38 | TGGTTGGGGGATTTTGAGGG | chr11: 43559089- | 141 |
| | MIRBr | 39 | AAACCTCCCCGCCTACCTAT | 43559229 | |
| | MIRCf | 40 | GCGGACGGTTTGGAGAAATG | chr11: 43559343- | 82 |
| | MIRCr | 41 | CGCGACTCAATCTCACCACT | 43559424 | |
| | MIRDf | 42 | GGAGGTTGGGTTTCGGGATT | chr11: 43559257- | 127 |
| | MIRDr | 43 | GCGCCCTAAAACTCGTATCT | 43559383 | |
| | MIREf | 44 | GCGGAGTGGTGAGATTGAGT | chr11: 43559401- | 113 |
| | MIREr | 45 | ACCGACTTCTTCGATTCGCC | 43559513 | |
| | MIRFf | 46 | ATAGGTAGGCGGGGAGGTTT | chr11: 43559205- | 139 |
| | MIRFr | 47 | CGATCCCCCAACTCAACCC | 43559343 | |
| | MIR eAf | 48 | TGAGTTGGCGGTTTCGTTTG | chr11: 43559004- | 122 |
| | MIR eAr | 49 | CCCGAATCCCCTCTTATCCC | 43559125 | |
| | MIR eBf | 50 | CGCGATTTTGTAGTCGGGGT | chr11: 43559156- | 96 |
| | MIR eBr | 51 | TTTCCTATCGCCCCAACACC | 43559251 | |
| | MIR eCf | 52 | GGAGGTTGGGTTTCGGGATT | chr11: 43559257- | 127 |
| | MIR eCr | 53 | GCGCCCTAAAACTCGTATCT | 43559383 | |
| | MIR eDf | 54 | GATTGAGTCGCGATGGAACG | chr11: 43559413- | 81 |
| | MIR eDr | 55 | GCCGCCTTCAACCCAAAATA | 43559494 | |
| ADCY4 | ADCYFf | 56 | CGCGAGCGTATAGAGTACGA | chr14: 23873573 | 163 |
| | ADCYFr | 57 | ACCCTAACCAACCCCGAAAC | 23873735 | |
| | ADCYGf | 58 | TAGCGTCGCGAGCGTATAGA | chr14: 23873567- | 188 |
| | ADCYGr | 59 | AAAAATAACCCGACGCCCGA | 23873754 | |
| | ADCYHf | 60 | GGTTTCGTAGAAGAGGTTTTC | chr14: 23873642- | 174 |
| | ADCYHr | 61 | CGCGAAATAATAACGACTTT | 23873815 | |
| | ADCY4 eAf | 62 | AGAAGAGGTTTTCGTTGGGGG | chr14: 23873650- | 80 |
| | ADCY4 eAr | 63 | ACCAACCCCGAAACTCGAAA | 23873729 | |
| | ADCY4 eBf | 64 | TAGGATTTGGGGTTGGTGCG | chr14: 23873975- | 141 |
| | ADCY4 eBr | 65 | AACGCAACGACGAACGTAAC | 23874115 | |
| | ADCY4 eCf | 66 | TGGTAGTGGGAGATCGAGG | chr14: 23874376- | 99 |
| | ADCY4 eCr | 67 | AAACGCCCCCAACTCTAACC | 23874474 | |
| DMBX1 | DMBAf | 68 | GTTGCGGACGGCGTAGAT | chr1: 46723984- | 149 |
| | DMBAr | 69 | ACGCTCCCCGAAACAATAACT | 46724132 | |
| | DMBBf | 70 | TTGTTAGTTTTGTTAGCGCGG | chr1: 46723919- | 75 |
| | DMBBr | 71 | CGTCCGCAACGATTCATCATC | 46723993 | |
| | DMBCf | 72 | TGTTTAGGAGATGGTTCGTGGT | chr1: 46723889- | 115 |
| | +DMBCr | 73 | GCATCTACGCCGTCCGCAAC | 46724003 | |
| | DMBCr | 74 | ATCTACGCCGTCCGCAAC | | |
| | DMBX1 eAf | 75 | TGTTTAGACGTGGGTTGGGG | chr1: 46723237- | 87 |
| | DMBX1 eAr | 76 | TCAACTCCACTCACCCCGTA | 46723323 | |
| | DMBX1 eBf | 77 | GAGGAGGGTGGAGAGGGTAG | chr1: 46723478- | 133 |
| | DMBX1 eBr | 78 | ATACCGCACGTACTCCCAAC | 46723610 | |

TABLE 15-continued

| Gene | Probe | SEQ ID NO. | 5'-3' Primer Sequence (Bisulfite) | Chr: Location | PCR Product Length |
|---|---|---|---|---|---|
| | DMBX1 eCf | 79 | GGAGTGGAGTAGGTAGCGGT | chr1: 46723635- | 117 |
| | DMBX1 eCr | 80 | TTCCTAACCCTCTCCGACCA | 46723751 | |
| | DMBX1 eDf | 81 | TTTTTGAGCGGTGAAGGGGA | chr1: 46723764- | 125 |
| | DMBX1 eDr | 82 | AATTATTAACGCGACCGCCG | 46723888 | |
| HOXA9 | HOXAAf | 83 | GTAATAATTTGGTGGTATCGGGGG | chr7: 27171666- | 100 |
| | HOXAAr | 84 | TCTACTAAACGAACACGTAACGC | 27171765 | |
| | HOXABf | 85 | ATAATTTGGTGGTATCGGGGG | chr7: 27171669- | 109 |
| | HOXABr | 86 | ACGCGTTATTATTCTACTAAACGAA | 27171777 | |
| | HOXACf | 87 | TGGGGTTTGTTTTAATTGTGGTT | chr7: 27171878- | 152 |
| | +HOXACr | 88 | GCGAAACCCGCGCCTTCTTAAT | 27172029 | |
| | HOXACr | 89 | GAAACCCGCGCCTTCTTAAT | | |
| | HOXADf | 90 | GGGGAAGTATAGTTATTTAATAAGTTG | chr7: 27171688- | 128 |
| | HOXADr | 91 | ACAAAACATCRAACCATTAATAA | 27171815 | |
| | HOXA9 eAf | 92 | TTCGCGAAGGAGAGCGTATC | chr7: 27171234- | 101 |
| | HOXA9 eAr | 93 | CCCTACGTACACCCCCAAAC | 27171334 | |
| | HOXA9 eBf | 94 | CGTTTGGGGGTGTACGTAGG | chr7: 27171314- | 88 |
| | HOXA9 eBr | 95 | AAACCCAATACACGCGACGA | 27171401 | |
| | HOXA9 eCf | 96 | TTTGTCGGGGAGGTTGGTTT | chr7: 27171478- | 82 |
| | HOXA9 eCr | 97 | TTCCTACTAAACGCCGACGC | 27171559 | |
| | HOXA9 eDf | 98 | TAGCGTTTGGTTCGTTCGGT | chr7: 27171611- | 123 |
| | HOXA9 eDr | 99 | ATAAAAACGCGAACGCCGAC | 27171733 | |
| SFRP5 | SFRAf | 100 | GCGGGCGTTTCGATTGATTT | | |
| | +SFRAf | 101 | TTGCGGGCGTTTCGATTGATTT | chr10: 99521730- | 131 |
| | SFRAr | 102 | TAAAAACCGCCCCCACTACC | 99521860 | |
| | SFRBf | 103 | TGTTCGGCGGTTTAGGTGTT | chr10: 99521628- | 124 |
| | SFRBr | 104 | AAATCAATCGAAACGCCCGC | 99521751 | |
| | SFRCf | 105 | TAGTTCGGGTTTCGTCGTGC | chr10: 99521776- | 90 |
| | +SFRCr | 106 | AAAACTAAAAACCGCCCCACT | 99521865 | |
| | SFRCr | 107 | AACTAAAAACCGCCCCACT | | |
| | SFRDf | 108 | GTGGGTGGTAGTTTGCGTTG | chr10: 99521713- | 135 |
| | SFRDr | 109 | CACTACCTCCCCGCCTTAAA | 99521847 | |
| | SFREf | 110 | GCGTGCGTTTTCGGTTTTGA | | |
| | +SFREf | 111 | CGGCGTGCGTTTTCGGTTTTGA | chr10: 99521649- | 83 |
| | SFREr | 112 | AACGCAAACTACCACCCACC | 99521731 | |
| | SFRP5 eAf | 113 | GGACGTTGGGTTGAGTTAGGA | chr10: 99520910- | 109 |
| | SFRP5 eAr | 114 | ACGACCCTACAACTCCCCTA | 99521018 | |
| | SFRP5 eBf | 115 | GGTGTTCGAATTGTACGGCG | chr10: 99521073- | 107 |
| | SFRP5 eBr | 116 | CTACGCGCCGCTCATAAAAA | 99521179 | |
| | SFRP5 eCf | 117 | GCGCGTACGGTTTCGTATAG | chr10: 99521183- | 75 |
| | SFRP5 eCr | 118 | ATACTCGCTCTTTACGCCCG | 99521257 | |
| | SFRP5 eDf | 119 | TAGAGCGGTAGGTCGGTAGG | chr10: 99521393- | 79 |
| | SFRP5 eDr | 120 | AACAAACCGAACCGCTACAC | 99521471 | |
| CHST11 | CHSAf | 121 | GCGGCGTGGGAATGAATTTT | | |
| | +CHSAf | 122 | GGGCGGCGTGGGAATGAATTTT | chr12: 103376278- | 120 |
| | CHSAr | 123 | CTTTCCCTCGCACCCCTAAA | 103376397 | |
| | CHSBf | 124 | TGCGAGGGAAAGTTTGGGTT | chr12: 103376386- | 123 |
| | CHSBr | 125 | CCGCGTTACCCGAAAAACTT | 103376508 | |
| | CHSCf | 126 | TTTTAGGGGTGCGAGGGAAA | chr12: 103376377- | 86 |
| | CHSCr | 127 | CGCAACCGAACTACTCACCC | 103376462 | |
| | CHSDf | 128 | GTGCGAGGGAAAGTTTGGGT | chr12: 103376385- | 126 |
| | CHSDr | 129 | ACCCGCGTTACCCGAAAAA | 103376510 | |
| | CHST11 eAf | 130 | TTTTTTTGGTTGTCGGGTC | chr12: 103375901- | 109 |
| | CHST11 eAr | 131 | CGAAACCCGAAACACGTA | 103376009 | |
| | CHST11 eBf | 132 | AGAGTGGTCGGGTGTTTAGC | chr12: 103376031- | 149 |
| | CHST11 eBr | 133 | ACGTAACCCAAAAACTCGAAA | 103376179 | |
| | CHST11 eCf | 134 | GTCGTTTTTAGGGGTGC | chr12: 103376371- | 99 |
| | CHST11 eCr | 135 | TAAACTTCGCAACCGAACTA | 103376469 | |
| | CHST11 eDf | 136 | TATTAAGTTTCGCGTTTGGGTC | chr12: 103376781- | 109 |
| | CHST11 eDr | 137 | AAAACCGTCTATCCCTACGC | 103376889 | |
| FOXA3 | FOXAf | 138 | CGAGGTAGGAAGTTTTGCGG | chr19: 51071936- | 103 |
| | FOXAr | 139 | CGACTCCTCCCGCGAAATAA | 51072038 | |
| | FOXBf | 140 | CGGGGTGTTGTTGTAGGGTT | chr19: 51072158- | 93 |
| | FOXBr | 141 | AATCACACCTACCCACGCC | 51072250 | |
| | FOXCf | 142 | TAGGGCGGTTAGGTTTGGGG | chr19: 51072076- | 128 |
| | FOXCr | 143 | GACGAATAACCCCACCCTCC | 51072203 | |
| | FOXDf | 144 | TTGTCGCGTTGGTTTTCGT | chr19: 51071765- | 103 |
| | FOXDr | 145 | ACCTTTCTCTCGACCCCAAT | 51071867 | |
| | FOXEf | 146 | CGTTTTGTCGGTTGCGTGTTA | chr19: 51071734- | 91 |
| | FOXEr | 147 | ATTCCCCGACCCTACCCAAAC | 51071824 | |
| | FOXA3 eAf | 148 | GGTAGGTGATAACGTTAGTGGGTT | chr19: 51068615- | 110 |
| | FOXA3 eAr | 149 | ACCTCCATCCCCTACCCAAC | 51068724 | |
| | FOXA3 eBf | 150 | AGTAGGGGAGGTGGTTTTG | chr19: 51069110- | 135 |

TABLE 15-continued

| Gene | Probe | SEQ ID NO. | 5'-3' Primer Sequence (Bisulfite) | Chr: Location | PCR Product Length |
|---|---|---|---|---|---|
| | FOXA3 eBr | 151 | TCCTCCTCCCCAACTTAACC | 51069244 | |
| | FOXA3 eCf | 152 | AGTTTGGGTGTGGCGGTTTA | chr19: 51070046- | 111 |
| | FOXA3 eCr | 153 | ACCAACTTCGCCATATTAACCA | 51070156 | |
| TTBK1 | TTBAf | 154 | CGCGGTGTATTGTGGGTAGT | chr6: 43319189- | 99 |
| | TTBAr | 155 | CCTTCCGACCCGAATCATCC | 43319287 | |
| | TTBBf | 156 | GGTCGTCGGAACGTGATGT | chr6: 43319101- | 86 |
| | TTBBr | 157 | GCCAACATCAACACCAACCC | 43319186 | |
| | TTBCf | 158 | TCGTTTTGTCGTTGTCGTCG | chr6: 43319212- | 107 |
| | TTBCr | 159 | TTAAATAACCCGCTCCCTCCG | 43319318 | |
| | TTBDf | 160 | GTCGTGATGTTAGAGCGGGC | chr6: 43319130- | 126 |
| | TTBDr | 161 | ACCCCGATCCTCCTTAAACG | 43319255 | |
| | TTBK1 eAf | 162 | TTAAGGAGGATCGGGGTC | chr6: 43319239- | 91 |
| | TTBK1 eAr | 163 | TCAATACGACGTTAAATAACCC | 43319329 | |
| | TTBK1 eBf | 164 | TGGAGTTAAGCGGGTGGTAG | chr6: 43319008- | 141 |
| | TTBK1 eBr | 165 | CCCGCTCTAACATCACGACTC | 43319148 | |
| TAL1 | pbTAL f | 166 | GTATTGTCGCGGGTTCGTTC | chr1: 47470631- | 129 |
| | pbTAL r | 167 | CTCAACCAATCCCCACTCCC | 47470738 | |
| | mbTAL f | 168 | GTTTTAGGTTTCGTTAGTATGGG | chr1: 47470570- | 129 |
| | +mbTAL r | 169 | CAAATTAAAATAAATCATTTAACCCATAA | 47470698 | |
| | mbTAL r | 170 | TTAAAATAAATCATTTAACCCATAA | | |
| DMRTA2 | pbDMRTA f | 171 | CGAAGATTTCGTAGGCGGGT | chr1: 50659325- | 145 |
| | +pbDMRTA r | 172 | ACGACGCAAATAACGCTACGCA | 50659469 | |
| | pbDMRTA r | 173 | GACGCAAATAACGCTACGCA | | |
| | mbDMRTA f | 174 | TGTTTTAGAAGCGGGAGAAAG | | |
| | mbDMRTA r | 175 | AAATAAAACCCCCGTATCCAAT | | |
| | +mbDMRTA f | 176 | AATGTTTTAGAAGCGGGAGAAAG | chr1: 50659041- | 113 |
| | +mbDMRTA r | 177 | AAAAATAAAACCCCCGTATCCAAT | 50659153 | |
| | DMRTAexp Af | 178 | GCGGCGGTTAGCGTTAGTTTTTCGGTAG | chr1: 50659366- | 124 |
| | DMRTAexp Ar | 179 | CGAAACGCCAACGTATCATAACGACGCA | 50659489 | |
| PDE4B | pbPDE f | 180 | ACGTTTTAGGGACGGCGAAT | chr1: 66030622- | 77 |
| | pbPDE r | 181 | AATCCCAACGACCGTCTACC | 66030698 | |
| | mbPDE f | 182 | TTTCGTTTTGTATTTATGGTAGATGT | chr1: 66030580- | 115 |
| | mbPDE r | 183 | CCAACGACCGTCTACCACTA | 66030694 | |
| BARHL2 | pbBARHL f | 184 | CGTGGTATGGATTTCGGGGT | chr1: 90967266- | 111 |
| | pbBARHL r | 185 | ACTCCTAACCCTAAACGCGA | 90967376 | |
| | mbBARHL f | 186 | GTTTTTTTCGGTTTTGTTCGA | | |
| | mbBARHL r | 187 | TTTCTCCCAATTCCAATATCCA | | |
| | +mbBARHL f | 188 | TGGTTTTTTTCGGTTTTGTTCGA | chr1: 90967815- | 86 |
| | +mbBARHL r | 189 | ACTTTCTCCCAATTCCAATATCCA | 90967900 | |
| TBX15 | pbTBX f | 190 | GCGATCGGCGATTGGTTTTT | chr1: 119331668- | 100 |
| | pbTBX r | 191 | GCGACGACACACGACCTAAA | 119331767 | |
| | mbTBX f | 192 | TGAGGTTTTAGGTCGTGTGT | | |
| | +mbTBX f | 193 | GGTGAGGTTTTAGGTCGTGTGT | chr1: 119331740- | 142 |
| | mbTBX r | 194 | AAAACCTTAATCGACTCAAATAAAA | 119331881 | |
| RUSC1, C1orf104 | pbRUSC f | 195 | GGGTGTAGTTGCGTAGCGTA | chr1: 153557280- | 142 |
| | pbRUSC r | 196 | CCGAACCCTCCTCACCAAAA | 153557421 | |
| | mbRUSC f | 197 | TAGTTGCGTAGCGTAGGGTA | chr1: 153557285- | 126 |
| | mbRUSC r | 198 | TCACCAAAATCCTCCTAAAAC | 153557410 | |
| GNG4 B | pbGNG f | 199 | ACGTAGTGTTGGTAAGATTTGTAGA | chr1: 233880823- | 149 |
| | pbGNG r | 200 | ACAAAAACCGCTTATAAACGACGA | 233880971 | |
| | mbGNG f | 201 | GTAGGTTTTTGCGTTGGAGATT | chr1: 233880677- | 141 |
| | mbGNG r | 202 | ATTTTCGTTACTTCTCTATTCCCAA | 233880817 | |
| POU3F3 | pbPOU3F f | 203 | GGGGTTTCGCGTTTTGAGTT | chr2: 104836866- | 79 |
| | pbPOU3F r | 204 | AACACCAAAACCCCCGCTAA | 104836944 | |
| | mbPOU3F f | 205 | AAAAGTAATTAATCGGAACGGT | chr2: 104836837- | 134 |
| | mbPOU3F r | 206 | ACACTTTCCCAAATACAAAAAAA | 104836970 | |
| BOLL B/C | pbBOLL f | 207 | TTTCGAGTCGGGGCGTTTTA | chr2: 198359264- | 138 |
| | pbBOLL r | 208 | TACCTAACCGCTCGCTCTCT | 198359401 | |
| | mbBOLL f | 209 | GTTCGGTTTTGGGATTTTT | | |
| | mbBOLL r | 210 | AATCCCAAAAACCGACTCT | | |
| | +mbBOLL f | 211 | GAGGGTTCGGTTTTGGGATTTTT | chr2: 198359331- | 131 |
| | +mbBOLL r | 212 | ACCAATCCCAAAAACCGACTCT | 198359461 | |
| TRIM71 | pbTRIM f | 213 | CGGAGGAATTTGTGTCGTCG | chr3: 32834331- | 110 |
| | pbTRIM r | 214 | CACCAAAACAACGCTACCCG | 32834440 | |
| | mbTRIM Af | 215 | TTGGGAATTTTTTTCGTTTAT | chr3: 32834188- | 150 |

TABLE 15-continued

| Gene | Probe | SEQ ID NO. | 5'-3' Primer Sequence (Bisulfite) | Chr: Location | PCR Product Length |
|---|---|---|---|---|---|
| | mbTRIM Ar | 216 | TCCTCCGAATAACTTAAAAACC | 32834337 | |
| | mbTRIM Bf | 217 | TCGTTGGATAGTGGTATTTAATGT | chr3: 32834348- | 150 |
| | mbTRIM Br | 218 | AAAATCACCGACTCACTCAA | 32834497 | |
| SLC2A2 | pbSLC f | 219 | CGGAGTACGGCGGTAGGAA | chr3: 172228914- | 80 |
| | +pbSLC r | 220 | AATACCCCGAAAACCCGCTAATA | 172228993 | |
| | pbSLC r | 221 | ACCCCGAAAACCCGCTAATA | | |
| | mbSLC f | 222 | ATGATATTTTGTAGGAAAGCGT | chr3: 172228748- | 103 |
| | mbSLC r | 223 | CAAATTCCGTTTCTAAAAAAC | 172228850 | |
| CYTL1 | pbCYTL f | 224 | GGGTTCGTATGCGGGAGTAG | chr4: 5071974- | 126 |
| | pbCYTL r | 225 | ACGAAACTACACCAACGCCT | 5072099 | |
| | mbCYTL f | 226 | GGGGGTTTTCGTTAGGAGTAG | chr4: 5072020- | 123 |
| | mbCYTL r | 227 | AAACCGCCCTAAACCACC | 5072142 | |
| SHISA3 | pbSHISA f | 228 | GAAGGGCGGTAGCGATAGTT | chr4: 42094543- | 108 |
| | +pbSHISA r | 229 | CTACGAATTCCGCAAACGAAA | 42094650 | |
| | pbSHISA r | 230 | ACGAATTCCGCAAACCGAAA | | |
| | mbSHISA f | 231 | ATTGTTTTGTCGGCGTT | chr4: 42094569- | 86 |
| | mbSHISA r | 232 | TACACTACGAATTCCGCAA | 42094654 | |
| GABRA4 | pbGAB f | 233 | GCGTGCGTATATTCGCGTTT | | |
| | +pbGAB f | 234 | CGGCGTGCGTATATTCGCGTTT | chr4: 46690291- | 95 |
| | pbGAB r | 235 | AAATTCCGCCTCCCCTAACC | 46690385 | |
| | mbGAB Af | 236 | TTTAGCGTTTAATGTGTATGTAGA | chr4: 46690411- | 135 |
| | +mbGAB Ar | 237 | CGAAATTACAATCGAAACAAACTTAC | 46690545 | |
| | mbGAB Ar | 238 | AAATTACAATCGAAACAAACTTAC | | |
| | mbGAB Bf | 239 | GTTTTGAGTAGGGTGCGAG | | |
| | mbGAB Br | 240 | AAAAAAACAAATTCCGCCT | | |
| | +mbGAB Bf | 241 | GATGTTTTGAGTAGGGTGCGAG | chr4: 46690248- | 151 |
| | +mbGAB Br | 242 | AAACGAAAAAAACAAATTCCGCCT | 46690398 | |
| EGFLAM | pbEGF f | 243 | TGGTAGCGTTGTAAGGTGGG | chr5: 38293231- | 129 |
| | pbEGF r | 244 | AAAAACAAACGCGACCCTCG | 38293359 | |
| | mbEGF f | 245 | TCGAGTTTTGGTAGCGTTGTAA | chr5: 38293223- | 84 |
| | +mbEGF r | 246 | AATACCCCGCAAAAAAATCTACA | 38293306 | |
| | mbEGF r | 247 | CCCCGCAAAAAAATCTACA | | |
| C5orf39 | pbC5orf f | 248 | ACGAGAAATTGGCGCGTTGA | chr5: 43076304- | 101 |
| | pbC5orf r | 249 | AACAACACCCTTTACGACGC | 43076404 | |
| | mbC5orf f | 250 | TGTTTGTTAGGGTTTTGTTTTAA | | |
| | mbC5orf r | 251 | CGCCAAAACGAATATTTATTTA | | |
| | +mbC5orf f | 252 | AATTGTTTGTTAGGGTTTTGTTTTAA | chr5: 43076267- | 124 |
| | +mbC5orf r | 253 | CGACGCCAAAACGAATATTTATTTA | 43076390 | |
| CDO1 B | pbCDO f | 254 | GGTAGCGTAGTGGATTCGGG | chr5: 115180192- | 142 |
| | pbCDO r | 255 | CTCGTCCTCCCTCCGAAAAC | 115180333 | |
| | mbCDO f | 256 | GTTTGTTTTATTTCGTGGGAG | chr5: 115179983- | 85 |
| | mbCDO r | 257 | CCAACTCCTTAACTCGCTCAA | 115180067 | |
| IRF4 B/C | pbIRF f | 258 | TCGCGGGAAACGGTTTTAGT | | |
| | pbIRF r | 259 | GCCCTTAACGACCCTCCG | | |
| | +pbIRF f | 260 | TTTTCGCGGGAAACGGTTTTAGT | chr6: 336451- | 100 |
| | +pbIRF r | 261 | GCGCCCTTAACGACCCTCCG | 336550 | |
| | mbIRF f | 262 | CGTTTTGTAAAGCGAAGTTT | | |
| | +mbIRF f | 263 | GGTTATACGTTTTGTAAAGCGAAGTTT | chr6: 336298- | 108 |
| | mbIRF r | 264 | AAACCAATCAATCACTAAACTACA | 336405 | |
| ID4 B | pbID Af | 265 | GGTTTTTGGGCGTCGTGTTA | chr6: 19945064- | 107 |
| | pbID Ar | 266 | AAATTCACTCTCCACCGCCC | 19945170 | |
| | pbID Bf | 267 | AGGCGAATAATGAAACGGAGGA | chr6: 19944950- | 134 |
| | pbID Br | 268 | TAACACGACGCCCAAAAACC | 19945083 | |
| | mbID f | 269 | ATTTTACGGATGGAGTGATG | | |
| | +mbID f | 270 | GGAATTTTACGGATGGAGTGATG | chr6: 19945031- | 118 |
| | mbID r | 271 | CTTATCCCGACTAAACTACTAAAAAA | 19945148 | |
| SCAND3, GPX5 | pbSCAND f | 272 | AATTCGTTTCGCGACGTGAG | | |
| | +pbSCAND f | 273 | TTAATTCGTTTCGCGACGTGAG | chr6: 28618249- | 111 |
| | pbSCAND r | 274 | ACACGCCTTAAAACCTACTCAT | 28618359 | |
| | mbSCAND f | 275 | CGTGAGGGAGAATTTAGGAG | chr6: 28618265- | 104 |
| | mbSCAND r | 276 | TAAAAAACACACGCCTTAAACCTA | 28618368 | |
| DDAH2 | pbDDAH f | 277 | TCGTTTAGCGAGCGTTGTTT | chr6: 31806112- | 99 |
| | pbDDAH r | 278 | GATCCGCCGTTACGCTATTC | 31806210 | |
| | mbDDAH f | 279 | TGTTAGAAATCGGTATCGTTTA | | |
| | mbDDAH r | 280 | TCTACGAAACGTTTACAACC | | |

TABLE 15-continued

| Gene | Probe | SEQ ID NO. | 5'-3' Primer Sequence (Bisulfite) | Chr: Location | PCR Product Length |
|---|---|---|---|---|---|
| | +mbDDAH f | 281 | TTTTTTGTTAGAAATCGGTATCGTTTA | chr6: 31806097-31806189 | 97 |
| | +mbDDAH r | 282 | AAAATCTACGAAACGTTTACAACC | | |
| COL11A2 | pbCOL f | 283 | TTTAGGGATCGCGTTCGGAG | chr6: 33269259-33269402 | 144 |
| | pbCOL r | 284 | AAACTCCTTTCCCCTCTCATAC | | |
| | mbCOL f | 285 | CGGAGT2TTTTAATCGGATAT | chr6: 33269274-33269415 | 142 |
| | mbCOL r | 286 | TCCCTTCTCTTTAAAACTCCT | | |
| NT5E B | mbNT5E f | 287 | GTCGGATTTTATTTTAATCGTG | | |
| | mbNT5E r | 288 | AAACAAAAAAATCTCAAAAACTAAAA | | |
| | +mbNT5E f | 289 | GTTGTCGGATTTTATTTTAATCGTG | chr6: 86215769-86215912 | 144 |
| | +mbNT5E r | 290 | CTTAAACAAAAAAATCTCAAAAACTAAAA | | |
| SIM1 B | pbSIM Af | 291 | GTTAGGGGCGAGGCGTTTAT | chr6: 101019614-101019695 | 82 |
| | pbSIM Ar | 292 | CGAAACCTAAACGCGCGAAA | | |
| | pbSIM Bf | 293 | AGGTTAATAGGTGGCGCGTT | chr6: 101019077-101019171 | 95 |
| | pbSIM Br | 294 | CCCGCAACTCCGCGATAATA | | |
| | pbSIM Cf | 295 | AGTCGTTTTTCGCGCGTTTA | | |
| | +pbSIM Cf | 296 | CGAGTCGTTTTTCGCGCGTTTA | chr6: 101019667-101019756 | 90 |
| | pbSIM Cr | 297 | GACCCGACACCCTAAACTCAT | | |
| | mbSIM Af | 298 | AGGCGTTTATTGGTTAATAGGG | chr6: 101019624-101019757 | 134 |
| | +mbSIM Ar | 299 | CGACCCGACACCCTAAACTCAT | | |
| | mbSIM Ar | 300 | ACCCGACACCCTAAACTCAT | | |
| | mbSIM Bf | 301 | TTTAATTTGGGTTTTAAGTTTGAGG | chr6: 101018944-101019075 | 132 |
| | mbSIM Br | 302 | ACGCTACTAAACCCCGCTTAT | | |
| RGS17 | RGS17 Af | 303 | GCGTTTAGGTAGCGACGC | chr6: 153493700-153493820 | 121 |
| | RGS17 Ar | 304 | ATACCCCGACGAAAACGAC | | |
| | RGS17 Bf | 305 | TTTGGGATTTGGTCGAGC | chr6: 153493620-153493730 | 111 |
| | RGS17 Br | 306 | AAAATTAAATCCCGCGTCG | | |
| CAPDS2 | CAPDS Af | 307 | CGTTTAGGTTTGTGGACGC | chr7: 121743823-121743951 | 129 |
| | CAPDS Ar | 308 | AAAAACGAAATCGCTAATACGC | | |
| MSC | MSC Af | 309 | TTTTTCGAATTTTTGCGC | | |
| | MSC Ar | 310 | AACACGCTCCGACTAACTTC | | |
| | +MSC Af | 311 | GGTTGTTTTTTCGAATTTTTGCGC | chr8: 72918397-72918531 | 135 |
| | +MSC Ar | 312 | TAAACACGCTCCGACTAACTTC | | |
| | MSC Bf | 313 | CGTTCGCGTTATTATTTGC | | |
| | MSC Br | 314 | CGCCCAATAACAACTCGT | | |
| | +MSC Bf | 315 | ATTATCGTTCGCGTTATTATTTGC | chr8: 72918698-72918852 | 155 |
| | +MSC Br | 316 | CCTCGCCCAATAACAACTCGT | | |
| SPAG6 | SPAG6 Af | 317 | GTCGAGTCGTCGTTACGATC | chr10: 22674453-22674529 | 77 |
| | SPAG6 Ar | 318 | CTACCCTCCTCGAACTCTACG | | |
| INA | INA Af | 319 | GTTTTCGGATGGGAAATTTTAG | | |
| | INA Ar | 320 | AAACCATCTACATCGAAATCGC | | |
| | +INA Af | 321 | GTGGTTTTCGGATGGGAAATTTTAG | chr10: 105026593-105026715 | 123 |
| | +INA Ar | 322 | AACAAAACCATCTACATCGAAATCGC | | |
| FLI | FLI Af | 323 | TTTTAGGAGTAAGTATTTTGTGTG | chr11: 128068870-128068981 | 112 |
| | FLI Ar | 324 | CCCTCTTCCTCCCCTACTAAT | | |
| ATP5G2 | ATP5G2 Af | 325 | TAGGTATATTTCGGTCGGC | chr12: 52357363-52357478 | 116 |
| | ATP5G2 Ar | 326 | AACTCGAAACCTCATCCG | | |
| USP44 | USP44 Af | 327 | ACGGGAGGGTAAATTTAGC | chr12: 94466977-94467090 | 114 |
| | USP44 Ar | 328 | TACCAAACAATTCGACGTTA | | |
| POU4F1 | POU4F1 Af | 329 | GCGTACGTCGGTTTATTC | | |
| | POU4F1 Ar | 330 | ACGCTCTACGCGATCAAA | | |
| | +POU4F1 Af | 331 | AAGTGCGTACGTCGGTTTATTC | chr13: 78075512-78075652 | 141 |
| | +POU4F1 Ar | 332 | GCGACGCTCTACGCGATCAAA | | |
| LHX1 | LHX Af | 333 | CGAGCGATTGTGGGGTTAGA | chr17: 32368543-32368624 | 82 |
| | LHX Ar | 334 | CAACTCGCGACCGCCTAAA | | |
| HINF1B | HINF Af | 335 | TTCGGGCGTTTATAGAGTTC | chr17: 33176898-33177017 | 120 |
| | HINF Ar | 336 | AAAATCAAAACGCGAACG | | |
| | HINF Bf | 337 | TAGCGTCGCGTTAGAAAGC | | |
| | HINF Br | 338 | ATCGCTCAAAACCTAACGAA | | |
| | +HINF Bf | 339 | TTTTAGCGTCGCGTTAGAAAGC | chr17: 33177225-33177341 | 117 |
| | +HINF Br | 340 | AAAAATCGCTCAAAACCTAACGAA | | |
| | HINF Cf | 341 | AGGTTTAGTTTCGAAATCGC | | |
| | HINF Cr | 342 | AACCGAACGATTCCCTAA | | |

TABLE 15-continued

| Gene | Probe | SEQ ID NO. | 5'-3' Primer Sequence (Bisulfite) | Chr: Location | PCR Product Length |
|---|---|---|---|---|---|
| | +HINF Cf | 343 | GTTAAGGTTTAGTTTCGAAATCGC | chr17: 33177654- | 120 |
| | +HINF Cr | 344 | CTAAAAAACCGAACGATTCCCTAA | 33177773 | |
| GALR1 | GALR1 Af | 345 | GAATTTTTGGAAAAGTCGGGA | | |
| | GALR1 Ar | 346 | CTCCTACAAAAAAAACTCCC | | |
| | +GALR1 Af | 347 | TTCGGAATTTTTGGAAAAGTCGGGA | chr18: 73090886- | 104 |
| | +GALR1 Ar | 348 | CGACTCCTACAAAAAAAACTCCC | 73090989 | |
| MAST1 | MAST1 Af | 349 | AGAAGGTGGTCGGTAAGC | | |
| | MAST1 Ar | 350 | ACGTAATTATAAAAAACACGCC | | |
| | +MAST1 Af | 351 | GGAGAAGGTGGTCGGTAAGC | chr19: 12839386- | 148 |
| | +MAST1 Ar | 352 | AAAACGTAATTATAAAAAACACGCC | 12839533 | |
| | MAST1 Bf | 353 | TAGTTTTTTGGAGGGAGAGG | chr19: 12839568- | 103 |
| | MAST1 Br | 354 | ATCCTCGTCCTCTTAAAAAC | 12839670 | |
| CPXM1 | CPXM1 Af | 355 | GTCGAGTTTGGGATTTTGGT | | |
| | CPXM1 Ar | 356 | AAACTCCTACTCGCCCTAACC | | |
| | +CPXM1 Af | 357 | GGGGTCGAGTTTGGGATTTTGGT | chr20: 2729097- | 118 |
| | +CPXM1 Ar | 358 | AAAAACTCCTACTCGCCCTAACC | 2729214 | |
| NEURL2 | NEURL2 Af | 359 | TCGAGTTGGATAAGGCGTAC | chr20: 43952304- | 142 |
| | NEURL2 Ar | 360 | CCGATAACACGACCGACATA | 43952445 | |
| | NEURL2 Bf | 361 | TGTATGTCGGTCGTGTTATC | chr20: 43952424- | 82 |
| | NEURL2 Br | 362 | TAAACGTACTACCTCCGACC | 43952505 | |
| ACVRL1 | ACVRL1f | 363 | GGATGTGGGAGGTTCGGTTCGGGTG | chr12:50587308- | 136 |
| | ACVRL1r | 364 | CCGCTCGCCCCTCGCTAAAACTACA | 50587443 | |
| AFF3 | AFF3f | 365 | GGCGCGAGGTAGTTTTAGTACGTAGTTTTT | chr2: 99542180- | 78 |
| | AFF3r | 366 | ATAACAACGTCGTCCTTTCCGCAAAACG | 99542257 | |
| AKR1B1 | AKR1B1f | 367 | GGGGATTTTGTAAGTTCGCGCGTGGTTT | chr7: 133794143- | 108 |
| | AKR1B1r | 368 | ACACTCTCCGCGCGACCTATATTAACGA | 133794250 | |
| | AKR1B1R_f | 369 | GGAGACGGTTTGTTATGGTTGTTCGTT | chr15: 43266838- | 122 |
| | AKR1B1R_r | 370 | ACGCCCTTTCTACCGACCTCACGAACTA | 43266959 | |
| ALDOC | ALDOCf | 371 | TTTTTCGGGGGCGTGGTTTGTATGTTT | chr17: 23928071- | 123 |
| | ALDOCr | 372 | TACCCTAACGAAACGCTCACTCCACCTCG | 23928193 | |
| ALOX5 | ALOX5f | 373 | TTTTGCGGTTAGGTGAAGGCGTAGAGGT | chr10: 45234654- | 106 |
| | ALOX5r | 374 | GACCGAATACCCCGCTTTCTCTCTCGAC | 45234759 | |
| | ALOX5R_f | 375 | GAGGTCGAGAGAGAAAGCGGGGTATTCG | chr10: 45234729- | 110 |
| | ALOX5R_r | 376 | AACGCTCTCAACCCAACCCCTAAACTCA | 45234838 | |
| ALX1 | ALX1f | 377 | AGGATAGTAGCGGTGAGTCGTTAGCGTT | chr12: 84198385- | 117 |
| | ALX1r | 378 | CGCTCCCACTTTTCTCCTTTCTCCCTCC | 84198501 | |
| ALX4 | ALX4f | 379 | TTTTGATAAAGTGGGGAGGGCGTAGGGG | chr11: 44289270- | 106 |
| | ALX4r | 380 | ACACTCTCAAATACCCGTCGCGCTCTAT | 44289375 | |
| C1orf230 | C1orf230f | 381 | TTTTGATAAAGTGGGGAGGGCGTAGGGG | chr1: 149960830- | 92 |
| | C1orf230r | 382 | ACACTCTCAAATACCCGTCGCGCTCTAT | 149960921 | |
| | C1orf230R_f | 383 | AGCGTAGCGTAGTTGGAGTAGTTGCGAA | chr1: 149960685- | 121 |
| | C1orf230R_r | 384 | CGACGACTCTCTTCCCAATCTAAAACCCCA | 149960805 | |
| C6orf186 | C6orf186f | 385 | CGGAGTTTAGAAGGGCGTTCGGTTACGG | chr6: 110785585- | 116 |
| | C6orf186r | 386 | CTCCACGAATCGCATCTTTCAATACCCA | 110785700 | |
| C17orf64 | C17orf64f | 387 | AAAGGTGGTTCGAGTGAGGAAATTGCGG | chr17: 55853711- | 79 |
| | C17orf64r | 388 | GCGTCCCTAAACGACACACGACGAAATC | 55853789 | |
| | C17orf64R_f | 389 | GTCGACGGCGGTTTTATCGTATTGTCGC | chr17: 55853578- | 112 |
| | C17orf64R_r | 390 | CCTTCTCCCGAACCTTCCTTCGTATCCT | 55853689 | |
| C19orf41 | C19orf41f | 391 | TTAGAGGTATGGCGGGGTTTTTGTGACG | chr19: 55358254- | 95 |
| | C19orf41r | 392 | AATACTCCCTAAACCTCCTAACCGCGCC | 55358348 | |
| CCDC67 | CCDC67f | 393 | GAGGTTTAATTGTTTCGTTGGTCGC | chr11: 92703424- | 123 |
| | CCDC67r | 394 | ACGCAAAACCGCGTATATCACCT | 92703546 | |
| CCDC8 | CCDC8f | 395 | GGTTTTAGGGACGCGGTTGGAATTTGGG | chr19: 51608460- | 89 |
| | CCDC8r | 396 | CCCAACGCCTCGACCATATTAAATAACTT | 51608548 | |
| CD38 | CD38f | 397 | GCGATTAAGGCGTATCGGTGGGTATTGC | chr4: 15389377- | 125 |
| | CD38r | 398 | AACACCACCCGACGAACTCTCGACTAAC | 15389501 | |

TABLE 15-continued

| Gene | Probe | SEQ ID NO. | 5'-3' Primer Sequence (Bisulfite) | Chr: Location | PCR Product Length |
|---|---|---|---|---|---|
| CD8A | CD8Af | 399 | TAGGACGTTGTTTGGTTCGAAGTTCGGG | chr2: 86871471-86871569 | 99 |
| | CD8Ar | 400 | CTCCGAACCGACCGAAAAACGCAACTTT | | |
| CDH23 | CDH23f | 401 | GGCGGGGTATTGTTTTGTTTC | chr10: 72826313-72826423 | 111 |
| | CDH23r | 402 | TCTACCGATATCATAACACCGACT | | |
| CDK5R2 | CDK5R2f | 403 | AAAGGTAGAGGGAAGGAGAGTTGTTTTT | chr2: 219532251-219532354 | 104 |
| | CDK5R2r | 404 | ACTCCTACCTCCTCCGAATCCTAAAACCT | | |
| CHST2 | CHST2f | 405 | CGGAATGAAGGTGTTTCGTAGGAAGGCG | chr3: 144322486-144322636 | 151 |
| | CHST2r | 406 | GCTACGACACCCAACGACCCATCGAAA | | |
| CLCN1 | CLCN1f | 407 | AATGATTTTGTTGGGTTCGGTGGAGCGG | chr7: 142752740-142752852 | 113 |
| | CLCN1r | 408 | CCGACAACTTCCGCGCCATCTCTTAAAC | | |
| | CLCN1R_f | 409 | TTGTGTTTTGAGCGTAGGTTGCGCGTAG | chr7: 142752798-142752874 | 77 |
| | CLCN1R_r | 410 | GCCTTCCCGTCGTAAAACAACTCCGACA | | |
| COL16Af | COL16A1f | 411 | GTTTTAGGGGGTTGGGGGTTTGTTAGGGA | chr1: 31942237-31942382 | 146 |
| | COL16A1r | 412 | AACCCGAAACGAAACTATACACCCCGCA | | |
| CPNE8 | CPNE8f | 413 | TCGATGTTCGTAGTGTTGTTGTAGCGGT | chr12: 37585569-37585689 | 121 |
| | CPNE8r | 414 | CCATCCCCGCCTAACGAAAACTAACCCT | | |
| DIO3 | DIO3f | 415 | CGTTTCGAGAAGAAGTTTCGCGGTTGGT | chr14: 101095917-101096005 | 89 |
| | DIO3r | 416 | ATCTAAACCCAAATCGAAAACCGCCGCC | | |
| DNM3 | DNM3f | 417 | TTGGAGTTGTCGTAGATCGTCGTGGTGG | chr1: 170077504-170077626 | 123 |
| | DNM3r | 418 | AAATCGCCCCACTACCGCATCCTTACTC | | |
| | DNM3R_f | 419 | GCGGTTAGGTGTGGTAAAGTAGTTGGCG | chr1: 170077283-170077405 | 123 |
| | DNM3R_r | 420 | GCGCACAACCAACCTATAAACTCCGACG | | |
| DUOX1 | DUOX1f | 421 | GGGATTTGTGAAGGCGGATTTG | chr15: 43209229-43209307 | 79 |
| | DUOX1r | 422 | AATATTCCGTCGATACCGAAAACCCGA | | |
| EMX1 | EMX1f | 423 | CGGTTGGAGCGCGTTTTCGAGAAGAAT | chr2: 73005041-73005163 | 123 |
| | EMX1r | 424 | AACGCAAAACAAACCGCGACCGAAAATA | | |
| EMX2OS | EMX2OSf | 425 | AGGAGAAGTCGTAGCGGGCGTC | chr10: 119291932-119292032 | 101 |
| | EMX2OSr | 426 | GACTAAACCTTCTACCGCCCACCG | | |
| ESPN | ESPNf | 427 | TAGTTGCGATGGGTGGGAAGTTACGTT | chr1: 6430246-6430357 | 112 |
| | ESPNr | 428 | AAAACCATCGCCATCCACGAAAACGACA | | |
| EVX1 | EVX1f | 429 | AGGAGGATGATAGTTTAGAAAGAAGAGGGT | chr7: 27248900-27249019 | 120 |
| | EVX1r | 430 | CGCGACCGCGACGATAACGATAAAAACT | | |
| FABP5 | FABP5f | 431 | GAAACGTGTAGGCGTCGGCGTTTATGAG | chr8: 82355078-82355157 | 80 |
| | FABP5r | 432 | CGACCTCTCGAACGCCTCCTACAAACAA | | |
| FBRSL1 | FBRSL1f | 433 | GTGGAGGAGGAAGTTCGTTTC | chr12: 131575948-131576052 | 105 |
| | FBRSL1r | 434 | AACTACTACCAAACACGAAACGCA | | |
| FLJ41350 | FLJf | 435 | GGTTAGAGTCGGTTGCGTAGTTT | chr10: 102979731-102979855 | 125 |
| | FLJr | 436 | TTTTTGTTAGGCGAAGTATAGAGAGCG | | |
| FOXG1 | FOXG1f | 437 | TTTTTCGATTGGTCGACGGCGAGAGAG | chr14: 28305617-28305740 | 124 |
| | FOXG1r | 438 | TTTCCGAACTACAAACGCACACTAAAAC | | |
| FOXL2 | FOXL2f | 439 | GATTCGTATGGGTTTTATCGAGTTTC | chr3: 140148670-140148764 | 95 |
| | FOXL2r | 440 | ACTTAAAAATAAACTCGCCCGTACG | | |
| FZD2 | FZD2f | 441 | TCGTTGGTGAAGGTGTAGTGTTCGTTCG | chr17: 39990814-39990938 | 125 |
| | FZD2r | 442 | TAACGCGCGCGCTCACAAATAAAACGAC | | |
| | FZD2R_f | 443 | TTTTTAGTGGTTCGAGCGTTTGCGTTGC | chr17: 39990969-39991059 | 91 |
| | FZD2R_r | 444 | TCCGTCCTCGAAATAATTCTAACCGACGC | | |
| HIF3A | HIF3Af | 445 | CGTGGTATAGTTAATCGCGCGGCGT | chr19: 51492066-51492190 | 125 |
| | HIF3Ar | 446 | TACAACCCCAACGCCATAACTCGCCAAT | | |
| HIVEP3 | HIVEP3f | 447 | TGTCGTCGTCGTCGGGGTTTTGTTATTT | chr1: 41901039-41901114 | 76 |
| | HIVEP3r | 448 | ACGACGATAACTCCCGCTAAACGAA | | |
| | HIVEP3R_f | 449 | GAACGAGGATTTGCGTTTTTGGATCGC | chr1: 41901096-41901175 | 80 |
| | HIVEP3R_r | 450 | CCTAAACTCCTCTACATATTCCTCTACCT | | |
| HLA-F | HLA-Ff | 451 | GAATGGTTGCGATATGGGGTTCGACGG | chr6: 946778-946902 | 125 |
| | HLA-Fr | 452 | CCACGATATCCGCCGCGATCCAAAAC | | |

TABLE 15-continued

| Gene | Probe | SEQ ID NO. | 5'-3' Primer Sequence (Bisulfite) | Chr: Location | PCR Product Length |
|---|---|---|---|---|---|
| HOTAIR | HOTAIRf | 453 | TAAGGGTCGGTTGTTGTTTTTTTC | chr12: 52645919-52646034 | 116 |
| | HOTAIRr | 454 | ACCGACGCCTTCCTTATAAAATACG | | |
| HOXA10 | HOXA10f | 455 | TGTGGGATAATTTGGCGAAGGGAGTAGA | chr7: 27180403-27180526 | 124 |
| | HOXA10r | 456 | AACTCGAAATTAACTACGAACGCCCGCC | | |
| HOXD11 | HOXD11f | 457 | GGCGGGGGTAGTTTTTGTATTAAGGCGA | chr2: 176680987-176681111 | 125 |
| | HOXD11r | 458 | CCTACGCTACTACTCTTCTCGACCCCCG | | |
| HOXD8 | HOXD8f | 459 | CGTTTCGTTCGTCGGTCGTAGCGATTG | chr2: 176702636-176702749 | 114 |
| | HOXD8r | 460 | CCGACGAAACATTTTCGCACCACAACAC | | |
| | HOXD8R_f | 461 | CGCGGTTTCGGGGTATACGGAGTTTTTG | chr2: 176702549-176702668 | 120 |
| | HOXD8R_r | 462 | GCAATTCAATCGCTACGACCGACGAACG | | |
| HSPA12B | HSPA12Bf | 463 | CGTCGTAGCGGGTACGGTTAACGAGTTG | chr20: 3661361-3661485 | 125 |
| | HSPA12Br | 464 | TTTCTCCACTCGAAACGCCCGACAACC | | |
| ISL1 | ISL1f | 465 | CGGGGGAGAACGGTTTGAGTTTCGAGTA | chr5: 50714776-50714885 | 110 |
| | ISL1r | 466 | TCATATTTCAACCTCGCCGCCGCTAAAC | | |
| Intergenic1 | Int1f | 467 | AGTAGGGATGGTCGTTCGTTGTTCGGTG | chr11: 68379573-68379679 | 107 |
| | Int1r | 468 | GACAAACGACCGAAAATACTCGCGCAAC | | |
| | Int1R_f | 469 | TTTTACGGTCGGGGCGATAGTTGAAGGT | chr11: 68379395-68379493 | 99 |
| | Int1R_r | 470 | TCACGCCAATACCCGCTAATCCCTCCTA | | |
| Intergenic2 | Int2f | 471 | GGGGATGGATAATTTTTAGGCGTTAAC | chr17: 69460223-69460339 | 117 |
| | Int2r | 472 | TAACCTCGTCTTTATCCCCGCG | | |
| Intergenic3 | Int3f | 473 | AGTGTGTAGTCGTTTGTGGGTGAGGAGTT | chr8: 95315865-95315994 | 130 |
| | Int3r | 474 | CACCGCGAAAAACGCCCACAATCTTACC | | |
| | Int3R_f | 475 | CGCGGGGGAGTTTATTTTTGAGGATTCGG | chr8: 95315775-95315892 | 118 |
| | Int3R_r | 476 | ACTCCTCACCCACAAACGACTACACACT | | |
| Intergenic4 | Int4f | 477 | TAGTATTTGTACGGAGTTTTTCGGCGGTC | chr5: 43054172-43054263 | 92 |
| | Int4r | 478 | TACGACGCAACCAACGATACTATCACCAA | | |
| Intergenic5 | Int5f | 479 | TAGTGATTGGTTATTTGGGCGCGGGGC | chr10: 43138416-43138530 | 115 |
| | Int5r | 480 | AAACGACATCCATCATCTCCCTCGACCC | | |
| Intergenic6 | Int6f | 481 | AGGTCGCGTTTTGGTCGTGC | chr3: 14827613-14827688 | 76 |
| | Int6r | 482 | ACTTAAAAATAAACTCGCCCGTACG | | |
| Intergenic7 | Int7f | 483 | ATTTTACGTAGGGTGGGGTTGAGGGCGT | chr12: 52897799-52897910 | 112 |
| | Int7r | 484 | ATCCTAACCGTCCCGCCTCAAAACCGTA | | |
| Intergenic8 | Int8f | 485 | CGTCGTAGTATTTGGCGGCGCGTTTC | chr2: 236737778-236737883 | 106 |
| | Int8r | 486 | AACGTACCTAATCCCCAAACCCACTCCT | | |
| Intergenic9 | Int9f | 487 | TCGTTGTGCGCGTTTCGTTTGTTGGATTA | chr6: 778755-778846 | 92 |
| | Int9r | 488 | TCGATAATATCTCCGTCGCCTCCGCAAA | | |
| Intergenic10 | Int10f | 489 | GCGCGTTTAATCGTGGGATTTTTGGGAG | chr2: 174899379-174899494 | 116 |
| | Int10r | 490 | CAAATTCGCGACACCCTACCCCAACAC | | |
| | Int10R_f | 491 | GGGTGTCGCGAATTTGGGTA | chr2: 174899479-174899602 | 124 |
| | Int10R_r | 492 | CTAAACCTCTCCCCTCCCAAATTTACCT | | |
| Intergenic12 | Int12f | 493 | ATCGAGTTTTTAGCGGTTTTTGGGCGG | chr1: 119344866-119344974 | 109 |
| | Int12r | 494 | ACTAACATCGCGCACTTAAATCTTTCCG | | |
| Intergenic13 | Int13f | 495 | GGTAGCGGCGGGTAAAAAGTC | chr7: 64675119-64675225 | 107 |
| | Int13r | 496 | TACAACTTTTTACCTCCGCCGC | | |
| Intergenic14 | Int14f | 497 | CGTCGATTTGCGGAATTTCGTCGTCGTT | chr1: 238227938-238228045 | 108 |
| | Int14r | 498 | ACATCCGCGTAAACTCGCCCTTTAACAC | | |
| | Int14R_f | 499 | TTTCGGGATTAGGGTTTCGGAGGGTGTC | chr1: 238227822-238227913 | 92 |
| | Int14R_r | 500 | CGTATCGATCCGTCCCTCCCGCTTAAAA | | |

TABLE 15-continued

| Gene | Probe | SEQ ID NO. | 5'-3' Primer Sequence (Bisulfite) | Chr: Location | PCR Product Length |
|---|---|---|---|---|---|
| Intergenic15 | Int15f | 501 | CGGTTTTGGTGGTAGTTTTGGTAATC | chr19: 48895723-48895802 | 80 |
| | Int15r | 502 | AAAACCTCCCGAACGACGAAATAATCCA | | |
| | Int15R_f | 503 | GTAGGCGGTCGGAACGTGAAC | chr19: 48895536-48895660 | 125 |
| | Int15R_r | 504 | CGATAAAAACTACAATAACTCGACAACCA | | |
| Intergenic16 | Int16f | 505 | GTTGTGAGGGTTTTCGGCGGTATC | chr1: 54713046-54713165 | 120 |
| | Int16r | 506 | CATAACAACGCGCGACCCCTA | | |
| Intergenic17 | Int17f | 507 | TGATTATAAATTAGGGGGTTTGGTCGTCG | chr12: 61311832-61311945 | 114 |
| | Int17r | 508 | AAACCCTCCACCCTCGCAATACTACTCC | | |
| Intergenic18 | Int18f | 509 | TGTAGGAGATAATGGGAGTGAAGAGGGA | chr6: 4971256-4971338 | 83 |
| | Int18r | 510 | TTCCACGAAACGCGCGACTTCCTAACTA | | |
| | Int18R_f | 511 | GTTGAGTTAGGAGAGGTCGATAGC | chr6: 4971467-4971570 | 104 |
| | Int18R_r | 512 | CCCGAAAACAACGACTATCGAAATCCAA | | |
| Intergenic19 | Int19f | 513 | ATAAGGTTTGGTGGAAGCGTAGGAGCGT | chr6: 3177175-3177289 | 115 |
| | Int19r | 514 | ACGCCGAATAAAAATCCCGCAACCACAA | | |
| Intergenic20 | Int20f | 515 | GGAGGGGAGGAGATAGCGTTATTTAGGG | chr10: 118912740-118912842 | 103 |
| | Int20r | 516 | AAACAAAACCCGAAACCCCACCTACACC | | |
| Intergenic21 | Int21f | 517 | GCGTGGTAGTTGAGGATGTAGACGTGGT | chr16: 45381613-45381736 | 124 |
| | Int21r | 518 | TCCGAACTACTTAAAAATCCCCGCCGCC | | |
| Intergenic22 | Int22f | 519 | TCGTTGGTTGTGATTTTTATGCGGGCGT | chr8: 68037259-68037357 | 99 |
| | Int22r | 520 | ACCTCTCCGATAAACCAAATCCTCCGCC | | |
| | Int22R_f | 521 | CGGGTGAGGTTTGTGGTTAATTTCGCGT | chr8: 68037556-68037675 | 120 |
| | Int22R_r | 522 | CTCAACCAAACTACAACGTTCCCGCCTC | | |
| Intergenic23 | Int23f | 523 | AATGGAGGCGTAGATTAACGAGCGGTGT | chr5: 42987147-42987254 | 108 |
| | Int23r | 524 | ATCCTTAACAACCCCGCCGACTAACGTC | | |
| | Int23R_f | 525 | ACGGGTACGGAGAAACGTCGGATTTAGT | chr5: 42987852-42987946 | 95 |
| | Int23R_r | 526 | TCCCCGCGACACTCTACCTATAACGTCC | | |
| KCNH8 | KCNH8f | 527 | CGTTTGGCGGGTATTGTTGTTC | chr3: 19164879-19164971 | 93 |
| | KCNH8r | 528 | CCCGACGCAAACTCCCTCTC | | |
| KCNJ2 | KCNJ2f | 529 | GAAGTTGTTTTTTAGGGGTTTGCGC | chr17: 65676355-65676440 | 86 |
| | KCNJ2r | 530 | ACTCAAATCTACCCTCGCTTCAACG | | |
| KCKN4 | KCKN4f | 531 | GCGCGGGGGTATTTTGGAGGGTTAGTTA | chr11: 63816449-63816549 | 101 |
| | KCKN4r | 532 | TCCCTACTCGCCCGCTACGACTATAACA | | |
| KCNK17 | KCNK17f | 533 | CGGATTTGTTTTCGGGAGTCGTTCGGG | chr6: 39390031-39390150 | 120 |
| | KCNK17r | 534 | AACTAAACGCCTAACCCTTCCCTCCCAC | | |
| KIAA1751 | KIAAf | 535 | TTCGTTTTGTTTTTCGGTTGGAGCGGGT | chr1: 1925171-1925288 | 118 |
| | KIAAr | 536 | TATAACCTAACCCTTCAACCGCGCCTCG | | |
| | KIAA1751R_f | 537 | AGGCGGCGGTTTTTGGCGATTGTTTTC | chr1: 1925065-1925140 | 76 |
| | KIAA1751R_r | 538 | TTCCGTTACCATAAAACTACCCGCCCC | | |
| LASS1 | LASS1f | 539 | GATTTCGCGTATCGTCGTGTC | chr19: 18868171-18868273 | 103 |
| | LASS1r | 540 | TAATATCCCCCGTACCCCCG | | |
| LOC255167 | LOCf | 541 | TTTCGATAATAGCGTTTTTGCGGCGTGG | chr5: 6636474-6636619 | 146 |
| | LOCr | 542 | CAAAAACACGCGACCTACGCCCTCCTAA | | |
| LRRC4 | LRRC4f | 543 | CGAGTCGGAGTGAGCGTTAAGTGAGGGG | chr7: 127459680-127459780 | 101 |
| | LRRC4r | 544 | CCTATCAACGACCACCCAACTACTCCCT | | |
| MIR155HG | MIR155HGf | 545 | TCGGGTTTAGCGTCGTTTGTAGTTTCGG | chr21: 25856335-25856430 | 96 |
| | MIR155HGr | 546 | AAAAACGTCTCCTTAATTCCCCGCGCTT | | |
| NEXN | NEXNf | 547 | GCGGTTGGAGTAGAAGTGTTAGCGGTTAGA | chr1: 78126913-78127036 | 124 |
| | NEXNr | 548 | TCACCCTACAAAAACCGATAACCGACGA | | |

TABLE 15-continued

| Gene | Probe | SEQ ID NO. | 5'-3' Primer Sequence (Bisulfite) | Chr: Location | PCR Product Length |
|---|---|---|---|---|---|
| NKX2-1 | NKX2-1f | 549 | AGTTGGTTATAGGCGGCGAATTGGGTTT | chr14: 36057307- | 91 |
| | NKX2-1r | 550 | TCAACACCCCCTCTCCTAACCTCTCCAA | 36057397 | |
| NKX6-2 | NXX6-2f | 551 | CGGGGAAGAGTTTCGGTTCGCGTTTTAG | chr10: 134449988- | 123 |
| | NXX6-2r | 552 | CCCTCCTATAACCCCGACCTACCCGAAA | 134450110 | |
| | NKX6-2R_f | 553 | GCGCGGTAGGTGTTTTTCGGGTTGTAAA | chr10: 1344419796- | 97 |
| | NKX6-2R_r | 554 | ACCTTTACCTAACTACACTCCCATCCAA | 134449892 | |
| NOTUM | NOTUMf | 555 | AGAGTAGGTCGTGGGGGATTC | chr17: 77512836- | 87 |
| | NOTUMr | 556 | CGCGCTAACCGCGATAAAAAC | 77512922 | |
| NRN1 | NRN1f | 557 | AGGAGCGGGAGAGGGAAAAATAGTTAAG | chr6: 5952635- | 125 |
| | NRN1r | 558 | ACTACGCCCAAAACTCAACTACTAAAT | 5952759 | |
| PLTP | PLTPf | 559 | TGGGAACGGGATAGGGACGCGTTTTAAT | chr20: 43974093- | 92 |
| | PLTPr | 560 | GAATCCCCTAAACTACCCGCCATCCCAC | 43974184 | |
| | PLTPR_f | 561 | TGTACGCGTATTTTTGGAGGGTGGTTTGC | chr20: 43973871- | 80 |
| | PLTPR_r | 562 | CGATCTAATCGACCACCTCCTCTCCTCC | 43973950 | |
| PRDM13 | PRDM13f | 563 | AAGTTTCGTCGAGTTGGGGTCGTTGGTT | chr6: 100168753- | 92 |
| | PRDM13r | 564 | GACCCTTCCCGACAACCATCTCGAACA | 100168844 | |
| PRDM15 | PRDM15f | 565 | GAAAATTGCGCGGTTGGGTTAGTAGGGG | chr21: 42110148- | 112 |
| | PRDM15r | 566 | ACCTACAAATACCGTCCCCACCCGAAAC | 42110259 | |
| PTGDR | TGDRf | 567 | AAGAGGGGTGTGATTCGCGAGTTTAGAT | chr14: 51804089- | 110 |
| | TGDRr | 568 | CCGCGCGCGACTCGAACGAAAAA | 51804198 | |
| RECK | RECKf | 569 | AAGGGTGCGATGTTTTCGTTTAGGATCG | chr9: 36027398- | 88 |
| | RECKr | 570 | TAACTAACTAAAACCGCGATAAAACGACT | 36027485 | |
| RTN4RL1 | RTN4f | 571 | TGGTAATCGCGTAGGTGTGTGATAGGGC | chr17: 1827825- | 107 |
| | RTN4r | 572 | AAAATACAAAATACGCCCCCGACCCCGA | 1827931 | |
| | RTN4RL1R_f | 573 | TGAGGAGAGATTCGGAGTAGTTAGTAGA | chr17: 1827743- | 109 |
| | RTN4RL1R_r | 574 | CCCTATCACACACCTACGCGATTACCAA | 1827851 | |
| SFRP5 | SFRP5f | 575 | TTTCGAAAAGTTGGTAGTCGGCGGTTGG | chr4: 154929548- | 123 |
| | SFRP5r | 576 | CATTCTACTCCCCCGAATCGAAACCCCC | 154929670 | |
| | SFRP5R_f | 577 | AAGAGGAAGAGTTCGCGCGTCGAGTTTA | chr4: 154929355- | 100 |
| | SFRP5R_r | 578 | GAAATCGCGCGCCCACGATACTACAAAA | 154929454 | |
| SHF | SHFf | 579 | TTATTAGTAGGCGGCGTCGGGGGTT | chr15: 43266978- | 150 |
| | SHFr | 580 | CGAAAACCCCTACTCCGAAAAATCGTCCG | 43267127 | |
| | SHFR_f | 581 | GTTGAGATATCGAGGGGTTCGGGTTAGG | chr15: 43266838- | 122 |
| | SHFR_r | 582 | CGCCAACAACGATAAAATAAATACCGCGCC | 43266959 | |
| SHOX2 | SHOX2f | 583 | CGTTTGTTCGATCGGGTCGTACGAGTAT | chr3: 159304063- | 100 |
| | SHOX2r | 584 | TTTCCGCCTCCTACCTTCTAACCCGACT | 159304162 | |
| SNCA | SNCAf | 585 | GGTTGGGGAGTGGGAGGTAAATTCGTT | chr4: 90977105- | 117 |
| | SNCAr | 586 | CTAAACGCTCCCTCACGCCTTACCTTCA | 90977221 | |
| SNX32 | SNX32f | 587 | TTGAGGGAAACGCGGTGGGAATCGTTTT | chr11: 65357939- | 119 |
| | SNX32r | 588 | CCGTAACTCGCCCGAAAAACTAACCGAA | 65358057 | |
| SP9 | SP9f | 589 | TGATTGGTTGCGGGGTAGTTTC | chr2: 174907826- | 86 |
| | SP9r | 590 | ACACCCGCTTTAAAATACCGCTAA | 174907911 | |
| STK33 | STK33f | 591 | GCGTTTCGGGTCGTTCGTTTTATTTCGC | chr11: 8572140- | 123 |
| | STK33r | 592 | CGACAACCTACGCCGAATATACGCACCT | 8572262 | |
| SYNGR3 | SYNGR3f | 593 | GAAGGGATGAGGTTGAGGTTGGAGGTCG | chr16: 1981075- | 121 |
| | SYNGR3r | 594 | ACCTCCTACCCACCAATTCCGAAAACAA | 1981195 | |
| T | Tf | 595 | TTACGGAGTTTTAGGCGGCGTTAC | chr6: 166501979- | 121 |
| | Tr | 596 | CATTTCCCTCTCTACGCGCGAAC | 166502099 | |
| THBS2 | THBS2f | 597 | CGTAGGTTTTGTTGGAGCGAGAGATCGG | chr6: 169395805- | 94 |
| | THBS2r | 598 | ACATATAAAACCGCGCTACCCGAAAACCG | 169395898 | |
| TLX1NB | TLX1NBf | 599 | TGAAAGGGAGAGGGGAATGTTATTGTT | chr10: 102871413- | 106 |
| | TLX1NBr | 600 | AATATTCTCGCAAACCCACCGCCAAACC | 102871518 | |
| TMEM22 | TMEM22f | 601 | AAAGAGATTCGTGTTGCGGCGGATGAAG | chr3: 138021575- | 117 |
| | TMEM22r | 602 | GATCAACACTCGAACCCGAACTTTCCGC | 138021691 | |

TABLE 15-continued

| Gene | Probe | SEQ ID NO. | 5'-3' Primer Sequence (Bisulfite) | Chr: Location | PCR Product Length |
|---|---|---|---|---|---|
| TNFRSF10D | TNFRSf | 603 | AAGGGAGGAGGGTGGATCGAAAGCGTTA | chr8: 23077397-23077475 | 79 |
| | TNIFRSr | 604 | CGAAAACCTTTACACGCGCACAAACTACG | | |
| TXNRD1 | TXNDR1f | 605 | TATGGGTTGCGTCGAGGGTAAGGTAGTG | chr12: 103133710-103133788 | 79 |
| | TXNDR1r | 606 | ACCATCGCCGTTCTTACCTTTCGTCTACA | | |
| VSTM2B | VSTM2Bf | 607 | TTTTTAATTCGGTTCGGCGTTGATTTGT | chr19: 34711435-34711559 | 125 |
| | VSTM2Br | 608 | ACAACCGCGCGCTCCCGATAC | | |
| ZFPM2 | ZFPM2f | 609 | TAGCGCGGAAGTTGTGAGTTTAAGGCG | chr8: 106401146-106401241 | 96 |
| | ZFPM2r | 610 | TCCTCTAAACACCATCGAAACCCCCGAAC | | |
| ZNF280B | ZNF280Bf | 611 | AGTGGCGTTCGTTGAGATTAGGGAAGGG | chr22: 21192757-21192877 | 121 |
| | ZNF280Br | 612 | ACCGTACGCTACCGAAACGACCTTTACA | | |
| LOC105378683 | LOC105 Af | 613 | GTTTGTAATTGGTATGAGCGGC | chr1: 43023566-43023673 | 108 |
| | LOC105 Ar | 614 | ATAACGAAACGACGCCTC | | |
| | LOC105 Bf | 615 | GTAATTGGTATGAGCGGCGT | chr1: 43023570-43023660 | 91 |
| | LOC105 Br | 616 | GCCTCCGCGAAATAAAACCAT | | |
| | LOC105 Cf | 617 | AGTTAGAGTGGGTTAGGGGAT | chr1: 43023464-43023613 | 150 |
| | LOC105 Cr | 618 | ACGCGTAACACAAACACGAC | | |
| NPHS2 | NPHS2 Af | 619 | GGGGGATTTTAAAGATCGTC | chr1: 177811721-177811842 | 122 |
| | NPHS2 Ar | 620 | GACGAACGCAATCCACAA | | |
| | NPHS2 Bf | 621 | TGGTGGAGTTGTGGATTGCG | chr1: 177811817-177811891 | 75 |
| | NPHS2 Br | 622 | TCCCACCCAAACCTCTCTCT | | |
| NR5A2 | NR5A2 Af | 623 | GGTGCGTTTACGGGTTTC | chr1: 198278389-198278538 | 150 |
| | NR5A2 Ar | 624 | ACCTAATCCGATATTTCCGA | | |
| | NR5A2 Bf | 625 | GGTAGGGTTTCGGTTGCGTA | chr1: 198278432-198278527 | 139 |
| | +NR5A2 Br | 626 | TATTTCCCGAAAACTCCACATCCA | | |
| | NR5A2 Br | 627 | TCCCGAAAACTCCACATCCA | | |
| PAX6 | PAX6 Af | 628 | ATTTGGATGTTTCGCGTTTC | | |
| | PAX6 Ar | 629 | TATCGCTACGACCCGACTAA | | |
| | +PAX6 Af | 630 | GTTAATTTGGATGTTTCGCGTTTC | chr11: 31783206-31783322 | 117 |
| | +PAX6 Ar | 631 | GTTTATCGCTACGACCCGACTAA | | |
| | PAX6 Bf | 632 | AGGGGAGTCGCGTTTTTAGG | chr11: 31782520-31782652 | 133 |
| | PAX6 Br | 633 | TCCCGACCGAAACCCAAATC | | |
| KCNE3 | KCNE3 Af | 634 | GAATAACGGCGTAAGTTTTTAC | chr11: 73855818-73855915 | 98 |
| | KCNE3 Ar | 635 | ATCCTCCCGAACGCAATA | | |
| | KCNE3 Bf | 636 | TTGTACGTTTGTGGGTGTGGA | chr11: 73855765-73855914 | 150 |
| | KCNE3 Br | 637 | TCCTCCCGAACGCAATAATCG | | |
| KCNA6 | KCNA6 Af | 638 | TTAACGGTTAGGTTAGATCGC | chr12: 4789322-4789421 | 100 |
| | KCNA6 Ar | 639 | CAATCTCTAAAACGCGACAC | | |
| | KCNA6 Bf | 640 | CGGGTGTCGCGTTTTAGAGAT | chr12: 4789399-4789482 | 84 |
| | KCNA6 Br | 641 | TTCTCCGATCTCATACCCCCT | | |
| TMEM132C | TMEM Af | 642 | GAGAAAAGTTGTTTCGGTC | | |
| | TMEM Ar | 643 | GCTACGTCTCTACTATCCGA | | |
| | +TMEM Af | 644 | CGGGAGAAAAGTTGTTTCGGTC | chr12: 127317663-127317786 | 124 |
| | +TMEM Ar | 645 | CCGCTACGTCTCTACTATCCGA | | |
| | TMEM Bf | 646 | TTCGGGGTGAGGGTAGTC | | |
| | TMEM Br | 647 | CCGACGCCCAACTAAAAA | | |
| | +TMEM Bf | 648 | GAGTTCGGGGTGAGGGTAGTC | chr12: 127318043-127318179 | 137 |
| | +TMEM Br | 649 | GAATCCCGACGCCCAACTAAAAA | | |
| | TMEM Cf | 650 | TTTTCGGGTTACGGGTCGTT | chr12: 127317330-127317424 | 95 |
| | TMEM Cr | 651 | ACGACTCCTCCGAAAATCCG | | |
| PDX1 | PDX1 Af | 652 | GTCGATTTTTGTTTTGAGC | chr13: 27390195-27390280 | 86 |
| | PDX1 Ar | 653 | TAAAAATAATCTACCGAATCGC | | |
| | PDX1 Bf | 654 | GGCGTTAGCGGGGATTTAGA | chr13: 27389563-27389694 | 132 |
| | PDX1 Br | 655 | CGCATCAAACGAAACCCTCC | | |
| | PDX1exp Af | 656 | CGGGAAGGTGTTCGTTTAATGGTTCGGT | chr13: 27389489-27389590 | 102 |
| | PDX1exp Ar | 657 | GTTTCCGCTCTAAATCCCCGCTAACGCC | | |
| | PDX1exp Bf | 658 | GGAAAAAGGAGGAGGATAAGAAGCGC | chr13: 27396588-27396685 | 98 |
| | PDX1exp Br | 659 | CTCGCCGAAAATCACGACGCAATCCTAC | | |
| EPSTI1 | EPSTI1 Af | 660 | TAGGGGAGGCGTCGAGTTC | chr13: 42464253-42464369 | 117 |
| | EPSTI1 Ar | 661 | ACTCGCTAAACGTCCCAACC | | |

TABLE 15-continued

| Gene | Probe | SEQ ID NO. | 5'-3' Primer Sequence (Bisulfite) | Chr: Location | PCR Product Length |
|---|---|---|---|---|---|
| A2BP1 | A2BP1 Af | 662 | GAGTTTAGGGGTCGCGTC | chr16: 6009425-6009564 | 140 |
| | A2BP1 Ar | 663 | CAATACCGCCGCCTCTACTA | | |
| | A2BP1 Bf | 664 | GAGAGAGTAGGAGCGGATCG | chr16: 6009706-6009842 | 137 |
| | A2BP1 Br | 665 | ACAAATCAACCCCGCCCTAA | | |
| CRYM | CRYM Af | 666 | AGTGAGTGTTCGGGAGTTTC | | |
| | CRYM Ar | 667 | TCATTTATTAAAAACGCGCG | | |
| | +CRYM Af | 668 | GCAGTGAGTGCTCGGGAGCCCC | chr16: 21202786-21202934 | 149 |
| | +CRYM Ar | 669 | GGTTTTCATTTGTTAGAGGCGCGCG | | |
| | CRYM Bf | 670 | CGGGTTCGCGTAGGATTAGG | chr16: 21202650-21202732 | 83 |
| | CRYM Br | 671 | ACTCCTCATCCCAACACCCT | | |
| PRKCB | PRKCB Af | 672 | GTTCGTAGTTCGCGGTTTC | | |
| | PRKCB Ar | 673 | CGATACTCTCCTCGCCCT | | |
| | +PRKCB Af | 674 | TCGGTTCGTAGTTCGCGGTTTC | chr16: 23754928-23755052 | 125 |
| | +PRKCB Ar | 675 | GCACGATACTCTCCTCGCCCT | | |
| | PRKCB Bf | 676 | TTGGGCGAGTGATAGTTTC | chr16: 23754821-23754909 | 89 |
| | PRKCB Br | 677 | GACCGCTACTACACCCGA | | |
| | PRKCB Cf | 678 | CGGTAGAAGAACGTGTATGAGGT | chr16: 23755076-23755216 | 141 |
| | PRKCB Cr | 679 | GCTACCCTCGAAAACCCGAA | | |
| IRF8 | IRF8 Af | 680 | GATTTTTTTTAAGGTCGCGC | chr16: 84490230-84490341 | 112 |
| | +IRF8 Af | 681 | TTACGATTTTTTTAAGGTCGCGC | | |
| | IRF8 Ar | 682 | ACTATACCTACCTACCGCCGTC | | |
| | IRF8 Bf | 683 | ATTTCGAAGAAGGCGGGTCG | chr16: 84490149-84490276 | 128 |
| | IRF8 Br | 684 | CTCCAAACGATACGCCAACG | | |
| SALL3 | SALL3 Af | 685 | TTTTGCGGGTAAGCGTTC | | |
| | SALL3 Ar | 686 | CCACAACTCTCTCGACGAC | | |
| | +SALL3 Af | 687 | TGTTTTTTGCGGGTAAGCGTTC | chr18: 74841456-74841551 | 96 |
| | +SALL3 Ar | 688 | GCCCACAACTCTCTCGACGAC | | |
| | SALL3 Bf | 689 | ATTTCGGGAAAGGGTGGGTC | chr18: 74840051-74840163 | 113 |
| | SALL3 Br | 690 | ACCCTAATCCCCCTTCACCA | | |
| | SALL3 Cf | 691 | TTTCGTTTCGTTTCGGTCGC | chr18: 74840452-74840573 | 122 |
| | SALL3 Cr | 692 | AACCCGCCCGAACTCAAATA | | |
| LYPD5 | LYPD5 Af | 693 | ATTAGGAGCGTACGTTTATTC | chr19: 49016646-49016788 | 143 |
| | LYPD5 Ar | 694 | TACGCACTCGAAACACAA | | |
| | LYPD5 Bf | 695 | CGGCGCGTTTTAAGGGTTTT | chr19: 49016738-49016863 | 126 |
| | LYPD5 Br | 696 | ATTACTCTCACCTCCGCACG | | |
| DPP10 | DPP10 Af | 697 | GATTGCGGGAAGAAGGTAC | | |
| | DPP10 Ar | 698 | AAACGAAACCAAACGACAA | | |
| | +DPP10 Af | 699 | CGGATTGCGGGAAGAAGGTAC | chr2: 115635638-115635739 | 102 |
| | +DPP10 Ar | 700 | GACGAAACGAAACCAAACGACAA | | |
| | DPP10 Bf | 701 | TTTTCGAGTTTGAAGCGTTC | | |
| | DPP10 Br | 702 | CGACTCTCACCTAATCCGC | | |
| | +DPP10 Bf | 703 | CGGTTTTCGAGTTTGAAGCGTTC | chr2: 115635947-115636088 | 142 |
| | +DPP10 Br | 704 | TACCGACTCTCACCTAATCCGC | | |
| | DPP10 Cf | 705 | TTACGACGGGGAGTTCGTTC | chr2: 115635821-115635943 | 123 |
| | +DPP10 Cr | 706 | CTTAACAACGTTCGCAAATCACGA | | |
| | DPP10 Cr | 707 | ACAACGTTCGCAAATCACGA | | |
| C20orf56 | C20orf Af | 708 | GTTCGTTATTCGGAATTC | chr20: 22507658-22507804 | 147 |
| | C20orf Ar | 709 | CCGACCGATAAAATATAATTC | | |
| | C20orf Bf | 710 | GGGGAGGGATTTAAGCGGGAG | chr20: 22507684-22507819 | 136 |
| | C20orf Br | 711 | CCCCCTTCACTAATCCCGAC | | |
| SOX2OT | SOX2OT Af | 712 | AGTGTTGAGAGTCGACGC | chr3: 182919951-182920042 | 92 |
| | SOX2OT Ar | 713 | AATAAAATAACCCGAACCGC | | |
| | SOX2OT Bf | 714 | GGGTTACGGTTTCGGGTTGT | chr3: 182919884-182919969 | 86 |
| | SOX2OT Br | 715 | CGCGTCGACTCTCAACACTA | | |
| CDKL2 | CDKL2 Af | 716 | GGTCGAGTCGAGTCGTTAC | | |
| | CDKL2 Ar | 717 | AAAACGCCTCCTAACGAA | | |
| | +CDKL2 Af | 718 | ATTGGTCGAGTCGAGTCGTTAC | chr4: 76774785-76774935 | 151 |
| | +CDKL2 Ar | 719 | ACAAAAAAACGCCTCCTAACGAA | | |
| | CDKL2 Bf | 720 | TATTTTGGGCGAAGGCGTTG | chr4: 76774698-76774806 | 109 |
| | CDKL2 Br | 721 | GTAACGACTCGACTCGACCA | | |
| MARCH11 | MARCH11 Af | 722 | TCGGCGTTTTCGTTTTTC | chr5: 16232623-16232697 | 75 |
| | MARCH11 Ar | 723 | CGACGACACAACCATAAACTTT | | |
| | MARCH11 Bf | 724 | AAGGTTTTGTAGTTGCGGCG | chr5: 16232839-16232935 | 97 |
| | MARCH11 Br | 725 | TCTCACGCGCAACCGAAT | | |

TABLE 15-continued

| Gene | Probe | SEQ ID NO. | 5'-3' Primer Sequence (Bisulfite) | Chr: Location | PCR Product Length |
|---|---|---|---|---|---|
| CCL28 | CCL28 Af | 726 | GTGGAGTTTTAGGTAGCGC | | |
| | CCL28 Ar | 727 | ACCCGCGATAAACTAAACC | | |
| | +CCL28 Af | 728 | AGGGTGGAGTTTTAGGTAGCGC | chr5: 43433001-43433128 | 128 |
| | +CCL28 Ar | 729 | AACAACCCGCGATAAACTAAACC | | |
| | CCL28 Bf | 730 | TGTAGTCGTGGTTGTCGTGG | chr5: 43432695-43432834 | 140 |
| | CCL28 Br | 731 | CCAAATAAACGACGTCCCGC | | |
| AP3B1 | AP3B1 Af | 732 | ATTTTATAGTCGCGTTAAAAGC | | |
| | AP3B1 Ar | 733 | ACTTTTATTACTCGCGATCC | chr5: 77304383-77304519 | 137 |
| | AP3B1 Bf | 734 | GGTAGGGTGAGTTTGGTCGG | chr5: 77304339-77304484 | 146 |
| | AP3B1 Br | 735 | CGCCGAACCACGTAAAAACT | | |
| CARD11 | CARD11 Af | 736 | ATTTGGGCGTTTATGTTTC | chr7: 3049825-3049944 | 120 |
| | CARD11 Ar | 737 | CCCTCGAAAAACGACTCC | | |
| | CARD11 Bf | 738 | AGGGGTTGTAGGGTCGGG | | |
| | +CARD11 Bf | 739 | TTTAGGGGTTGTAGGGTCGGG | chr7: 3049955-3050087 | 133 |
| | CARD11 Br | 740 | ATTTTACATTTCCCTCCCCCGC | | |
| BLACE | BLACE Af | 741 | AGAATAAAAGTAGGCGGC | chr7: 154859246-154859384 | 139 |
| | BLACE Ar | 742 | TCTCGAAACCAAAATAAACG | | |
| | BLACE Bf | 743 | AGTAGGCGGCGGATTTGTAG | chr7: 154859254-154859357 | 104 |
| | BLACE Br | 744 | CCGAAAATACGCGAAATCAACC | | |
| PTPRN2 | PTPRN2 Af | 745 | GAGGAGATAAAGGTGTCGC | | |
| | PTPRN2 Ar | 746 | AACGTACCTAACCCGAAAAC | | |
| | +PTPRN2 Af | 747 | TCGGAGGAGATAAAGGTGTCGC | chr7: 157176188-157176342 | 155 |
| | +PTPRN2 Ar | 748 | CCAACGTACCTAACCCGAAAAC | | |
| | PTPRN2 Bf | 749 | GACGGTTTCGGTAGGGTC | | |
| | PTPRN2 Br | 750 | CCGAACCGAATATAAAACGA | | |
| | +PTPRN2 Bf | 751 | CGGACGGTTTCGGTAGGGTC | chr7: 157176379-157176463 | 85 |
| | +PTPRN2 Br | 752 | GCGCCGAACCGAATATAAAACGA | | |
| RUNX1T1 | RUNX1T1 Af | 753 | TTAGGTTCGTAAAGAGGGC | chr8: 93183286-93183401 | 116 |
| | RUNX1T1 Ar | 754 | TTAAAACCACGTCCGAATA | | |
| | RUNX1T1 Bf | 755 | TTTCGGGCGGGAGTTATAGG | chr8: 93183412-93183529 | 118 |
| | RUNX1T1 Br | 756 | ACGCGCTCTAAACTCAACCG | | |
| L1TD1 | L1TD1 Af | 757 | GCGCGTGGGGYFCGTAGCGTTTTAAG | chr1: 62433357-62433465 | 109 |
| | L1TD1 Ar | 758 | TTACCCGAAACACCCCGCGCCCTTC | | |
| PPFIA3 | PPFIA3 Af | 759 | AGATACGGAGATTTAGCGCGAGATCGGT | chr19: 54337953-54338094 | 143 |
| | PPFIA3 Ar | 760 | AAATTAACCGCCGAACACTCACAATACG | | |
| FILIP1L | FILIP1L Af | 761 | TTGTAGTGTCGCGTTGCGAGTCGATTGT | chr3: 101077651-101077753 | 103 |
| | FILIP1L Ar | 762 | ACAATAACGTAACGCCCATAAACCGAACG | | |
| NUDT16P | NUDT Af | 763 | GAGGACGGGTTGAATCGTGGTTTGTTGG | chr3: 132563775-132563858 | 84 |
| | NUDT Ar | 764 | ACTACGATAATCAAAACGCTCCACGCGA | | |
| TOP2P1 | TOP Af | 765 | GTGCGCGTTTTAGTAGGGCGAGAATGG | chr6: 28283268-28283417 | 150 |
| | TOP Ar | 766 | CGAAAACCAAATCCGAACCACCGTCTCC | | |
| | TOP Bf | 767 | TGATTTGGGTGGATGTAGAGGTTGTGGT | chr6: 28283447-28283568 | 122 |
| | TOP Br | 768 | TTTCGAATAACGCTACTCCGAACCGCGA | | |
| UNKWN1 | UNKWN1 Af | 769 | TTGAGAGTAGGGATTGTGGTGCGTCGTC | chr5: 72634694-72634838 | 145 |
| | UNKWN1 Ar | 770 | CTAACTCCCGAACGCTACATTCGCTCCA | | |
| GALR3 | GALR3 Af | 771 | GGTTGTGGTGAGTTTGGTTTACGGGCG | chr22: 36550907-36551049 | 143 |
| | GALR3 Ar | 772 | CGTAAAACGCGACCACCGCCAACATA | | |
| PRSS27 | PRSS Af | 773 | GGGAGGTTATTCGTAGGATTTGGCGCGG | chr16: 2705610-2705748 | 139 |
| | PRSS Ar | 774 | ATCCTAACGACTACGCACTACTTCCGCA | | |
| SLC7A4 | SLC Af | 775 | GAGTTCGTTTAGTTCGTCGGCGTC | chr22: 19716858-19717005 | 148 |
| | SLC Ar | 776 | AACCCCGATAAACTCCGATAACGACCT | | |
| LEF1 | LEF1 Af | 777 | AGAGTTGGGGCGGTATAGTTAGGGTGT | chr4: 109307444-109307547 | 104 |
| | LEF1 Ar | 778 | TTCAATCCCTACGACCCCAACGCCTAAA | | |
| NFIC | NFIC Af | 779 | CGTGGATACGAGTTTTGGCGGCGATTAT | chr19: 3386117-3386219 | 103 |
| | NFIC Ar | 780 | GCCACCAACCCTACCTCCTTCCATATCC | | |
| | NFIC Bf | 781 | TTTTTCGGTTTGAGTTATCGTGGCGGGA | chr19: 3386234-3386379 | 146 |
| | NFIC Br | 782 | CGAACCGTACTTCCAACCAAACGCAACT | | |

TABLE 15-continued

| Gene | Probe | SEQ ID NO. | 5'-3' Primer Sequence (Bisulfite) | Chr: Location | PCR Product Length |
|---|---|---|---|---|---|
| TMEM90B | TMEM90 Af | 783 | TAGGAAGGGGTCGATGTTGGTTTGGGTT | chr20: 24398648-24398747 | 100 |
|  | TMEM90 Ar | 784 | TCTCACCAACTCCCATCGAATTCGCACA |  |  |
|  | TMEM90 Bf | 785 | GTTTTGGTTTCGTTTCGGAGCGCGTAGA | chr20: 24398510-24398642 | 133 |
|  | TMEM90 Br | 786 | TTTCTCTACCGACTCAACTCCCCCTCCC |  |  |
| UBD | UBD Af | 787 | TCGGTTGCGTAAATCGCGTTTTTGGTTG | chr6: 29629437-29629564 | 128 |
|  | UBD Ar | 788 | TTCTCGATAATATCTCCGTCGCCTCCGC |  |  |
| GIPC2 | GIPC Af | 789 | GTTTAGGGGTGGAGGTCGGGGTTTTGA | chr1: 78284199-78284289 | 91 |
|  | GIPC Ar | 790 | CCGAACCCCGCGCAAATAAAAACAACCT |  |  |
| EFNA4 | ERNA Af | 791 | GGGGCGCGTTTTTATGGAAAGTTAGGGT | chr1: 153310423-153310549 | 127 |
|  | ERNA Ar | 792 | CTACGCCCTAAAACACGCCTCGACTTCT |  |  |
|  | ERNA Bf | 793 | TGTGCGAAAGAGACGCGGGGTTTAGTTA | chr1: 153310139-153310288 | 150 |
|  | ERNA Br | 794 | CCCGTAATCGCTAAAACATCCGCCCTTA |  |  |
| DRD4 | DRD4 Af | 795 | CGTCGGGCGATGTTGGTTTGTTCGTG | chr11: 627035-627175 | 141 |
|  | DRD4 Ar | 796 | GCGACGCTCCACCGTAAACCCAATATTA |  |  |
| TCTEX1D1 | TCTEX Af | 797 | CGGGGAGGGTCGAGGGTTTTGTTTGAG | chr1: 66990668-66990782 | 101 |
|  | TCTEX Ar | 798 | GCGTCCCAAACTTCATTCAACCGACGAC |  |  |
| PHOX2B | PHOX Af | 799 | GCGGACGTAGTAATGGATTAAACGGGGA | chr4: 41447111-41447255 | 145 |
|  | PHOX Ar | 800 | AAATCCGACTCCCTACACTCCCGACTTT |  |  |
| TSPAN33 | TSPAN Af | 801 | GGGGGTTGTGTTAGTTGTTTGTTTAGCGA | chr7: 128596487-128596593 | 107 |
|  | TSPAN Ar | 802 | CGAAACTATTTCCCGCCAAACCGAACCC |  |  |
| CA9 | CA9 Af | 803 | TTTCGGGCGGGAGTATCGGGTTTTGTAG | chr9: 35666101-35666239 | 139 |
|  | CA9 Ar | 804 | GCTCCTTTACCCCTTCTCGACCAACTCC |  |  |
| UNKWN2 | UNKWN2 Af | 805 | TTACGGATTTTATTTGTATTCGGAATCGTA | chr10: 102409232-102409335 | 104 |
|  | UNKWN2 Ar | 806 | ACGCATCAAACTCGACACAAAATTTCATC |  |  |
| WT1 | WT1 Af | 807 | GGTGTTTTCGTAAGACGGGGTAGTGGGT | chr11: 32406776-32406869 | 94 |
|  | WT1 Ar | 808 | TTCTCCTCCGCTAAAAATCCGAATACGA |  |  |
| OTX2 | OTX2 Af | 809 | AGGGATTGTATTTCGAGGTGGTCGAGGT | chr14: 56331673-56331781 | 109 |
|  | OTX2 Ar | 810 | CCGACAAATCGAAACCTTCGCCCGAAAC |  |  |
| HOXB13 | HOXB13 Af | 811 | TCGCGGGTTATAAATATTTGGTTGCGGC | chr17: 44157793-44157885 | 93 |
|  | HOXB13 Ar | 812 | GACCGCCACTACCTCGAAAACATTTCCC |  |  |
| BRCA1 | BRCA1 Af | 813 | GGTAACGGAAAAGCGCGGGAATTATAGA | chr17: 38530874-38530968 | 95 |
|  | BRCA1 Ar | 814 | CCCACAACCTATCCCCCGTCCAAAAA |  |  |
| ITPRIPL1 | ITPRIPL1f | 815 | TTTTGTACGTTGGGTTACGGGGGTTTGG | chr2: 96354715-96354857 | 143 |
|  | ITPRIPL1r | 816 | TAAACGCGATAAACCCCTACGACCCCCA |  |  |
| HES5 | HES5-F | 817 | TATCGGTTTTCGTAGTTGCGGGAGGAGG | Chr1: 2451323-2451386 | 118 |
|  | HES5-R | 818 | CCGAATAAATACCAAACTCGCCCGACGC |  |  |
| CSRP1/LOC376693 | CSRP1/LOC3766-F | 819 | CGGGTAGAGGGGAGGTAGGAATTGGAGA | Chr1: 199775889-199775914 | 80 |
|  | CSRP1/LOC3766-R | 820 | CCGAATAAACGTCACCCCTACACACCGC |  |  |
| ALOX5 | ALOX5-F | 821 | TTTTGCGGTTAGGTGAAGGCGTAGAGGT | Chr10: 45234681-45234732 | 106 |
|  | ALOX5-R | 822 | GACCGAATACCCCGCTTTCTCTCTCGAC |  |  |
| PPM1H/MON2 | PPM1H/MON2-F | 823 | AGGAGTAGTATTGCGAGGGTGGAGGGT | Chr12: 61311943-61312001 | 112 |
|  | PPM1H/MON2-R | 824 | TAAACCCGAAAAACAACGCCAATCCCGC |  |  |
| KIAA0984 | KIAA0984-F | 825 | GGGGATTTGTTGTAGAGTCGTAGGAGAA | Chr12: 63515983-63516043 | 62 |
|  | KIAA0984-R | 826 | CCGCATCCCACCCTTTAAAACTCTA |  |  |
| TXNRD1 | TXNRD1-F | 827 | TATGGGTTGCGTCGAGGGTAAGGTAGTG | Chr12: 103133737-103133768 | 86 |
|  | TXNRD1-R | 828 | TACGACGACCATCGCCGTTCTTACCTTT |  |  |
| CHST11 | CHST11-F | 829 | AAATTTGGATTGGGGGAGGGACGAGGTT | Chr12: 103376469-103376538 | 124 |
|  | CHST11-R | 830 | CTTCGCAACCGAACTACTCACCCCCGAC |  |  |
| EFS | EFS-F | 831 | GGTCGTTGGAGTGGTCGTTTCGGTTTAG | Chr14: 22904743-22904785 | 98 |
|  | EFS-R | 832 | CCTCAAACCCCCGAACGCGCTAAATAAA |  |  |

TABLE 15-continued

| Gene | Probe | SEQ ID NO. | 5'-3' Primer Sequence (Bisulfite) | Chr: Location | PCR Product Length |
|---|---|---|---|---|---|
| ANXA2 | ANXA2-F | 833 | GTTCGGGGAGGGAGGGAGATTCGTTTTG | Chr15: 58478046- | 107 |
|  | ANXA2-R | 834 | AACTCCCGACTTTAACCTCCCAACCCAA | 58478098 |  |
| RHCG | RHCG-F | 835 | GTTGTAGGGGTGTTTGGTCGGGTTGGTA | Chr15: 87840807- | 118 |
|  | RHCG-R | 836 | ATCAACTACTCCGTACCCCACGTAACCG | 87840869 |  |
| RARA | RARA-F | 837 | AGTCGGGGTTGGTTGGTGGAAGAGG | Chr17: 35718896- | 137 |
|  | RARA-R | 838 | CCCTCTCAACTCGATTCAAAATTCCCCC | 35718981 |  |
| PTRF | PTRF-F | 839 | AAAGTAATAAGTGGTTTCGGGCGGAGTC | Chr17: 37827277- | 104 |
|  | PTRF-R | 840 | ACCCCGCATACCTACGAAAACGAAACC | 37827326 |  |
| RND2 | RND2-F | 841 | CGGGATTATGGAGGGGTAGAGCGGTCG | Chr17: 38430910- | 99 |
|  | RND2-R | 842 | ACGTCCTTAACGAACACCTACAACACG | 38430955 |  |
| TMP4 | TMP4-F | 843 | AGGTTTTGTAGTAGTAGGCGGACGAGGC | Chr19: 16048446- | 121 |
|  | TMP4-R | 844 | ACGAATACGAAACCCGAAACCGAAACGC | 16048512 |  |
| HIF3A | HIF3A-F | 845 | CGTGGTATAGTTAATCGCGCGGCGT | Chr19: 51492259- | 118 |
|  | HIF3A-R | 846 | TACAACCCCAACGCCATAACTCGCCAAT | 51492376 |  |
| KLK5 | KLK4-F | 847 | TAGCGGGGATTTATTAGGGGAGAGGTGG | Chr19: 56107959- | 123 |
|  | KLK4-R | 848 | ATCACCTACGAACACTATCCCTCACCCG | 56108027 |  |
| AMOTL2 | AMOTL2-F | 849 | GCGGAATAGTTCGCGGTTTTGGAATGTT | Chr3: 135565786- | 125 |
|  | AMOTL2-R | 850 | AAACGTTTCCGCTCCCCGAAAAACGAAT | 135565856 |  |
| SCGB3A1 | SCGB3A1-F | 851 | GGAGATAGTTTTGAGAGGGGGAGGTCGC | Chr5: 179950858- | 120 |
|  | SCGB3A1-R | 852 | CGCTACCTACGCCGATCGTAAATCCCAA | 179950923 |  |
| HLA-F | HLA-F-F | 853 | GAATGGTTGCGATATGGGGTTCGACGGA | Chr6: 29799978- | 112 |
|  | HLA-F-R | 854 | CGCGATCCAAAAACGCAAATCCTCGTTC | 29800035 |  |
| HLA-J-1 | HLA-J, NCRNA00171-1-F | 855 | GGTTTTGGTCGAGATTTGGGCGGGTGAG | Chr6: 30082430- 30082476 | 101 |
|  | HLA-J, NCRNA00171-1-R | 856 | CCCGAATCCTACGCCCCAACCAAATAAA |  |  |
| HLA-J-3 | HLA-J, NCRNA00171-2-F | 857 | TGAGTGATTTCGGTTCGGGGCGTAGATT | Chr6: 30083115- 30083168 | 125 |
|  | HLA-J, NCRNA00171-2-R | 858 | CGAAAATCTCTACAAATCCCGCAACCTCG |  |  |
| PON3 | PON3-F | 859 | ATGGTTTCGGGGTGTTTAGCGGCGATTG | Chr7: 94863624- | 105 |
|  | PON3-R | 860 | AACGAAACCGAACGAACCCCAATCCGTA | 94863674 |  |
| LRRC4/SND1 | LRRC4-F | 861 | GAGTCGGAGTGAGCGTTAAGTGAGGGG | Chr7: 127459707- | 77 |
|  | LRRC4-R | 862 | TCCCTCCGACCGACCCAAATAACTACG | 127459730 |  |
| PAH | PAH-F | 863 | TTCGTTGTTCGTTTTGGGTAAAGGGAAG | Chr12: 101835348- | 116 |
|  | PAH-R | 864 | AAACTCGCTTCCCAAACTTCTAAAAATC | 101835409 |  |
| EPSTI1 | EPSTI1-F | 865 | GGGGAGGCGTCGAGTTCGGAGTTTATTA | Chr13: 42464282- | 117 |
|  | EPSTI1-R | 866 | AAAACTCGCTAAACGTCCCAACCGCATC | 42464345 |  |
| ADCY4 | ADCY4-F | 867 | CGGGTATTGTTGGTTTAGGTTGTAGTAGGT | Chr14: 23873644- | 123 |
|  | ADCY4-R | 868 | CGACCCTAACCAACCCCGAAACTCGAAA | 23873710 |  |
| HAPLN3 | HAPLN3-F | 869 | AGGGTAGAAAGGAAGCGGTAGTAGAAAA | Chr15: 87239811- | 116 |
|  | HAPLN3-R | 870 | ACAACAACTCCTCCCTTCGAACCCAACC | 87239872 |  |
| HSF4 | HSF4-F | 871 | TGTGGGAGGGAAGGGAAATCGAGATTGG | Chr16: 65762053- | 113 |
|  | HSF4-R | 872 | ACGACAAAACGAAACCCACAATCCTACCC | 65762164 |  |
| NBR1/ TMEM106 A | NBR1/TMEM106A-F | 873 | ATTCGGATTGGTTAGTTTTTGCGGAAGT | Chr17: 38719260- | 91 |
|  | NBR1/TMEM106A-R | 874 | TTCGCCACGCAACAACCTAAAACGCTAC | 38719296 |  |
| HAAO | HAAO-F | 875 | GGTTGCGGCGTTTATTTAGCGGGAAGTC | Chr2: 42873761- | 114 |
|  | HAAO-R | 876 | CTCGCCGAACCCGCGACGAAATCTAC | 42873822 |  |
| RARB | RARB-F | 877 | TAGAGGAATTTAAAGTGTGGGTTGGGGG | Chr3: 25444371- | 125 |
|  | RARB-R | 878 | ACCAACTTCTCTCCCTTTACGCCTTTTT | 25444441 |  |
| ALDH1L1 | ALDH1L1-F | 879 | TGGGTTAAGTATTTGTTATGTGTTACGGA | Chr3: 127382511- | 121 |
|  | ALDH1L1-R | 880 | CGCTATCCACCCGAATACGCAACT | 127382580 |  |

TABLE 15-continued

| Gene | Probe | SEQ ID NO. | 5'-3' Primer Sequence (Bisulfite) | Chr: Location | PCR Product Length |
|---|---|---|---|---|---|
| HIST1H3G | HIST1H3G-F | 881 | GCGCGGCGTTTTGTTATCGGTGGATT | Chr6: 26379588-26379647 | 60 |
|  | HIST1H3G-R | 882 | TCTAAAATAACCCGCACCAAACAAACTACA |  |  |
| ZSCAN12 | ZSCAN12-F | 883 | TTATAAAGGTCGGAAGCGGTTACGGGGG | Chr6: 28475534-28475572 | 93 |
|  | ZSCAN12-R | 884 | AACCCCTTTCGCTCCCTTCCTAAAACGA |  |  |
| HCG4P6 | HCG4P6-F | 885 | GTATGGTTGCGATTTGGGGTTGGAAGGG | Chr6: 30002983-30003042 | 114 |
|  | HCG4P6-R | 886 | GCCGCGATCCAAAAACGCAAATCCTAAT |  |  |
| HLA-J-3 | HLA-J, NCRNA00171-3-F | 887 | TAGGGAATGTTTGGTTGCGATTTGGGG | Chr6: 30083115-30083168 | 80 |
|  | HLA-J, NCRNA00171-3-R | 888 | TCCTTACCGTCGTAAACATACTACTCAT |  |  |
| EYA4 | EYA4-F | 889 | GCGTAAGTGCGAGGTTGTCGGTAGC | Chr6: 133604154-133604229 | 125 |
|  | EYA4-R | 890 | TTTCCCGCAACTCTTTCCCCCTCTCT |  |  |
| HOXA7 | HOXA7-F | 891 | TGCGGTTAAAGAATTCGTTCGCGTTCGG | Chr7: 27162955-27162982 | 82 |
|  | HOXA7-R | 892 | CTAAACGCTCCCGCGAAACCTCCAAATC |  |  |
| USP44 | USP44/p-F | 893 | TTCGGGTATTTTGAGGTTGTCGTCGGGA | Chr12: 94466379-94466481 | 103 |
|  | USP44/p-R | 894 | GACGACGACGCGTCCGACGAATTTTA |  |  |
| CYP27A1 | CYP27A1/p-F | 895 | GTTTTGGTCGGGGCGTCGTGGATATTTT | Chr2: 219354932-219355042 | 111 |
|  | CYP27A1/p-R | 896 | AAAAACCAACTAAACCCCTTCCCGCTCG |  |  |
| PRSS3 | PRSS3/p-F | 897 | GTGTGGAAAGGGTTTGGCGGTTGTTAGG | Chr9: 33740574-33740686 | 113 |
|  | PRSS3/p-R | 898 | CTCGCCAAATACGTCCACCCAAAAACGA |  |  |
| C18orf62 | C18orf62/p-F | 899 | TAGGAGGGGACGTAGAGTTTACGGCGAA | Chr18: 71296729-71296833 | 105 |
|  | C18orf62/p-R | 900 | GAATACCCGACCCGACCCATCCATCAC |  |  |
| SFRP2 | SFRP2/p-1-F | 901 | TGCGTTTGTAGGAGAAGTCGGGTGGTT | Chr4: 154929326-154929408 | 83 |
|  | SFRP2/p-1-R | 902 | ACTCTTCCTCGCCTCGCACTACTACCTA |  |  |
|  | SFRP2/p-2-F | 903 | GTGCGATTCGGGGTTTCGAAAAGTTGGT | Chr4: 154929535-154929641 | 107 |
|  | SFRP2/p-2-R | 904 | GAAACTACGCGCGAACTTACAACGCCTC |  |  |
| SLCO4C1 | SLCO4C1/p-F | 905 | GAGCGTAGAGCGTTGAGCGGGG | Chr5: 101660047-101660169 | 123 |
|  | SLCO4C1/p-R | 906 | CGCCGCCGAATAACACGCCCAC |  |  |
| CORO1C | CORO1C/p-1-F | 907 | AGCGGGGATTTTCGGAGTTGGAGAGTTT | Chr12: 107686622-107686733 | 112 |
|  | CORO1C/p-1-R | 908 | CTCCATCCGCCCGACCTAACCCTAAAA |  |  |
|  | CORO1C/p-2-F | 909 | GGGAAGTGGCGTAGTGGGCGTTTGTATC | Chr12: 107686752-107686848 | 97 |
|  | CORO1C/p-2-R | 910 | TACCTCCAACGACCACGCCCACAAAATA |  |  |
| KJ904227 | KJ904227/p-F | 911 | TGGAGCGTTGAGTCGAAGTTTTGATTTT | Chr3: 127489474-127489582 | 109 |
|  | KJ904227/p-R | 912 | TCTTACCCGAACTTTAACCCCAACCGCT |  |  |
| C6orf141 | C6orf141/p-1-F | 913 | GGTTGGGAGTTCGGAGTTGTAGTAGAGG | Chr6: 49626357-49626455 | 99 |
|  | C6orf141/p-1-R | 914 | CTTTAACCGATTCAAACAACAAACGCCT |  |  |
|  | C6orf141/p-2-F | 915 | GTAGGGCGCGGGGTTTCGTTAGTTTC | Chr6: 49626570-49626668 | 99 |
|  | C6orf141/p-2-R | 916 | ATCTACCGTTCTATCCTCGTAACCGCCG |  |  |
| BC030768 | BC030768/p-F | 917 | TCGTTTGGGAGGGATCGTTTTTGGGAGA | Chr1: 26424688-26424767 | 80 |
|  | BC030768/p-R | 918 | AACCCGAATACTATCCAACTACCGCCGC |  |  |
| DMRTA2 | DMRTA2/p-F | 919 | CGAGCGTGGGTATTAAGTCGGTAGTGGA | Chr1: 50657067-50657169 | 103 |
|  | DMRTA2/p-R | 920 | GACCTCAACCCCCTACGCCTAACCTACT |  |  |
| HFE | HFE/p-1-F | 921 | GTAGATCGCGGTTTTGTAGGGGCGTTTG | Chr6: 26195692-26195783 | 92 |
|  | HFE/p-1-R | 922 | CTAATTTCGATTTTTCCACCCCCGCCGC |  |  |
|  | HFE/p-2-F | 923 | GAGTGTTTGTCGAGAAGGTTGAGTAAAT | Chr6: 26196140-26196221 | 82 |
|  | HFE/p-2-R | 924 | CACCGCCCAACGCATTCGTTCTAAAATA |  |  |
| CADPS2 | CADPS2/p-F | 925 | ATAAAAGTGGGGTGGGTGGCGGAGGG | Chr7: 121744063-121744166 | 104 |
|  | CADPS2/p-R | 926 | GCGCCGAAATAACAACCCAACCTACCAA |  |  |
| CYTH4 | CYTH4/p-F | 927 | TTTATCGGGGAAGTTTTCGAGGGTGGGC | Chr22: 36050993-36051112 | 120 |
|  | CYTH4/p-R | 928 | TCCCAACTACCTCCTACGCACGAACGAT |  |  |
| Intergenic (Chr4) | Chr4/p-1-F | 929 | ATGAAATGTGGTTCGTGGAAGGTGTTTGT | Chr4: 186174475-186174549 | 75 |
|  | Chr4/p-1-R | 930 | ACGACCCGAACGTTAATCCTCTTACTAC |  |  |

TABLE 15-continued

| Gene | Probe | SEQ ID NO. | 5'-3' Primer Sequence (Bisulfite) | Chr: Location | PCR Product Length |
|---|---|---|---|---|---|
| NHLH2 | NHLH2/p-F | 931 | ACGTAGTTTTCGAGTTAGTGTCGTTAGAA | Chr1: 116172677-116172793 | 117 |
| | NHLH2/p-R | 932 | GACAAACGCCTCAAACCCGACCG | | |
| NRN1 | NRN1/p-F | 933 | AGGAGCGGGAGAGGGAAAAATAGTTAAG | Chr6: 5952635-5952767 | 133 |
| | NRN1/p-R | 934 | CGCTCCAAACTACGCCCAAAACTCAA | | |
| HMGCLL1 | HMGCLL1/p-F | 935 | ATTAGAGTTGTTTTGCGTATTGCGGCGG | Chr6: 55551934-55552030 | 97 |
| | HMGCLL1/p-R | 936 | CAAATACCCCGTACACCCGCTACCCCAA | | |
| Me3 | Me3/p-1-F | 937 | GGGAGTTGAGGTTTACGCGGTTTCGTTG | Chr11: 86061026-86061124 | 99 |
| | Me3/p-1-R | 938 | GACCGCCAACGCGATCCACCCATTAAC | | |
| | Me3/p-2-F | 939 | AGTTTTGGAAGTAGATTCGGTGCGGGTG | Chr11: 86060867-86060948 | 82 |
| | Me3/p-2-R | 940 | GCCGCGCAATCGCCTCTTTTTCAC | | |
| Intergenic (Chr3) | Chr3/p-1-F | 941 | AGACGATAGATGGCGGGTAGGAAGGGAG | Chr3: 135608250-135608374 | 125 |
| | Chr3/p-1-R | 942 | GCCGCCTACAACCGACGAACTACAAATC | | |
| Intergenic (Chr8) | Chr8/p-1-F | 943 | TCGCGGGTGAGGTTTGTGGTTAATTTCG | Chr8: 68037553-68037676 | 124 |
| | Chr8/p-1-R | 944 | GCTCAACCAAACTACAACGTTCCCGCCT | | |
| NBPF1 | NBPF1/p-F | 945 | TGAGAGGCGTATTTTGTTGGTTACGGTT | Chr1: 146219493-146219574 | 82 |
| | NBPF1/p-R | 946 | CGAAAACCATTCCGCTACCCTTCCAACT | | |
| Intergenic (Chr10) | Chr10/p-1-F | 947 | GGGGCGTTGGGTTATGGAGATTACGTTTT | Chr10: 42748953-42749053 | 101 |
| | Chr10/p-1-R | 948 | GTCCCGCGCTTAACGAATTCTACGAACG | | |
| ASAP1 | ASAP1/p-F | 949 | GTTCGGGTAGGGGTCGGGGGTC | Chr8: 131524437-131524546 | 110 |
| | ASAP1/p-R | 950 | CCCGAAACGACGTACTTAACGACCCGAA | | |
| Intergenic (Chr1) | Chr1/p-1-F | 951 | GGGAGGTTTGAGCGTCGAAGTTTTCGTT | Chr1: 119352428-119352549 | 122 |
| | Chr1/p-1-R | 952 | GCCCACTACCCCGCGAAACCTTATCAAC | | |
| PPP2R5C | PPP2R5C/p-F | 953 | AGTCGTTAGGTTGTTAAGGCGCGTTGTG | Chr14: 101317476-101317534 | 59 |
| | PPP2R5C/p-R | 954 | ACAAAAATAAAATCGAACCTAACCCCACG | | |
| Intergenic (Chr2) | Chr2/p-1-F | 955 | CGTATTAAGGGTTAAGCGGCGCGGT | Chr22: 44883312-44883404 | 93 |
| | Chr2/p-1-R | 956 | AACTTTCTCGAACGACTCGATAAACCTAA | | |
| KRT78 | KRT78/p-F | 957 | AGGTTTTGGGAATTTGGAAGTTCGCGGG | Chr12: 51554274-51554370 | 97 |
| | KRT78/p-R | 958 | AAAAACGCTCGAACCCAACCAATCGACG | | |
| LINC240 | LINC240/p-1-F | 959 | AAAGGAAGATCGTGGGTAGTTCGTGCG | Chr6: 27167780-27167859 | 80 |
| | LINC240/p-1-R | 960 | ACTACAACTCACGTTTCCCCTCCAACAC | | |
| | LINC240/p-2-F | 961 | AGGTTTATTTGACGTTTTAGGTCGATAGT | Chr6: 27172709-27172830 | 122 |
| | LINC240/p-2-R | 962 | CGATCTCTCCCTTTCTTCCGCTTCCTAA | | |
| Intergenic (Chr16) | Chr16/p-1-F | 963 | GGCGTCGGTTGCGGTTTTAGAT | Chr16: 53648145-53648269 | 125 |
| | Chr16/p-1-R | 964 | ACGCGAAAATCTACCTTTTAATTACGAACC | | |
| HIST1H3G/1H2BI | HIST1H3G/1H2BI/p-F | 965 | TCGTCGGTGGTCGGCGCGTTTTT | Chr6: 26379488-26379589 | 102 |
| | HIST1H3G/1H2BI/p-R | 966 | AACCCGCACCAAACAAACTACACGCAAA | | |
| PPM1H | PPM1H/p-1-F | 967 | GAATGGTAGCGAGAGGTTGCGGGTTAGG | Chr12: 61312222-61312310 | 89 |
| | PPM1H/p-1-R | 968 | CTCTACCCTCAAAATCGCGACGCAAACG | | |
| | PPM1H/p-2-F | 969 | AGGAGTAGTATTGCGAGGGTGGAGGGTT | Chr12: 61311917-61312012 | 96 |
| | PPM1H/p-2-R | 970 | CGCCAATCCCGCTCCGACACTATAACAA | | |
| TUBB2B | TUBB2B/p-F | 971 | ATAAGGTTTGGTGGAAGCGTAGGAGCGT | Chr12: 3177175-3177262 | 88 |
| | TUBB2B/p-R | 972 | ACGATATTCTAACCTCCGCCGCGAAACT | | |
| C2CD4A | C2C5F | 973 | GGTAGAGGGATAGGGAAGAGTTTGGCGT | Chr15: 60146378-60146528 | 150 |
| | C2C5R | 974 | ATTCAAAACGCGCGCGACGAAATTCAAC | | |
| COL19A1 | COL2F | 975 | GCGGAGTGGGAGGGTTATATTGGGAGAG | Chr6: 70633134-70633240 | 106 |
| | COL2R | 976 | CCGAACAAAACTACGACACCGCCGAAAA | | |
| DCDC2 | DCD5F | 977 | ACGACGGGTTGAGATAGGTGGTTGGATT | Chr6: 24465938-24466027 | 90 |
| | DCD5R | 978 | CCCGACGCGAAACAACGAACTAAAACGA | | |

TABLE 15-continued

| Gene | Probe | SEQ ID NO. | 5'-3' Primer Sequence (Bisulfite) | Chr: Location | PCR Product Length |
|---|---|---|---|---|---|
| DHRS3 | DGR2F | 979 | TTTTTGTACGTTTTCGGGGTCGGAGGAG | Chr1: 12601840- | 102 |
|  | DHR2R | 980 | AATCGCCGTCTAAACAAATCGCGAACTA | 12601942 |  |
| GALNT3 | GAL1F | 981 | CGGCGGTCGCGGTTTGTAGTTTAGAATTG | Chr2: 166358281- | 150 |
|  | GAL1R | 982 | ACGCGCTTCCACTCCGACTAACAAATTA | 166358431 |  |
|  | GAL3F | 983 | GGCGTCGTTCGGGTTAAGTTTGGTTGT | Chr2: 166359152- | 78 |
|  | GAL3R | 984 | CACAACTTACGCGAAACAACAACCTCGC | 166359230 |  |
| HES5 | HES1F | 985 | TGGGTTGGTGTCGCGCGAATTTTTGTTT | Chr1: 2451234- | 116 |
|  | HES1R | 986 | CCTCCTCCCGCAACTACGAAAACCGATA | 2451350 |  |
|  | HES3F | 987 | GTTGGGGGTTATGTTTGGCGCGGAATAG | Chr1: 2451478- | 144 |
|  | HES3R | 988 | CGCCTATATAAAACGTCGACGCGCGAAA | 2451622 |  |
|  | HES4F | 989 | GTTCGGGCGTCGCGGTCGTTTTTATATT | Chr1: 2453144- | 122 |
|  | HES4R | 990 | AAAACGCCCATTATACCCGCGCCAATTC | 2453266 |  |
| KILLIN | KIL5F | 991 | TAAGAATCGGCGGTAGTTAGTAGGCGGG | Chr10: 89611638- | 145 |
|  | KIL5R | 992 | TCCTACGCCGCGACGAAAACAAAAACTC | 89611783 |  |
|  | KIL6F | 993 | AGGTGGGGCGCGTTTATTAGTTTAGGGG | Chr10: 89611428- | 150 |
|  | KIL6R | 994 | ACCTCTCCATCGCTAATACCCTACCGCT | 89611578 |  |
| MUC21 | MUC2F | 995 | GAGTGTTTCGAGGGTAGGAGGTTGTCGG | Chr6: 31031426- | 133 |
|  | MUC2R | 996 | CAAAAACCGCCCGCAAAACGAAACCTAA | 31031559 |  |
| NR2E1/ OSTM1 | OST3F | 997 | ACGGATCGATCGCGGTTTTGGTAAGGAT | Chr6: 108542828- | 87 |
|  | OST3R | 998 | CGCAAAAACGAAAAACTACGTACGCGCT | 108542915 |  |
|  | OST4F | 999 | GTTGTTTGAGGACGGGTCGTTTAGCGG | Chr6: 108543090- | 99 |
|  | OST4R | 1000 | ACCCCTATCCTACAACCCTACGAACGCA | 108543189 |  |
| PAMR1 | PAM4F | 1001 | TTTCGGGAGGTGTGGTTACGTTTGGAGA | Chr11: 35503958- | 119 |
|  | PAM4R | 1002 | CCCCTCCTCCCAACACCCAACACTAAAA | 35504077 |  |
| SCRN1 | SCR2F | 1003 | GGTTGTGGTTTTTAAAAGGGAAAATTCGGG | Chr7: 29996282- | 106 |
|  | SCR2R | 1004 | TAAACGCCGAAACCCGAACGTAACAACC | 29996388 |  |
| SEZ6 | SEZ3F | 1005 | AGGTGATTAGAAGGGAGAGGGGGAGGTT | Chr17: 24371083- | 97 |
|  | SEZ3R | 1006 | TCATTATACACGACGCGCCCCTCCAAAT | 24371180 |  |
|  | SEZ5F | 1007 | TACGTGGGTGTAGGTTAGGTCGGGTTGA | Chr17: 24371224- | 121 |
|  | SEZ5R | 1008 | ACCACGCGACTACCGTATAAACAACCGAA | 24371345 |  |

EQUIVALENTS

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1. How K A, Nielsen H M, Tost J. DNA methylation based biomarkers: practical considerations and applications. Biochimie 2012; 94:2314-37.
2. Mikeska T, Craig J M. DNA methylation biomarkers: cancer and beyond. Genes (Basel) 2014; 5:821-64.
3. Noehammer C, Pulverer W, Hassler M R, Hofner M, Wielscher M, Vierlinger K, et al. Strategies for validation and testing of DNA methylation biomarkers. Epigenomics. 2014; 6:603-22.
4. Warton K, Samimi G. Methylation of cell-free circulating DNA in the diagnosis of cancer. Front Mol. Biosci. 2015; 2:13.
5. Wittenberger T, Sleigh S, Reisel D, Zikan M, Wahl B, Alunni-Fabbroni M, et al. DNA methylation markers for early detection of women's cancer: promise and challenges. Epigenomics. 2014; 6:311-27.
6. Usadel H, Brabender J, Danenberg K D, Jeronimo C, Harden S, Engles J, et al. Quantitative adenomatous polyposis coli promoter methylation analysis in tumour tissue, serum, and plasma DNA of patients with lung cancer. Cancer Res. 2002; 62:371-5.
7. Esteller M, Sanchez-Cespedes M, Rosell R, Sidransky D, Baylin S B, Herman J G. Detection of aberrant promoter hypermethylation of tumour suppressor genes in serum DNA from non-small cell lung cancer patients. Cancer Res. 1999; 59:67-70.
8. Mazurek A, Pierzyna M, Giglok M, Dworzecka U, Suwinski R, Ma U E. Quantification of concentration and assessment of EGFR mutation in circulating DNA. Cancer Biomark. 2015; 15:515-24.
9. Ostrow K L, Hoque M O, Loyo M, Brait M, Greenberg A, Siegfried J M, et al. Molecular analysis of plasma DNA for the early detection of lung cancer by quantitative methylation-specific PCR. Clin. Cancer Res. 2010; 16:3463-72.
10. Powrozek T, Krawczyk P, Kucharczyk T, Milanowski J. Septin 9 promoter region methylation in free circulating DNA-potential role in noninvasive diagnosis of lung cancer: preliminary report. Med. Oncol. 2014; 31:917.
11. Lin P C, Lin J K, Lin C H, Lin H H, Yang S H, Jiang J K, et al. Clinical Relevance of Plasma DNA Methylation in Colorectal Cancer Patients Identified by Using a Genome-Wide High-Resolution Array. Ann. Surg. Oncol. 2014.

12. Philipp A B, Nagel D, Stieber P, Lamerz R, Thalhammer I, Herbst A, et al. Circulating cell-free methylated DNA and lactate dehydrogenase release in colorectal cancer. BMC. Cancer 2014; 14:245.
13. Chimonidou M, Strati A, Malamos N, Georgoulias V, Lianidou E S. SOX17 promoter methylation in circulating tumour cells and matched cell-free DNA isolated from plasma of patients with breast cancer. Clin. Chem. 2013; 59:270-9.
14. Chimonidou M, Tzitzira A, Strati A, Sotiropoulou G, Sfikas C, Malamos N, et al. CST6 promoter methylation in circulating cell-free DNA of breast cancer patients. Clin. Biochem. 2013; 46:235-40.
15. Martinez-Galan J, Torres-Torres B, Nunez M I, Lopez-Penalver J, Del M R, Ruiz De Almodovar J M, et al. ESR1 gene promoter region methylation in free circulating DNA and its correlation with estrogen receptor protein expression in tumour tissue in breast cancer patients. BMC. Cancer 2014; 14:59.
16. Matuschek C, Bolke E, Lammering G, Gerber P A, Peiper M, Budach W, et al. Methylated APC and GSTP1 genes in serum DNA correlate with the presence of circulating blood tumour cells and are associated with a more aggressive and advanced breast cancer disease. Eur. J. Med. Res. 2010; 15:277-86.
17. Fackler M J, Lopez B Z, Umbricht C, Teo W W, Cho S, Zhang Z, et al. Novel methylated biomarkers and a robust assay to detect circulating tumour DNA in metastatic breast cancer. Cancer Res. 2014; 74:2160-70.
18. Avraham A, Uhlmann R, Shperber A, Birnbaum M, Sandbank J, Sella A, et al. Serum DNA methylation for monitoring response to neoadjuvant chemotherapy in breast cancer patients. Int. J. Cancer 2012; 131: E1166-E1172.
19. Sharma G, Mirza S, Parshad R, Gupta S D, Ralhan R. DNA methylation of circulating DNA: a marker for monitoring efficacy of neoadjuvant chemotherapy in breast cancer patients. Tumour. Biol. 2012; 33:1837-43.
20. Legendre C, Gooden G C, Johnson K, Martinez R A, Liang W S, Salhia B. Whole-genome bisulfite sequencing of cell-free DNA identifies signature associated with metastatic breast cancer. Clin. Epigenetics. 2015; 7:100.
21. Jones P A. Functions of DNA methylation: islands, start sites, gene bodies and beyond. Nat. Rev. Genet. 2012; 13:484-92.
22. Cope L M, Fackler M J, Lopez-Bujanda Z, Wolff A C, Visvanathan K, Gray J W, et al. Do breast cancer cell lines provide a relevant model of the patient tumour methylome? PLoS. One. 2014; 9: e105545.
23. Becker D, Lutsik P, Ebert P, Bock C, Lengauer T, Walter J. BiQ Analyzer HiMod: an interactive software tool for high-throughput locus-specific analysis of 5-methylcytosine and its oxidized derivatives. Nucleic Acids Res. 2014; 42: W501-W507
24. Lutsik P, Feuerbach L, Arand J, Lengauer T, Walter J, Bock C. BiQ Analyzer HT: locus-specific analysis of DNA methylation by high-throughput bisulfite sequencing. Nucleic Acids Res. 2011; 39: W551-W556.
25. Soreide K. Receiver-operating characteristic curve analysis in diagnostic, prognostic and predictive biomarker research. J. Clin. Pathol. 2009; 62:1-5.
26. Madic, J. et al. Pyrophosphorolysis-activated polymerization detects circulating tumor DNA in metastatic uveal melanoma. Clinical Cancer Research: an official journal of the American Association for Cancer Research. 2012; 18:3934-3941.
27. Bidard, F. C. et al. Detection rate and prognostic value of circulating tumor cells and circulating tumor DNA in metastatic uveal melanoma. International Journal of Cancer 2014; 134:1207-1213.
28. The Molecular Taxonomy of Primary Prostate Cancer. Cell. 2015; 163 (4): 1011-25.

All references referred to herein are expressly incorporated by reference in their entireties.

The invention claimed is:

1. A method of detecting the presence of uveal cancer, comprising:
   amplifying multiple regions of tumour DNA extracted from a cell-free sample obtained from a human subject with a plurality of PCR primer pairs;
   wherein the multiple regions are either
   (a) the regions amplified by primer pairs as set forth in SEQ ID NOs: 977-978 and 979-980, or
   (b) the regions amplified by primer pairs as set forth in SEQ ID NOs: 973-1008;
   wherein individual primer pairs of the plurality of PCR primer pairs are modified to include non-native DNA sequences corresponding to methylation specific versions of the multiple regions by selecting C residues to be replaced with T residues according to their methylation status within individual regions of the multiple selected regions;
   generating sequencing reads from the amplified regions;
   aligning the sequencing reads with a reference sequence for each region with a computer, wherein the reference sequence is obtained from a sample obtained from a healthy human subject; and
   detecting signals by using the computer to determine methylation status of CpG residues in each of the two or more selected regions;
   wherein the presence of uveal cancer in the subject is indicated when a level of methylation of CpG residues within the two or more selected regions is greater than a level of methylation of CpG residues within the two or more selected regions for subjects without uveal cancer.

2. The method of claim 1, further comprising determining sites of hydroxymethylation.

3. The method of claim 2, wherein:
   amplifying is carried out with at least one primer set designed to amplify at least one methylation site having a methylation value at or below −0.1, −0.2, −0.3, −0.4, or −0.5 in normal tissue; or
   amplifying is carried out with at least one primer set designed to amplify at least one methylation site having a difference between the average methylation value in the cancer and the normal tissue of greater than 0.1, 0.2, 0.3, 0.4, or 0.5; or
   amplifying is carried out with at least one primer set comprising primer pairs amplifying at least one methylation site having at least one adjacent methylation site within 200 base pairs that also has:
   a methylation value at or below −0.1, −0.2, −0.3, −0.4, or −0.5 in normal tissue, and
   a difference between the average methylation value in the cancer and the normal tissue of greater than 0.1, 0.2, 0.3, 0.4, or 0.5.

4. The method of claim 1, wherein the detection of at least one signal is indicative of the presence of uveal cancer during one or more of:
   determining response to treatment;
   monitoring tumour load;
   detecting residual tumour post-surgery;
   detecting relapse;
   performing a secondary screening;
   performing a primary screening;
   monitoring cancer development; and
   monitoring cancer risk.

5. The method of claim 1, further comprising either
   (i) determining a distribution of signals across the multiple regions; and
   comparing the distribution to at least one pattern associated with uveal cancer;
   wherein similarity between the distribution and the pattern is indicative of uveal cancer; or
   (ii) comparing the distribution to a plurality of patterns, each one associated with uveal cancer;
   wherein similarity between the distribution and one of the plurality of patterns is indicative of the uveal cancer.

6. A kit for detecting the presence of uveal cancer in tumour DNA extracted from a cell-free sample obtained from a human subject, the kit comprising:
   reagents for carrying out a method of detecting uveal cancer, the reagents comprising either
   (a) primer pairs as set forth in SEQ ID NOs: 977-978 and 979-980, or
   (b) primer pairs as set forth in SEQ ID NOs: 973-1008.

7. A method of detecting the presence of uveal cancer and treating uveal cancer, comprising:
   amplifying multiple regions of tumour DNA extracted from a cell-free sample obtained from a human subject, with a plurality of PCR primer pairs;
   wherein the multiple regions are either
   (a) the regions amplified by primer pairs as set forth in SEQ ID NOs: 977-978 and 979-980, or
   (b) the regions amplified by primer pairs as set forth in SEQ ID NOs: 973-1008;
   wherein individual primer pairs of the plurality of PCR primer pairs are modified to include non-native DNA sequences corresponding to methylation specific versions of the multiple regions by selecting C residues to be replaced with T residues according to their methylation status within individual regions of the multiple selected regions;
generating sequencing reads from the amplified regions;
aligning the sequencing reads with a reference sequence for each region with a computer, wherein the reference sequence is obtained from a sample obtained from a healthy human subject; and
detecting signals by using the computer to determine methylation status of CpG residues in each of the two or more selected regions;
determining that a level of methylation within the two or more selected regions is greater than a level of methylation within the two or more selected regions in subjects without uveal cancer which is indicative of the human subject having uveal cancer; and
administering an anti-uveal cancer treatment to the human subject determined to have uveal cancer.

8. A method of detecting the presence of uveal cancer, comprising:
amplifying multiple regions of tumour DNA extracted from a cell-free sample obtained from a human subject, with either
 (a) primer pairs as set forth in SEQ ID NOs: 977-978 and 979-980, or
 (b) primer pairs as set forth in SEQ ID NOs: 973-1008;
wherein individual primer pairs of the plurality of PCR primer pairs are modified to include non-native DNA sequences corresponding to methylation specific versions of the multiple regions by selecting C residues to be replaced with T residues according to their methylation status within individual regions of the multiple selected regions;
generating sequencing reads from the amplified regions;
aligning a computer to align the sequencing reads with a reference sequence for each region with a computer, wherein the reference sequence is obtained from a sample obtained from a healthy human subject; and
detecting signals by using the computer to determine methylation status of CpG residues in each of the two or more selected regions;
wherein the presence of uveal cancer in the subject is indicated when a level of methylation of CpG residues within the two or more selected regions is greater than a level of methylation of CpG residues within the two or more selected regions for subjects without uveal cancer.

9. A method, comprising:
amplifying multiple regions of tumour DNA extracted from a cell-free sample obtained from a human subject with a plurality of PCR primer pairs;
wherein the multiple regions are either
 (a) the regions amplified by primer pairs as set forth in SEQ ID NOs: 977-978 and 979-980, or
 (b) the regions amplified by primer pairs as set forth in SEQ ID NOs: 973-1008;
wherein individual primer pairs of the plurality of PCR primer pairs are modified to include non-native DNA sequences corresponding to methylation specific versions of the multiple regions by selecting C residues to be replaced with T residues according to their methylation status within individual regions of the multiple selected regions;
generating sequencing reads from the amplified regions;
aligning the sequencing reads with a reference sequence for each region with a computer, wherein the reference sequence is obtained from a sample obtained from a healthy human subject; and
detecting signals by using the computer to determine methylation status of CpG residues in each of the two or more selected regions.

* * * * *